US 8,685,974 B2

(12) United States Patent
Sudau et al.

(10) Patent No.: US 8,685,974 B2
(45) Date of Patent: Apr. 1, 2014

(54) THIENYLPYRI(MI)DINYLAZOLE

(75) Inventors: Alexander Sudau, Leichlingen (DE); Mazen Es-Sayed, Couzon au Mont d'Or (FR); Julia Neumann, Düsseldorf (DE); Catherine Sirven, Langenfeld (DE); Jürgen Benting, Leichlingen (DE); Christoph Andreas Braun, Düsseldorf (DE); Ruth Meissner, Leverkusen (DE); Anne-Sophie Rebstock, Lyons (FR); Samir Bennabi, Caluire (FR); Philippe Desbordes, Lyons (FR); Arounarith Tuch, Lyons (FR); Philippe Rinolfi, Chatillon d'Azerous (FR); Stephane Brunet, Saint André de Corcy (FR); Hiroyuki Hadano, Tochigi (JP); Marie-Claire Grosjean-Cournoyer, Curis au Mont d'Or (FR)

(73) Assignee: Bayer CropScience AG, Monheim (DE)

( * ) Notice: Subject to any disclaimer, the term of this patent is extended or adjusted under 35 U.S.C. 154(b) by 437 days.

(21) Appl. No.: 12/974,978

(22) Filed: Dec. 21, 2010

(65) Prior Publication Data

US 2011/0237588 A1    Sep. 29, 2011

Related U.S. Application Data

(60) Provisional application No. 61/288,566, filed on Dec. 21, 2009.

(30) Foreign Application Priority Data

Dec. 21, 2009 (EP) .................................. 09180177

(51) Int. Cl.
*A61K 31/535* (2006.01)
(52) U.S. Cl.
USPC ........ 514/236.5; 514/314; 514/274; 514/341; 514/256; 514/275; 544/331; 544/333; 544/124; 544/316; 546/275.4; 546/167; 546/276.1
(58) Field of Classification Search
USPC ........... 514/235.8, 275, 236.5, 314, 274, 341, 514/256; 544/122, 331, 333, 124, 316; 546/275.4, 167, 276.1
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 5,876,739 A | 3/1999 | Turnblad et al. | |
| 6,096,901 A | 8/2000 | Marfat et al. | |
| 6,335,336 B1 | 1/2002 | Anantanarayan et al. | |
| 6,511,997 B1 | 1/2003 | Minami et al. | |
| 6,979,686 B1 | 12/2005 | Naraian et al. | |
| 7,091,352 B2 | 8/2006 | Kimura et al. | |
| 7,294,625 B2 | 11/2007 | Hagihara et al. | |
| 2003/0176428 A1 | 9/2003 | Schneidersmann et al. | |
| 2009/0018156 A1 | 1/2009 | Tang et al. | |
| 2009/0062252 A1 | 3/2009 | Kaplan et al. | |

FOREIGN PATENT DOCUMENTS

| | | |
|---|---|---|
| EP | 1 553 096 A1 | 7/2005 |
| EP | 1 382 603 B1 | 7/2008 |
| WO | WO 89/10396 A1 | 11/1989 |
| WO | WO 95/31451 A1 | 11/1995 |
| WO | WO 96/33270 A1 | 10/1996 |
| WO | WO 98/52937 A2 | 11/1998 |
| WO | WO 98/52940 A1 | 11/1998 |
| WO | WO 00/31063 A1 | 6/2000 |
| WO | WO 00/39116 A1 | 7/2000 |

(Continued)

OTHER PUBLICATIONS

Bénard, S., et al., "Copper-Mediated N-Cyclopropylation of Azoles, Amides, and Sulfonamides by Cyclopropylboronic Acid," *J. Org. Chem.* 73:6441-44, American Chemical Society, United States (2008).

(Continued)

*Primary Examiner* — Jason M Sims
*Assistant Examiner* — Ibrahim D Bori
(74) *Attorney, Agent, or Firm* — Sterne, Kessler, Goldstein & Fox PLLC

(57) ABSTRACT

Thienylpyri(mi)dinylazole of the formula (I)

in which $R^1$ to $R^8$ and $X^1$ have the meanings given in the description, and agrochemically active salts, to their use and to methods and compositions for controlling phytopathogenic harmful fungi in and/or on plants or in and/or on seed of plants and for reducing mycotoxins in plants and parts of the plants, to processes for preparing such compounds and compositions and treated seed and also to their use for controlling phytopathogenic harmful fungi in agriculture, horticulture, forestry, in animal husbandry, in the protection of materials, in the domestic and hygiene field and for the reduction of mycotoxins in plants and parts of the plants.

10 Claims, No Drawings

(56) References Cited

FOREIGN PATENT DOCUMENTS

| | | |
|---|---|---|
| WO | WO 01/30154 A2 | 5/2001 |
| WO | WO 02/28186 A2 | 4/2002 |
| WO | WO 02/057265 A1 | 7/2002 |
| WO | WO 02/080675 A1 | 10/2002 |
| WO | WO 03/049542 A1 | 6/2003 |
| WO | WO 03/095455 A2 | 11/2003 |
| WO | WO 2004/014913 A2 | 2/2004 |
| WO | WO 2004/029043 A1 | 4/2004 |
| WO | WO 2005/028434 A2 | 3/2005 |
| WO | WO 2005/040155 A1 | 5/2005 |
| WO | WO 2005/077363 A1 | 8/2005 |
| WO | WO 2006/054151 A1 | 5/2006 |
| WO | WO 2006/081072 A1 | 8/2006 |
| WO | WO 2006/108591 A1 | 10/2006 |
| WO | WO 2007/024782 A2 | 3/2007 |
| WO | WO 2007/024843 A2 | 3/2007 |
| WO | WO 2007/027777 A2 | 3/2007 |
| WO | WO 2007/039112 A1 | 4/2007 |
| WO | WO 2007/104538 A1 | 9/2007 |
| WO | WO 2007/143597 A2 | 12/2007 |
| WO | WO 2008/006509 A1 | 1/2008 |
| WO | WO 2008/008747 A1 | 1/2008 |
| WO | WO 2008/088692 A2 | 7/2008 |
| WO | WO 2009/076440 A2 | 6/2009 |
| WO | WO 2009/158380 A1 | 12/2009 |

OTHER PUBLICATIONS

Draber, W. and Wegler, R., "Naturliche Pflanzenwuchsstoffe—Phytohormone: 2. Gibberelline," in *Chemie der Pflanzenschutz- and Schadlingsbekampfungsmittel*, vol. 2, Wegler, R., ed., pp. 401-412, Springer-Verlag, Germany (1970).

Emmitte, K.A., et al., "Discovery of thiophene inhibitors of polo-like kinase," *Bioorg. Med. Chem. Lett. 19*:1018-21, Elsevier Ltd., England (2009).

Eskildesen, J., et al., "Halogen dance in pyrazole 1-oxides: synthesis of pyrazolo[3,4-c]quinoline 1-oxides," *Tetrahedron 58*:7635-44, Elsevier Science Ltd., England (2002).

Gérard, A.-L., et al., "Efficient and simple synthesis of 3-aryl-1*H*-pyrazoles," *Tetrahedron Lett. 47*:4665-69, Elsevier Ltd., England (2006).

Guthrie, D.A. and Tovar, J.D., "Conformationally Complex π-Conjugated Molecular and Polymeric Materials: New Challenges for Organic Synthesis," *Chem. Eur. J. 15*:5176-85, Wiley-VCH Verlag GmbH, Germany (2009).

Huang, X. and Buchwald, S.L., "New Ammonia Equivalents for the Pd-Catalyzed Amination of Aryl Halides," *Org. Lett. 3*(21):3417-19, American Chemical Society, United States.

Hussein, A.M., et al., "β-Oxoanilides in Heterocyclic Synthesis: An Expeditious Synthesis of New Polyfunctionally Substituted Pyridine and Pyrazole Derivatives," *J. Heterocyclic Chem. 45*:1819-23, John Wiley & Sons, Inc., United States (2008).

Iddon, B., et al., "The *N*-vinyl group as a protection group of the preparation of 3(5)-substituted pyrazoles via bromine-lithium exchange," *Tetrahedron 63*:56-61, Elsevier Ltd., England (2007).

Ivachtchenko, A.V., et al., "Synthesis of Pinacol Esters of 1-Alkyl-1*H*- pyrazol-5-y1- and 1-Alkyl-1*H*-pyrazol-4-ylboronic Acids," *J. Heterocyclic Chem. 41*: 931-9, John Wiley & Sons, Inc., United States (2004).

Karpov, A.S. and Müller, T.J.J., "Straightforward Novel One-Pot Enaminone and Pyrimidine Syntheses by Coupling-Addition-Cyclocondensation Sequences," *Synthesis 18*:2815-26, Georg Thieme Verlag, Germany (2003).

Ley, S.V., et al., "A polymer-supported thionating reagent," *J. Chem. Soc., Perkin Trans. 1*:358-61, The Royal Society of Chemistry, England (2001).

Li, H., et al., "Discovery of (*R*)-6-Cyclopentyl-6-(2-(2,6-diethylpyridin-4-yl)ethyl)-3-((5,7-dimethyl-[1,2,4]triazolo[1,5-α]pyrimidin-2-yl)methyl)-4-hydroxy-5,6-dihydropyran-2-one (PF-00868554) as a Potent and Orally Available Hepatitis C Virus Polymerase Inhibitor," *J. Med. Chem. 52*:1255-58, American Chemical Society, United States (2009).

Liang, B., et al., "Pd-Catalyzed Copper-Free Carbonylative Sonogashira Reaction of Aryl Iodides with Alkynes for the Synthesis of Alkynyl Ketones and Flavones by Using Water as a Solvent," *J. Org. Chem. 70*:6097-6100, American Chemical Society, United States (2005).

Liu, H.-L., et al., "One-pot three-component synthesis of pyrazoles through a tandem coupling-cyclocondensation sequence," *Tetrahedron Lett. 49*:3805-09, Elsevier Ltd., England (2008).

Liu, Z., et al., "Synthesis of novel 5,6-substituted furo[2,3-d]pyrimidines via Pd-catalyzed cyclization of alkynylpyrimidinols with aryl iodides," *Tetrahedron 63*:1931-36, Elsevier Ltd., England (2007).

Matsumoto, Y., et al., "Novel Potassium Channel Activators: Synthesis and Structure-Activity Relationship Studies of 3,4-Dihydro-2*H*-1,4-benzoxazine Derivatives," *Chem. Pharm. Bull. 44*(1):103-14, Pharmaceutical Society of Japan, Japan 1996.

Millen, L., "Abstract: *Chemie der Pflanzenschutz- and Schadlingsbekampfungsmittel*," CAB Direct, http://www.cabdirect.org/abstracts/19712302897.html, retrieved Mar. 17, 2011.

Mitchell, T.N., "Palladium-Catalysed Reactions of Organotin Compounds," *Synthesis 9*:803-15, Thieme, Germany (1992).

Mittendorf, J., et al., "Discovery of Riociguat (BAY 63-2521): A Potent, Oral Stimulator of Soluble Guanylate Cyclase for the Treatment of Pulmonary Hypertension," *ChemMedChem 4*:853-65, Wiley-VCH, Germany (2009).

Miyaura, N., "Organoboron Compounds," *Top Curr. Chem. 219*:11-59, Springer-Verlag, Germany (2002).

More, M.S., et al., "Synthesis and characterization of some 2-(1-phenyl-3-(thiophen-2-yl)-1*H*-pyrazol-4-yl)-4*H*-chromon-4-ones, 4-(2-hydroxyphenyl)-6-(1-phenyl-3-(thiophen-2-yl)-1*H*-pyrazol-4-yl)pyrimidine-2-(1*H*)-thione, 2-(5-(1-phenyl-3-(thiophen-2-yl)-1*H*-pyrazol-4-yl)-1*H*-pyrazol-3-yl)phenol and 2-(2,3-dihydro-2-(1-phenyl-3-(thiophen-2-yl)-1*H*-pyrazol-4-yl)-benzo[b][1,4]thiazepin-4-yl)-phenol," *Indian J. Chem. 46B*:360-65, National Institute of Science Communication and Information Resources, India (2007).

Mosrin, M., et al., "Regio- and chemoselective magnesiation of protected uracils and thiouracils using TMPMgCl•LiCl and TMP₂Mg•2LiCl," *Org. Biomol. Chem. 6*:3237-39, Royal Society of Chemistry, England (2008).

Naganuma, K., et al., "Discovery of selective PDE4B inhibitors," *Bioorg. Med. Chem. Lett. 19*:3174-76, Elsevier Ltd., England (2009).

Nakamura, T., et al., "Pyrazole and Isoxazole Derivatives as New, Potent, and Selective 20-Hydroxy-5,8,11,14-eicosatetraenoic Acid Synthase Inhibitors," *J. Med Chem. 46*:5416-27, American Chemical Society, United States (2003).

Palimkar, S.S., et al., "Copper-, ligand- and solvent-free synthesis of ynones by coupling acid chlorides with terminal alkynes," *Tetrahedron Lett. 47*:5527-30, Elsevier Ltd., England (2006).

Ralph, J.M., et al., "Two convenient regioselective syntheses of 1-*N*-alkyl-3-aryl-4-[pyrimidin-4-yl]-pyrazoles," *Tetrahedron Lett. 50*:1377-80, Elsevier Ltd., England (2009).

Sandosham, J. and Undheim, K., "Stannylation in the Electrophilic 2- and 4/6-Pyrimidine Position and the Use of Stannylpyrimidines in Coupling and Tin-Lithium Exchange Reactions," *Tetrahedon 50*(1):275-84, Pergamon Press Ltd., England (1994).

Sawyer, J.S., et al., "Synthesis and Activity of New Aryl- and Heteroaryl-Substituted Pyrazole Inhibitors of the Transforming Growth Factor-β Type I Receptor Kinase Domain," *J Med Chem. 46*(19):3953-56, American Chemical Society, United States (2003).

Stevens, K.L., et al., "Pyrazolo[1,5-a]pyridines as p38 Kinase Inhibitors," *Org. Lett. 7*(21):4753-56, American Chemical Society, United States (2005).

Stockmann, V., et al., "Formation of new 4-isocyanobut-2-enenitriles by thermal ring cleavage of 3-pyridyl azides," *Tetrehedron 65*:3668-72, Elsevier Ltd., England (2009).

Suzuki, A., "Recent Advances in the cross-coupling reactions of organoboron derivatives with organic electrophiles, 1995-1998," *J. Organomet. Chem. 576*:147-68, Elsevier Science S.A., England (1999).

(56) References Cited

OTHER PUBLICATIONS

Tambade, P. J., et al., "Copper-Catalyzed, Palladium-Free Carbonylative Sonogashira Coupling Reaction of Aliphatic and Aromatic Alkynes with Iodoaryls," *Synlett 6*:886-88, Georg Thieme Verlag, Germany (2008).

Tyrrell, E. and Brookes, P., "The Synthesis and Applications of Heterocyclic Boronic Acids," *Synthesis 4*:469-83, Georg Thieme Verlag, Germany (2004).

Ueyama, N., et al., "Nonpeptide Angiotensin II Receptor Antagonists. I. Synthesis and Biological Activity of Pyridine Derivatives," *Chem. Pharm. Bull. 42*(9):1841-49, Pharmaceutical Society of Japan, Japan (1994).

Vidal, B., et al., "Discovery and Characterization of 4'-(2-Furyl)-*N*-pyridin-3-yl-4,5'-bipyrimidin-2'-amine (LAS38096), a Potent, Selective, and Efficacious $A_{2B}$ Adenosine Receptor Antagonist," *J. Med. Chem. 50*:2732-36, American Chemical Society, United States (2007).

Vors, J.-P., et al., "The structure of the agrochemical fungicidal 4-chloro-3-(3-5-dichlorophenyl)-1*H*-pyrazole (RPA 406194) and related compounds," *Tetrahedron 59*:555-60, Elsevier Science Ltd., England (2003).

Wiles, J.A., et al., "Biological evaluation of isothiazoloquinolones containing aromatic heterocyles at the 7-position: In vitro activity of a series of potent antibacterial agents that are effective against methicillin-resistant *Staphylococcus aureus*," *Bioorg. Med. Chem. Lett. 16*1277-81, Elsevier Ltd., England (2006).

Willy, B. and Müller, T.J.J., "Regioselective Three-Component Synthesis of Highly Fluorescent 1,3,5-Trisubstituted Pyrazoles," *Eur. J. Org. Chem. 39*:4157-68, Wiley-VCH, Germany (2008).

Wuts, P.G.M. and Greene, T.W., *Greene's Protective Groups in Organic Synthesis*, Fourth Edition, pp. 756, 757, and 887, John Wiley & Sons, Inc., United States (2007).

European Search Report, application No. EP 09 18 0177.9, mailed Mar. 17, 2010, European Patent Office, Munich, Germany.

International Search Report, application No. PCT/EP2010/070219, mailed Jan. 20, 2011, European Patent Office, Rijswijk, Netherlands.

THIENYLPYRI(MI)DINYLAZOLE

The invention relates to novel Thienylpyri(mi)dinylazole and their agrochemically active salts, to their use and to methods and compositions for controlling phytopathogenic harmful fungi in and/or on plants or in and/or on seed of plants and for reducing mycotoxins in plants and parts of the plants, to processes for preparing such compounds and compositions and treated seed and also to their use for controlling phytopathogenic harmful fungi in agriculture, horticulture, forestry, in animal husbandry, in the protection of materials, in the domestic and hygiene field and for the reduction of mycotoxins in plants and parts of the plants.

It is already known that certain Arylpyrazoles can be employed as fungicidal crop protection agents (see WO 03/49542 and WO 01/30154). However, the fungicidal activity of these compounds is, in particular at low application rates, not always sufficient.

Since the ecological and economic demands made on modern crop protection agents are increasing constantly, for example with respect to activity spectrum, toxicity, selectivity, application rate, formation of residues and favourable manufacture, and there can furthermore be problems, for example, with resistance, there is a constant need to develop novel crop protection agents, in particular fungicides which, at least in some areas, have advantages over the known fungicides.

Surprisingly, it has now been found that the present Thienylpyri(mi)dinylazole solve at least in some aspects the problems mentioned above and are suitable for use as crop protection agents, in particular as fungicides.

Some Arylazoles are already known as pharmaceutically active compounds (see for example WO 98/52937, EP-A 1 553 096, WO 04/29043, WO 98/52940, WO 00/31063, WO 95/31451, WO 02/57265 and WO 00/39116), but not their surprising fungicidal activity.

The invention provides compounds of the formula (I),

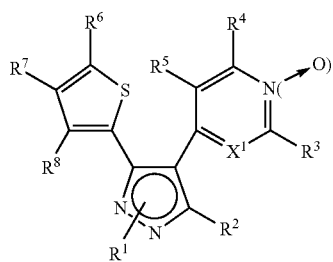
(I)

in which the symbols have the following meanings:

$X^1$ represents C—H or N, $R^1$ represents $C_1$-$C_6$-alkyl, $C_2$-$C_6$-alkenyl, $C_2$-$C_6$-alkinyl, $C_1$-$C_6$-alkoxy, $C_3$-$C_6$-cycloalkyl, $C_3$-$C_8$-allenyl, $C_3$-$C_8$-trialkylsilyl, $C_4$-$C_8$-cycloalkenyl, $C_1$-$C_6$-alkoxy-$C_1$-$C_6$-alkyl, acyloxy-$C_1$-$C_6$-alkyl, heteroaryl-$C_1$-$C_6$-alkyl, aryl-$C_1$-$C_6$-alkyl, $C_1$-$C_6$-alkylthio-$C_1$-$C_6$-alkyl, $C_1$-$C_4$-alkyl-C(O)—$C_1$-$C_6$-alkyl, $C_3$-$C_6$-cycloalkyl-C(O)—$C_1$-$C_4$-alkyl, heterocyclyl-C(O)—$C_1$-$C_4$-alkyl, $C_1$-$C_4$-alkyl-C(O)O—$C_1$-$C_6$-alkyl, $C_3$-$C_6$-cycloalkyl-C(O)O—$C_1$-$C_4$-alkyl, heterocyclyl-C(O)O—$C_1$-$C_4$-alkyl, heterocyclyl-$C_1$-$C_6$-alkyl, $C_5$-$C_{10}$-aryl, heterocyclyl, heteroaryl, each of which is optionally mono- or polysubstituted by identical or different substituents from the group consisting of $R^{16}$
or represents H, C(O)NR$^{17}$R$^{18}$, C(O)R$^{17}$, C(O)OR$^{17}$, S(O)$_2$R$^{17}$, C(S)NR$^{17}$R$^{18}$, C(S)R$^{17}$, S(O)$_2$NR$^{17}$R$^{18}$, $R^2$ represents H, cyano, halogen
or represents $C_1$-$C_6$-alkyl, $C_3$-$C_6$-cycloalkyl, heterocyclyl, $C_2$-$C_8$-alkenyl, $C_2$-$C_8$-alkinyl, $C_1$-$C_8$-alkoxy, $C_2$-$C_8$-alkynyloxy, $C_1$-$C_8$-alkylthio, $C_3$-$C_8$-trialkylsilyl, each of which is optionally mono- or polysubstituted by identical or different substituents from the group consisting of halogen, cyano, amino, dimethylamino or methoxy
and furthermore represents $C_6$-$C_{14}$-aryl which is optionally mono- or polysubstituted by identical or different substituents from the group consisting of halogen, cyano, $C_1$-$C_6$-alkyl, $C_1$-$C_6$-alkylamino, $C_1$-$C_6$-dialkylamino, NH$_2$, heterocyclyl, C(O)OC$_1$-$C_6$-alkyl, OC(O)C$_1$-$C_6$-alkyl, $C_1$-$C_4$-alkoxy, $C_6$-$C_{14}$-aryl
and furthermore represents $C_1$-$C_6$-alkyl, $C_3$-$C_6$-cycloalkyl, $C_2$-$C_8$-alkenyl, $C_2$-$C_8$-alkinyl, $C_1$-$C_8$-alkoxy, $C_2$-$C_8$-alkynyloxy, $C_1$-$C_8$-alkylthio, $C_3$-$C_8$-trialkylsilyl each of which is optionally mono- or polysubstituted by identical or different substituents from the group consisting of $C_1$-$C_6$-alkyl, $C_1$-$C_6$-alkylamino, $C_1$-$C_6$-dialkylamino, heterocyclyl, C(O)OC$_1$-$C_6$-alkyl, OC(O)C$_1$-$C_6$-alkyl, $C_2$-$C_4$-alkoxy, $C_6$-$C_{14}$-aryl,
and furthermore represents heterocyclyl which is optionally mono- or polysubstituted by identical or different substituents from the group consisting of $C_1$-$C_6$-alkylamino, $C_1$-$C_6$-dialkylamino, heterocyclyl, C(O)OC$_1$-$C_6$-alkyl, OC(O)C$_1$-$C_6$-alkyl, $C_2$-$C_4$-alkoxy, $C_6$-$C_{14}$-aryl, $R^3$ represents H, halogen, cyano, OR$^{11}$, C(O)OR$^{11}$, C(O)SR$^{11}$, C(S)OR$^{11}$, C(O)R$^{11}$, C(S)R$^{11}$, SR$^{11}$, NR$^9$R$^{10}$, C(O)NR$^{11}$R$^{20}$, C(S)NR$^{11}$R$^{20}$, N(R$^{17}$)C(O)OR$^{11}$, N═CH—NR$^{17}$R$^{18}$, NH—CH—NR$^{17}$R$^{18}$, N═CR$^{17}$R$^{18}$, N(C$_1$-$C_6$-alkyl)-NHR$^{17}$, N═C(H)OR$^{17}$, N═C(OR$^{17}$)R$^{18}$, N═C(SR$^{17}$)R$^{18}$, C(═NR$^{17}$)NR$^{17}$R$^{18}$, SO(═NR$^{17}$)R$^{18}$, SO$_2$NR$^{11}$R$^{20}$
or represents $C_1$-$C_6$-alkyl, $C_3$-$C_8$-cycloalkyl, $C_2$-$C_6$-alkenyl, $C_2$-$C_8$-alkynyl, $C_6$-$C_{14}$-aryl, heterocyclyl, heteroaryl, each of which is optionally mono- or polysubstituted by identical or different substituents from the group consisting of $R^{16}$,
or represents SO$_2$R$^{11}$,
excluded are compounds with $R^3$ equals aniline if $X^1$ equals N, $R^4$ and $R^5$ represent independently of each other H, F, Cl, Br, I, cyano, nitro, OH, SH
and furthermore represent NH$_2$
or represent $C_1$-$C_6$-alkyl, $C_3$-$C_6$-cycloalkyl, $C_2$-$C_6$-alkenyl, $C_2$-$C_6$-alkinyl, $C_6$-$C_{14}$-aryl, alkoxy, O—($C_6$-$C_{14}$-aryl), S—($C_1$-$C_4$-alkyl), S(O)—($C_1$-$C_6$-alkyl), C(O)—($C_1$-$C_6$-alkyl), $C_3$-$C_8$-trialkylsilyl, heteroaryl, heterocyclyl, each of which is optionally mono- or polysubstituted by identical or different substituents from the group consisting of $R^{16}$
or form together with the carbon atoms, which they are attached to, an optionally mono- or multi identical or different by halogen, oxygen, cyano or $C_1$-$C_4$-alkyl, $C_1$-$C_4$-alkoxy, $C_1$-$C_6$-haloalkyl, $C_1$-$C_4$-haloalkoxy, $C_3$-$C_6$-cycloalkyl substituted cycle with 5 to 8 ring atoms, whereas the cycle consists of carbon atoms but may also contain 1 to 4 heteroatoms selected from oxygen, sulphur or NR$^{19}$, $R^6$ represents H, halogen, OH, nitro, cyano, C(O)NR$^{11}$R$^{20}$, C(O)OR$^{11}$, SO$_2$R$^{11}$, SR$^{11}$, S(O)R$^{11}$, C(S)R$^{11}$, C(S)NR$^{11}$R$^{20}$, SO$_2$NR$^{11}$R$^{20}$, NR$^9$R$^{10}$, N═CR$^{17}$R$^{18}$, C(═NR$^{17}$)R$^{18}$, OR$^{11}$, C(O)SR$^{11}$, C(S)OR$^{11}$, C(O)OC(O)R$^{11}$, C(O)R$^{11}$, N(R$^{17}$)C(O)R$^{11}$, N(R$^{17}$)C(O)OR$^{11}$, N═C—NR$^{17}$R$^{18}$, N(C$_1$-$C_6$-alkyl)-NR$^{17}$, N═C(H)OR$^{17}$, N=C(OR$^{17}$)R$^{18}$, N=C(SR$^{17}$)R$^{18}$, C(=NR$^{17}$)NR$^{17}$R$^{18}$, SO(=NR$^{17}$)R$^{18}$, SO$_2$NR$^{11}$R$^{20}$ or represents C$_1$-C$_6$-alkyl, C$_3$-C$_8$-cycloalkyl, C$_2$-C$_8$-alkenyl, C$_2$-C$_8$-alkinyl, C(O)—C$_1$-C$_6$-alkyl, C$_1$-C$_8$-alkoxy, C$_1$-C$_8$-alkylthio, C$_1$-C$_8$-halogenalkoxy, C$_1$-C$_6$-alkylsulphenyl, C$_1$-C$_6$-alkylsulfanyl, C$_3$-C$_8$-trialkylsilyl, C$_6$-C$_{10}$-aryl, heteroaryl, heterocyclyl, C$_6$-C$_{10}$-aryloxy, each of which is optionally mono- or polysubstituted by identical or different substituents from the group consisting of R$^{16}$, R$^7$ represents H, halogen, cyano, nitro, C$_1$-C$_6$-alkyl, C$_3$-C$_6$-cycloalkyl, C$_2$-C$_6$-alkenyl, C$_2$-C$_6$-alkinyl, C$_5$-C$_{10}$-aryl, heteroaryl, heterocyclyl, or R$^6$ and R$^7$ together can form a 5- to 7-membered ring which can optionally be substituted with one or more substituents selected from: C$_1$-C$_4$-alkyl, C$_1$-C$_4$-halogenoalkyl, C$_1$-C$_4$-alkoxy, C$_1$-C$_4$-halogenoalkoxy, halogen, hydroxyl, amino, cyano or nitro, whereas the cycle consists of carbon atoms but may also contain 1 to 4 heteroatoms selected from oxygen, sulphur or NR$^{19}$, R$^8$ represents H, halogen, cyano, C$_1$-C$_6$-alkyl, C$_3$-C$_6$-cycloalkyl, C$_2$-C$_6$-alkenyl, C$_2$-C$_6$-alkinyl, C$_6$-C$_{10}$-aryl, heteroaryl, heterocyclyl, or R$^7$ and R$^8$ together can form a 5- to 7-membered ring which can optionally be substituted with one or more substituents selected from: C$_1$-C$_4$-alkyl, C$_1$-C$_4$-halogenoalkyl, C$_1$-C$_4$-alkoxy, C$_1$-C$_4$-halogenoalkoxy, halogen, hydroxyl, amino, cyano or nitro, whereas the cycle consists of carbon atoms but may also contain 1 to 4 heteroatoms selected from oxygen, sulphur or NR$^{19}$, R$^9$ and R$^{10}$ represent H, C(S)R$^{14}$, C(O)R$^{14}$, SO$_2$R$^{14}$, C(O)OR$^{14}$, OR$^{14}$ oder C(O)NR$^{14}$R$^{15}$ or represent C$_1$-C$_6$-alkyl, C$_3$-C$_6$-cycloalkyl, C$_2$-C$_6$-alkenyl, C$_2$-C$_6$-alkinyl, C$_3$-C$_8$-cycloalkyl, C$_6$-C$_{14}$-aryl, heterocyclyl or heteroaryl, each of which is optionally mono- or polysubstituted by identical or different substituents from the group consisting of F, Cl, Br, OH, cyano, C$_1$-C$_6$-alkyl, O—C(O)R$^{17}$, O—P(O)(OR$^{17}$)$_2$, O—B(OR$^{17}$)$_2$ or O—(C$_1$-C$_4$-alkyl)

and furthermore represent C$_3$-C$_8$-cycloalkyl-C$_1$-C$_6$-alkyl, C$_6$-C$_{14}$-aryl-C$_1$-C$_6$-alkyl, heterocyclyl-C$_1$-C$_6$-alkyl, or heteroaryl-C$_1$-C$_6$-alkyl, each of which is optionally mono- or polysubstituted by identical or different substituents from the group consisting of F, Cl, Br, OH, cyano, C$_1$-C$_6$-alkyl, O—C(O)R$^{17}$, O—P(O)(OR$^{17}$)$_2$, O—B(OR$^{17}$)$_2$ or O—(C$_1$-C$_4$-alkyl), R$^{11}$ and R$^{20}$ represent H, C(S)R$^{12}$, C(O)R$^{12}$, SO$_2$R$^{12}$, C(O)OR$^{12}$, OR$^{12}$ or C(O)NR$^{12}$R$^{13}$, or represents C$_1$-C$_6$-alkyl, C$_2$-C$_6$-alkenyl, C$_2$-C$_6$-alkinyl, C$_3$-C$_8$-cycloalkyl, C$_6$-C$_{14}$-aryl, heterocyclyl or heteroaryl, each of which is optionally mono- or polysubstituted by identical or different substituents consisting of F, Cl, Br, OH, cyano, C$_1$-C$_6$-alkyl, O—C(O)R$^{17}$, O—P(O)(OR$^{17}$)$_2$, O—B(OR$^{17}$)$_2$ or O—(C$_1$-C$_4$-alkyl), R$^{12}$ and R$^{13}$ represent H, or represents C$_1$-C$_6$-alkyl, C$_3$-C$_6$-cycloalkyl, C$_2$-C$_6$-alkenyl, C$_2$-C$_6$-alkinyl, C$_3$-C$_8$-cycloalkyl, C$_6$-C$_{14}$-aryl, heterocyclyl oder heteroaryl, each of which is optionally mono- or polysubstituted by identical or different substituents from the group consisting of F, Cl, Br, I, OH, carbonyl, cyano, C$_1$-C$_6$-alkyl or C$_1$-C$_4$-alkoxy, R$^{14}$ and R$^{15}$ represent H, or represent C$_1$-C$_6$-alkyl, C$_3$-C$_6$-cycloalkyl, C$_2$-C$_6$-alkenyl, C$_2$-C$_6$-alkinyl, C$_3$-C$_8$-cycloalkyl, C$_6$-C$_{14}$-aryl, heterocyclyl oder heteroaryl, each of which is optionally mono- or polysubstituted from the group consisting of F, Cl, Br, I, OH, cyano, methoxy, nitro, trifluormethyl, difluormethyl and furthermore represent C$_3$-C$_8$-cycloalkyl-C$_1$-C$_6$-alkyl, C$_6$-C$_{14}$-aryl-C$_1$-C$_6$-alkyl, heterocyclyl-C$_1$-C$_6$-alkyl, or heteroaryl-C$_1$-C$_6$-alkyl, each of which is optionally mono- or polysubstituted by identical or different substituents from the group consisting of F, Cl, Br, I, OH, cyano, methoxy, nitro, trifluormethyl, difluormethyl, C$_1$-C$_6$-alkyl, O—C(O)R$^{17}$, O—P(O)(OR$^{17}$)$_2$, O—B(OR$^{17}$)$_2$ or O—(C$_1$-C$_4$-alkyl)

and furthermore represent C$_1$-C$_6$-alkyl, C$_3$-C$_6$-cycloalkyl, C$_2$-C$_6$-alkenyl, C$_2$-C$_6$-alkinyl, C$_3$-C$_8$-cycloalkyl, C$_6$-C$_{14}$-aryl, heterocyclyl or heteroaryl, each of which is optionally mono- or polysubstituted by identical or different substituents from the group consisting of C$_1$-C$_6$-alkyl, O—C(O)R$^{17}$, O—P(O)(OR$^{17}$)$_2$, O—B(OR$^{17}$)$_2$ or O—(C$_1$-C$_4$-alkyl), R$^{16}$ represents OH, F, Cl, Br, I, cyano, NH—C(O)R$^{17}$, NR$^{17}$R$^{18}$, C(O)R$^{17}$, C(O)OR$^{17}$, C(O)NR$^{17}$R$^{18}$, SO$_2$R$^{17}$, OC(O)R$^{17}$ or represents C$_1$-C$_6$-alkyl, C$_2$-C$_6$-alkenyl, C$_2$-C$_6$-alkinyl, C$_3$-C$_8$-cycloalkyl, C$_1$-C$_4$-alkoxy, S—(C$_1$-C$_4$-alkyl), O—(C$_3$-C$_8$-cycloalkyl), S—(C$_3$-C$_8$-cycloalkyl), C$_6$-C$_{14}$-aryl, O—(C$_6$-C$_{14}$-aryl), S—(C$_6$-C$_{14}$-aryl), heterocyclyl or heteroaryl, each of which is optionally mono- or polysubstituted by identical or different substituents from the group consisting of F, Cl, Br, I, OH, carbonyl, cyano, C$_1$-C$_6$-alkyl or C$_1$-C$_4$-alkoxy R$^{17}$ and R$^{18}$ represents C$_1$-C$_6$-alkyl, C$_3$-C$_6$-cycloalkyl, C$_2$-C$_6$-alkenyl, C$_2$-C$_6$-alkinyl, benzyl, each of which is optionally mono- or polysubstituted by identical or different substituents from the group consisting of F, Cl, Br, OH, cyano or represents H, or represents aryl, R$^{19}$ represents H, C$_1$-C$_6$-alkyl, C$_3$-C$_6$-cycloalkyl, C$_2$-C$_6$-alkenyl, C$_2$-C$_6$-alkinyl, C(S)R$^{14}$, C(O)R$^{14}$, SO$_2$R$^{14}$, C(O)OR$^{14}$, and also agrochemically active salts thereof, whereas 4-[3-(2-thienyl)-1H-pyrazol-4-yl]quinoline and phenyl substituted 4-phenyl-6-[1-phenyl-3-(2-thienyl)-1H-pyrazol-4-yl]pyrimidine-2(1H)-thiones are excluded.

The invention also provides the use of the compounds of the formula (I) as fungicides.

Thienylpyri(mi)dinylazole of the formula (I) according to the invention and also their agrochemically active salts are highly suitable for controlling phytopathogenic harmful fungi and for the reduction of mycotoxins. The compounds according to the invention mentioned above have in particular strong fungicidal activity and can be used both in crop protection, in the domestic and hygiene field, in the protection of materials and for the reduction of mycotoxins in plants and parts of the plants.

The compounds of the formula (I) can be present both in pure form and as mixtures of various possible isomeric forms, in particular of stereoisomers, such as E and Z, threo and erythro, and also optical isomers, such as R and S isomers or atropisomers, and, if appropriate, also of tautomers. What is claimed are both the E and the Z isomers, and the threo and erythro, and also the optical isomers, mixtures of these isomers, and also the possible tautomeric forms.

Preference is given to compounds of the formula (I) in which one or more of the symbols have one of the meanings below:

X$^1$ represents CH, N

R$^1$ represents methyl, ethyl, n-propyl, iso-propyl, n-butyl, iso-butyl, sec-butyl, tert-butyl, n-pentyl, —CH=CH$_2$, —CH$_2$CH=CH$_2$, —CH$_2$C≡CH, —C≡CH, —CH=CHCH$_3$, —C≡CCH$_3$, but-2-en-1-yl, but-3-en-2-yl, but-2-yn-1-yl, cyclopropyl, cyclobutyl, cyclopentyl, cyclohexyl, —CH=C=CH$_2$, trimethylsilyl, tert-butyldimethylsilyl, cyclohexenyl, methoxymethyl, ethoxymethyl, methoxyethyl, tert-butoxy-methyl, trifluormethyl, difluormethyl, trifluoromethoxy, difluoromethoxy, methylacetate, ethylacetate, pyridin-2-ylmethyl, pyridin-3-ylmethyl, pyridin-4-ylmethyl, (1,3-thiazol-5-yl)methyl, (1,3-thiazol-4-yl)methyl, 1,3-thiazol-3-yl)methyl, (1,3-oxazol-5-yl)methyl, (1,3-oxa-4-yl)methyl, 1,3-oxa-3-yl)methyl, phenylmethyl, phenylethyl, methylthio, ethylthio, n-propylthio, iso-propylthio, tertbutylthio, n-butylthio, sec-butylthio, iso-butylthio, methylthioalkyl, phenyl, benzyl, naphthalenyl, oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydro-pyridazinyl, 4-hexahydropyridazinyl, 2-hexahydropyrimidinyl, 4-hexahydropyrimidinyl, 5-hexahydropyrimidinyl, 2-piperazinyl, furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, morpholine, each of which is optionally mono- or polysubstituted by identical or different substituents from the group consisting of R$^{16}$ or represents H, C(O)NR$^{17}$R$^{18}$, C(O)R$^{17}$, C(O)OR$^{17}$, S(O)$_2$R$^{17}$, C(S)NR$^{17}$R$^{18}$, C(S)R$^{17}$, S(O)$_2$NR$^{17}$R$^{18}$, R$^2$ represents H, cyano, Br, Cl, F, or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH$_2$CH=CH$_2$, —C≡CH, —C≡CCH$_3$, —CH$_2$C≡CH, methoxy, ethoxy, n-propoxy, iso-propoxy, n-butoxy, tert-butoxy, —O—CH$_2$C≡CH, methylthio, ethylthio, n-propylthio, iso-propylthio, tertbutylthio, n-butylthio, sec-butylthio, iso-butylthio, trimethylsilyl, each of which is optionally mono- or polysubstituted by identical or different substituents from the group consisting of F, Cl, Br, cyano, amino, dimethylamino or methoxy R$^3$ represents H, F, Cl, Br, cyano, OR$^{11}$, C(O)OR$^{11}$, C(O)R$^{11}$, NR$^9$R$^{10}$, C(O)NR$^{11}$R$^{20}$, N=C(OR$^{17}$)R$^{18}$, N=C(SR$^{17}$)R$^{18}$, SO(=NR$^{17}$)R$^{18}$, N(C$_1$-C$_6$-alkyl)-NHR$^{17}$, or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, —CH=CHCH$_3$, —C≡CCH$_3$, but-2-en-1-yl, but-3-en-2-yl, but-2-yn-1-yl, phenyl, benzyl, each of which is optionally mono- or polysubstituted by identical or different substituents from the group consisting of R$^{16}$ R$^4$, R$^5$ represents independently of each other H, F, Cl, Br, cyano, nitro, OH, SH, or represents methyl, ethyl, cyclopropyl, CH=CH$_2$, —CH$_2$CH=CH$_2$, —CH$_2$C≡CH, —C≡CH, phenyl, methoxy, each of which is optionally mono- or polysubstituted by identical or different substituents from the group consisting of R$^{16}$ or form together with the carbon atoms, which they are attached to, an optionally mono- or multi identical or different by F, Cl, Br, oxygen, cyano or methyl, ethyl, methoxy, trifluormethyl, difluormethyl, trifluormethoxy, cyclopropyl substituted cycle with 5 to 8 ring atoms, whereas the cycle consists of carbon atoms but may also contain 1 to 4 heteroatoms selected from oxygen, sulphur or NR$^{19}$, R$^6$ represents H, F, Cl, Br, OH, nitro, cyano, C$_2$-alkinyl, or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, methoxy, ethoxy, n-propoxy, iso-propoxy, n-butoxy, tert-butoxy, methylthio, ethylthio, n-propylthio, iso-propylthio, tertbutylthio, n-butylthio, sec-butylthio, iso-butylthio, each of which is optionally mono- or polysubstituted by identical or different substituents from the group consisting of R$^{16}$ R$^7$ represents H, F, Cl, Br, cyano, nitro, methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, R$^8$ represents H, F, Cl, Br, cyano, methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, or R$^7$ and R$^8$ together can form a 5- to 7-membered ring which can optionally be substituted with one or more substituents selected from: methyl, ethyl, trifluoromethyl, methoxy, trifluoromethoxy, F, Cl, Br, hydroxyl, amino, cyano or nitro, whereas the cycle consists of carbon atoms but may also contain 1 to 4 heteroatoms selected from oxygen, sulphur or NR$^{19}$, R$^9$ and R$^{10}$ represent H, C(S)R$^{14}$, C(O)R$^{14}$, SO$_2$R$^{14}$, C(O)OR$^{14}$, OR$^{14}$ oder C(O)NR$^{14}$R$^{15}$ or represents in each case optionally mono- or multi identical or different by F, Cl, Br, OH, cyano, methyl, methoxy substituted methyl, ethyl, isopropyl, sec-butyl, iso-butyl, tert-butyl, cyclopropyl, CH=CH$_2$, —CH$_2$CH=CH$_2$, —CH$_2$C≡CH, —C≡CH, —CH=CHCH$_3$, —C≡CCH$_3$, but-2-en-1-yl, but-3-en-2-yl, but-2-yn-1-yl, phenyl, oxetanyl, methylcyclopropyl, benzyl, R$^{11}$ and R$^{20}$ represent H, C(S)R$^{12}$, C(O)R$^{12}$, SO$_2$R$^{12}$, C(O)OR$^{12}$, OR$^{12}$ oder C(O)NR$^{12}$R$^{13}$ or represent methyl, ethyl, n-propyl, iso-propyl, n-butyl, iso-butyl, sec-butyl, tert-butyl, n-pentyl, O—C(O)Me, O—C(O)Et, O—P(O)(OMe)$_2$, O—B(OMe)$_2$, O—B(OEt)$_2$ oder, methoxy, ethoxy, n-propoxy, iso-propoxy, n-butoxy, tert-butoxy substituted methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, phenyl, each of which is optionally mono- or polysubstituted by identical or different substituents from the group consisting of F, Cl, Br, OH, cyano, $R^{12}$ and $R^{13}$ represent H or represent methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, phenyl, each of which is optionally mono- or polysubstituted by identical or different substituents from the group consisting of F, Cl, Br, I, OH, carbonyl, cyano, methyl, ethyl, n-propyl, iso-propyl, n-butyl, iso-butyl, sec-butyl, tert-butyl, n-pentyl or methoxy, ethoxy, n-propoxy, iso-propoxy, n-butoxy, tert-butoxy, $R^{14}$ and $R^{15}$ represent methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, phenyl, each of which is optionally mono- or polysubstituted by identical or different substituents from the group consisting of F, Cl, Br, I, OH, Cyano, methoxy, nitro, trifluoromethyl, difluormethyl, cyclopropylmethyl, benzyl, 3-thienyl, 2-thienyl or represent hydrogen, $R^{16}$ represents OH, F, Cl, Br, I, cyano, NH—C(O)R$^{17}$, NR$^{17}$R$^{18}$, C(O)R$^{17}$, C(O)OR$^{17}$, C(O)NR$^{17}$R$^{18}$, SO$_2$R$^{17}$ or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, phenyl, methoxy, ethoxy, tetrahydrofuranyl, 3-tetrahydrofuranyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-Isoxazolin-4-yl, 4-Isoxazolin-4-yl, 2-Isoxazolin-5-yl, 3-Isoxazolin-5-yl, 4-Isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2-piperidinyl, 3-piperidinyl, 4-piperidinyl, 2-piperazinyl, furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, Imidazol-1-yl, Imidazol-2-yl, Imidazol-4-yl, Pyridin-2-yl, Pyridin-3-yl, pyridin-4-yl, pyridazin-3-yl, pyridazin-4-yl, pyrimidin-2-yl, pyrimidin-4-yl, pyrimidin-5-yl, pyrazin-2-yl, each of which is optionally mono- or polysubstituted by identical or different substituents from the group consisting of F, Cl, Br, I, OH, carbonyl, cyano, methyl, ethyl, methoxy, $R^{17}$ and $R^{18}$ represent methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, benzyl, each of which is optionally mono- or polysubstituted by identical or different substituents from the group consisting of F, Cl, Br, OH, cyano or represent H, $R^{19}$ represents H, methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, C(S)R$^{14}$, C(O)R$^{14}$, SO$_2$R$^{14}$, C(O)OR$^{14}$, and also agrochemically active salts thereof.

Particular preference is given to compounds of the formula (I) in which one or more of the symbols have one of the meanings below:

$X^1$ represents CH, N, $R^1$ represents H, methyl, ethyl, propan-2-yl, isobutyl, butan-2-yl, 2-methylpropyl, prop-2-in-1-yl, 3-methylbut-2-en-1-yl, 4-methylpentan-2-yl, 3-methylbutyl, 2,2-dimethylpropyl, pentan-3-yl, tertbutyl, 4-methylpentan-2-yl, 3-dimethylbutan-2-yl, 3-methylbutan-2-yl, 2,2,2-trifluoroethyl, 2-chloroethyl, 2-fluoroethyl, 2-methoxyethyl, methoxymethyl, 1-methoxypropan-2-yl, 2-(trifluormethoxy)ethyl, cyanomethyl, benzyl, 2-phenylethyl, —CH$_2$C(O)OEt, tetrahydrofuran-2-ylmethyl, ethylmorpholine, 3-dimethylamino-2-methylpropyl, Allyl, 3,3-dichloroprop-2-en-1-yl, but-3-en-2-yl, prop-2-yn-1-yl, but-2-yn-1-yl, cyclohexyl, cyclopropyl, cyclobutyl, cyclopentyl, (2,2-dichlorcyclopropyl)methyl, cyclopropylmethyl, cyano ethyl, 2,2-difluoro ethyl, ethoxyethyl, orthocyanobenzyl, orthofluorobenzyl, methoxyethoxyethyl, trifluoromethoxyethyl, cyclopropylmethyl, tetrahydro-2H-pyran-2-yl, phenyl, 2-fluorobenzyl, acetyl, ethoxycarbonyl, methylsulfonyl, isopropylaminocarbonyl, 2-Cyanoethyl, 2,2-difluoro ethyl, 2-ethoxyethyl, cyclopropylmethyl, 2-cyanobenzyl, 2,3-difluorobenzyl, $R^2$ represents H, cyano, cyclopropyl, methyl, Br, methylthio, trimethylsilyl, methyl, prop-1-ynyl, propyl, F, Cl $R^3$ represents H, Cl, Br, cyano, isopropylcarbamoyl, methoxy, propylamine, dimethylamino, hydrazine, benzylamino, amino, acetylamino, prop-2-yn-1-ylamino, N-Bis(cyclopropylcarbonyl)amino, N-benzyl-N-isopropylcarbonylamino, n-propionylamino, isobutyrylamino, (cyclobutylcarbonyl)amino, (cyclopropylcarbonyl)amino, (methoxyacetyl)amino, 2-methoxypropanoyl, (2-methylbutanoyl)amino, but-2-enoylamino, prop-2-inoylamino, 3-(dimethylamino)prop-2-enoyl]amino, (3,3,3-trifluorpropanoyl)amino, 3,3-difluorpropanoylamino, 2-(cyclopropylethynyl), (cyclopropylacetyl)amino, (3-methylbutanoyl)amino, 2-hydroxypropanoylamino, acetylacetamido, 3-oxetanylamino, cyclopropylamino, benzoylamino, 2,2-dimethylpropanoylamino, (3-thienylcarbonyl)amino, (2-thienylcarbonyl)amino, isopropylamino, allylamino, cyclopropylmethylamino, 1-methyl-2-methoxyethylamino, 1-methylpropylamino, formamido, $R^4$ represents H, $R^5$ represents H, $R^6$ H, Cl, F, acetyl, N-butylcarboxamido, methyl, cyano, $C_2$-$C_8$-alkynyl, $C_3$-$C_8$-cycloalkyl, $R^7$ represents H, Cl, $R^8$ represents H, Cl, and also agrochemically active salts thereof.

Very particular is given to compounds of the formula (I) in which one or more of the symbols have one of the meanings below:

$X^1$ represents CH, N, $R^1$ represents propan-2-yl, butan-2-yl, 2-methylpropyl, prop-2-in-1-yl, cyclopropyl, cyclobutyl, cyclopentyl, 2,2,2-trifluorethyl, 2-fluorobenzyl, 2-(trifluormethoxy)ethyl, 2-fluoroethyl, ethyl, but-1-en-3-yl, cyanomethyl, 3-pentyl, 2-chloroethyl, methoxymethyl, 2-cyanoethyl, 2,2-difluoroethyl, 2-ethoxyethyl, cyclopropylmethyl, 2-cyanobenzyl, 2,3-difluorobenzyl, methyl, $R^2$ represents H, methyl, prop-1-ynyl, $R^3$ represents H, acetylamino, n-propionylamino, isobutyrylamino, (cyclopropylcarbonyl)amino, (methoxyacetyl)amino, 2-methoxypropanoylamino, (2-methylbutanoyl)

amino, but-2-enoylamino, prop-2-inoylamino, 3-(dimethylamino)prop-2-enoylamino, 3,3,3-trifluorpropanoylamino, 3,3-difluorpropanoylamino, amino, (cyclobutylcarbonyl)amino, (cyclopropylacetyl)amino, (3-methylbutanoyl)amino, 2-hydroxypropanoylamino, acetylacetamido, 3-oxetanylamino, cyclopropylamino, benzoylamino, 2,2-dimethylpropanoylamino, $R^4$ represents H,
$R^5$ represents H,
$R^6$ represents Cl, F,
$R^7$ represents H,
$R^8$ represents H
and also agrochemically active salts thereof.

Very particular preference is furthermore given to compounds of the formula (I) in which
$X^1$ represents N,
where the other substituents have one or more of the meanings mentioned above,
and to the agrochemically active salts thereof.

Very particular preference is furthermore given to compounds of the formula (I) in which
$X^1$ represents CH,
where the other substituents have one or more of the meanings mentioned above,
and to the agrochemically active salts thereof.

Very particular preference is furthermore given to compounds of the formula (I) in which
$R^1$ represents Propan-2-yl, Butan-2-yl, 2-Methylpropyl, Cyclobutyl, Cyclopentyl, But-1-en-3-yl, 2-Fluoroethyl, methyl, ethyl,
where the other substituents have one or more of the meanings mentioned above,
and to the agrochemically active salts thereof.

Very particular preference is furthermore given to compounds of the formula (I) in which
$R^2$ represents H, methyl,
where the other substituents have one or more of the meanings mentioned above,
and to the agrochemically active salts thereof.

Very particular preference is furthermore given to compounds of the formula (I) in which
$R^3$ represents NHCO-methyl, NHCO-isopropyl, NHCO-cyclopropyl, NHCO-ethyl, NHCO-cyclobutyl, NHCO-methoxymethyl, NHCO-methylcyclopropyl, NHCO-(2-methylpropyl), NHCO-(1-hydroxyethyl), N(CO-methyl) CO-methyl, NH$_2$, NH-(3-oxetanyl)
where the other substituents have one or more of the meanings mentioned above,
and to the agrochemically active salts thereof.

Very particular preference is furthermore given to compounds of the formula (I) in which
$R^4$ represents H,
where the other substituents have one or more of the meanings mentioned above,
and to the agrochemically active salts thereof.

Very particular preference is furthermore given to compounds of the formula (I) in which
$R^5$ represents H,
where the other substituents have one or more of the meanings mentioned above,
and to the agrochemically active salts thereof.

Very particular preference is furthermore given to compounds of the formula (I) in which
$R^6$ represents Cl, F
where the other substituents have one or more of the meanings mentioned above,
and to the agrochemically active salts thereof.

Very particular preference is furthermore given to compounds of the formula (I) in which
$R^7$ represents H,
where the other substituents have one or more of the meanings mentioned above,
and to the agrochemically active salts thereof.

Very particular preference is furthermore given to compounds of the formula (I) in which
$R^8$ represents H,
where the other substituents have one or more of the meanings mentioned above,
and to the agrochemically active salts thereof.

The radical definitions given above can be combined with one another as desired. Moreover, individual definitions may not apply.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis. If the compounds of the formula (I) carries hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $(C_1-C_4)$-alkyl groups, mono-, di- and trialkanolamines of $(C_1-C_4)$-alkanols, choline and also chlorocholine.

The salts obtainable in this manner also have fungicidal, herbicidal and insecticidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as NaHSO$_4$ and KHSO$_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in various valencies that they can assume.

Optionally substituted groups may be mono- or polysubstituted, where in the case of polysubstitution the substituents may be identical or different.

In the definitions of the symbols given in the formulae above, collective terms were used which are generally representative for the following substituents:
halogen: fluorine, chlorine, bromine and iodine;

aryl: an unsubstituted or optionally substituted 5- to 15-membered partially or fully unsaturated mono-, bi- or tricyclic ring system having up to 3 ring members selected from the groups C(=O), (C=S), where at least one of the rings of the ring system is fully unsaturated, such as, for example (but not limited thereto) benzene, naphthalene, tetrahydronaphthalene, anthracene, indane, phenanthrene, azulene;

alkyl: saturated, straight-chain or branched hydrocarbon radicals having 1 to 8 carbon atoms, for example (but not limited thereto) $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkenyl: unsaturated, straight-chain or branched hydrocarbon radicals having 2 to 8 carbon atoms and a double bond in any position, for example (but not limited thereto) $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 8 carbon atoms and a triple bond in any position, for example (but not limited thereto) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkoxy: saturated, straight-chain or branched alkoxy radicals having 1 to 8 carbon atoms, for example (but not limited thereto) $C_1$-$C_6$-alkoxy, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

alkylthio: saturated, straight-chain or branched alkylthio radicals having 1 to 8 carbon atoms, for example (but not limited thereto) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

alkoxycarbonyl: an alkoxy group having 1 to 6 carbon atoms (as mentioned above) which is attached to the skeleton via a carbonyl group (—CO—);

alkylsulphinyl: saturated, straight-chain or branched alkylsulphinyl radicals having 1 to 8 carbon atoms, for example (but not limited thereto) $C_1$-$C_6$-alkylsulphinyl, such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentyl sulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl;

alkylsulphonyl: saturated, straight-chain or branched alkylsulphonyl radicals having 1 to 8 carbon atoms, for example (but not limited thereto) $C_1$-$C_6$-alkylsulphonyl, such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl;

cycloalkyl: monocyclic, saturated hydrocarbon groups having 3 to 10 carbon ring members, for example (but not limited thereto) cyclopropyl, cyclopentyl and cyclohexyl;

haloalkyl: straight-chain or branched alkyl groups having 1 to 8 carbon atoms (as mentioned above), where in these groups some or all of the hydrogen atoms may be replaced by halogen atoms as mentioned above, for example (but not limited thereto) $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromo ethyl, 1-fluoro ethyl, 2-fluoro ethyl, 2,2-difluoro ethyl, 2,2,2-trifluoro ethyl, 2-chloro-2-fluoro ethyl, 2-chloro-2,2-difluoro ethyl, 2,2-dichloro-2-fluoro ethyl, 2,2,2-trichloro ethyl, pentafluoroethyl and 1,1,1-trifluoroprop-2-yl;

haloalkoxy: straight-chain or branched alkoxy groups having 1 to 8 carbon atoms (as mentioned above), where in these groups some or all of the hydrogen atoms may be replaced by halogen atoms as mentioned above, for example (but not limited thereto) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloro ethoxy, 1-bromo ethoxy, 1-fluoroethoxy, 2-fluoro ethoxy, 2,2-difluoro ethoxy, 2,2,2-trifluoro ethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

haloalkylthio: straight-chain or branched alkylthio groups having 1 to 8 carbon atoms (as mentioned above), where in these groups some or all of the hydrogen atoms may be replaced by halogen atoms as mentioned above, for example (but not limited thereto) $C_1$-$C_3$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

heteroaryl: a 5 or 6-membered completely unsaturated monocyclic ring system which contains one to four heteroatoms from the group consisting of oxygen, nitrogen and sulphur; if the ring contains a plurality of oxygen atoms, these are not directly adjacent;

5-membered heteroaryl which contains one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

5-membered heteroaryl which is attached via nitrogen and contains one to four nitrogen atoms, or benzo-fused 5-membered heteroaryl which is attached via nitrogen and contains one to three nitrogen atoms: 5-membered heteroaryl groups which, in addition to carbon atoms, may contain one to four nitrogen atoms and one to three nitrogen atoms, respectively, as ring members and in which two adjacent carbon ring members or a nitrogen and an adjacent carbon ring member may be bridged by a buta-1,3-dien-1,4-diyl group in which one or two carbon atoms may be replaced by nitrogen atoms, where these rings are attached to the skeleton via one of the nitrogen ring members, for example (but not limited thereto) 1-pyrrolyl, 1-pyrazolyl, 1,2,4-triazol-1-yl, 1-imidazolyl, 1,2,3-triazol-1-yl, 1,3,4-triazol-1-yl;

6-membered heteroaryl which contains one to four nitrogen atoms: 6-membered heteroaryl groups which, in addition to carbon atoms, may contain one to three or one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 5-membered heteroaryl which contains one to three nitrogen atoms or one nitrogen atom and one oxygen or sulphur atom: for example (but not limited thereto) 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl and 1,3-benzoxazol-2-yl, benzo-fused 6-membered heteroaryl which contains one to three nitrogen atoms: for example (but not limited thereto) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, and isoquinolin-8-yl;

heterocyclyl: a three- to fifteen-membered saturated or partially unsaturated heterocycle which contains one to four heteroatoms from the group consisting of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, these are not directly adjacent; such as, for example (but not limited thereto), oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydroopyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydro oxazol-4-yl, 3,4-dihydro oxazol-5-yl, 3,4-dihydrooxazol-2-yl, 3,4-dihydro oxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

leaving group: $S_N1$ or $S_N2$ leaving group, for example halogen (chlorine, bromine, iodine), alkylsulphonates (–$OSO_2$- alkyl, for example —OSO$_2$CH$_3$, —OSO$_2$CF$_3$) or arylsulphonates (-OSO$_2$-aryl, for example —OSO$_2$Ph, —OSO$_2$PhMe).

Not included are combinations which contradict natural laws and which the person skilled in the art would therefore have excluded based on his expert knowledge. Excluded are, for example, ring structures having three or more adjacent oxygen atoms.

The present invention furthermore relates to a process for preparing thienylpyrazoles of the formula (I) according to the invention. A general summary of the synthesis paths is shown in Schemes 1 to 8.

A compound of the general formula (IVa) can be reacted with a compound of the formula (V) to give a compound of formula (IIIa) (Scheme 1). This compound can be subjected to a reaction with a formylating agent to afford a compound of general formula (IIa). The reaction of a compound of formula (IIa) with a substrate of general formula $R^1$—NH—NH$_2$ can afford the pyrazole of formula (Ia, $R^2$=H). A compound of general formula (Ib) where $R^1$=H can be further alkylated, acylated or subjected to N—C coupling or subjected to sulfonyl chloride, carbamoyl chloride, isocyanate to afford a compound of formula (I) (Scheme 2). The compound of formula (Ip) where $R^{3b}$ is a leaving group can be submitted to nucleophilic substitution or Buchwald coupling to give the amino derivative of formula (Ic) (Scheme 3). In case $R^{10}$=H (Ica) this compound can be further subjected to alkylation or acylation to afford the compound of general formula (Icb). In case $R^{3c}$ is a protected amino group (Icc) this compound can be deprotected to afford the corresponding amine of the general formula (Icd) (Scheme 3) which can be further subjected to alkylation and/or acylation or subjected to sulfonyl chloride, carbamoyl chloride, isocyanate to afford the compound of general formula (Ice). The compound of formula (Ip) where $R^{3b}$ is a leaving group can also be subjected to various transition metal catalysed C—C coupling to afford (Ig) (Scheme 4). The pyrazole of formula (Iaa) ($R^1$ and $R^2$=H) can be halogenated to afford the halogeno compound of formula (II) (Scheme 5). Protection of the nitrogen of the pyrazole leads to the compound of formula (Ik) ($R^1$=PG$^2$). The compound of formula (Ik) is subjected to transition metal catalysed C—C coupling to afford the compound of formula (Ij). Alternatively, it is subjected to metallation to generate an organometallic which could then be trapped by an electrophile to afford the compound of formula (Ij). Deprotection of this compound can give the compound of formula (Iba) ($R^1$=H). Further alkylation or acylation of this compound gives the compound of formula (Ih). The compound of formula (Iq) where $R^{6a}$ is an halogen can be subjected to transition metal catalysed C—C coupling to afford the compound of formula (Im). Alternatively, it can be subjected to metallation to generate an organometallic which could then be trapped by an electrophile to afford the compound of formula (Im). (Scheme 6).

Scheme 1

Process A

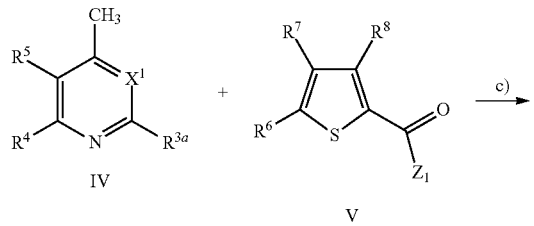

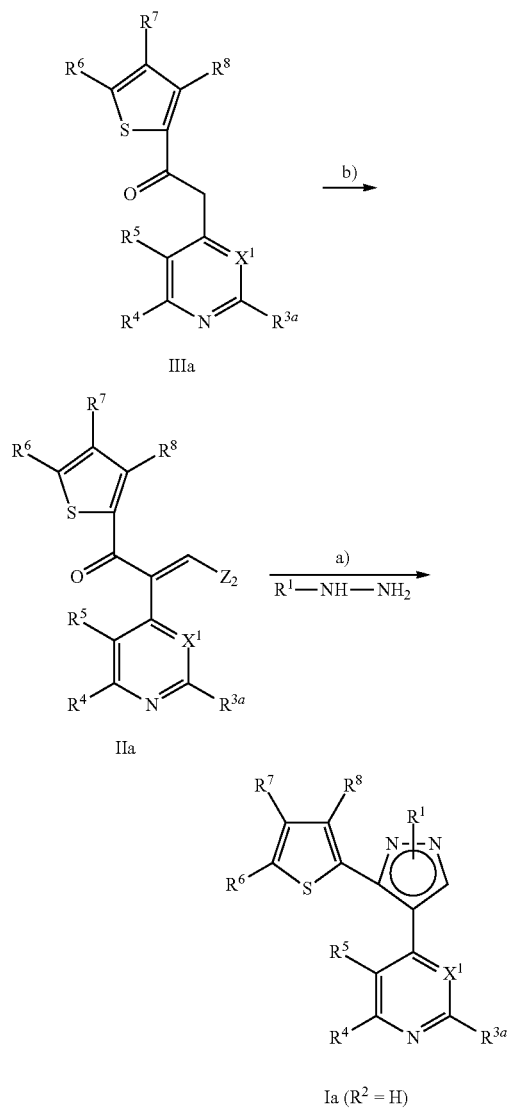

$Z_1$ = OMe, OEt, N(OMe)Me
$Z_2$ = Me$_2$N, OAlkyl, OH
$R^{3a}$ = H, Halogen, OAlk, SAlk, Aryl, amino-derivative Scheme 2

Process B

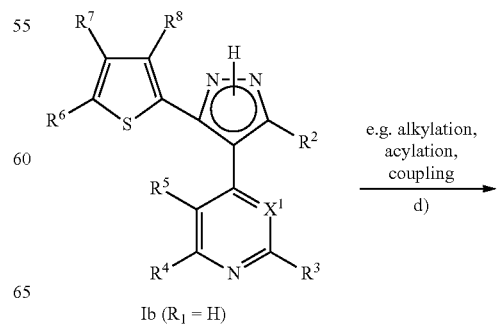

17

-continued

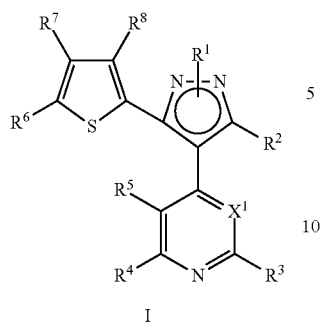

I

Scheme 3

Process C

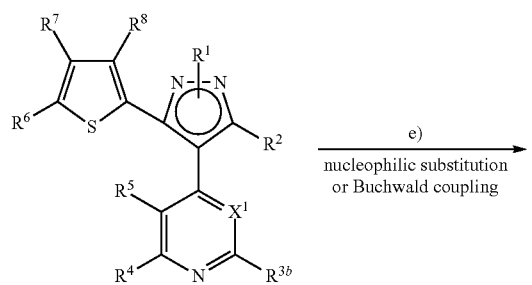

e)
nucleophilic substitution
or Buchwald coupling
→

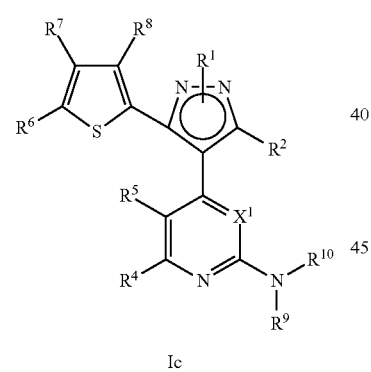

Ic

For $R_{10}$ = H:

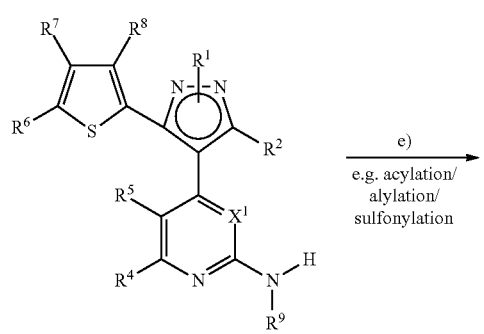

Ica

18

-continued

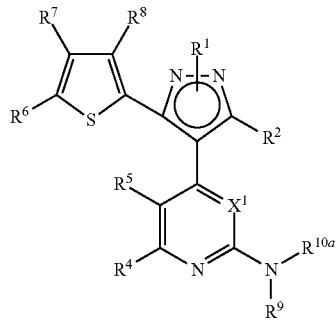

Icb

For $R_{10}$ = $PG^1$ and $R^9$ = H:

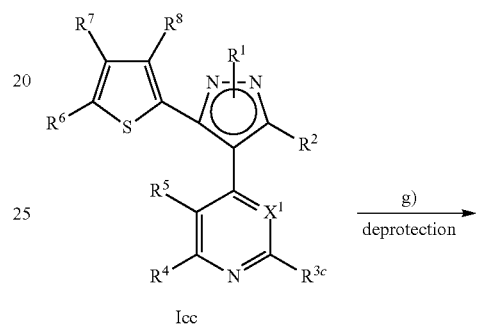

Icc g)
deprotection
→

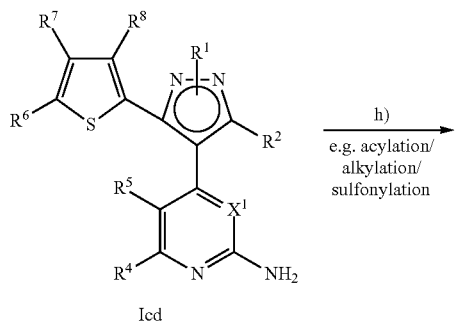

Icd h)
e.g. acylation/
alkylation/
sulfonylation
→

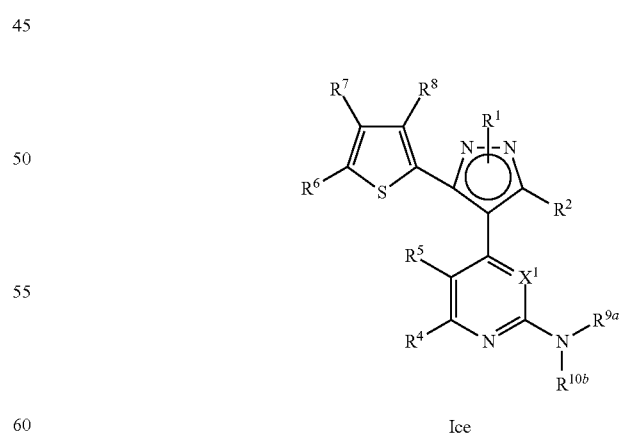

Ice e)
e.g. acylation/
alylation/
sulfonylation
→

$R^{3b}$ = halogen, OTf, S(O)$_2$Me
$R^{3c}$ = protected amino group (acetylamino, benzylamino, diphenylmethyleneamino)
$R^{9a}$, $R_{10}a$ = e.g. optionally substituted alkyl, cycloalkyl, C(O)R$^{14}$, C(O)(OR$^{14}$), S(O)$_2$R$^{14}$, C(O)NR$_{11}$R$^{20}$
$R^{10b}$ = $R^{9a}$ or H Scheme 4

Process D

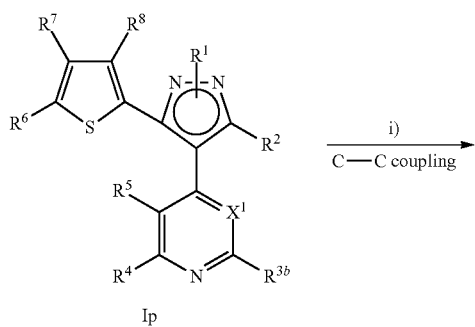

Ip i) C—C coupling →

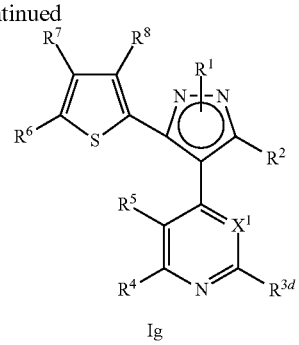

Ig $R^{3b}$ = halogen, OTf, S(O)2Me
$R^{3d}$ = cyano, alkynyl, amide, alkyl, cycloalkyl, aryl, alkenyl, heteroaryl, dialkylamide, alkylamide Scheme 5

Process E

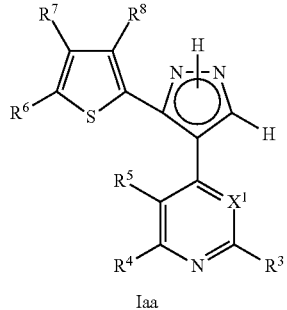

Iaa halogenation n) → II → protection m) →

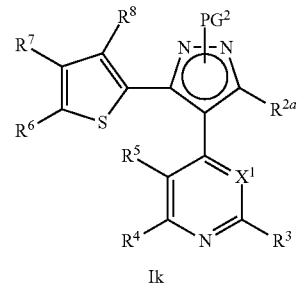

Ik l) metallation or C—C-coupling

↓

Ij k) deprotection

↓

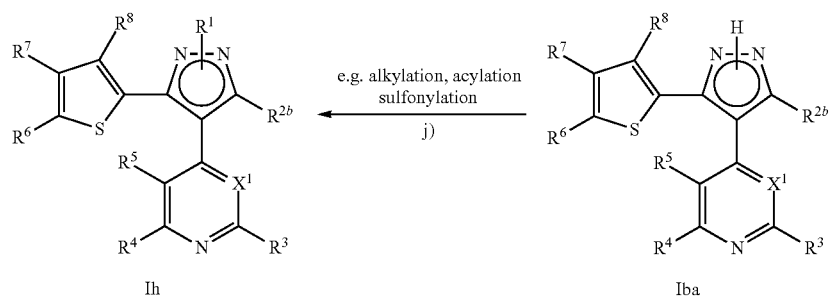

Ih   ← e.g. alkylation, acylation sulfonylation j) —   Iba $R^{2a}$ = halogen
$R^{2b}$ = alkyl, cycloalkyl, alkynyl, cyano, alkylthio, trialkylsilyl, halogen, alkenyl
$PG^2$ = PMG (para-methoxybenzyl), THP (tetrahydropyranyl)

Scheme 6

Process F

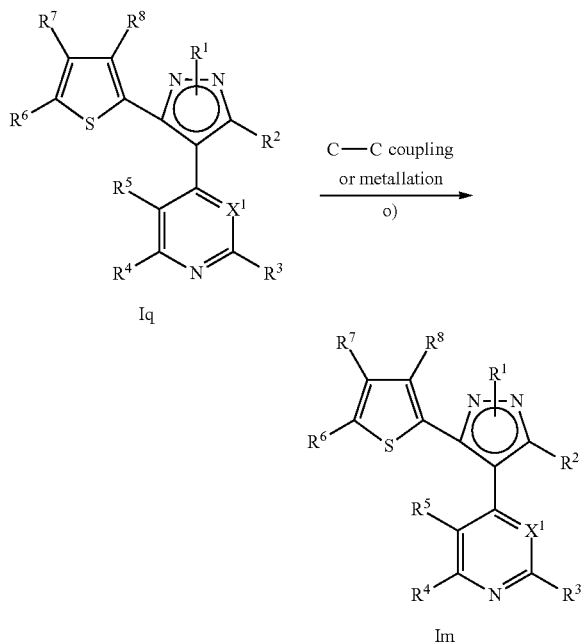

$R^{6a}$ = halogen
$R^{6b}$ = alkyl, cycloalkyl, alkynyl, cyano, alkenyl, amide, aryl, heteroaryl, alkylthio, halogen, trialkylsilyl Other possible routes of preparing compounds of the formula (I) are based on cross coupling strategy as shown in scheme 7. A compound of formula (XI) can be reacted subsequently with a substrate of general formula $R^2CC(OR)_2NMe_2$ and hydrazine to afford the corresponding pyrazole of formula (X). Alternatively compound of formula (XI) can be reacted subsequently with a substrate of general formula $R^{2c}C(O)(OR)$ in the presence of a base and hydrazine to afford the corresponding pyrazole of formula (X) (Scheme 7). This compound can then be alkylated to afford the compound of formula (IX). Halogenation of this compound can give the halogenated compound of formula (VIII) (Scheme 7) which can be subjected to a transition metal catalysed cross coupling with the compound of formula (XII) to afford the bisarylpyrazole of general formula (Iz) (Scheme 7). Alternatively the compound of general formula (Iz) can be prepared by a cross coupling reaction between the compound of general formula (VI) and the organometallic compound (VII) (Scheme 7) which can be generated from the halogeno compound (VIII) (Scheme 7).

Scheme 7

Process G

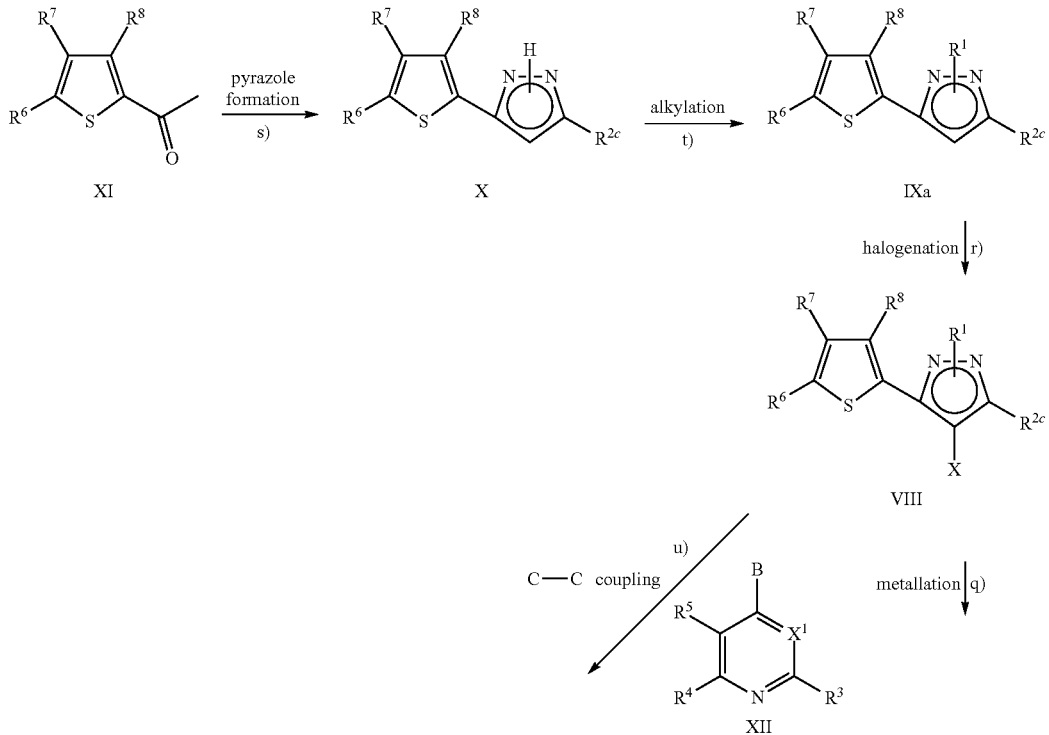

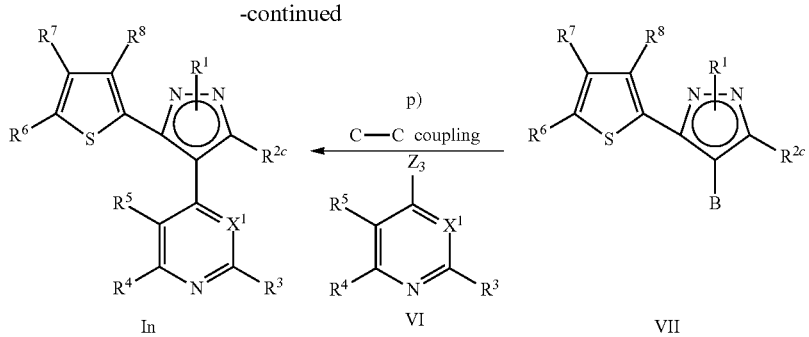

In        VI        VII $R^{2c}$ = alkyl, haloalkyl, OH, O-alkyl
X = Br, I, Cl
B = Sn(bu)$_3$, B(OH)$_2$, B(O-methyl)$_2$, B(O-ethyl)$_2$,
$Z_3$ = Bl, Br, I, OTf

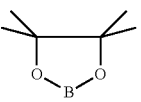

Another possibility can be to start with the bromopyrazole (XVII). The protection of this compound can afford the compound of formula (XVI) which can then be subjected to a transition metal catalysed cross coupling with the compound of formula (XII) to give the arylpyrazole of formula (XV) (Scheme 8). This compound can be metallated to afford the organometallic (XIV) which could then undergo a cross coupling reaction with the compound of general formula (XIII) to give the compound of formula (Io) where $R^1$ is a protecting group, PG$^2$ (Scheme 8). Deprotection of this compound afforded the compound of formula (Ib) where $R^1$ is hydrogen which can be alkylated or acylated or subjected to sulfonyl chloride, carbamoyl chloride or isocyanate to give a compound of general formula (I).

Scheme 8

Process H

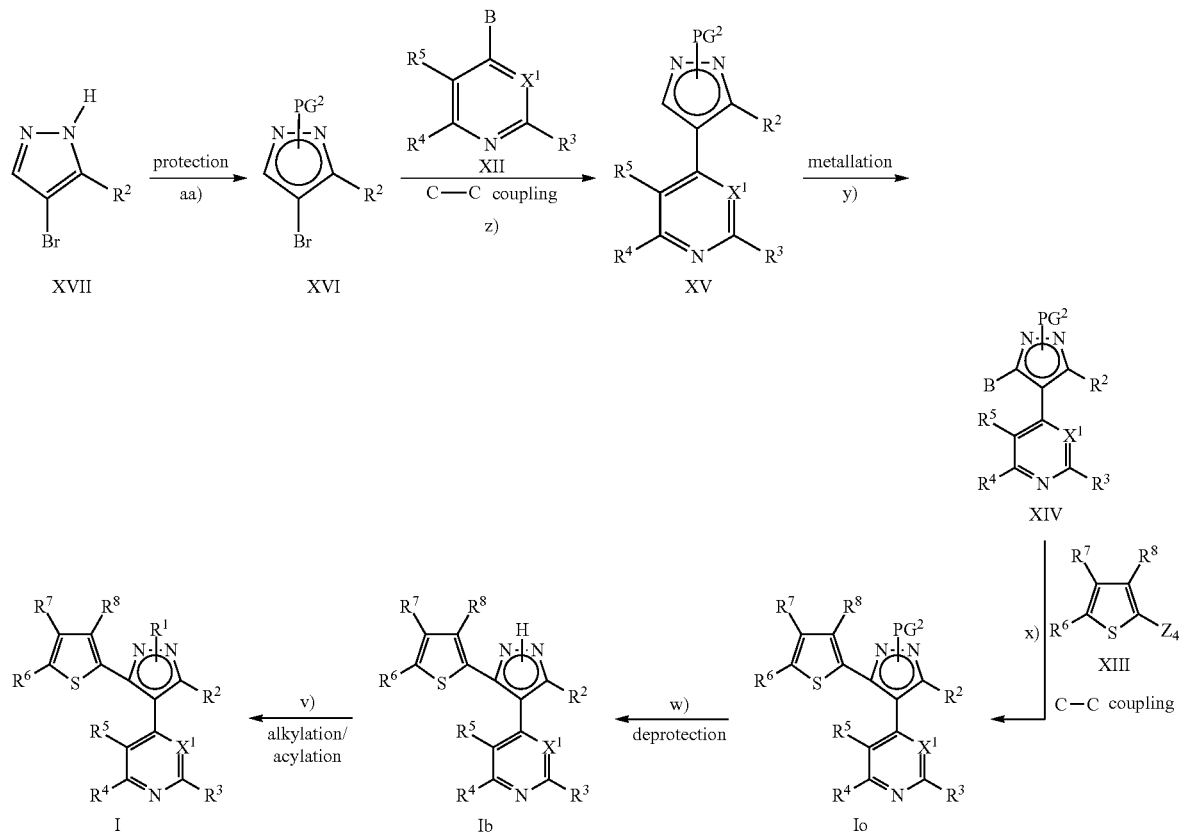

$Z_4$ = Cl, Br
$PG^2$ = THP, PMB
B = Sn(Bu)$_3$, B(OH)$_2$, B(O-methyl)$_2$, B(O-ethyl)$_2$,

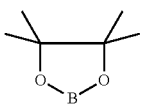

The following compounds of the schemes above are novel and therefore also part of the present invention:

Thienylpyrazole-derivatives of the formula (IXc),

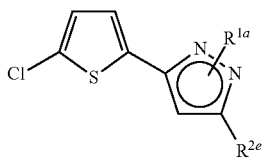

(IX-c)

in which
$R^{2e}$ represents optionally substituted $C_1$-$C_6$-alkyl, $C_1$-$C_6$-haloalkyl, OH, $C_1$-$C_6$-alkoxy, $C_3$-$C_6$-cycloalkyl, heterocyclyl, $C_2$-$C_6$-alkenyl, $C_1$-$C_6$-alkylC(O)OC$_1$-$C_6$-alkyl, $C_1$-$C_6$-alkyl-OC(O)C$_1$-$C_6$-alkyl, tri($C_1$-$C_6$-alkyl)silyl, $C_6$-$C_{14}$-aryl, $C_6$-$C_{14}$-heteroaryl,
$R^{1a}$ represents $C_1$-$C_6$-alkyl and $C_1$-$C_6$-haloalkyl,
as well as salts thereof,
$R^{1a}$ preferably represents methyl, ethyl, propan-2-yl, butan-2-yl, pentan-3-yl, 2-methylpropyl, 2,2-difluoroethyl,
$R^2$ preferably represents H or methyl, Thienylpyrazole-derivatives of the formula (VIIIa),

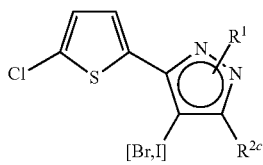

(VIII-a)

in which
$R^1$ and $R^{2c}$ have the above-mentioned meaning,
as well as salts thereof,
$R^{2c}$ preferably represents H or methyl, Thienylpyrazole-derivatives of the formula (VII),

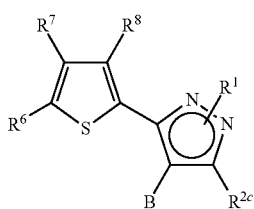

(VII)

in which
$R^1$, $R^6$, $R^7$, $R^8$, B, $R^{2c}$ have the above-mentioned meaning as well as salts thereof,
$R^{2c}$ preferably represents H or methyl,
excluded are compounds with $R^1$ equals trityl.

Process A a) Compounds of the general formula (Ia) may be obtained, according to known literature methods (U.S. Pat. No. 6,335,336 A; Journal of Medicinal Chemistry, 2003, 46, 5416-5427), by reacting a compound of general formula (IIa) with a hydrazine of general formula $R^1$—NH—NH$_2$ or a hydrated form thereof. Inert solvent such as cyclic or acyclic ethers (e.g. diethyl ether, tetrahydrofuran, dioxane), alcohols (e.g. methanol or ethanol) can be used. The reaction can be carried out in mixtures of two or more of these solvents. A base e.g. triethylamine may be used if desired. The reaction temperature can be varied from 10° C. to 50° C. but room temperature is preferred. The reaction time varies depending on the scale of the reaction and the reaction temperature, but is generally between a couple of minutes and 48 hours. The reaction can be performed in a microwave apparatus (e.g. CEM Explorer) at elevated temperature, which may shorten the reaction time. After the reaction has ended, compounds (Ia) are removed from the reaction mixture using one of the customary separation techniques. If required, the compounds are purified by recrystallisation, distillation or chromatography.

b) Compounds of the general formula (IIa) may be obtained, according to known literature methods (J. Med. Chem. 2007, 50, 2732-2736; Journal of Heterocyclic Chemistry, 2008, 45, 1819-1823 and WO 05/040155) by reacting a compound of general formula (Ma) with a formylating agent such as an alkyl formiate (e.g. methyl formiate), a trialkyl orthoformiate (e.g. trimethyl orthoformiate) or an acetal of N,N-dialkylformamide. A solvent is used optionally. Typical solvents include alcohols (e.g. ethanol), esters (e.g. ethyl acetate), ethers (e.g. THF) and also more polar solvents such as DMF or NMP. The reaction temperature can be varied from room temperature to the boiling point of the reaction mixture. The reaction time varies depending on the scale of the reaction and the reaction temperature, but is generally between a couple of minutes and 48 hours.

After the reaction has ended, compounds (IIa) are removed from the reaction mixture using one of the customary separation techniques. If required, the compounds are purified by recrystallisation, distillation or chromatography, or they can, if appropriate, also be used for the next step without prior purification.

c) Compounds of the general formula (Ma) may be prepared, according to known literature methods (J. Med. Chem. 2007, 50, 2732-2736 and WO 05/040155) by reacting a compound of the general formula (IVa) with an ester, dialkylamide or N,O-dialkylamide of general formula (V) under the influence of a strong base.

Typical bases used in this reaction are alkoxides (e.g. potassium tert-butoxide or sodium tert-butoxide), lithium amides (e.g. LDA or LiHMDS) and metal hydride (e.g. potassium or sodium hydride).

Typical solvents are ethers (e.g. diethylether, glyme and THF). In certain cases the use of more polar solvents (e.g. DMF, DMSO and HMPT) is preferred. The reaction can be carried out in mixtures of two or more of these solvents. The preferred solvent is tetrahydrofuran.

The starting materials are employed in equimolar amounts. The reaction is usually carried out at temperatures of −78° C. to the boiling point of the solvent and preferably at 0° C.-25° C. The reaction time varies depending on the scale of the reaction and the reaction temperature, but is generally between a couple of minutes and 48 hours.

After the reaction has ended, compounds (IIIa) are removed from the reaction mixture using one of the customary separation techniques. If required, the compounds are purified by recrystallisation, distillation or chromatography, or they can, if appropriate, also be used for the next step without prior purification.

Compounds of general formula (V) are either commercially available or are prepared by state of the art procedures from the corresponding acid, nitrile or methyl derivative by esterification, hydrolysis or oxidation or can be prepared using known organic synthesis techniques.

Methylpyrimidines (IVa) might be prepared via cyclisation of the corresponding amidines as described in the literature (ChemMedChem, 2009, 4, 853-865 or Tetrahedron, 2007, 63, 1931-1936). On the other hand methylpyridines could be obtained via metallation and subsequent reaction of the anion with MeX with X representing a leaving group e.g. iodine (as described in WO 08/006,509). These compounds may also be obtained by nucleophilic substitution using e.g. MeMgCl (as described in WO 06/054151), or palladocatalysed coupling using e.g. MeB(OH)$_2$ (as described in WO 05/028434).

Compounds of formula (Inc) where $R^3$ is $NR^{9c}R^{10c}$ can be prepared from the compound of the general formula (IIIaa) where $R^{3d}$ is halogen as described in scheme 15.

Scheme 15

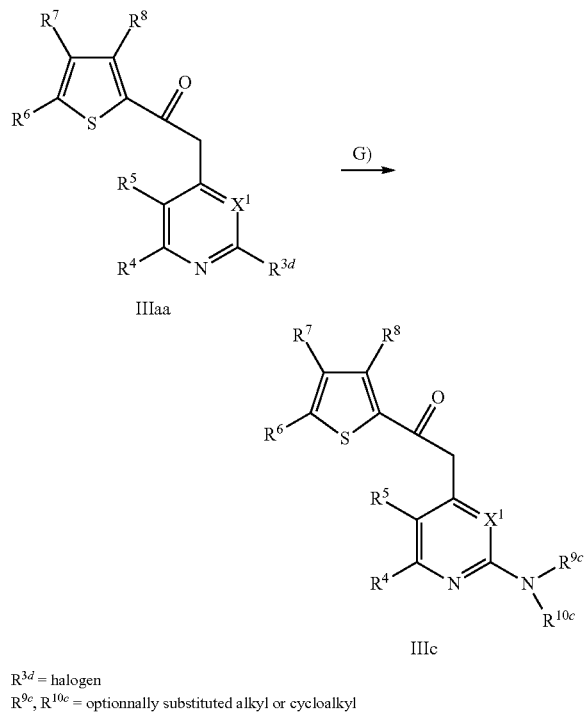

$R^{3d}$ = halogen
$R^{9c}$, $R^{10c}$ = optionnally substituted alkyl or cycloalkyl Compounds of formula (IIIc) may also be prepared by nucleophilic substitution which means by direct treatment of compounds of formula (IIIaa), where $R^{3d}$ represents a leaving group such as chlorine with an amine of general formula $HNR^{9c}R^{10c}$ under thermal or microwave conditions, if appropriate in the presence of a solvent and if appropriate in the presence of a base.

Suitable for use as solvents are all customary solvents which are inert under the reaction conditions, such as cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), amides (e.g. N,N-dimethylformamide) and nitriles (e.g. acetonitrile), or the reaction can be carried out in mixtures of two or more of these solvents. Preferably the reaction can be performed without solvent.

The reaction is usually carried out at temperatures of 20° C.-160° C. and preferably at 110° C. in the microwave oven. The reaction time varies depending on the scale of the reaction and the reaction temperature, but is generally between a couple of minutes and 48 hours.

After the reaction has ended, compound (Inc) is removed from the reaction mixture using one of the customary separation techniques. If required, the compounds are purified by recrystallisation, distillation or chromatography.

Process B d) Compounds of formula (I) may be obtained by alkylation, acylation, N—C coupling or by reaction with sulfonyl chloride, carbamoyl chloride, isocyanate of compounds of formula (Ib) where $R^1$ is hydrogen, as shown in Scheme 2.

The alkylation can be performed with an alkylating agent of formula $R^1$-$LG^1$ (where $LG^1$ is a leaving group such as halogen, triflate, mesylate) in the presence of a base. Suitable for use as solvents are all customary solvents which are inert under the reaction conditions, such as cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), amides (e.g. N,N-dimethylformamide) and nitriles e.g. acetonitrile) or the reaction can be carried out in mixtures of two or more of these solvents. The preferred solvents are N,N-dimethylformamide and acetonitrile.

At least one equivalent of base (e.g. cesium carbonate or sodium hydride) is employed, based on the starting material of the general formula (Ib).

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (I) are removed from the reaction mixture using one of the customary separation techniques. If required, the compounds are purified by recrystallisation, distillation or chromatography.

The acylation is performed in the presence of an acylating agent such as $R^{17}C(O)Cl$ in the presence of an acid scavenger/base.

Suitable for use as solvents are all customary solvents which are inert under the reaction conditions, such as, for example, cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene) and nitriles (e.g. acetonitrile), or the reaction can be carried out in mixtures of two or more of these solvents. The preferred solvents are tetrahydrofuran and dichloromethane.

At least one equivalent of an acid scavenger/a base (e.g. Hünig base, triethylamine or commercially available polymeric acid scavengers) is employed, based on the starting material of the general formula (Ib). If the starting material is a salt, at least two equivalents of the acid scavenger are required.

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (I) are removed from the reaction mixture using one of the customary separation techniques. If required, the compounds are purified by recrystallisation, distillation or chromatography.

Alternatively the compound of general formula (Ib) can be subjected to a reactant of general formula LG-C(O)NR$^{17}$R$^{18}$, LG-C(O)OR$^{17}$, LG-S(O)$_2$R$^{17}$, LG-S(O)$_2$NR$^{17}$R$^{18}$, R$^{17}$N=C=O or R$^{17}$N=C=S, where LG is a leaving group, in similar conditions as described above for the acetylation reaction to provide the compound of general formula (I).

If R$^1$ contains a carbonyl function, it can be subjected to thionation in the presence of a thionating agent like for example sulphur (S), sulfhydric acid (H$_2$S), sodium sulfide (Na$_2$S), sodium hydrosulfide (NaHS), boron trisulfide (B$_2$S$_3$), bis(diethylaluminium) sulfide ((AlEt$_2$)$_2$S), ammonium sulfide ((NH$_4$)$_2$S), phosphorous pentasulfide (P$_2$S$_5$), Lawesson's reagent (2,4-bis(4-methoxyphenyl)-1,2,3,4-dithiadiphosphetane 2,4-disulfide) or a polymer-supported thionating reagent such as described in J. Chem. Soc. Perkin 1, (2001), 358.

One possibility for the synthesis of compounds of formula (I) in which R1 stands for cyclopropyl is the reaction of a compound of general formula (Ib) with cyclopropyl boronic acid according to known literature methods (Journal of Organic Chemistry, 73(16), 6441-6444, 2008; WO 08/088, 692). The reaction can be performed in the presence of a base (e.g. triethylamine, pyridine, sodium carbonate, potassium phosphate or cesium carbonate) and Cu(II)-salt (e.g. Cu(OAc)$_2$ or CuCl$_2$). In addition, a suitable ligand (e.g. pyridine or 2,2'-Bipyridin, N,N,N',N'-tetramethylethylenediamine or 1.10-Phenanthridin) can be added.

Suitable for use as solvents are all customary solvents which are inert under the reaction conditions, such as cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene) and the reaction can be carried out in mixtures of two or more of these solvents. The preferred solvent is dichloromethane.

The reaction temperature is in the range of 50° C. to the boiling point of the reaction mixture. The reaction time varies depending on the scale of the reaction and the reaction temperature, but is generally between a couple of minutes and 48 hours. The reaction can be performed in a microwave apparatus (e.g. CEM Explorer) at elevated temperature, which may shorten the reaction time.

After the reaction has ended, compounds (I) are isolated from the reaction mixture using one of the customary separation techniques. If required, the compounds are purified by recrystallisation, distillation or chromatography.

Analogously to the methods described above, the compounds of the general formula (Ih) can be synthesized from corresponding compounds (Iba) as shown in scheme 5 step j). The compounds of the general formula (I) can be synthesized from the corresponding compounds (Ib) as shown in scheme 8 step v) (step v)=step d)).

Process C e) Compounds of formula (Ic) can be prepared from (Ip), where R$^{3b}$ represents a leaving group by Buchwald amination or amidation reaction (Scheme 3). The reaction can be performed in the presence of a primary amide or amine, of a palladium (II) catalyst such as palladium diacetate, a ligand such as Xantphos, a base such as potassium or cesium carbonate in an aprotic solvent such as dioxane or THF under thermal or microwave conditions (see Org. Lett. 2001, 3 (21) 3417). The reaction is usually carried out at temperatures of 20° C.-140° C. and preferably at 60° C.-100° C. The reaction time varies depending on the scale of the reaction and the reaction temperature, but is generally between a couple of minutes and 48 hours. After the reaction has ended, the compounds (Ic) are removed from the reaction mixture using one of the customary separation techniques. If required, the compounds are purified by recrystallisation, distillation or chromatography.

Compounds of formula (Ic) may also be prepared by nucleophilic substitution which means by direct treatment of compounds of formula (Ip), where R$^{3b}$ represents a leaving group such as chlorine with an amine of general formula HNR$^9$R$^{10}$ under thermal or microwave conditions, if appropriate in the presence of a solvent and if appropriate in the presence of a base.

Suitable for use as solvents are all customary solvents which are inert under the reaction conditions, such as cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), amides (e.g. N,N-dimethylformamide) and nitriles (e.g. acetonitrile), or the reaction can be carried out in mixtures of two or more of these solvents. Preferably the reaction can be performed without solvent.

The reaction is usually carried out at temperatures of 20° C.-160° C. and preferably at 140° C. in the microwave oven. The reaction time varies depending on the scale of the reaction and the reaction temperature, but is generally between a couple of minutes and 48 hours.

After the reaction has ended, compound (Ic) is removed from the reaction mixture using one of the customary separation techniques. If required, the compounds are purified by recrystallisation, distillation or chromatography.

For compounds where X1=N and R$^{3b}$=SMe, it may be necessary to generate the sulfone using an oxidating agent like for example meta-chloroperbenzoic acid in a solvent like for example dichloromethane (see Tetrahedron Letters, 2009, 50, 1377-1380) to facilitate the nucleophilic substitution.

For compounds where X1=CH and R$^{3b}$=Cl, it may be necessary to generate the N-oxide using an oxidating agent like for example meta-chloroperbenzoic acid in a solvent like for example dichloromethane (as described in WO 07/143, 597) to facilitate the nucleophilic substitution. Compound of the general formula (Ic) would then be obtained after reduction of the N-oxide using a reducing agent like for example PCl$_3$ (see Chemical & Pharmaceutical Bulletin, 1996, 44, 103-14).

f) Compounds of formula (Ica) with R$^{10}$=H can be reacted with an alkylating agent of formula R$^{10a}$-LG$^2$ (LG$^2$ is a leaving group such as halogen, triflate, mesylate) in the presence of a base to generate a compound of formula (Icb).

Suitable for use as solvents are all customary solvents which are inert under the reaction conditions, such as cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), amides (e.g. N,N-dimethylformamide) and nitriles (e.g. acetonitrile), or the reaction can be carried out in mixtures of two or more of these solvents. The preferred solvents are N,N-dimethylformamide and acetonitrile.

The reaction is usually carried out at temperatures of 20° C.-100° C. and preferably at 60° C.-80° C., but it can also be carried out at the reflux temperature of the reaction mixture. The reaction time varies depending on the scale of the reaction and the reaction temperature, but is generally between a couple of minutes and 48 hours.

After the reaction has ended, the compounds (Icb) are removed from the reaction mixture using one of the customary separation techniques. If required, the compounds are purified by recrystallisation, distillation or chromatography.

Compounds of formula (Icb) where $R^3$ is $NR^9C(O)R^{14}$ may be obtained by acylation of a compound of general formula (Ica) with $R^{10}$=H, in the presence of an acylating agent such as $R^{14}C(O)Cl$, in the presence of an acid scavenger/a base.

Suitable for use as solvents are all customary solvents which are inert under the reaction conditions, such as, for example, cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene) and nitriles (for example acetonitrile), or the reaction can be carried out in mixtures of two or more of these solvents. The preferred solvents are tetrahydrofuran and dichloromethane.

At least one equivalent of an acid scavenger/a base (for example pyridine) is employed, based on the starting material of the general formula (Ica). If the starting material is a salt, at least two equivalents of the acid scavenger are required.

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (Icb) are removed from the reaction mixture using one of the customary separation techniques. If required, the compounds are purified by recrystallisation, distillation or chromatography.

Alternatively the compound of general formula (Ica) can be subjected to a reactant of general formula LG-C(O) $NR^{14}R^{15}$, LG-C(O)$OR^{14}$, LG-S(O)$_2R^{14}$, $R^{14}N$=C=O or $R^{14}N$=C=S, where LG is a leaving group, in similar conditions as described above for the acetylation reaction to provide the compound of general formula (Icb).

If $R^9$ and/or $R^{10}$ contain a carbonyl function, it can be subjected to thionation in the presence of a thionating agent like for example sulphur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in J. Chem. Soc. Perkin 1, (2001), 358.

Analogously to the methods described above, the compounds (Ice) can be synthesized from corresponding compounds (Icd) where $R^3$ is a free amino group.

g) Compounds of formula (Icc) where $R^3$ is a protected amino function can be deprotected under state of the art methods depending on the nature of the protective group to generate the compound of formula (Icd) where $R^3$ is a free amine (see "Protective groups in organic chemistry" Green and Wuts $4^{th}$ edition, Wiley Interscience). As an example benzyl as protective group can be deprotected under acidic condition such as concentrated sulphuric acid or hydrogenation condition.

h) The intermediate (Icd) can be further alkylated or acylated using the same procedure as describe above to afford compounds of formula (Ice) where $R^3$ is $NHR^{9a}$ or $NR^{9a}R^{9a}$. Another alkylation or acylation will provide, under the same conditions, compounds where $R^3$ is $NR^{9a}R^{10a}$ as previously described.

Process D i) Compounds of formula (Ig) wherein $R^{3c}$ is an optionally substituted alkyl, cycloalkyl, alkenyl, alkynyl, alkylamide, dialkylamide, aryl, heteroaryl or cyano group is prepared via coupling of compounds of general formula (Ip) where $R^{3b}$ is a leaving group (e.g. chlorine or bromine) with a reactant of the general formula $R^{3c}$-M. M represents MgCl, MgBr, ZnCl, ZnBr, ZnCN, B(OH)$_2$, BF$_3$K, B(C$_1$-C$_8$-alkoxy)$_2$, SnMe$_3$, SnBu$_3$, CuCl, CuBr, CuCN, AgCl, AgBr. Compound of the general formula $R^{3c}$-M can be either prepared in situ or prior to the reaction.

Suitable for use as solvents are all customary solvents which are inert under the reaction conditions, such as, for example, cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), carboxylic esters (for example ethyl acetate), amides (for example N,N-dimethylformamide, N,N-dimethylacetamide), dimethyl sulphoxide and 1,3-dimethyl-2-imidazolinone, and the reaction can be carried out in mixtures of two or more of these solvents.

The reaction should be carried out in the presence of additives depending on the type of coupling that is performed. For example, if Sonogashira reaction is performed triethylamine (at least one equivalent based on the compound (Ip)) and copper(I) iodide (at least 0.1 equivalent based on the compound (Ip)) is added.

Suitable catalyst for carrying out the above mentioned process according to the invention may be chosen as being a metal salt or complex. Suitable metal derivatives for this purpose are based on palladium. Suitable metal salts or complexes for this purpose are palladium chloride, palladium acetate, tetrakis(triphenylphosphine)palladium, bis(triphenylphosphine)palladium dichloride or 1,1'-bis(diphenylphosphino) ferrocenepalladium(II) chloride.

It is also possible to generate a palladium complex in the reaction mixture by separate addition to the reaction of a palladium salt and a ligand or salt, such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino) benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine) ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino) ferrocene, tris-(2,4-tert-butylphenyl)-phosphite, (R)-(−)-1-

[(S)-2-(diphenylphosphino)ferrocenyl]ethyldi-tert-butylphosphine, (S)-(+)-1-[(R)-2-(diphenylphosphino)ferrocenyl]ethyldicyclohexylphosphine, (R)-(−)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine or 1,3-bis(2,4,6-trimethylphenyl)imidazolium chloride.

The amount of catalyst used is at least 1% to an excess based on the starting material (Ip).

The reaction is usually carried out at temperatures of 20° C.-160° C. and preferably at 20° C.-120° C. The reaction time varies depending on the scale of the reaction and the reaction temperature, but is generally between a couple of minutes and 48 hours.

The reaction is generally carried out under atmospheric pressure but it is also possible to operate under elevated pressure.

After the reaction has ended, the compounds (Ig) are removed from the reaction mixture using one of the customary separation techniques. If required, the compounds are purified by recrystallisation, distillation or chromatography.

Analogously to the method described above, the compounds (Ij) can be synthesized from corresponding compounds (Ik), where $R^2$ is a leaving group, as shown in scheme 5 step 1).

Intermediate Synthesis (Alternatives)

Compounds of formula (Ipa) where $R^{3d}$ is halogen (e.g. chlorine, bromine) can be prepared using the general method as described in scheme 8. It can alternatively be generated from the compound of the general formula (Ir) where $R^3$ is hydrogen as described in scheme 9.

Scheme 9

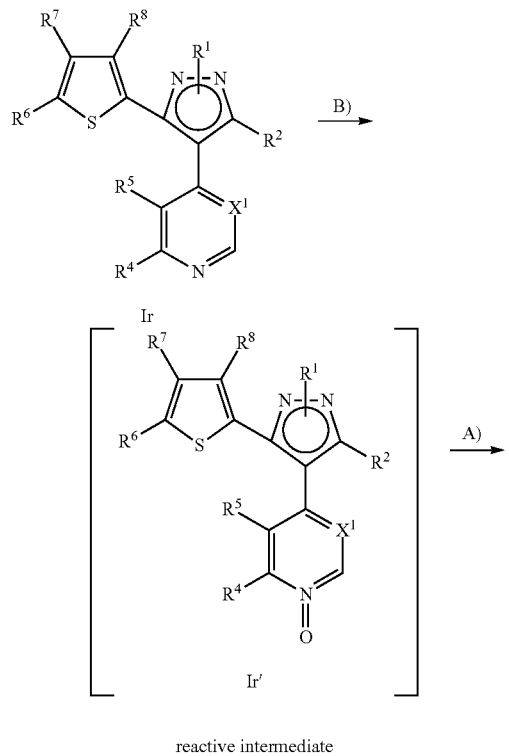

reactive intermediate $R^{3d}$ = halogen

A) Compounds of formula (Ipa) where $R^{3d}$ is bromide or chloride can be prepared by treating the corresponding N-oxide with POCl$_3$ or POBr$_3$ under conditions used in state of the art methodology (e.g. chlorination of substituted pyridines in Chem. and Pharm. Bull. 1994, 42(9), 1841).

B) The N-oxyde (Ir') can be prepared by treating (Ir) ($R^3$=H) for example with an oxidating agent, e.g. meta-chloroperbenzoic acid, in a solvent such as dichloromethane as described in WO 07/143,597.

Scheme 10

C) Compound of the general formula (Is) where $R^3$ is chlorine can be reacted with a brominating agent like a hydrobromic acid solution in acetic acid to generate the corresponding bromo compound of the general formula (It) according to WO 06/081072.

Process E j) The intermediate (Iba) can be alkylated or acylated using the same procedures as described for Process B, step d) to afford compounds of formula (Ih).

k) Compounds of formula (Iba) may be obtained by deprotection of compounds of formula (Ij) under state of the art methods depending on the nature of the protective group. As an example paramethoxybenzyl as protective group can be deprotected under acidic condition such as TFA or hydrogenation condition (see "Protective groups in organic chemistry" Green and Wuts 4$^{th}$ edition, Wiley Interscience). It is to be noted that weak deprotecting group may be deprotected during the course of the reaction.

l) Compounds of formula (Ij) with $R^{2b}$ is alkyl, cycloalkyl, alkynyl, alkenyl or cyano can be prepared using similar conditions as previously described for Process D, step i) starting from compounds of general formula (Ik) with $R^2$ is halogen.

Alternatively, compounds of general formula (Ij) with $R^{2b}$ is halogen, trialkylsilyl, alkylthio or alkyl can be prepared by metalation of the haloheterocycle (Ik) with a base (e.g. n-butyllithium or isopropylmagnesium chloride) in a solvent (e.g. diethyl ether or tetrahydrofurane) and subsequent reaction with an electrophile (e.g. trimethylsilyl chloride or dimethyldisulfide) according to known literature methods (Tetrahedron, 2006, 63, 56; Tetrahedron, 2002, 58, 7635 or WO 05/077363).

At least one equivalent of base (e.g. butyl lithium or isopropylmagnesium chloride) is employed, based on the starting material of the general formula (Ik).

The reaction is usually carried out at temperatures of −80° C.-20° C. depending on the base used to perform the reaction. During the reaction a change in temperature may be beneficial or necessary to ensure the reaction with the second reactant. The reaction time varies depending on the scale of the reaction and the reaction temperature, but is generally between a couple of minutes and 48 hours.

After the reaction has ended, the compounds (Ij) are removed from the reaction mixture using one of the customary separation techniques. If required, the compounds are purified by recrystallisation, distillation or chromatography, or they can, if appropriate, also be used for the next step without prior purification.

Analogously to the method described above, the compounds (Im) can be synthesized from corresponding compounds (Iq), where $R^{6a}$ is a leaving group, as shown in Scheme 6, step o).

m) Compounds of formula (Ik) (where $PG^2$ is a protective group such as paramethoxybenzyl or tetrahydropyranyl) may be obtained by protection of a compound of general formula (II) (see "Protective groups in organic chemistry" Green and Wuts 4$^{th}$ edition, Wiley Interscience).

n) The intermediate of formula (II) with $R^{2a}$ is halogen can be synthesized by halogenation of a compound of formula (Iaa) where $R^2$ and $R^1$ are hydrogen using a suitable halogenating agent in an appropriate solvent.

Suitable for use as solvents are all customary solvents which are inert under the reaction conditions, such as, for example, alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), carboxylic esters (e.g. ethyl acetate), amides (e.g. N,N-dimethylformamide, N,N-dimethylacetamide), dimethyl sulphoxide, 1,3-dimethyl-2-imidazolinone, water and acetic acid, or the reaction can be carried out in mixtures of two or more of these solvents. Preferred solvents for this reaction is N,N-dimethylformamide.

Suitable for use as halogen source are, e.g., N-bromosuccinimide, N-chlorosuccinimide, N-iodosuccinimide, pyridinium tribromide, or bromine The reaction can, if appropriate, be carried out using an acid, such as for example acetic acid, sulphuric acid, hydrobromic acid or hydrochloric acid.

The starting materials and the halogenating agent are employed in equimolar amounts. The halogenating agent can also be used in excess. The reaction is usually carried out at temperatures of 0° C.-60° C. and preferably at 0° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (Iaa) are removed from the reaction mixture using one of the customary separation techniques. If required, the compounds are purified by recrystallisation, distillation or chromatography, or they can, if appropriate, also be used for the next step without prior purification.

Process F o) Compounds of formula (Im) with $R^{6b}$ is alkynyl, alkenyl, cycloalkyl, alkyl, cyano, aryl, alkylsulfanyl, halogen or trialkylsilyl can be prepared using analoguous conditions as previously described for Process E, step 1) starting from compounds of general formula (Iq) with $R^{6a}$ is an halogen.

For $R^{6b}$ is cyano, the compound can be further modified by state of the art methods to generate all the possible derivatives of the cyanide group: e.g., hydrolysis to form the acid or amide, reduction to form the amine or aldehyde, addition on cyanide of an alkyl or aryl Grignard to generate the ketone.

Process G p) Compounds of general formula (Iz) can be obtained for example by coupling a compound of the general formula (VII) with heterocycles of the general formula (VI) (Scheme 7). B represents e.g. a boronic ester (e.g. pinacol borane) or a boronic acid. $Z^3$ represents a leaving group such as chlorine, bromine, iodine or OTf. The reaction can be performed in the presence of a catalyst, a base and a suitable solvent at an appropriate temperature according to known literature procedures (Top Curr. Chem 2002, 219, 11, b-A. Suzuki, Org. Chem. 1999, 28, 147 and literature cited therein).

Suitable catalyst for carrying out the above mentioned process may be chosen as being a metal salt or complex. Suitable metal derivatives for this purpose are based on palladium. Suitable metal salts or complexes for this purpose are palladium chloride, palladium acetate, tetrakis(triphenylphosphine)palladium, bis(triphenylphosphine)palladium dichloride or 1,1'-bis(diphenylphosphino) ferrocene-palladium(II) chloride.

It is also possible to generate a palladium complex in the reaction mixture by separate addition to the reaction of a palladium salt and a ligand or salt, such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino) benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)-ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino) ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino) ferrocenyl]ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine or 1,3-bis(2,4,6-trimethylphenyl)imidazolium chloride.

The amount of catalyst used is at least 1% to an excess based on the starting material (VI).

The reaction is usually carried out at temperatures of 20° C.-160° C. and preferably at 20° C.-120° C. The reaction time varies depending on the scale of the reaction and the reaction temperature, but is generally between a couple of minutes and 48 hours.

The reaction is generally carried out under atmospheric pressure but it is also possible to operate under elevated pressure.

After the reaction has ended, the compounds (Iz) are removed from the reaction mixture using one of the customary separation techniques. If required, the compounds are purified by recrystallisation, distillation or chromatography.

Compounds of the general formula (VI) are commercially available or can be prepared using known organic synthesis techniques, e.g. metallation and subsequent trapping with a halogenating agent of the corresponding pyri(mi)dine (as described in Tetrahedron, 2009, 65, 3668 or in Org. and Biomol. Chem., 2008, 6, 3237) or via halogenation of the corresponding pyri(mi)done (as described in J. Med. Chem., 2009, 52, 1255 or in Bioorg. Med. Chem. Lett., 2008, 19, 3174)

q) Compounds of general formula (VII) can be prepared according to scheme 7. They are prepared by reacting the bromopyrazole (VIII) with boron derivatives in the presence of a catalyst (e.g. dichlorobis(diphenylphosphinoferrocene-palladium) in the presence of a base and a suitable solvent following procedure described in literature (U.S. Pat. No. 0,018,156 A, WO 07/024,843 or EP-A 1,382,603).

Suitable solvents for carrying out this reaction are customary inert organic solvents, such as Sulfoxides (e.g. dimethylsulfoxide), cyclic ethers (e.g. dioxane) and amides (e.g. N,N-dimethylformamide). The reaction can also be carried out in mixtures of two or more of these solvents. The preferred solvents are dimethyl sulfoxide and dioxane.

The reaction is usually carried out at temperatures between 80° C. and 120° C., the preferred reaction temperature is 85° C.-90° C. The reaction time varies depending on the scale and temperature of the reaction, but is generally between one hour and 16 hours.

Other synthesis methods described in literature can be used to produce the compounds of the formula (VII). For example, compounds of the formula (VII) can be prepared by metallation of bromopyrazole (VIII) with bases such as n-butyl lithium and reaction with trialkylborate. The resulting boronic ester can be used as such in the coupling reaction, treated with diol like pinacol to afford the corresponding cyclic boronic ester (as described in J. Het. Chem., 2004, 41, 931-940, or EP-A 1 382 603) or hydrolysed following standard procedure to generate the corresponding boronic acid.

At least one equivalent of base (e.g. butyl lithium or isopropylmagnesium chloride) is employed, based on the starting material of the general formula (VIII).

The reaction is usually carried out at temperatures of −80° C.-20° C. depending on the base used to perform the reaction. During the reaction a change in temperature may be beneficial or necessary to ensure the reaction with the second reactant. The reaction time varies depending on the scale of the reaction and the reaction temperature, but is generally between a couple of minutes and 48 hours.

After the reaction has ended, the compounds (VII) are removed from the reaction mixture using one of the customary separation techniques. If required, the compounds are purified by recrystallisation, distillation or chromatography, or they can, if appropriate, also be used for the next step without prior purification.

r) The intermediate of formula (VIII) can be synthesized by halogenation of a compound of formula (IXa) using a suitable halogenating agent in an appropriate solvent.

Suitable for use as solvents are all customary solvents which are inert under the reaction conditions, such as, for example, alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), carboxylic esters (e.g. ethyl acetate), amides (e.g. N,N-dimethylformamide, N,N-dimethylacetamide), dimethyl sulphoxide, 1,3-dimethyl-2-imidazolinone, water and acetic acid, or the reaction can be carried out in mixtures of two or more of these solvents. Preferred solvents for this reaction is N,N-dimethylformamide.

Suitable for use as halogen source are, e.g., N-bromosuccinimide, N-chlorosuccinimide, N-iodosuccinimide, pyridinium tribromide, or bromine The reaction can, if appropriate, be carried out using an acid, such as for example acetic acid, sulphuric acid, hydrobromic acid or hydrochloric acid.

The starting materials and the halogenating agent are employed in equimolar amounts. The halogenating agent can also be used in excess. The reaction is usually carried out at temperatures of 0° C.-60° C. and preferably at 0° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (VIII) are removed from the reaction mixture using one of the customary separation techniques. If required, the compounds are purified by recrystallisation, distillation or chromatography, or they can, if appropriate, also be used for the next step without prior purification.

t) The compounds of general formula (IXa) can be prepared according to scheme 7. They are obtained by alkylation of compounds of formula (X). The reaction can be performed with an alkylating agent of formula R1-Y (where Y is a leaving group such as halogen, triflate, mesylate and the like) in the presence of a base. Suitable for use as solvents are all customary solvents which are inert under the reaction conditions, such as, for example, cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), amides (e.g. N,N-dimethylformamide) and nitriles (e.g. acetonitrile), or the reaction can be carried out in mixtures of two or more of these solvents. The preferred solvents are N,N-dimethylformamide and acetonitrile. At least one equivalent of base (e.g. cesium carbonate or sodium hydride) is employed, based on the starting material of the general formula (X).

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (IXa) are removed from the reaction mixture using one of the customary separation techniques. If required, the compounds are purified by recrystallisation, distillation or chromatography, or they can, if appropriate, also be used for the next step without prior purification.

s) Compounds of the general formula (X) can be prepared according to known procedure (Tetrahedron, 2003, 59, 555-560) for example using acetylthiophenyl of general formula (XI) and react it with a substrate of general formula $R^{2c}C(OR)_2NMe_2$ and subsequently with hydrazine. Alternatively it can be subjected to a substrate of general formula $R^{2c}C(O)(OR)$ in the presence of a base (as described for example in WO2009158380 or in US200962252) and subsequently with hydrazine.

Acetylthiophenyl of general formula (XI) are commercially available or can be prepared for example by addition of Methylmagnesium bromide on the corresponding weinreb amide (as described in Bioorganic & Medicinal Chemistry Letters, 19(3), 1018-1021; 2009).

u) Compounds of the general formula (Iz) may alternatively be prepared according to scheme 7. They are prepared for example by coupling the bromopyrazole (VIII) with metallated heterocycles of general formula (XII) (where B represents a boronic ester such as pinacol borane or a boronic acid) in the presence of a catalyst, a base and a ligand if appropriate and a suitable solvent at an appropriate temperature according to known literature procedures (Top Curr. Chem. 2002, 219, 11; Org. Lett. 2005, 7, 21, 4753-4756; Org. Chem. 1999, 28, 147 and the literature cited therein).

Compounds of the formula (Iz) can also be prepared by coupling the bromopyrazole (VIII) with metallated heterocycles of general formula (XII) where B represents trialkyltin such as for example tributyltin. The reaction can be performed in the presence of a catalyst, and a ligand if appropriate and a suitable solvent at an appropriate temperature according to known literature procedures produce (Synthesis 1992, 803-815).

Suitable catalyst for carrying out the above mentioned processes according to the invention may be chosen as being a metal salt or complex. Suitable metal derivatives for this purpose are based on palladium. Suitable metal salts or complexes for this purpose are palladium chloride, palladium acetate, tetrakis(triphenylphosphine)palladium, bis(triphenylphosphine)palladium dichloride or 1,1'-bis(diphenylphosphino) ferrocenepalladium(II) chloride.

It is also possible to generate a palladium complex in the reaction mixture by separate addition to the reaction of a palladium salt and a ligand or salt, such as a phosphine, for example triethylphosphine, tri-tert-butylphosphine, tricyclohexylphosphine, 2-(dicyclohexylphosphine)biphenyl, 2-(ditert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino) benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine) ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino) ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino) ferrocenyl]ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine or 1,3-bis(2,4,6-trimethylphenyl)imidazolium chloride. The amount of catalyst used is at least 1% to an excess based on the starting material (VIII). The reaction is usually carried out at temperatures of 20° C.-160° C. and preferably at 20° C.-120° C. The reaction time varies depending on the scale of the reaction and the reaction temperature, but is generally between a couple of minutes and 48 hours.

The reaction is generally carried out under atmospheric pressure but it is also possible to operate under elevated pressure. After the reaction has ended, the compounds (Iz) are removed from the reaction mixture using one of the customary separation techniques. If required, the compounds are purified by recrystallisation, distillation or chromatography.

Compounds of formula (VIII) can be prepared using the general method as described in scheme 7. It can alternatively be generated from the compound of the general formula (VIIIa) where $R^1$ is hydrogen, namely by alkylation as described in scheme 13. Compounds of formula (VIIIa) can be prepared from the compound of the general formula (X) by halogenation.

Scheme 13

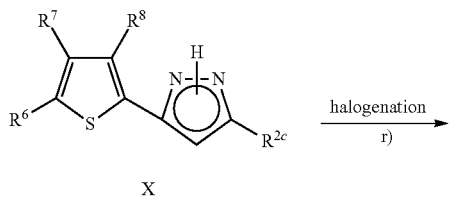

X

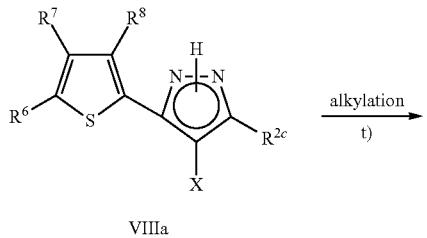

VIIIa

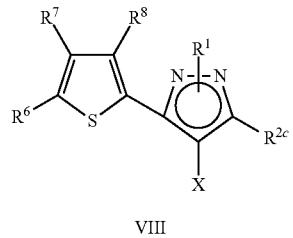

VIII

Compounds of formula (IXb) can be generated from the compound of the general formula (XIX) where $R^{2d}$ is $C_1$-$C_6$-alkyl, $C_3$-$C_6$-cycloalkyl, heterocyclyl, $C_2$-$C_6$-alkenyl, $C_1$-$C_6$-alkylC(O)OC$_1$-$C_6$-alkyl, $C_1$-$C_6$-alkyl-OC(O)C$_1$-$C_6$-alkyl, tri ($C_1$-$C_6$-alkyl)silyl, $C_6$-$C_{14}$-aryl, $C_6$-$C_{14}$-heteroaryl, each of which optionally mono- or polysubstituted by identical or different substituents from the group consisting of halogen, cyano, $C_1$-$C_6$-alkyl, $C_1$-$C_6$-alkylamino, $C_1$-$C_6$-dialkylamino, NH$_2$, heterocyclyl, C(O)OC$_1$-$C_6$-alkyl, OC(O)C$_1$-$C_6$-alkyl, $C_1$-$C_4$-alkoxy, $C_6$-$C_{14}$-aryl by condensation with a hydrazine derivative as described in scheme 14. Compounds of formula (XIX) can be prepared in situ or in isolated form from the compound of the general formula (XX) by C—C coupling.

Scheme 14

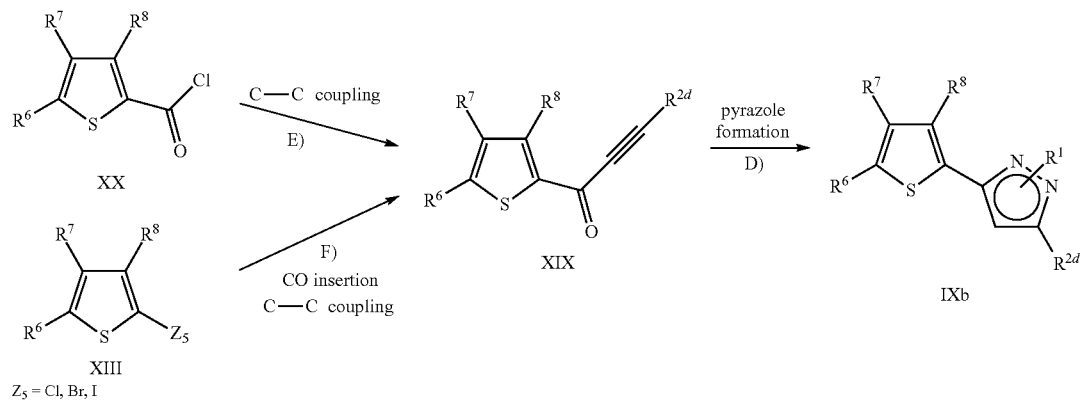

D) Compounds of formula (IXb) where $R^{2d}$ (definition see above) can be prepared by treating the alkynone of formula XIX with a hydrazine derivative under conditions used in state of the art methodology (e.g. in Eur. J. Org. Chem. 2008, 4157-4168 or Tetrahedron Lett. 2008, 49, 3805-3809).

E) The alkynone (XIX) can be prepared by treating acid chloride (XX) with an alkyne for example by transition-metal catalysis e.g. as described in Tetrahedron Lett. 2006, 47, 5527-5530 or in Synthesis 2003, 18, 2815-2826.

F) Alternatively, the alkynone (XIX) can be prepared by carbonylative C—C coupling using thiophene halides (XIII) with an alkyne employing carbon monoxide as described e.g. in Synlett 2008, 6, 886-888 or J. Org. Chem. 2005, 70, 6097-6100.

Compounds of general formula (XII) (where $B^a$ is a boron derivative) are commercially available or can be prepared as described in scheme 11.

Scheme 11

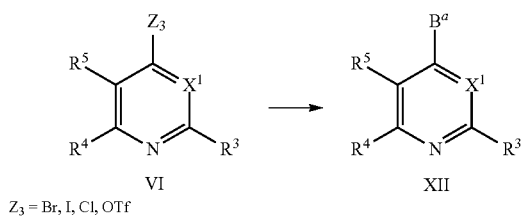

A method for preparing (XII) is the reaction of Halogenoheterocycles of general formula (VI) with bispinacolatodiboron in the presence of a catalyst (e.g. palladium acetate) and a ligand (e.g. diphenylphosphinoferrocene), a base (e.g. potassium acetate) and a solvent (e.g. dimethyl sulfoxide) according to literature procedure (Bioorg. Med. Chem. Lett. 2006, 16, 5, 1277-1281, and WO 04/014913).

Suitable solvents for carrying out this reaction are customary inert organic solvents, such as for example Sulfoxides (e.g. dimethylsulfoxide), cyclic ethers (e.g. Dioxane) and amides (e.g. N,N-dimethylformamide). The reaction can also be carried out in mixtures of two or more of these solvents. The preferred solvents are dimethyl sulfoxide and dioxane.

The reaction is usually carried out at temperatures between 80° C. and 120° C., the preferred reaction temperature is 85° C.-90° C. The reaction time varies depending on the scale and temperature of the reaction, but is generally between one hour and 16 hours.

Alternatively, compounds of general formula (XII) can be prepared by metalation of the haloheterocycle (VI) with a base (e.g. n-butyllithium) in a solvent (e.g. diethyl ether or tetrahydrofurane) and subsequent reaction with a trialkylborate (e.g. $B(Oi-Pr)_3$ or $B(OMe)_3$) according to known literature methods (Synthesis 2004, 4, 469-483, and references described therein).

At least one equivalent of base (e.g. butyl lithium or isopropylmagnesium chloride) is employed, based on the starting material of the general formula (VI).

The reaction is usually carried out at temperatures of −80° C.-20° C. depending on the base used to perform the reaction. During the reaction a change in temperature may be beneficial or necessary to ensure the reaction with the second reactant. The reaction time varies depending on the scale of the reaction and the reaction temperature, but is generally between a couple of minutes and 48 hours.

After the reaction has ended, the compounds (XII) are removed from the reaction mixture using one of the customary separation techniques. If required, the compounds are purified by recrystallisation, distillation or chromatography, or they can, if appropriate, also be used for the next step without prior purification.

Compounds of general formula (XII) (where B is a tin derivative) are commercially available or can be prepared according to the following scheme.

Scheme 12

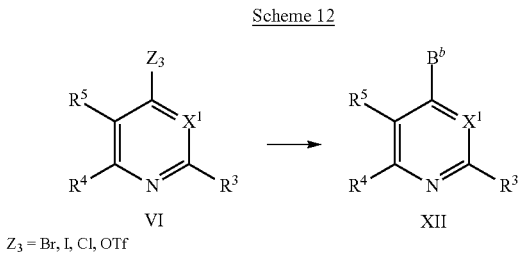

A method for preparing compounds of general formula (XII) is the reaction of Haloheterocyclen of general formula (VI) with Hexaalkylditin (e.g. 1,1,1,2,2,2-Hexabutylditin) in the presence of a catalyst (e.g. dichlorobis(triphenylphoshine)palladium), when appropriate with a fluoride ion source in a solvent (e.g. tetrahydrofuran or diethyl ether) according to literature methods (WO 03/095455 or WO 07/104,538).

Alternatively, compounds of general formula (XII) can be prepared by metalation of the haloheterocycle (VI) with a base (e.g. n-butyllithium) in a solvent (e.g. diethyl ether or tetrahydrofurane) and subsequent reaction with a trialkyltin chloride (e.g. tributyltin chloride) according to known literature methods (WO 08/08747 and Tetrahedron 1994, 275-284).

At least one equivalent of base (e.g. butyl lithium or isopropylmagnesium chloride) is employed, based on the starting material of the general formula (VI).

The reaction is usually carried out at temperatures of $-80°$ C.-20° C. depending on the base used to perform the reaction. During the reaction a change in temperature may be beneficial or necessary to ensure the reaction with the second reactant. The reaction time varies depending on the scale of the reaction and the reaction temperature, but is generally between a couple of minutes and 48 hours.

After the reaction has ended, the compounds (XII) are removed from the reaction mixture using one of the customary separation techniques. If required, the compounds are purified by recrystallisation, distillation or chromatography, or they can, if appropriate, also be used for the next step without prior purification.

Process H v) Compound of general formula (I) are prepared according to scheme 8 via alkylation or acylation of a compound of general formula (Ib) using the same procedures as describe for process B, step d) in scheme 3.

w) Compounds of formula (Ib) may be obtained by deprotection of compounds of formula (Io) under stated of the art methods depending on the nature of the protective group. As an example tetrahydropyranyl as protective group can be deprotected under acidic condition. It is to be noted that weak deprotecting group may be deprotected during the course of the reaction.

x) Compounds of general formula (Io) can be for prepared by coupling the pyrazoles of general formula (XIV) (where B represents a boronic ester or boronic acid) with compounds of formula (XIII) (where $Z^4$ is a leaving group such as chlorine, iodine, bromine or triflate) in the presence of a catalyst, a base, a ligand and a suitable solvent at an appropriate temperature according to known literature procedures (Top Curr. Chem. 2002, 219, 11; A. Suzuki, Org. Chem. 1999, 28, 147 and literature cited therein, Org. Lett. 2005, 7, 21, 4753-4756).

Compounds of general formula (Io) can alternatively be prepared by coupling the pyrazoles of general formula (XIV) (where B represents for trialkyltin) with compounds of formula (XIII) (where Z4 is a leaving group such as chlorine, bromine) in the presence of a catalyst, an inorganic or organic halide salt if appropriate, optionally a ligand and a suitable solvent at an appropriate temperature according to known literature procedures (Synthesis 1992, 803-815).

Suitable catalyst for carrying out the above mentioned processes according to the invention may be chosen as being a metal salt or complex. Suitable metal derivatives for this purpose are based on palladium. Suitable metal salts or complexes for this purpose are palladium chloride, palladium acetate, tetrakis(triphenylphosphine)palladium, bis(triphenylphosphine)palladium dichloride or 1,1'-bis(diphenylphosphino) ferrocenepalladium(II) chloride.

It is also possible to generate a palladium complex in the reaction mixture by separate addition to the reaction of a palladium salt and a ligand or salt, such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino) benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine) ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino) ferrocene, tris-(2,4-tert-butylphenyl)-phosphite, (R)-(−)-1-[(S)-2-(diphenylphosphino)ferrocenyl]ethyldi-tert-butyl-phosphine, (S)-(+)-1-[(R)-2-(diphenylphosphino) ferrocenyl]ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine or 1,3-bis(2,4,6-trimethylphenyl)imidazolium chloride.

The amount of catalyst used is at least 1% to an excess based on the starting material (XIII)

The reaction is usually carried out at temperatures of 20° C.-160° C. and preferably at 20° C.-120° C. The reaction time varies depending on the scale of the reaction and the reaction temperature, but is generally between a couple of minutes and 48 hours.

The reaction is generally carried out under atmospheric pressure but it is also possible to operate under elevated pressure.

After the reaction has ended, the compounds (Io) are removed from the reaction mixture using one of the customary separation techniques. If required, the compounds are purified by recrystallisation, distillation or chromatography, or they can, if appropriate, also be used for the next step without prior purification.

Compounds of general formula (XIII) are commercially available or can be prepared using known organic synthesis techniques like for example via metallation (as described in Chem. A Eur. J., 2009, 15, 5176) or via halogenation with an halogenating agent like for example N-bromosuccinimide (as described in WO 07/143,597).

y) Compounds of general formula (XIV) where $B^a$ is a boron derivative can be prepared by metalation of the protected pyrazole (XV) with a base (e.g. n-butyllithium) in a solvent (e.g. diethyl ether or tetrahydrofurane) and subsequent reaction with a trialkylborate (e.g. $B(Oi-Pr)_3$ or $B(OMe)_3$) according to known literature methods (Tetrahedron Letters 2006, 47, 27, 2006, 4665-4669, and literature described therein). At least one equivalent of base (for example butyl lithium or isopropylmagnesium chloride) is employed, based on the starting material of the general formula (XV), (Scheme 8).

The reaction is usually carried out at temperatures of $-80°$ C.-20° C. depending on the base used to perform the reaction. During the reaction a change in temperature may be beneficial or necessary to ensure the reaction with the second reactant. The reaction time varies depending on the scale of the reaction and the reaction temperature, but is generally between a couple of minutes and 48 hours.

After the reaction has ended, the compounds (XIV) are removed from the reaction mixture using one of the customary separation techniques. If required, the compounds are purified by recrystallisation, distillation or chromatography, or they can, if appropriate, also be used for the next step without prior purification.

Alternatively, compounds of general formula (XIV) where $B^b$ is a tin derivative can be prepared by metalation of the protected pyrazole (XV) with a base (e.g. n-butyllithium) in a solvent (e.g. diethyl ether or tetrahydrofurane) and subsequent reaction with a trialkyltin chloride (e.g. tributyltin chloride) according to known literature methods (WO 06/108591).

At least one equivalent of base (e.g. butyl lithium or isopropylmagnesium chloride) is employed, based on the starting material of the general formula (XV).

The reaction is usually carried out at temperatures of −80° C.-20° C. depending on the base used to perform the reaction. During the reaction a change in temperature may be beneficial or necessary to ensure the reaction with the second reactant. The reaction time varies depending on the scale of the reaction and the reaction temperature, but is generally between a couple of minutes and 48 hours.

After the reaction has ended, the compounds (XIV) are removed from the reaction mixture using one of the customary separation techniques. If required, the compounds are purified by recrystallisation, distillation or chromatography, or they can, if appropriate, also be used for the next step without prior purification.

z) Compounds of general formula (XV) can be prepared for example by coupling the bromopyrazole (XVI) with metallated heterocycles of general formula (XII) (where M represents a boronic ester such as pinacol borane or a boronic acid) in the presence of a catalyst, a base and a ligand if appropriate and a suitable solvent at an appropriate temperature according to known literature procedures produce (Top Curr. Chem. 2002, 219, 11; Org. Lett. 2005, 7, 21, 4753-4756; Org. Chem. 1999, 28, 147 and the literature cited therein).

Compounds of the formula (XV) can also be prepared by coupling the bromopyrazole (XVI) with metallated heterocycles of general formula (XII) where M represents trialkyltin (e.g. tributyltin). The reaction can be performed in the presence of a catalyst, and a ligand if appropriate and a suitable solvent at an appropriate temperature according to known literature procedures produce (Synthesis 1992, 803-815).

Suitable catalyst for carrying out the above mentioned processes according to the invention may be chosen as being a metal salt or complex. Suitable metal derivatives for this purpose are based on palladium. Suitable metal salts or complexes for this purpose are palladium chloride, palladium acetate, tetrakis(triphenylphosphine)palladium, bis(triphenylphosphine)palladium dichloride or 1,1'-bis(diphenylphosphino) ferrocenepalladium(II) chloride.

It is also possible to generate a palladium complex in the reaction mixture by separate addition to the reaction of a palladium salt and a ligand or salt, such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl]ethyldicyclohexylphosphine, (R)-(−)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine or 1,3-bis(2,4,6-trimethylphenyl)imidazolium chloride.

The amount of catalyst used is at least 1% to an excess based on the starting material (XVI).

The reaction is usually carried out at temperatures of 20° C.-160° C. and preferably at 20° C.-120° C. The reaction time varies depending on the scale of the reaction and the reaction temperature, but is generally between a couple of minutes and 48 hours.

The reaction is generally carried out under atmospheric pressure but it is also possible to operate under elevated pressure.

After the reaction has ended, the compounds (XV) are removed from the reaction mixture using one of the customary separation techniques. If required, the compounds are purified by recrystallisation, distillation or chromatography, or they can, if appropriate, also be used for the next step without prior purification.

aa) Compounds of formula (XVI) (where $PG^2$ is a protective group such as THP or PMB) may be obtained by protection of a compound of general formula (XVII) (see "Protective groups in organic chemistry" Green and Wuts $4^{th}$ edition, Wiley Interscience).

The intermediate of formula (XVII) can be synthesized by halogenation of a compound of formula (XVIII) using a suitable halogenating agent such as N-bromosuccinimide, bromine or the like in an appropriate solvent such as dimethylformamide, acetic acid, mixtures thereof or the like.

The invention furthermore provides the non-medicinal use of the heterocyclyl-substituted thiazoles according to the invention for controlling unwanted microorganisms.

The invention furthermore relates to a composition for controlling unwanted microorganisms which comprises at least one heterocyclyl-substituted thiazole according to the present invention.

Moreover, the invention relates to a method for controlling unwanted microorganisms, characterized in that the heterocyclyl-substituted thiazoles according to the invention are applied to the microorganisms and/or in their habitat.

The invention furthermore relates to a seed treated with at least one heterocyclyl-substituted thiazole according to the invention.

A last subject-matter of the invention relates to a method for protecting seed against unwanted microorganisms by using seed treated with at least one heterocyclyl-substituted thiazole according to the present invention.

The compounds according to the invention have strong microbicidal action and can be used for controlling unwanted microorganisms, such as fungi and bacteria, in crop protection and in the protection of materials.

The heterocyclyl-substituted thiazoles of the formula (I) according to the invention have very good fungicidal properties and can be used in crop protection, for example, for controlling *Plasmodiophoromycetes, Oomycetes, Chytridiomycetes, Zygomycetes, Ascomycetes, Basidiomycetes* and *Deuteromycetes*.

In crop protection, bactericides can be used for controlling, for example, Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by varietal property rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, cuttings and seeds.

The following plants may be mentioned as plants which can be treated according to the invention: cotton, flax, grapevines, fruit, vegetables, such as *Rosaceae* sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceae* sp., *Moraceae* sp., *Oleaceae* sp., Actinidaceae sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such *Gramineae* sp. (for example maize, lawn, cereals such as wheat, rye, rice, barley, oats, millet and triticale), *Asteraceae* sp. (for example sunflowers), *Brassicaceae* sp. (for example white cabbage, red cabbage, broccoli, cauliflowers, brussels sprouts, pak Choi, kohlrabi, garden radish, and also oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugarbeet, fodderbeet, swiss chard, beetroot); crop plants and ornamental plants in garden and forest; and also in each case genetically modified varieties of these plants. Preferably, cereal plants are treated according to the invention.

Some pathogens of fungal diseases which can be treated according to the invention may be mentioned by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita, Puccinia graminis* or *Puccinia striformis*; *Uromyces* species, such as, for example, *Uromyces appendiculatus*;

Diseases caused by pathogens from the group of the Oomycetes, such as, for example, *Albugo* species such as, for example, *Albugo cundida, Bremia* species, such as, for example, *Bremia lactucae*; *Peronospora* species, such as, for example, *Peronospora pisi* or *P. brassicae*; *Phytophthora* species, such as, for example *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

Leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, Syn: *Helminthosporium*) or *Cochliobolw miyabeanus*; *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola, Mycosphaerella arachidicola* or *Mycosphaerella fijiensis*; *Phaeosphaeria* species, such as, for example, *Phaeosphaeria nodorum*; *Pyrenophora* species, such as, for example, *Pyrenophora teres* or *Pyrenophora tritici repentis*; *Ramularia* species, such as, for example, *Ramularia collocygni* or *Ramulania areola*; *Rhynchosporium* species, such as, for example, *Rhynchosporium secalis*; *Septoria* species, such as, for example, *Septoria apii* or *Septoria lycopersici*; *Stagonospora* species, such as, for example, *Stagonospora nodorum*; *Typhula* species, such as, for example, *Typhula incarnata*; *Venturia* species, such as, for example, *Venturia inaequalis*;

Root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Plasmodiophora* species, such as, for example, *Plasmodiophora brassicae*; *Rhizoctonia* species, such as, for example *Rhizoctonia solani*; *Sarocladium* species, such as, for example, *Sarocladium oryzae*; *Sclerotium* species, such as, for example, *Sclerotium oryzae*; *Tapesia* species, such as, for example, *Tapesia acuformis*; *Thielaviopsis* species, such as, for example, *Thielaviopsis basicola*;

Ear and panicle diseases (including maize cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Stagonospora* species, such as for example, *Stagonospora nodorum*;

Diseases caused by smut fungi, such as, for example, *Sphacelotheca* species, such as, for example, *Sphacelotheca reiliana*; *Tilletia* species, such as, for example, *Tilletia caries* or *Tilletia controversa*; *Urocystis* species, such as, for example, *Urocystis occulta*; *Ustilago* species, such as, for example, *Ustilago nuda*;

Fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* or *Penicillium purpurogenum*; *Rhizopus* species, such as, for example, *Rhizopus stolonifer*; *Sclerotinia* species, such as, for example, *Sclerotinia sclerotiorum*; *Verticilium* species, such as, for example, *Verticilium alboatrum*;

Seed- and soil-borne rot and wilt diseases, and also diseases of seedlings, caused, for example, by *Alternaria* species, such as, for example, *Alternaria brassicicola*; *Aphanomyces* species, such as, for example, *Aphanomyces euteiches*; *Ascochyta* species, such as, for example, *Ascochyta lentis*; *Aspergillus* species, such as, for example, *Aspergillus flavus*; *Cladosporium* species, such as, for example, *Cladosporium herbarum*; *Cochliobolus* species, such as, for example, *Cochliobolus sativus* (conidia form: *Drechslera*, *Bipolaris* syn: *Helminthosporium*); *Colletotrichum* species, such as, for example, *Colletotrichum coccodes*; *Fusarium* species, such as, for example, *Fusarium culmorum*; *Gibberella* species, such as, for example, *Gibberella zeae*; *Macrophomina* species, such as, for example, *Macrophomina phaseolina*; *Microdochium* species, such as, for example, *Microdochium nivale*; *Monographella* species, such as, for example, *Monographella nivalis*; *Penicillium* species, such as, for example, *Penicillium expansum*; *Phoma* species, such as, for example, *Phoma lingam*; *Phomopsis* species, such as, for example, *Phomopsis sojae*; *Phytophthora* species, such as, for example, *Phytophthora cactorum*; *Pyrenophora* species, such as, for example, *Pyrenophora graminea*; *Pyricularia* species, such as, for example, *Pyricularia oryzae*; *Pythium* species, such as, for example, *Pythium ultimum*; *Rhizoctonia* species, such as, for example, *Rhizoctonia solani*; *Rhizopus* species, such as, for example, *Rhizopus oryzae*; *Sclerotium* species, such as, for example, *Sclerotium rolfsii*; *Septoria* species, such as, for example, *Septoria nodorum*; *Typhula* species, such as, for example, *Typhula incarnata*; *Verticillium* species, such as, for example, *Verticillium dahliae*;

Cancerous diseases, galls and witches' broom caused, for example, by *Nectria* species, such as, for example, *Nectria galligena*;

Wilt diseases caused, for example, by *Monilinia* species, such as, for example, *Monilinia laxa*;

Deformations of leaves, flowers and fruits caused, for example, by *Exobasidium* species, such as, for example, *Exobasidium vexams*; *Taphrina* species, such as, for example, *Taphrina deformans*;

Degenerative diseases of woody plants caused, for example, by *Esca* species, such as, for example, *Phaeomoniella chlamydospora, Phaeoacremonium aleophilum* or *Fomitiporia mediterranea*; *Ganoderma* species, such as, for example, *Ganoderma boninense*;

Diseases of flowers and seeds caused, for example, by *Botrytis* species, such as, for example, *Botrytis cinerea*;

Diseases of plant tubers caused, for example, by *Rhizoctonia* species, such as, for example, *Rhizoctonia solani*; *Helminthosporium* species, such as, for example, *Helminthosporium solani*;

Diseases caused by bacterial pathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*.

Preference is given to controlling the following diseases of soya beans:

Fungal diseases on leaves, stems, pods and seeds caused, for example, by *alternaria* leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also show a strong invigorating action in plants. Accordingly, they are suitable for mobilizing the internal defenses of the plant against attack by unwanted microorganisms.

In the present context, plant-invigorating (resistance-inducing) substances are to be understood as meaning substances which are capable of stimulating the defence system of plants such that, when the treated plants are subsequently inoculated with unwanted microorganisms, they display substantial resistance to these microorganisms.

In the present case, undesired microorganisms are understood as meaning phytopathogenic fungi and bacteria. Thus, the substances according to the invention can be employed for protecting plants against attack by the abovementioned pathogens within a certain period of time after the treatment. The period of time within which their protection is effected is generally extended from 1 to 10 days, preferably 1 to 7 days, after the plants have been treated with the active compounds.

The fact that the active compounds, at the concentrations required for the controlling of plant diseases, are well tolerated by plants permits the treatment of above-ground plant parts, of vegetative propagation material and seed, and of the soil.

In this context, the active compounds according to the invention can be employed particularly successfully for controlling diseases in viticulture and in the cultivation of fruit, potatoes and vegetables, such as, for example, in particular against powdery mildew fungi, Oomycetes, such as, for example, *Phytophthora, Plasmopara, Pseudoperonospora* and *Pythium* species.

The active compounds according to the invention are also suitable for increasing the yield. Moreover, they display a low degree of toxicity and are well tolerated by plants.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as insecticides. If appropriate, they can also be employed as intermediates or precursors for the synthesis of other active compounds.

The active compounds according to the invention, in combination with good plant tolerance and favourable toxicity to warm-blooded animals and being tolerated well by the environment, are suitable for protecting plants and plant organs, for increasing harvest yields and for improving the quality of harvested material in agriculture, in horticulture, in animal husbandry, in forests, in gardens and leisure facilities, in the protection of stored products and of materials, and in the hygiene sector. They are preferably employed as crop protection agents. They are active against normally sensitive and resistant species and against all or some stages of development.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for wet seed treatment, a water-soluble powder for slurry treatment, by encrusting, by coating with one or more coats, etc. It is furthermore possible to apply the active compounds by the ultra-low-volume method or to inject the active compound preparation or the active compound itself into the soil.

In the protection of materials, the compositions or active compounds according to the invention can furthermore be employed for protecting industrial materials against attack and destruction by unwanted microorganisms, such as, for example, fungi.

In the present context, industrial materials are understood as meaning nonliving materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably timber. The compositions or active compounds according to the invention can prevent disadvantageous effects such as rotting, decay, discoloration, decoloration or the formation of mould.

The method according to the invention for controlling unwanted fungi can also be employed for protecting storage goods. Here, storage goods are to be understood as meaning natural substances of vegetable or animal origin or process products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compounds according to the invention can prevent disadvantageous effects, such as rotting, decay, discoloration, decoloration or the formation of mould.

Microorganisms capable of degrading or changing the industrial materials which may be mentioned are, for example, bacteria, fungi, yeasts, algae and slime organisms. The active compounds according to the invention preferably act against fungi, in particular moulds, wood-discoloring and wood-destroying fungi (*Basidiomycetes*) and against slime organisms and algae. Microorganisms of the following genera may be mentioned as examples: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

The present invention furthermore relates to a composition for controlling unwanted microorganisms comprising at least one of the heterocyclyl-substituted thiazoles according to the invention. These are preferably fungicidal compositions comprising auxiliaries, solvents, carriers, surfactants or extenders suitable for use in agriculture.

According to the invention, a carrier is a natural or synthetic, organic or inorganic substance with which the active compounds are mixed or bonded for better applicability, in particular for application to plants or parts of plants or seed. The carrier, which may be solid or liquid, is generally inert and should be suitable for use in agriculture.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite and dolomite, and also synthetic granules of inorganic and organic meals, and granules of organic material, such as paper, sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol/POE and/or POP ethers, acid and/or POP/POE esters, alkylaryl and/or POP/POE ethers, fat and/or POP/POE adducts, POE and/or POP polyol derivatives, POE and/or POP/sorbitan or sugar adducts, alkyl or aryl sulphates, sulphonates and phosphates, or the corresponding PO ether adducts. Furthermore suitable oligo- or polymers, for example those derived from vinylic monomers, from acrylic acid, from EO and/or PO alone or in combination with, for example, (poly)alcohols or (poly)amines It is also possible to employ lignin and its sulphonic acid derivatives, unmodified and modified celluloses, aromatic and/or aliphatic sulphonic acids and their adducts with formaldehyde.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and also microencapsulations in polymeric substances.

The active compounds can be used as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspension-emulsion concentrates, natural materials impregnated with active compound, synthetic materials impregnated with active compound, fertilizers and also microencapsulations in polymeric substances. Application is carried out in a customary manner, for example by pouring, spraying, atomizing, broadcasting, dusting, foaming, painting-on, etc. It is furthermore possible to apply the active compounds by the ultra-low-volume method or to inject the preparation of active compound or the active compound itself into the soil. It is also possible to treat the seed of the plants.

The formulations mentioned can be prepared in a manner known per se, for example by mixing the active compounds with at least one customary extender, solvent or diluent, emulsifier, dispersant and/or binder or fixative, wetting agent, water repellant, if appropriate siccatives and UV stabilizers and if appropriate colorants and pigments, antifoams, preservatives, secondary thickeners, glues, gibberellins and other processing auxiliaries.

The compositions according to the invention include not only formulations which are already ready to use and can be applied to the plant or the seed using a suitable apparatus, but also commercial concentrates which have to be diluted with water prior to use.

The active compounds according to the invention can be present as such or in their (commercial) formulations and also in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are liquids which are gaseous at ambient temperature and under atmospheric pressure, for example aerosol propellants, such as halogenated hydrocarbons, and also butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible to use, for example, organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may additionally comprise further components, such as, for example, surfactants. Suitable surfactants are emulsifiers and/or foamformers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is required if one of the active compounds and/or one of the inert carriers is insoluble in water and the application is carried out in water. The proportion of surfactants is between 5 and 40 percent by weight of the compositions according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

Other possible additives are perfumes, mineral or vegetable oils, if appropriate modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

If appropriate, it is also possible for other additional components to be present, for example protective colloids, binders, glues, thickeners, thixotropic agents, penetrants, stabilizers, sequestrants, complex fomers. In general, the active compounds can be combined with any solid or liquid additive customarily used for formulation purposes.

The formulations generally comprise between 0.05 and 99% by weight, 0.01 and 98% by weight, preferably between 0.1 and 95% by weight, particularly preferably between 0.5 and 90% by weight, of active compound, very particularly preferably between 10 and 70 percent by weight.

The formulations described above can be employed in a method according to the invention for controlling unwanted microorganisms where the heterocyclyl-substituted thiazoles according to the invention are applied to the microorganisms and/or their habitat.

The active compounds according to the invention, as such or in their formulations, can also be used in a mixture with known fungicides, bactericides, acaricides, nematicides or insecticides, for example to broaden the activity spectrum or to prevent the development of resistance.

Suitable mixing partners are, for example, known fungicides, insecticides, acaricides, nematicides or else bactericides (see also Pesticide Manual, 13th ed.).

A mixture with other known active compounds, such as herbicides, or with fertilizers and growth regulators, safeners and/or semiochemicals is also possible.

Application is carried out in a manner adapted to the use forms.

The invention furthermore comprises a method for treating seed.

A further aspect of the present invention relates in particular to seed treated with at least one of the heterocyclyl-substituted thiazoles according to the invention. The seed according to the invention is used in methods for protecting seed against phytopathogenic harmful fungi. In these methods, seed treated with at least one active compound according to the invention is used.

The compositions and active compounds according to the invention are also suitable for treating seed. A large part of the damage to crop plants which is caused by harmful organisms occurs when the seed is attacked during storage or after the seed is introduced into the soil, and also during and after germination of the plant. This phase is particularly critical since the roots and shoots of the growing plant are particularly sensitive and even minor damage can lead to the death of the whole plant. Protecting the seed and the germinating plant by the use of suitable compositions is therefore of great interest.

The control of phytopathogenic harmful fungi by treating the seed of plants has been known for a long time and is subject-matter of continuous improvements. However, in the treatment of seed, a number of problems are encountered which can not always by resolved in a satisfactory manner. Thus, it is desirable to develop methods for protecting the seed and the germinating plant which dispense with the additional application of crop protection agents after sowing or after the emergence of the plants or where additional applications are at least significantly reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates to a method for the protection of seed and germinating plants from attack by animal pests and/or phytopathogenic harmful fungi, by treating the seed with a composition according to the invention. The invention likewise relates to the use of the compositions according to the invention for the treatment of seed for protecting the seed and the germinating plant from phytopathogenic fungi. Furthermore, the invention relates to seed which has been treated with a composition according to the invention so as to afford protection from phytopathogenic fungi.

Animal pests and/or phytopathogenic harmful fungi which damage the plant after emergence are primarily controlled by treating the soil and the above-ground parts of the plants with crop protection agents. Owing to concerns with a possible impact of the crop protection agents on the environment and human and animal health, there are efforts to reduce the amount of active compounds applied.

One of the advantages of the present invention is that the particular systemic properties of the compositions according to the invention mean that treatment of the seed with these compositions not only protects the seed itself, but also the resulting plants after emergence, from animal pests and/or phytopathogenic harmful fungi. In this manner, the immediate treatment of the crop at the time of sowing or shortly thereafter can be dispensed with.

It is also to be considered advantageous that the compositions and active compounds according to the invention can be used in particular also for transgenic seed, where the plant growing from this seed is capable of expressing a protein which acts against pests. By treating such a seed with the compositions and active compounds according to the invention, is possible to control certain pests even by the expression of the, for example, insecticidal protein. Surprisingly, a further synergistic effect may be observed here, which further improves the effectiveness of the protection against attack by pests.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawns and ornamental plants. The treatment of seed of cereals (such as wheat, barley, rye and oats), maize and rice is of particular importance.

As also described below, the treatment of transgenic seed with the compositions or active compounds according to the invention is also of particular importance. This takes the form of seed of plants which comprise at least one heterologous gene which governs the expression of a polypeptide or protein with insecticidal properties. The heterologous gene in transgenic seed may be derived, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., the gene product having activity against the European corn borer and/or the Western corn root worm. It is particularly preferably a heterologous gene derived from *Bacillus thuringiensis*.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and also water.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations rhodamine B, C.I. Pigment Red 112, and C.I. Solvent Red 1.

Suitable wetting agents that may be present in the seed dressing formulations which can be used according to the invention include all substances which promote wetting and are customary in the formulation of active agrochemical compounds. With preference it is possible to use alkylnaphthalene-sulphonates, such as diisopropyl- or diisobutylnaphthalene-sulphonates.

Suitable dispersants and/or emulsifiers that may be present in the seed dressing formulations which can be used according to the invention include all nonionic, anionic, and cationic dispersants which are customary in the formulation of active agrochemical compounds. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Suitable defoamers that may be present in the seed dressing formulations which can be used according to the invention include all foam-inhibiting substances which are customary in the formulation of active agrochemical compounds. With preference it is possible to use silicone defoamers and magnesium stearate.

Suitable preservatives that may be present in the seed dressing formulations which can be used according to the invention include all substances which can be used for such purposes in agrochemical compositions. By way of example, mention may be made of dichlorophen and benzyl alcohol hemiformal.

Suitable secondary thickeners that may be present in the seed dressing formulations which can be used according to the invention include all substances which can be used for such purposes in agrochemical compositions. Preferred suitability is possessed by cellulose derivatives, acrylic acid derivatives, xanthan, modified clays, and finely divided silica.

Suitable adhesives that may be present in the seed dressing formulations which can be used according to the invention include all customary binders which can be used in seed dressing. With preference, mention may be made of polyvinylpyrrolidone, polyvinyl acetate, polyvinyl alcohol and tylose.

Suitable gibberellins that may be present in the seed dressing formulations which can be used according to the invention are preferably the gibberellins A1, A3 (=gibberellinic acid), A4 and A7; particularly preferably, gibberellinic acid is used. The gibberellins are known (cf. R. Wegler "Chemie der Pflanzenschutz- and Schädlingsbekämpfungsmittel", Vol. 2, Springer Verlag, 1970, pp. 401-412).

The seed dressing formulations which can be used according to the invention may be used directly or after dilution with water beforehand to treat seed of any of a very wide variety of types. For instance, the concentrates or the preparations obtainable therefrom by dilution with water may be used to dress the seed of cereals, such as wheat, barley, rye, oats, and triticale, and also the seed of maize, rice, oilseed rape, peas, field beans, cotton, sunflowers, and beets, or else vegetable seed of any of a very wide variety of kinds. The seed dressing formulations which can be used according to the invention or their dilute preparations may also be used to dress seed of transgenic plants. In this context, additional synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The application rate of the seed dressing formulations which can be used according to the invention may be varied within a relatively wide range. It depends on the respective content of the active compounds in the formulations and on the seed. In general, the application rates of active compound combination are between 0.001 and 50 g per kilogram of seed, preferably between 0.01 and 15 g per kilogram of seed.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi does by no means limit the mycotic spectrum which can be covered, but is only for illustration.

Accordingly, the active compounds of the formula (I) according to the invention can be used both in medical and in non-medical applications.

The active compounds can be applied as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, painting-on, etc. It is also possible to apply the active compounds by the ultra-low-volume method or to inject the preparation of active compound or the active compound itself into the soil. It is also possible to treat the seed of the plants.

When using the active compounds according to the invention as fungicides, the application rates can be varied within a relatively wide range, depending on the type of application. The application rate of the active compounds according to the invention is

- in the treatment of parts of plants, for example leaves: from 0.1 to 10 000 g/ha, preferably from 10 to 1000 g/ha, particularly preferably from 50 to 300 g/ha (when the application is by watering or dripping, it is possible to reduce the application rate even more, in particular when inert substrates such as rock wool or perlite are used);
- in the treatment of seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed;
- in soil treatment: from 0.1 to 10 000 g/ha, preferably from 1 to 5000 g/ha.

These application rates are mentioned only in an exemplary manner and are not limiting for the purpose of the invention.

In the veterinary sector and in animal keeping, the active compounds according to the invention are applied in the known manner by enteral administration in the form of, for example, tablets, capsules, drinks, drenches, granules, pastes, boluses, the feed-through method, suppositories, by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When used for livestock, poultry, domestic animals and the like, the active compounds of the formula (I) can be applied as formulations (for example powders, emulsions, flowables) which comprise the active compounds in an amount of from 1 to 80% by weight, either directly or after 100- to 10 000-fold dilution, or else as a chemical bath.

If appropriate, the ready-to-use compositions may comprise further insecticides and, if appropriate, one or more further fungicides.

With respect to possible additional mixing partners, reference is made to the insecticides and fungicides mentioned above.

The compounds according to the invention can also be used for protecting objects which come into contact with salt water or brackish water, such as hulls, screens, nets, buildings, moorings and signalling systems, against colonization.

The compounds according to the invention, alone or in combination with other active compounds, can furthermore be employed as antifouling agents.

The treatment method according to the invention can be used for treating genetically modified organisms (GMOs), for example plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which is/are present in the plant (using for example, antisense technology, cosuppression technology or RNA interference (RNAi) technology. A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, the following effects, which exceed the effects which were actually to be expected, are possible: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the active compound combinations according to the invention may also have a strengthening effect in plants. Accordingly, they are also suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably treated according to the invention include all plants with genetic material which bestows upon these plants particularly advantageous useful properties (whether this was achieved by breeding and/or biotechnology is immaterial).

Plants and plant cultivars which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stress factors. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients or shade avoidance.

Plants and plant cultivars which may also be treated according to the invention are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore by affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or the hybrid effect which results in generally higher yield, vigour, health and resistance towards biotic and abiotic stress factors. Such plants are typically made by crossing an inbred male sterile parent line (the female parent) with another inbred male fertile parent line (the male parent). Hybrid seed is typically harvested from the male sterile plants and sold to growers. Male sterile plants can sometimes (e.g. in corn) be produced by detasseling, (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide-resistant plants are plants that are made tolerant to acetolactate synthase (ALS) inhibitors. Known ALS-inhibitors include, for example, sulphonylurea, imidazolinone, triazolopyrimidines, pyrimidinyloxy(thio)benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:
1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A. 105 protein produced by maize event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604;
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1a and VIP2A proteins;
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
a. plants which contain a transgene capable of reducing the expression and/or the activity of the poly(ADP-ribose) polymerase (PARP) gene in the plant cells or plants.
b. plants which contain a stress tolerance-enhancing transgene capable of reducing the expression and/or the activity of the PARG encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as, for example:
1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications.
2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan.
3) transgenic plants which produce hyaluronan.

Plants or plant cultivars (that can be obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes,
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;

e) plants, such as cotton plants, wherein the timing of the plasmodesmatal gating at the basis of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated according to the invention are plants which comprise one or more genes which encode one or more toxins, are the following which are sold under the trade names: YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names: Roundup Ready® (tolerance to glyphosate, for example maize, cotton, soya beans), Liberty Link® (tolerance to phosphinothricin, for example oilseed rape), IMF) (tolerance to imidazolinone) and SCS CD (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

According to the invention, the plants listed can be treated particularly advantageously with the compounds of the general formula (I) or the active compound mixtures according to the invention. The preferred ranges indicated above for the active compounds and mixtures also apply to the treatment of these plants. Particular emphasis is given to treating the plants with the compounds and mixtures specifically indicated in the present text.

The compositions or active compounds according to the invention can also be used to protect plants for a certain period after treatment against attack by the pathogens mentioned. The period for which protection is provided generally extends over 1 to 28 days, preferably over 1 to 14 days, particularly preferably over 1 to 10 days, very particularly preferably over 1 to 7 days, after the treatment of the plants with the active compounds, or over up to 200 days after seed treatment.

Preparation and use of the active compounds of the formula (I) according to the invention is shown in the examples below. However, the invention is not limited to these examples.

General remarks: Unless indicated otherwise, all chromatographic purification and separation steps were carried out on silica gel using a solvent gradient from 0:100 ethyl acetate/cyclohexane to 100:0 ethyl acetate/cyclohexane Preparation of Starting Materials of the Formula (III)

1-(5-chloro-2-thienyl)-2-(pyridin-4-yl)ethanone

To a solution of 4-methylpyridine (32.3 mmol) and ethyl 5-chlorothiophene-2-carboxylate (35.5 mmol) in anhydrous THF (58 mL) at 0° C., under $N_2$ was added dropwise a solution of lithium bis(trimethylsilyl)amide (1 molar solution in hexanes, 64.5 mmol). The mixture was stirred 3 h at 5° C. The resulting precipitate was filtered and acidified with 6 molar HCl. The precipitate was then filtered and dried to afford 2.9 g (35% yield) of 1-(5-chloro-2-thienyl)-2-(pyridin-4-yl)ethanone.

logP (pH2.7): 1.17
MS (ESI): 238.1 ([M+H]$^+$)
$^1$H-NMR (400 MHz, $d_6$-DMSO): δ=8.53 (d, 2H), 8.09 (d, 1H), 7.40 (d, 1H), 7.34 (d, 2H), 4.39 (s, 2H) ppm 1-(5-chloro-2-thienyl)-2-(2-chloropyridin-4-yl)ethanone To a solution of 2-chloro-4-methylpyridine (15.6 mmol) and ethyl 5-chlorothiophene-2-carboxylate (17.2 mmol) in anhydrous THF (17 mL) at 0° C., under $N_2$ was added dropwise a solution of lithium bis(trimethylsilyl)amide (1 molar solution in hexanes, 31.3 mmol). The mixture was stirred 2 h at 5° C. The solvent was then evaporated and the residue was dissolved in a mixture of water and dichloromethane. The organic layer was separated, and the aqueous layer was extracted with dichloromethane. The combined organic layers were washed with brine, dried with $MgSO_4$, and concentrated under reduced pressure to afford 4.3 g (96% yield) of 1-(5-chloro-2-thienyl)-2-(2-chloropyridin-4-yl)ethanone.

logP (pH2.7): 2.94
MS (ESI): 272.0 ([M+H]$^+$)
$^1$H-NMR (400 MHz, $d_6$-DMSO): δ=8.48 (d, 1H), 8.09 (d, 1H), 7.51 (s, 1H), 7.40 (d, 1H), 7.36 (d, 1H), 4.48 (s, 2H) ppm 1-(5-Chloro-2-thienyl)-2-[2-(methylsulfanyl)pyrimidin-4-yl]ethanone To a solution of 4-methyl-2-(methylsulfanyl)pyrimidine (1 eq, 235 mmol) and ethyl 5-chlorothiophene-2-carboxylate (1.11 eq, 261 mmol) in anhydrous THF (400 mL) at 0° C., under $N_2$ was added dropwise a solution of lithium bis(trimethylsilyl)amide (1M solution in hexanes, 1.6 eq, 376 mmol). The resulting mixture was stirred for 3 h at 0° C. and then stirred at room temperature overnight. A solution of HCl 1M (750 mL) was then added till pH=1. The aqueous layer was extracted with ethyl acetate and the combined organic extracts were washed with brine, dried over MgSO4, filtered and concentrated. The residue was diluted with diisopropylether and the resulting precipitate was filtered and to afford 29.5 g (43% yield) of 1-(5-chloro-2-thienyl)-2-[2-(methylsulfanyl)pyrimidin-4-yl]ethanone.

logP (pH2.7): 2.98
MS (ESI): 285 ([M+H]$^+$)
$^1$H-NMR (400 MHz, $d_6$-DMSO): δ=8.61 (d, 1H), 8.04 (d, 1H), 7.39 (d, 1H), 7.23 (d, 1H), 4.48 (s, 2H), 3.43 (s, 3H) ppm 1-(3-Chloro-2-thienyl)-2-(pyridin-4-yl)ethanone To a solution of 4-methylpyridine (1 eq, 75 mmol) in anhydrous THF (50 mL) was added n-butyl lithium 2.5 M solution (1.3 eq, 98 mmol) at −50° C. under nitrogen. The reaction mixture was stirred for 30 min at −50° C. To the mixture was slowly added a solution of methyl 3-chloro-2-thiophenecarboxylate (1 eq, 75 mmol, synthesis described in Heterocycles, 2007, 71(1), 87) in anhydrous THF (50 mL) at −50° C. The reaction mixture was stirred at −50° C. for 30 min, then allowed to warm to room temperature and stirred for 2 h. The mixture was quenched with aqueous saturated ammonium chloride solution (150 mL). The organic layer was separated and the aqueous phase was extracted with ethyl acetate (3×100 mL). The combined extracts were washed with water, brine, dried over Na2SO4 and concentrated. The obtained dark brown residue was purified by column chromatography on silica gel (DCM:MeOH, 100:1 to 80:1) to afford 4 g of 1-(3-chloro-2-thienyl)-2-(pyridin-4-yl)ethanone (22% yield).

$^1$H-NMR (400 MHz, CDCl$_3$): δ=8.57 (d, 2H), 7.60 (d, 1H), 7.22 (d, 2H), 7.06 (d, 1H), 4.36 (s, 2H) ppm 2-(2-Chloropyrimidin-4-yl)-1-(5-chloro-2-thienyl) ethanone To a solution of 2-chloro-4-methylpyrimidine (1 eq, 46.7 mmol) and ethyl 5-chlorothiophene-2-carboxylate (1.1 eq, 51.3 mmol) in anhydrous THF (50 mL) at 0° C., under N$_2$ was added dropwise a solution of lithium bis(trimethylsilyl)amide (1 molar solution in hexanes, 2 eq, 93.3 mmol). The mixture was stirred 2 h at 5° C. Water was then added followed by 300 mL of dichloromethane. The organic layer was separated and the yellow precipitate was then filtered and dried to afford 10.7 g (84% yield) of 2-(2-chloropyrimidin-4-yl)-1-(5-chloro-2-thienyl)ethanone.

logP (pH2.7): 2.60
MS (ESI): 273 ([M+H]$^+$)
$^1$H-NMR (400 MHz, d$_6$-DMSO): δ=8.08 (d, 1H), 7.69 (d, 1H), 7.20 (d, 1H), 6.99 (d, 1H), 5.48 (s, 1H) ppm Preparation of Intermediate of the Formula (IIIa) where R$^3$ is an Amino Derivative 1-(2-Chloro-2-thienyl)-2-[2-(isopropylamino)pyrimidin-4-yl]ethanone A mixture of 2-(2-chloropyrimidin-4-yl)-1-(5-chloro-2-thienyl)ethanol (1 eq, 14.6 mmol) in 20 mL of isopropylamine was stirred at 110° C. in the microwave for 70 min. The solvent was evaporated and HCl 1M was added until pH=1. The resulting white precipitate was filtered and dried to afford 4.25 g of 1-(5-chloro-2-thienyl)-2-[2-(isopropylamino)pyrimidin-4-yl]ethanone (98% yield).

logP (pH2.7): 2.37
MS (ESI): 296 ([M+H]$^+$)

Preparation of Starting Materials of the Formula (II)

1-(5-chloro-2-thienyl)-3-(dimethylamino)-2-(pyridin-4-yl)prop-2-en-1-one

To a suspension of 1-(5-chloro-2-thienyl)-2-(pyridin-4-yl)ethanone (21 mmol) in 13 mL N,N-dimethylformamide, was added N,N-dimethylformamide dimethyl acetal (71.5 mmol). The mixture was refluxed for 3 h and then allowed to cool to room temperature. The solvent was evaporated under reduced pressure and the residue was partitioned between ethyl acetate and water. The aqueous layer was extracted with ethyl acetate and the combined organic extracts were dried over MgSO$_4$ filtered and concentrated. The residue was purified by chromatography on silica gel (dichloromethane:methanol 100:1 to 20:1) to afford 3.3 g (51% yield) of 1-(5-chloro-2-thienyl)-3-(dimethylamino)-2-(pyridin-4-yl)prop-2-en-1-one.

logP (pH2.7): 1.07
MS (ESI): 293.0 ([M+H]$^+$)
$^1$H-NMR (400 MHz, d$_6$-DMSO): δ=8.49 (d, 2H), 7.64 (bs, 1H), 7.16 (d, 2H), 7.04 (d, 1H), 6.88 (d, 1H), 2.81 (bs, 6H) ppm 1-(5-chloro-2-thienyl)-3-(dimethylamino)-2-(2-chloropyridin-4-yl)prop-2-en-1-one To a suspension of 1-(5-chloro-2-thienyl)-2-(2-chloropyridin-4-yl)ethanone (15.8 mmol) in 10 mL N,N-dimethylformamide, was added N,N-dimethylformamide dimethyl acetal (53.7 mmol). The mixture was refluxed for 2 h and then allowed to cool to room temperature. The solvent was evaporated under reduced pressure and the residue was partitioned between ethyl acetate and water. The aqueous layer was extracted with ethyl acetate and the combined organic extracts were dried over MgSO$_4$ filtered and concentrated. The residue was purified by chromatography on silica gel (ethyl acetate:heptane 6:4 to 1:0) to afford 3.3 g (60% yield) of 1-(5-chloro-2-thienyl)-3-(dimethylamino)-2-(2-chloropyridin-4-yl)prop-2-en-1-one.

logP (pH2.7): 2.58
MS (ESI): 327.0 ([M+H]$^+$)
$^1$H-NMR (400 MHz, d$_6$-DMSO): δ=8.28 (bs, 1H), 7.69 (bs, 1H), 7.23 (s, 1H), 7.12 (m, 2H), 7.08 (d, 1H), 2.80 (bs, 6H) ppm 3-(Dimethylamino)-1-(5-chloro-2-thienyl)-2-[2-(methylsulfanyl)pyrimidin-4-yl]prop-2-en-1-one A solution of 1-(5-chloro-2-thienyl)-2-[2-(methylsulfanyl)pyrimidin-4-yl]ethanone (1 eq, 104 mmol) in 290 mL N,N-dimethylformamide dimethyl acetal was stirred at 80° C. for 1 h40 min and then stirred overnight at room temperature. The solvent was evaporated under reduced pressure and the residue was purified by chromatography on silica gel (heptane/ethyl acetate 1:1 to 3:7) to afford 32.7 g (86% yield) of 3-(dimethylamino)-1-(5-chloro-2-thienyl)-2-[2-(methylsulfanyl)pyrimidin-4-yl]prop-2-en-1-one.

logP (pH2.7): 2.27
MS (ESI): 340 ([M+H]$^+$)
$^1$H-NMR (400 MHz, d$_6$-DMSO): δ=8.24 (d, 1H), 7.82 (s, 1H), 7.15 (m, 2H), 6.92 (d, 1H), 2.93 (bs, 6H), 2.36 (s, 3H) ppm 1-(3-Chlorothiophen-2-yl)-3-(dimethylamino)-2-(pyridin-4-yl)prop-2-en-1-one To a solution of 1-(3-chlorothiophen-2-yl)-2-(pyridin-4-yl)prop-2-en-1-one (1 eq, 27 mmol) in anhydrous N,N-dimethylformamide (40 mL) was added N,N-dimethylformamide dimethyl acetal (4 eq, 108 mmol). The reaction mixture was stirred under reflux for 1.5 h. The mixture was diluted with water (600 mL) and extracted with dichloromethane (4×200 mL) and ethylacetate (4×200 mL). The combined extracts were washed with water, brine, dried over Na2SO4 and concentrated. The obtained residue was purified by column chromatography on silica gel (DCM:MeOH, 40:1 to 20:1) to afford intermediate 5.9 g of 1-(3-chlorothiophen-2-yl)-3-(dimethylamino)-2-(pyridin-4-yl)prop-2-en-1-one (74% yield).

$^1$H-NMR (400 MHz, d$_6$-DMSO): δ=8.51 (d, 2H), 7.41 (s 1H), 7.34 (d, 1H), 7.14 (d, 2H), 6.86 (d, 1H), 2.95 (s, 3H), 2.88 (s, 3H) ppm

3-(Dimethylamino)-1-(5-chloro-2-thienyl)-2-[2-(isopropylamino)pyrimidin-4-yl]prop-2-en-1-one To a suspension of 1-(5-chloro-2-thienyl)-2-[2-(isopropylamino)pyrimidin-4-yl]ethanon (1 eq, 13.5 mmol) in 6 mL N,N-dimethylformamide, was added of N,N-dimethylformamide dimethyl acetal (3.4 eq, 46 mmol). The mixture was stirred at 100° C. for 2 h and then allowed to cool to room temperature. The solvent was evaporated to afford 4.5 g (95% yield) of 3-(dimethylamino)-1-(5-chloro-2-thienyl)-2-[2-(isopropylamino)pyrimidin-4-yl]prop-2-en-1-one which was used in the next step without further purification.

logP (pH2.7): 1.67
MS (ESI): 351 ([M+H]$^+$)

Preparation of Compound of the Formula (Ia)

4-[3-(5-chloro-2-thienyl)-1H-pyrazol-4-yl]pyridine

A mixture of 1-(5-chloro-2-thienyl)-3-(dimethylamino)-2-(pyridin-4-yl)prop-2-en-1-one (5.1 mmol), hydrazine hydrate (7.6 mmol) and triethylamine (7.6 mmol) in 25 mL ethanol was refluxed for 3 h. The solvent was evaporated under reduced pressure and the residue was purified by chromatography on silica gel (dichloromethane:methanol 50:1 to 20:1) to afford 1.16 g 4-[3-(5-chloro-2-thienyl)-1H-pyrazol-4-yl]pyridine (83% yield).

logP (pH2.7): 0.90
MS (ESI): 262.0 ([M+H]$^+$)
$^1$H-NMR (400 MHz, d$_6$-DMSO): δ=13.43 (bs, 1H), 8.58 (d, 2H), 8.17 (d, 1H), 7.41 (d, 2H), 7.11 (d, 1H), 6.90 (s, 1H) ppm

4-[1-sec-Butyl-3-(5-chloro-2-thienyl)-1H-pyrazol-4-yl]pyridine and 4-[1-sec-butyl-5-(5-chloro-2-thienyl)-1H-pyrazol-4-yl]pyridine A mixture of 1-(5-chloro-2-thienyl)-2-(pyridin-4-yl)ethanone (0.68 mmol), secbutylhydrazin (1.37 mmol) and triethylamine (1.37 mmol) in 5 mL dichloromethane was refluxed for 2.5 h. The solvent was evaporated under reduced pressure and the residue was partitioned between ethyl acetate and water. The aqueous layer was extracted with ethyl acetate and the combined organic extracts were dried over MgSO$_4$ filtered and concentrated. The residue was purified by chromatography on silica gel (dichloromethane:methanol 100:1 to 20:1) to afford 37 mg of 4-[1-sec-butyl-3-(5-chloro-2-thienyl)-1H-pyrazol-4-yl]pyridine (16% yield) and 48 mg of 4-[1-sec-butyl-5-(5-chloro-2-thienyl)-1H-pyrazol-4-yl]pyridine (21% yield).

4-[1-sec-Butyl-3-(5-chloro-2-thienyl)-1H-pyrazol-4-yl]pyridine logP (pH2.7): 2.10
MS (ESI): 318.1 ([M+H]$^+$)
$^1$H-NMR (400 MHz, d$_6$-DMSO): δ=8.52 (d, 2H), 8.23 (s, 1H), 7.40 (d, 2H), 7.07 (d, 1H), 6.88 (d, 1H), 4.30 (m, 1H), 1.81 (m, 2H), 1.44 (d, 3H), 0.81 (t, 3H) ppm

4-[1-sec-Butyl-5-(5-chloro-2-thienyl)-1H-pyrazol-4-yl]pyridine logP (pH2.7): 1.94
MS (ESI): 318.1 ([M+H]$^+$)
$^1$H-NMR (400 MHz, d$_6$-DMSO): δ=8.48 (d, 2H), 8.13 (s, 1H), 7.34 (d, 1H), 7.23 (m, 3H), 4.12 (m, 1H), 1.90 (m, 1H), 1.71 (m, 1H), 1.37 (d, 3H), 0.67 (t, 3H) ppm

2-Chloro-4-[3-(5-chloro-2-thienyl)-1H-pyrazol-4-yl]pyridine

A mixture of 1-(5-chloro-2-thienyl)-3-(dimethylamino)-2-(2-chloropyridin-4-yl)prop-2-en-1-one (10 mmol), hydrazine hydrate (20 mmol) in 90 mL ethanol was stirred at 80° C. for 1.5 h. The solvent was evaporated under reduced pressure to afford 3 g 2-chloro-4-[3-(5-chloro-2-thienyl)-1H-pyrazol-4-yl]pyridine (95% yield).

logP (pH2.7): 2.75
MS (ESI): 296.0 ([M+H]$^+$)
$^1$H-NMR (400 MHz, d$_6$-DMSO): δ=13.20 (bs, 1H), 8.39 (d, 1H), 8.28 (s, 1H), 7.56 (s, 1H), 7.43 (d, 1H), 7.14 (d, 1H), 6.98 (d, 1H) ppm

4-[3-(5-Chloro-2-thienyl)-1H-pyrazol-4-yl]-2-(methylsulfanyl)pyrimidine

To a mixture of 3-(dimethylamino)-1-(5-chloro-2-thienyl)-2-[2-(methylsulfanyl)pyrimidin-4-yl]prop-2-en-1-one (1 eq, 96 mmol) in 300 mL ethanol was added dropwise hydrazine hydrate (1.5 eq, 144 mmol) and then triethylamine (1.5 eq, 144 mmol). The mixture was heated under reflux for 2 h and then overnight at room temperature. The solvent was then slowly poured in 1 L of water. The resulting precipitate was filtered and dried to afford 24 g of 4-[3-(5-chloro-2-thienyl)-1H-pyrazol-4-yl]-2-(methylsulfanyl)pyrimidine (80% yield).

logP (pH2.7): 2.78
MS (ESI): 309 ([M+H]$^+$)
$^1$H-NMR (400 MHz, d$_6$-DMSO): δ=13.61 (bs, 1H), 8.57 (d, 1H), 8.51 (s, 1H), 7.58 (d, 1H), 7.40 (d, 1H), 7.14 (d, 1H), 2.48 (s, 3H) ppm

4-(3-(3-Chloro-2-thienyl)-1H-pyrazol-4-yl)pyridine

To a solution of 3-(dimethylamino)-1-(3-chloro-2-thienyl)-2-(pyrimidin-4-yl)prop-2-en-1-one (1 eq, 20 mmol) in ethanol (60 mL) was added hydrazine hydrate (1.5 eq, 30 mmol) and triethylamine (1.5 eq, 30 mmol). The reaction mixture was stirred at reflux for 2 h. The mixture was evaporated under reduced pressure. The obtained residue was dissolved in dichloromethane (100 mL) and methanol (10 mL), washed with brine (3×50 mL), dried over Na2SO4 and concentrated. The crude product was suspended in ethylacetate, filtered and dried to afford 2.9 g of 4-(3-(3-chloro-2-thienyl)-1H-pyrazol-4-yl)pyridine (55% yield).

MS (ESI): 262 ([M+H]$^+$)
$^1$H-NMR (400 MHz, d$_6$-DMSO): δ=13.59 (bs, 1H), 8.44 (m, 3H), 7.81 (d, 1H), 7.19 (m, 3H) ppm

4-[3-(5-Chloro-2-thienyl)-1H-pyrazol-4-yl]-2-(isopropylamino)pyrimidine

A mixture of 3-(dimethylamino)-1-(5-chloro-2-thienyl)-2-[2-(isopropylamino)pyrimidin-4-yl]prop-2-en-1-one (1 eq, 12.8 mmol), hydrazine hydrate (1.1 eq, 14.1 mmol) in 78 mL ethanol was stirred overnight at room temperature. The solvent was evaporated and purified by chromatography on silica gel (heptane/ethyl acetate) to afford 1.19 g of 4-[3-(5-chloro-2-thienyl)-1H-pyrazol-4-yl]-2-(methylsulfanyl)pyrimidin (29% yield).

logP (pH2.7): 1.79
MS (ESI): 320 ([M+H]$^+$)
$^1$H-NMR (400 MHz, d$_6$-DMSO): δ=13.37 (bs, 1H), 8.34 (s, 1H), 8.21 (d, 1H), 7.07 (d, 1H), 6.91 (d, 1H), 6.73 (d, 1H), 4.05 (m, 1H), 1.16 (d, 6H) ppm

4-[3-(5-Fluoro-2-thienyl)-1H-pyrazol-4-yl]pyridine

To a solution of 4-methylpyridine (14.8 mmol) and ethyl 5-fluorothiophene-2-carboxylate (16.3 mmol, synthesis described in U.S. Pat. No. 6,096,901 A) in anhydrous THF (15 mL) at 0° C., under $N_2$ was added dropwise a solution of lithium bis(trimethylsilyl)amide (1 molar solution in hexanes, 29.6 mmol). The mixture was stirred 3 h at 5° C. Water and ethyl acetate were added, the layers were separated and the aqueous layer was extracted with ethyl acetate. The combined organic layers were washed with brine, dried with $MgSO_4$ and evaporated.

The residue was dissolved in 60 mL of N,N-dimethylformamide and N,N-dimethylformamide dimethylacetal (49.1 mmol) was added. The mixture was refluxed for 3 h. The solvent was evaporated. Water and ethyl acetate were added, the layers were separated and the aqueous layer was extracted with ethyl acetate. The combined organic layers were washed with brine, dried with $MgSO_4$ and evaporated.

The residue was dissolved in 100 mL of absolute ethanol and hydrazine hydrate (20.6 mmol) and triethylamine (20.6 mmol) were added. The resulting mixture was stirred at reflux for 3 h. The solvent was then evaporated and the residue was purified by column chromatography on silica gel (dichloromethane:methanol 1:0 to 20:1) to afford 2.52 g of 4-[3-(5-Fluoro-2-thienyl)-1H-pyrazol-4-yl]pyridine (70% yield).

logP (pH2.7): 0.57
MS (ESI): 246.1 ([M+H]$^+$)
$^1$H-NMR (400 MHz, $d_6$-DMSO): δ=13.34 (bs, 1H), 8.55 (d, 2H), 8.17 (s, 1H), 7.42 (d, 2H), 6.68 (m, 2H) ppm

4-[3-(3-Thieno[3,2-b]thiophen-2-yl)-1H-pyrazol-4-yl]pyridine

To a solution of 4-methylpyridine (1 eq, 22.6 mmol) and methyl 3-thieno[3,2-b]thiophene-2 carboxylate (1.12 eq, 25.3 mmol) in anhydrous tetrahydrofurane (20 mL) at 0° C., under $N_2$ was added dropwise a solution of lithium bis(trimethylsilyl)amide (1 molar solution in tetrahydrofurane, 2 eq, 45.1 mmol). The mixture was stirred 3 h at 5° C. and overnight at room temperature. The resulting precipitate was filtered, washed with diisopropylether and dried to afford a yellow solid (7.4 g).

This solid was dissolved in 150 mL of water and a 1M solution of hydrochloric acid was carefully added until pH reached 5. The resulting precipitated was filtered and dried to afford a green solid (5.3 g). This solid was dissolved in N,N-dimethylformamide dimethylacetal (30 mL). The mixture was refluxed for 1 h. The solvent was evaporated. The residue was purified by column chromatography on silica gel (ethyl acetate) to afford 3.8 g of a brown solid.

This solid was dissolved in 80 mL of absolute ethanol and hydrazine hydrate (17.2 mmol) and triethylamine (17.2 mmol) were added. The resulting mixture was stirred at reflux for 3 h. The solvent was then evaporated and the residue was suspended in 50 mL of ethanol. The resulting precipitate was filtered and dried to afford 2.8 g of 4-[3-(3-thieno[3,2-b]thiophen-2-yl)-1H-pyrazol-4-yl]pyridine (44% yield).

$^1$H-NMR (400 MHz, $d_6$-DMSO): δ=13.42 (bs, 1H), 8.56 (d, 2H), 8.23 (s, 1H), 7.67 (d, 1H), 7.45 (m, 3H), 7.37 (s, 1H) ppm

4-[3-(5-Bromo-2-thienyl)-1H-pyrazol-4-yl]pyridine

To a solution of 4-methylpyridine (1 eq, 100 mmol) and methyl 5-bromothiophene-2-carboxylate (1.2 eq, 120 mmol, synthesis described in WO2007/39112) in anhydrous THF (100 mL) at −10° C., under $N_2$ was added dropwise a solution of lithium bis(trimethylsilyl)amide (1 molar solution in tetrahydrofurane, 2 eq, 200 mmol). The mixture was stirred 3 h at 0° C. and overnight at room temperature. The resulting precipitate was filtered, washed with diisopropylether and dried overnight at 40° C. under vacuum to afford 29 g of a yellow solid. This solid was diluted with 1 L of water and HCl concentrate until pH=5/6. The precipitate was filtered washed with water and dried overnight at 40° C. under vacuum to afford 18.5 g of 1-(5-Chloro-2-thienyl)-2-(pyrimidin-4-yl)ethanone which was used in the next step without further purification.

The resulting solid was dissolved in 95 mL of N,N-dimethylformamide dimethylacetal. The mixture was refluxed for 1 h30. After filtration of the precipitate, the solvent was evaporated. Pentane was then added and the resulting precipitate was filtered and dried overnight at 40° C. to afford 15.9 g (47 mmol) of 3-(dimethylamino)-1-(5-chloro-2-thienyl)-2-(pyrimidin-4-yl)prop-2-en-1-one which was used in the next step without further purification.

The solid was dissolved in 300 mL of absolute ethanol and hydrazine hydrate (1.5 eq, 71 mmol) and triethylamine (1.5 eq, 71 mmol) were added. The resulting mixture was stirred at reflux for 1 h30. The solvent was then evaporated and the residue was diluted with water, filtered and dried to afford 13.9 g of a brown solid which was purified by column chromatography on silica gel (dichloromethane:methanol 1:0 to 20:1) to afford 8.6 g of 4-[3-(5-bromo-2-thienyl)-1H-pyrazol-4-yl]pyridine (28% yield).

logP (pH2.7): 0.94
MS (ESI): 306 ([M+H]$^+$)
$^1$H-NMR (400 MHz, $d_6$-DMSO): δ=13.42 (bs, 1H), 8.53 (d, 2H), 8.17 (s, 1H), 7.39 (d, 2H), 7.16 (d, 1H), 6.83 (s, 1H) ppm Preparation of Compounds of the Formula (I)

4-[1-Isopropyl-3-(5-chloro-2-thienyl)-1H-pyrazol-4-yl]pyridine and 4-[1-isopropyl-5-(5-chloro-2-thienyl)-1H-pyrazol-4-yl]pyridine To a solution of 4-[3-(5-chloro-2-thienyl)-1H-pyrazol-4-yl]pyridine (1.9 mmol) in 10 mL N,N-dimethylformamide were added 2-iodopropane (2.9 mmol) and cesium carbonate (2.1 mmol). The reaction mixture was stirred overnight at room temperature and the solvent was then evaporated. The residue was diluted with water and extracted three times with ethyl acetate. The combined organic extracts were dried over MgSO4 filtered and concentrated. The residue was purified by chromatography on silica gel (dichloromethane:ethyl acetate 20:1 to 5:1) to afford 0.37 g of 4-[1-isopropyl-3-(5-chloro-2-thienyl)-1H-pyrazol-4-yl]pyridine (61% yield) and 63 mg of 4-[1-isopropyl-5-(5-chloro-2-thienyl)-1H-pyrazol-4-yl]pyridine (10% yield).

4-[1-Isopropyl-3-(5-chloro-2-thienyl)-1H-pyrazol-4-yl]pyridine logP (pH2.7): 1.82
MS (ESI): 304.1 ([M+H]$^+$)
$^1$H-NMR (400 MHz, $d_6$-DMSO): δ=8.54 (d, 2H), 8.25 (s, 1H), 7.41 (d, 2H), 7.07 (d, 1H), 6.88 (d, 1H), 4.55 (m, 1H), 1.48 (d, 6H) ppm

4-[1-Isopropyl-5-(5-chloro-2-thienyl)-1H-pyrazol-4-yl]pyridine logP (pH2.7): 1.70
MS (ESI): 304.1 ([M+H]$^+$)
$^1$H-NMR (400 MHz, $d_6$-DMSO): δ=8.48 (d, 2H), 8.12 (s, 1H), 7.35 (d, 1H), 7.29 (d, 1H), 7.22 (d, 2H), 4.42 (m, 1H), 1.39 (d, 6H) ppm

4-[1-Cyclopropyl-3-(5-chloro-2-thienyl)-1H-pyrazol-4-yl]pyridine

To a suspension of 4-[3-(5-chloro-2-thienyl)-1H-pyrazol-4-yl]pyridine (0.57 mmol), cyclopropylboronic acid (1.14 mmol) and sodium carbonate (1.14 mmol) in 2 mL of dichloroethane, was added a suspension of copper acetate (0.57 mmol) and 2,2'-bipyridyn (0.57 mmol) in 4 mL of hot dichloroethane. The mixture was warmed up to 70° C. and stirred for 3 h under air. The resulting mixture was cooled to room temperature, and a saturated ammonium chloride solution was added, followed by water. The organic layer was separated, and the aqueous layer was extracted with dichloromethane. The combined organic layers were washed with brine, dried with $MgSO_4$, and concentrated under reduced pressure. The residue was purified by chromatography on basic alumina (heptane/ethyl acetate 20:1 to 10:1) to afford 43 mg (24% yield) of 4-[1-cyclopropyl-3-(5-chloro-2-thienyl)-1H-pyrazol-4-yl]pyridine.

logP (pH2.7): 1.62
MS (ESI): 302.1 ([M+H]$^+$)
$^1$H-NMR (400 MHz, $d_6$-DMSO): δ=8.56 (d, 2H), 8.23 (s, 1H), 7.39 (d, 2H), 7.06 (d, 1H), 6.86 (d, 1H), 3.80 (m, 1H), 1.13 (m, 2H), 1.02 (m, 2H) ppm

2-Chloro-4-[1-isobutyl-3-(5-chloro-2-thienyl)-1H-pyrazol-4-yl]pyridine and 2-chloro-4-[1-isobutyl-5-(5-chloro-2-thienyl)-1H-pyrazol-4-yl]pyridine To a solution of 2-chloro-4-[3-(5-chloro-2-thienyl)-1H-pyrazol-4-yl]pyridine (6.7 mmol) in 53 mL N,N-dimethylformamide were added bromoisobutyle (10.1 mmol) and cesium carbonate (7.4 mmol). The reaction mixture was stirred overnight at room temperature and the solvent was then evaporated. The residue was diluted with water and extracted three times with ethyl acetate. The combined organic extracts were dried over $MgSO_4$, filtered and concentrated. The residue was purified by chromatography on silica gel (heptane:ethyl acetate 1:0 to 1:1) to afford 2.21 g of a mixture of 2-chloro-4-[1-isobutyl-3-(5-chloro-2-thienyl)-1H-pyrazol-4-yl]pyridine and 2-chloro-4-[1-isobutyl-5-(5-chloro-2-thienyl)-1H-pyrazol-4-yl]pyridine (8:2; 88% yield). The mixture was used as such in the next step.

80 mg of this mixture was purified again by chromatography on silica gel to afford 50 mg of 2-chloro-4-[1-isobutyl-3-(5-chloro-2-thienyl)-1H-pyrazol-4-yl]pyridine and 6 mg of 2-chloro-4-[1-isobutyl-5-(5-chloro-2-thienyl)-1H-pyrazol-4-yl]pyridine.

2-Chloro-4-[1-isobutyl-3-(5-chloro-2-thienyl)-1H-pyrazol-4-yl]pyridine logP (pH2.7): 4.85
MS (ESI): 352.1 ([M+H]$^+$)
$^1$H-NMR (400 MHz, $CDCl_3$): δ=8.53 (d, 1H), 7.52 (s, 1H), 7.38 (d, 1H), 7.22 (d, 1H), 6.83 (m, 2H), 3.96 (d, 2H), 2.30 (m, 1H), 1.01 (d, 6H) ppm

2-Chloro-4-[1-isobutyl-5-(5-chloro-2-thienyl)-1H-pyrazol-4-yl]pyridine logP (pH2.7): 4.62
MS (ESI): 352.1 ([M+H]$^+$)
$^1$H-NMR (400 MHz, $CDCl_3$): δ=8.20 (d, 1H), 7.78 (s, 1H), 7.15 (d, 1H), 6.98 (m, 2H), 6.83 (d, 1H), 3.82 (d, 2H), 2.21 (m, 1H), 0.83 (d, 6H) ppm

4-[3-(5-Chloro-2-thienyl)-1-isopropyl-1H-pyrazol-4-yl]-2-(methylsulfanyl)pyrimidine To a solution of 4-[3-(5-chloro-2-thienyl)-1H-pyrazol-4-yl]-2-(methylsulfanyl)pyrimidin (1 eq, 16.2 mmol) in 120 mL N,N-dimethylformamide were added 2-iodopropane (1.5 eq, 24.3 mmol) and cesium carbonate (1.1 eq, 17.8 mmol). The reaction mixture was stirred at room temperature for 4 h and the solvent was then evaporated. The residue was diluted with water and dichloromethane. The layers were separated and the aqueous layer was extracted three times with dichloromethane. The combined organic extracts were dried over MgSO4 filtered and concentrated. The residue was purified by chromatography on silica gel (dichloromethane) to afford 4.2 g of 4-[3-(5-chloro-2-thienyl)-1-isopropyl-1H-pyrazol-4-yl]-2-(methylsulfanyl)pyrimidin (70% yield).

logP (pH2.7): 4.44
MS (ESI): 351 ([M+H]$^+$)
$^1$H-NMR (400 MHz, $CDCl_3$): δ=8.59 (s, 1H), 8.52 (d, 1H), 7.55 (d, 1H), 7.31 (d, 1H), 7.10 (d, 1H), 4.57 (m, 1H), 2.47 (s, 3H), 1.49 (d, 6H) ppm

4-[(3/5)-(5-Chloro-2-thienyl)-1-cyclopentyl-1H-pyrazol-4-yl]-2-(isopropylamino)pyrimidine To a solution of 4-[3-(5-chloro-2-thienyl)-1H-pyrazol-4-yl]-2-(isopropylamino)pyrimidine (1 eq, 0.22 mmol) in 3 mL N,N-dimethylformamide were added 2-iodocyclopentane (1.5 eq, 0.33 mmol) and cesium carbonate (1.5 eq, 0.33 mmol). The reaction mixture was heated at 40° C. for 3 h and stirred overnight at room temperature. Water and dichloromethane were added. The layers were separated and the aqueous layer was extracted three times with dichloromethane. The combined organic extracts were dried over MgSO4 filtered and purified by preparative HPLC (SunFire™ C18 OBD 5 μm 30×150, water/acetonitrile/formic acid) to afford 83 mg of 4-[(3/5)-(5-Chloro-2-thienyl)-1-ethyl-1H-pyrazol-4-yl]-2-(isopropylamino)pyrimidine (95% yield, mixture of isomers 90:10).

logP (pH2.7): 3.61 (3.33 minor isomer)
MS (ESI): 388 ([M+H]$^+$)

4-[1-sec-butyl-3-(5-fluoro-2-thienyl)-1H-pyrazol-4-yl]pyridine and 4-[1-secbutyl-5-(5-fluoro-2-thienyl)-1H-pyrazol-4-yl]pyridine To a solution of 4-[3-(5-fluoro-2-thienyl)-1H-pyrazol-4-yl]pyridine (0.61 mmol) in 3 mL N,N-dimethylformamide were added 2-bromobutane (0.91 mmol) and cesium carbonate (0.67 mmol). The reaction mixture was stirred overnight at room temperature and the solvent was then evaporated. The residue was diluted with water and extracted three times with ethyl ether. The combined organic extracts were dried over MgSO4 filtered and concentrated. The residue was purified by chromatography on silica gel (dichloromethane:ethyl acetate 20:1 to 5:1) to afford 112 mg of 4-[1-secbutyl-3-(5-fluoro-2-thienyl)-1H-pyrazol-4-yl]pyridine (60% yield) and 30 mg of 4-[1-secbutyl-5-(5-fluoro-2-thienyl)-1H-pyrazol-4-yl]pyridine (16% yield).

4-[1-sec-butyl-3-(5-fluoro-2-thienyl)-1H-pyrazol-4-yl]pyridine logP (pH2.7): 1.78
MS (ESI): 302.1 ([M+H]$^+$)
$^1$H-NMR (400 MHz, $d_6$-DMSO): δ=8.55 (d, 2H), 8.22 (s, 1H), 7.41 (d, 2H), 6.68 (m, 2H), 4.30 (m, 1H), 1.84 (m, 1H), 1.79 (m, 1H), 1.46 (d, 3H), 0.80 (t, 3H) ppm

4-[1-sec-butyl-5-(5-fluoro-2-thienyl)-1H-pyrazol-4-yl]pyridine logP (pH2.7): 1.84
MS (ESI): 302.1 ([M+H]$^+$)
$^1$H-NMR (400 MHz, d$_6$-DMSO): δ=8.46 (d, 2H), 8.14 (s, 1H), 7.26 (d, 1H), 7.07 (t, 1H), 6.96 (m, 1H), 4.16 (m, 1H), 1.89 (m, 1H), 1.73 (m, 1H), 1.39 (d, 3H), 0.67 (t, 3H) ppm

4-[1-Isopropyl-3-(5-fluoro-2-thienyl)-1H-pyrazol-4-yl]pyridine and 4-[1-isopropyl-5-(5-fluoro-2-thienyl)-1H-pyrazol-4-yl]pyridine To a solution of 4-[3-(5-fluoro-2-thienyl)-1H-pyrazol-4-yl]pyridine (0.61 mmol) in 3 mL N,N-dimethylformamide were added 2-iodopropane (0.91 mmol) and cesium carbonate (0.67 mmol). The reaction mixture was stirred overnight at room temperature and the solvent was then evaporated. The residue was diluted with water and extracted three times with ethyl ether. The combined organic extracts were dried over MgSO$_4$ filtered and concentrated. The residue was purified by chromatography on silica gel (dichloromethane:ethyl acetate 20:1 to 5:1) to afford 114 mg of 4-[1-isopropyl-3-(5-fluoro-2-thienyl)-1H-pyrazol-4-yl]pyridine (64% yield) and 4 mg of 4-[1-isopropyl-5-(5-fluoro-2-thienyl)-1H-pyrazol-4-yl]pyridine (3% yield).

4-[1-Isopropyl-3-(5-fluoro-2-thienyl)-1H-pyrazol-4-yl]pyridine logP (pH2.7): 1.53
MS (ESI): 288.1 ([M+H]$^+$)
$^1$H-NMR (400 MHz, d$_6$-DMSO): δ=8.54 (d, 2H), 8.23 (s, 1H), 7.41 (d, 2H), 6.69 (m, 2H), 4.53 (m, 1H), 1.48 (d, 6H) ppm

4-[1-Isopropyl-5-(5-fluoro-2-thienyl)-1H-pyrazol-4-yl]pyridine logP (pH2.7): 1.51
MS (ESI): 288.1 ([M+H]$^+$)
$^1$H-NMR (400 MHz, CDCl$_3$): δ=8.40 (d, 2H), 7.79 (s, 1H), 7.09 (d, 2H), 6.67 (t, 1H), 6.52 (m, 1H), 4.46 (m, 1H), 1.43 (d, 6H) ppm

4-[1-isobutyl-(3/5)-(3-thieno[3,2-b]thiophen-2-yl)-1H-pyrazol-4-yl]pyridine

To a solution of 4-[(3/5)-(3-thieno[3,2-b]thiophen-2-yl)-1H-pyrazol-4-yl]pyridine (1 eq, 0.3 mmol) in 5 mL N,N-dimethylformamide were added 2-iodopropane (3 eq, 0.9 mmol) and cesium carbonate (1.1 eq, 0.33 mmol). The reaction mixture was heated at 40° C. for 3 h and stirred at room temperature for 72 h. Water and dichloromethane were added. The layers were separated and the aqueous layer was extracted three times with dichloromethane. The combined organic extracts were dried over MgSO4 filtered and purified by preparative HPLC (SunFire C18 OBD 5 μm 30×150, water/acetonitrile/formic acid) to afford 24 mg of 4-[1-isobutyl-(3/5)-(3-thieno[3,2-b]thiophen-2-yl)-1H-pyrazol-4-yl]pyridine (23% yield, mixture of isomer 95:5).

logP (pH2.7): 2.07 (2.02 minor isomer)
MS (ESI): 340 ([M+H]$^+$)

4-[1-Isopropyl-(3/5)-(5-bromo-2-thienyl)-1H-pyrazol-4-yl]pyridine

To a solution of 4-[3-(5-bromo-2-thienyl)-1H-pyrazol-4-yl]pyridine (1 eq, 9.8 mmol) in 50 mL N,N-dimethylformamide were added 2-iodopropane (1.2 eq, 11.8 mmol) and cesium carbonate (1.5 eq, 14.7 mmol). The reaction mixture was stirred overnight at room temperature and the solvent was then evaporated. The residue was diluted with water and extracted three times with ethyl acetate. The combined organic extracts were dried over MgSO4 filtered and concentrated to afford 3.53 g of 4-[1-isopropyl-(3/5)-(5-bromo-2-thienyl)-1H-pyrazol-4-yl]pyridine (98% yield, mixture of isomer 82:18).

logP (pH2.7): 1.88 (1.76 minor isomer)
MS (ESI): 3481 ([M+H]$^+$)
$^1$H-NMR (400 MHz, d$_6$-DMSO): δ=8.55 (d, 2H$^{major}$), 8.25 (s, 1H$^{major}$), 8.11 (s, 1H$^{minor}$), 7.39 (d, 2H$^{major}$), 7.16 (d, 1H$^{major}$), 6.84 (d, 1H$^{major}$), 4.54 (m, 1H$^{major}$), 1.48 (d, 6H$^{major}$), 1.39 (s 6H$^{minor}$) ppm

4-[1-isobutyl-3-(5-bromo-2-thienyl)-1H-pyrazol-4-yl]pyridine

To a solution of 4-[3-(5-bromo-2-thienyl)-1H-pyrazol-4-yl]pyridine (1 eq, 8.8 mmol) in 50 mL N,N-dimethylformamide were added 1-bromo-2-methylpropane (1.5 eq, 13.2 mmol) and cesium carbonate (1.1 eq, 9.7 mmol). The reaction mixture was stirred overnight at room temperature and poured in 500 mL of water. The resulting precipitate was filtered and dried. The solid was then recrystallised in a mixture diisopropylether:dichloromethane to afford 1.81 g of 4-[1-isobutyl-3-(5-bromo-2-thienyl)-1H-pyrazol-4-yl]pyridine (53% yield).

logP (pH2.7): 2.04
MS (ESI): 362 ([M+H]$^+$)
$^1$H-NMR (400 MHz, d$_6$-DMSO): δ=8.55 (dd, 2H), 8.17 (s, 1H), 7.39 (dd, 2H), 7.16 (d, 1H), 6.84 (d, 1H), 3.96 (d, 2H), 2.17 (m, 1H), 0.90 (d, 6H) ppm Preparation of Intermediate of the Formula (Ia) where R$^3$ is an Halogen

4-[1-sec-butyl-3-(5-chloro-2-thienyl)-1H-pyrazol-4-yl]pyridine N oxide

To a solution of 4-[1-sec-butyl-3-(5-chloro-2-thienyl)-1H-pyrazol-4-yl]pyridine (1 eq, 7.2 mmol) in 23 mL of dichloromethane was added metachloroperbenzoic acid 70% (1.5 eq, 10.9 mmol) in small portion at 0° C. The reaction was then stirred at room temperature overnight. Sodium sulfite (1.5 eq, 10.9 mmol) was then added and the organic layer was then washed with a 2M solution of potassium carbonate, dried over MgSO4, filtered and concentrated to afford 2.25 g of 4-[1-sec-butyl-3-(5-chloro-2-thienyl)-1H-pyrazol-4-yl]pyridine N oxide (83% yield) which was used in the next step without further purification.

logP (pH2.7): 2.5
MS (ESI): 334.1 ([M+H]$^+$)

2-Chloro-4-[1-sec-butyl-3-(5-chloro-2-thienyl)-1H-pyrazol-4-yl]pyridine

4-[1-sec-butyl-3-(5-chloro-2-thienyl)-1H-pyrazol-4-yl]pyridine-N-oxide (6.1 mmol) was stirred in 20 mL of phosphorous oxychloride at 120° C. for 5 h. The solvent was then evaporated and the residue was treated with methanol and evaporated again. The residue was purified by chromatography on silica gel (hepthane:ethyl acetate 5:1 to 3:1) to afford 623 mg of 2-Chloro-4-[1-sec-butyl-3-(5-chloro-2-thienyl)-1H-pyrazol-4-yl]pyridine (29% yield).

logP (pH2.7): 4.90
MS (ESI): 352.1 ([M+H]$^+$)
$^1$H-NMR (400 MHz, d$_6$-DMSO): δ=8.37 (m, 2H), 7.54 (s, 1H), 7.42 (d, 1H), 7.10 (d, 1H), 6.94 (d, 1H), 4.30 (m, 1H), 1.84 (m, 1H), 1.79 (m, 1H), 1.46 (d, 3H), 0.80 (t, 3H) ppm

2-Bromo-4-[1-sec-butyl-3-(5-chloro-2-thienyl)-1H-pyrazol-4-yl]pyridine

To 2-Chloro-4-[1-sec-butyl-3-(5-chloro-2-thienyl)-1H-pyrazol-4-yl]pyridine (0.57 mmol) was added slowly 0.5 mL of a 33% solution hydrobromic acid in acetic acid. The resulting mixture was stirred in the microwave at 140° C. for 20 min. After cooling to room temperature, potassium carbonate (2 molar solution) was added and the aqueous layer was extracted with ethyl acetate. The organic layers were combined, dried over $MgSO_4$ and evaporated. The residue was purified by chromatography on silica gel (hepthane:ethyl acetate 5:1 to 2:1) to afford 178 mg of 2-bromo-4-[1-sec-butyl-3-(5-chloro-2-thienyl)-1H-pyrazol-4-yl]pyridine (79% yield).

logP (pH2.7): 5.03
MS (ESI): 396.0 ([M+H]$^+$)
$^1$H-NMR (400 MHz, $d_6$-DMSO): δ=8.37 (s, 1H), 8.34 (d, 1H), 7.67 (s, 1H), 7.44 (d, 1H), 7.10 (d, 1H), 6.94 (d, 1H), 4.30 (m, 1H), 1.86 (m, 1H), 1.77 (m, 1H), 1.46 (d, 3H), 0.80 (t, 3H) ppm

Preparation of Compound of the Formula (Ic)

2-Chloro-4-[3-(5-chloro-2-thienyl)-1H-pyrazol-4-yl]pyridine N oxyde

To a mixture of 2-chloro-4-[3-(5-chloro-2-thienyl)-1H-pyrazol-4-yl]pyridine (0.67 mmol) in 1 mL of dichloromethane, was added under argon metachloroperbenzoic acid (1.35 mmol). The mixture was then stirred for 24 h at room temperature. Sodium sulfite (0.4 mmol) was then added followed by $K_2CO_3$ 2 molar and dichloromethane. The layers were separated and the aqueous layer was extracted with dichloromethane. The organic layers were combined, dried over $MgSO_4$ and evaporated. The residue was purified by chromatography on silica gel (dichloromethane:methanol 1:0 to 9:1) to afford 43 mg 2-chloro-4-[3-(5-chloro-2-thienyl)-1H-pyrazol-4-yl]pyridine N oxide (19% yield).

logP (pH2.7): 1.57
MS (ESI): 312.0 ([M+H]$^+$)
$^1$H-NMR (400 MHz, $d_6$-DMSO): δ=13.44 (bs, 1H), 8.41 (d, 1H), 8.24 (s, 1H), 7.83 (d, 1H), 7.38 (dd, 1H), 7.09 (d, 1H), 6.98 (d, 1H) ppm

2-Chloro-4-[1-isobutyl-(3/5)-(5-chloro-2-thienyl)-1H-pyrazol-4-yl]pyridine N oxide To a mixture of metachloroperbenzoic acid (12.5 mmol) in 17 mL dichloromethane was slowly added at 0° C. a solution of 2-chloro-4-[1-isobutyl-(3/5)-(5-chloro-2-thienyl)-1H-pyrazol-4-yl]pyridine (6.2 mmol) in 2 mL dichloromethane. The mixture was stirred 24 h at room temperature. Sodium sulfite (12.5 mmol) was then added and the organic layer was then washed with a 2 molar solution of potassium carbonate, dried over $MgSO_4$, filtered and concentrated. The residue was purified by chromatography on silica gel (dichloromethane:methanol 9:1) to afford 1.2 g of a mixture of 2-chloro-4-[1-isobutyl-3-(5-chloro-2-thienyl)-1H-pyrazol-4-yl]pyridine-N-oxide and 2-chloro-4-[1-isobutyl-5-(5-chloro-2-thienyl)-1H-pyrazol-4-yl]pyridine-N-oxide (8:2; 52% yield). The mixture was used as such in the next step.

2-Chloro-4-[1-isobutyl-3-(5-chloro-2-thienyl)-1H-pyrazol-4-yl]pyridine-N-oxide logP (pH2.7): 2.82
MS (ESI): 368.0 ([M+H]$^+$)

2-Chloro-4-[1-isobutyl-5-(5-chloro-2-thienyl)-1H-pyrazol-4-yl]pyridine-N-oxyde logP (pH2.7): 3.06
MS (ESI): 368.0 ([M+H]$^+$)

2-Propargylamino-4-[1-isobutyl-(3/5)-(5-chloro-2-thienyl)-1H-pyrazol-4-yl]pyridine N oxide A mixture of 2-propargylamino-4-[1-isobutyl-(3/5)-(5-chloro-2-thienyl)-1H-pyrazol-4-yl]pyridine N oxide (0.54 mmol) in 1 mL propargylamine was irradiated at 140° C. for 30 min in the microwave. The solvent was then evaporated and the residue was purified by chromatography on silica gel (dichloromethane:methanol 1:0 to 97:3) to afford 113 mg of 2-propargylamino-4-[1-isobutyl-3-(5-chloro-2-thienyl)-1H-pyrazol-4-yl]pyridine-N-oxide (48% yield) and 21 mg 2-propargylamino-4-[1-isobutyl-5-(5-chloro-2-thienyl)-1H-pyrazol-4-yl]pyridine-N-oxide (8% yield).

2-Propargylamino-4-[1-isobutyl-5-(5-chloro-2-thienyl)-1H-pyrazol-4-yl]pyridine-N-oxyde logP (pH2.7): 2.92
MS (ESI): 387.1 ([M+H]$^+$)

2-Propargylamino-4-[1-isobutyl-3-(5-chloro-2-thienyl)-1H-pyrazol-4-yl]pyridine-N-oxyde logP (pH2.7): 2.70
MS (ESI): 387.1 ([M+H]$^+$)

2-Propargylamino-4-[1-isobutyl-3-(5-chloro-2-thienyl)-1H-pyrazol-4-yl]pyridine A mixture of 2-propargylamino-4-[1-isobutyl-3-(5-chloro-2-thienyl)-1H-pyrazol-4-yl]pyridine-N-oxide (1 eq, 0.23 mmol), phosphorous trichloride (3 eq, 0.69 mmol) in 1 mL dichloromethane was stirred 5 h30 at room temperature. A 30% solution of sodium hydroxide was the added dropwise. The mixture was the diluted with dichloromethane and water was added. The organic layer was separated, dried over MgSO4 and filtered. The solvent was then evaporated to afford 40 mg 2-propargylamino-4-[1-isobutyl-3-(5-chloro-2-thienyl)-1H-pyrazol-4-yl]pyridine (37% yield).

logP (pH2.7): 2.30
MS (ESI): 371.20 ([M+H]$^+$)
$^1$H-NMR (400 MHz, $d_6$-DMSO): δ=8.01 (m, 2H), 7.05 (d, 1H), 6.92 (m, 2H), 6.58 (m, 2H), 4.06 (bs, 2H), 3.95 (d, 2H), 3.05 (s, 1H), 2.19 (m, 1H), 0.90 (d, 6H) ppm

2-Benzylamino-4-[1-isobutyl-(3/5)-(5-chloro-2-thienyl)-1H-pyrazol-4-yl]pyridine N oxide A mixture of 2-chloro-4-[1-isobutyl-(3/5)-(5-chloro-2-thienyl)-1H-pyrazol-4-yl]pyridine N oxide (1.35 mmol) in 5 ml benzylamine was irradiated in the microwave at 130° C. for 30 min. The mixture was diluted with ethyl acetate and water was added. The organic layer was separated, washed with water, dried over MgSO$_4$ and filtered. The solvent was then evaporated and the residue was purified by chromatography on silica gel (dichloromethane:methanol 1:0 to 97:3) to afford 450 mg of 2-benzylamino-4-[1-isobutyl-(3/5)-(5-chloro-2-thienyl)-1H-pyrazol-4-yl]pyridine N oxide (70% yield) which was used in the next step without further purification. 140 mg of the mixture was purified again by chromatography on silica gel to afford 98 mg of 2-benzylamino-4-[1-isobutyl-3-(5-chloro-2-thienyl)-1H-pyrazol-4-yl]pyridine N oxide and 29 mg of 2-benzylamino-4-[1-isobutyl-5-(5-chloro-2-thienyl)-1H-pyrazol-4-yl]pyridine N oxide.

2-Benzylamino-4-[1-isobutyl-3-(5-chloro-2-thienyl)-1H-pyrazol-4-yl]pyridine N oxide logP (pH2.7): 3.65
MS (ESI): 439.1 ([M+H]$^+$)
$^1$H-NMR (400 MHz, d$_6$-DMSO): δ=8.12 (d, 1H), 8.01 (s, 1H), 7.82 (t, 1H), 7.34 (m, 2H), 7.26 (m, 3H), 6.92 (d, 1H), 6.80 (d, 1H), 6.68 (s, 1H), 6.62 (d, 1H), 4.48 (d, 2H), 3.95 (d, 2H), 2.14 (m, 1H), 0.90 (d, 6H) ppm 2-Benzylamino-4-[1-isobutyl-5-(5-chloro-2-thienyl)-1H-pyrazol-4-yl]pyridine N oxide logP (pH2.7): 3.48
MS (ESI): 439.1 ([M+H]$^+$)
$^1$H-NMR (400 MHz, d$_6$-DMSO): δ=8.04 (d, 1H), 7.96 (s, 1H), 7.78 (t, 1H), 7.40-7.20 (m, 6H), 7.12 (d, 1H), 6.570 (d, 1H), 6.43 (d, 1H), 4.32 (d, 2H), 3.79 (d, 2H), 2.08 (m, 1H), 0.78 (d, 6H) ppm 4-[3-(5-Chloro-2-thienyl)-1-isobutyl-1H-pyrazol-4-yl]-N-propylpyridin-2-amine 1-oxide A mixture of 2-chloro-4-[1-isobutyl-(3/5)-(5-chloro-2-thienyl)-1H-pyrazol-4-yl]pyridineN oxide (0.19 mmol) in 0.5 mL of propylamine was stirred in the microwave for 15 min at 140° C. The solvent was then evaporated and the residue was purified by chromatography on silica gel (dichloromethane:methanol 1:0 to 97:3) to afford 8 mg of 4-[3-(5-chloro-2-thienyl)-1-isobutyl-1H-pyrazol-4-yl]-N-propylpyridin-2-amine 1-oxide (12% yield).
logP (pH2.7): 1.90
MS (ESI): 335.0 ([M+H]$^+$)
$^1$H-NMR (400 MHz, CDCl$_3$): δ=7.97 (d, 1H), 7.63 (s, 1H), 6.85 (d, 1H), 6.78 (d, 1H), 6.50 (m, 2H), 3.06 (t, 2H), 1.58 (m, 2H), 0.92 (t, 3H) ppm 4-[3-(5-Chloro-2-thienyl)-1-isopropyl-1H-pyrazol-4-yl]-2-(methylsulfonyl)pyrimidine To a solution of 4-[3-(5-chloro-2-thienyl)-1-isopropyl-1H-pyrazol-4-yl]-2-(methylsulfanyl)pyrimidine (1 eq, 12 mmol) in 315 mL of dichloromethane was added meta chloroperbenzoic acid 77% (2 eq, 24 mmol). The mixture was stirred at room temperature for 72 h and then quenched with water. Sodium sulfite (2.1 eq, 25 mmol) was added and the layers were separated. The organic layer was then washed twice with a 2M solution of potassium carbonate, dried over MgSO4 filtered and concentrated to afford 4 g of 4-[3-(5-Chloro-2-thienyl)-1-isopropyl-1H-pyrazol-4-yl]-2-(methylsulfonyl)pyrimidine (65% yield) in a 8:2 mixture with the corresponding sulfoxide. The crude material was used in the next step without further purification.
logP (pH2.7): 3.15

MS (ESI): 383 ([M+H]$^+$)
$^1$H-NMR (400 MHz, d$_6$-DMSO): δ=8.97 (d, 1H$^{major}$), 8.81 (s, 1H$^{major}$), 8.76 (s, 1H$_{minor}$), 8.14 (d, 1H$_{minor}$), 7.98 (d, 1H$_{major}$), 7.93 (d, 1H$_{major}$), 7.82 (d, 1H$_{minor}$), 7.10 (d, 1H$_{major}$), 7.07 (d, 1H$_{minor}$), 4.60 (m, 1H$_{major}$), 3.38 (s, 3H$_{major}$), 1.51 (d, 6H$_{major}$) ppm N-Benzyl-4-[3-(5-chloro-2-thienyl)-1-isopropyl-1H-pyrazol-4-yl]pyrimidin-2-amine A mixture of 4-[3-(5-chloro-2-thienyl)-1-isopropyl-1H-pyrazol-4-yl]-2-(methylsulfonyl)pyrimidine (1 eq, 5.2 mmol) in 25 mL benzylamine was stirred overnight at room temperature. The solvent was evaporated and the residue was diluted in dichloromethane and washed three times with HCl 1M. The organic layer was then dried over MgSO4 and evaporated to afford 2.3 g of N-benzyl-4-[3-(5-chloro-2-thienyl)-1-isopropyl-1H-pyrazol-4-yl]pyrimidin-2-amine (96% yield).
logP (pH2.7): 3.81
MS (ESI): 410 ([M+H]+)

N-Isopropyl-4-[3-(5-chloro-2-thienyl)-1-isopropyl-1H-pyrazol-4-yl]pyrimidin-2-amine A mixture of 4-[3-(5-chloro-2-thienyl)-1-isopropyl-1H-pyrazol-4-yl]-2-(methylsulfonyl)pyrimidine (1 eq, 0.39 mmol) in 2 mL isopropylamine was stirred overnight at room temperature. The solvent was evaporated and the residue was purified by chromatography on silica gel (dichloromethane:acetonitrile 1:0 to 95:5) to afford 115 mg of N-isopropyl-4-[3-(4-fluorphenyl)-1-isopropyl-1H-pyrazol-4-yl]pyrimidin-2-amin (77% yield).
logP (pH2.7): 2.82
MS (ESI): 362 ([M+H]$^+$)
$^1$H-NMR (400 MHz, d$_6$-DMSO): δ=8.37 (s, 1H), 8.21 (d, 1H), 7.61 (bd, 1H), 7.07 (d, 1H), 6.91 (d, 1H), 6.71 (d, 1H), 4.55 (m, 1H), 4.08 (m, 1H), 1.48 (d, 6H), 1.15 (d, 6H) ppm 4-[(3/5)-(5-Chloro-2-thienyl)-1-isopropyl-1H-pyrazol-4-yl]-N-(diphenylmethylene)pyridin-2-amine To a mixture of 4-[3-(5-chloro-2-thienyl)-1-isopropyl-1H-pyrazol-4-yl]-2-chloropyridine (1 eq, 10.7 mmol), 1,1-diphenylmethanamine (1.1 eq, 11.8 mmol), sodium tert-butylate (2 eq, 21.5 mmol), tris(dibenzylidenacetone)dipalladium (0.05 eq, 0.5 mmol) and 2,2'-bis(diphenylphosphino)-1,1'-binaphthyl (0.065 eq, 0.7 mmol) was added under argon anhydrous toluene (45 mL). The resulting mixture was stirred at 70° C. for 3 h. The solvent was then evaporated and the residue was purified by chromatography on silica gel (heptane:ethyl acetate 10:1 to 2:1) to afford 4.41 g of 4-[(3/5)-(5-chloro-2-thienyl)-1-isopropyl-1H-pyrazol-4-yl]-N-(diphenylmethylene)pyridin-2-amine as a 7:1 mixture of isomers (72% yield).
logP (pH2.7): 4.46 (3.96)
MS (ESI): 483 ([M+H]+)
1H-NMR (400 MHz, d$_6$-DMSO): δ=8.19 (d, 1H), 9.10 (s, 1H), 7.69 (d, 2H), 7.58 (m, 1H), 7.52 (m, 2H), 7.17 (m, 2H), 7.34 (d, 1H), 6.93 (dd, 1H), 6.72 (d, 1H), 6.54 (d, 1H), 4?50 (m, 1H), 1.45 (d, 6H) ppm N-{4-[1-sec-butyl-3-(5-chloro-2-thienyl)-1H-pyrazol-4-yl]pyridin-2-yl}acetamide To a solution of 2-bromo-4-[1-sec-butyl-3-(5-chloro-2-thienyl)-1H-pyrazol-4-yl]pyridine (0.12 mmol) in 1.2 mL of dioxane were added under nitrogen acetamide (0.25 mmol), palladium acetate (0.006 mmol), cesium carbonate (0.37 mmol) and Xantphos (0.012 mmol). The resulting mixture was stirred for 4 h in a sealed tube at 160° C. The solvent was filtered, evaporated. The residue was purified by column chromatography on silica gel (dichloromethane:ethyl acetate 5:1 to 3:1) to afford 15.2 mg of N-{4-[1-sec-butyl-3-(5-chloro-2-thienyl)-1H-pyrazol-4-yl]pyridin-2-yl}acetamide (28% yield).

logP (pH2.7): 2.94
MS (ESI): 375.1 ([M+H]$^+$)
$^1$H-NMR (400 MHz, CDCl$_3$): δ=8.45 (bs, 1H), 8.19 (s, 1H), 8.093 (d, 1H), 7.53 (s, 1H), 7.00 (d, 1H), 6.80 (d, 1H), 6.73 (d, 1H), 4.19 (m, 1H), 2.14 (s, 3H), 1.77 (m, 2H), 0.82 (t, 3H) ppm Preparation of Compound of the Formula (Icd)

2-Amino-4-[1-isobutyl-(3/5)-(5-chloro-2-thienyl)-1H-pyrazol-4-yl]pyridine N oxide A mixture of 2-benzylamino-4-[1-isobutyl-(3/5)-(5-chloro-2-thienyl)-1H-pyrazol-4-yl]pyridine N oxide (1 eq, 0.78 mmol) in 1.2 mL sulfuric acid was stirred at room temperature overnight. Ice was then added and the mixture was basified using 30% sodium hydroxide. The aqueous layer was extracted with ethyl acetate. The combined organic extracts were dried over MgSO4, filtered and concentrated to afford 170 mg of 2-amino-4-[1-isobutyl-(3/5)-(5-chloro-2-thienyl)-1H-pyrazol-4-yl]pyridine N oxide (59% yield) as a mixture of both isomers (8:2)

2-Amino-4-[1-isobutyl-5-(5-chloro-2-thienyl)-1H-pyrazol-4-yl]pyridine N oxide logP (pH2.7): 2.21
MS (ESI): 349.1 ([M+H]$^+$)

2-Amino-4-[1-isobutyl-3-(5-chloro-2-thienyl)-1H-pyrazol-4-yl]pyridine N oxide logP (pH2.7): 2.39
MS (ESI): 349.1 ([M+H]$^+$)

2-Amino-4-[1-isobutyl-(3/5)-(5-chloro-2-thienyl)-1H-pyrazol-4-yl]pyridine

A mixture of 2-amino-4-[1-isobutyl-(3/5)-(5-chloro-2-thienyl)-1H-pyrazol-4-yl]pyridine-N-oxide (0.34 mmol) and phosphorous trichloride (1.03 mmol) in 2 mL dichloromethane was stirred overnight at room temperature. A 30% solution of sodium hydroxide was the added dropwise. The mixture was the diluted with dichloromethane and water was added. The organic layer was separated, dried over MgSO$_4$ and filtered. The solvent was then evaporated to afford 82 mg 2-amino-4-[1-isobutyl-(3/5)-(5-chloro-2-thienyl)-1H-pyrazol-4-yl]pyridine (68% yield) as a mixture 8:2 of both isomers.

logP (pH2.7): 1.93 (minor isomer); 2.04 (major isomer)
MS (ESI): 333.1 ([M+H]$^+$)
$^1$H-NMR (400 MHz, d$_6$-DMSO): δ=8.00 (s, 1H$^{major}$), 7.91 (d, 1H$^{major}$), 7.89 (s, 1H$^{minor}$), 7.78 (d, 1H$^{minor}$), 7.30 (d, 1H$^{minor}$), 7.18 (d, 1H$^{minor}$), 7.02 (d, 1H$^{major}$), 6.89 (d, 1H$^{major}$), 6.48 (m, 2H$^{major}$), 6.36 (s, 1H$_{minor}$), 6.34 (d, 1H$^{minor}$), 5.94 (s, 2H$^{major}$), 5.82 (s, 2H$^{minor}$), 3.97 (d, 2H$^{major}$), 3.87 (d, 2H$^{minor}$), 2.13 (m, 1H$^{major}$ and 1H$^{minor}$), 0.89 (d, 6H$^{major}$), 0.79 (d, 6H$^{minor}$) ppm 4-[3-(5-chloro-2-thienyl)-1-isopropyl-1H-pyrazol-4-yl]pyrimidin-2-amine A mixture of N-benzyl-4-[3-(5-chloro-2-thienyl)-1-isopropyl-1H-pyrazol-4-yl]pyrimidin-2-amine (1 eq, 3.1 mmol) in 11 mL sulfuric acid was stirred at room temperature overnight. Ice was added followed by water and a solution of NaOH 30% until pH=9. The aqueous layer was extracted with dichloromethane and the combined organic extracts were dried over MgSO4 filtered and concentrated to afford 0.55 g of 4-[3-(5-chloro-2-thienyl)-1-isopropyl-1H-pyrazol-4-yl]pyrimidin-2-amine (50% yield).

logP (pH2.7): 2.35
MS (ESI): 334 ([M+H]$^+$)
1H-NMR (400 MHz, d6-DMSO): δ=8.33 (s, 1H), 8.19 (d, 1H), 7.83 (d, 1H), 7.05 (d, 1H), 6.71 (d, 1H), 6.66 (bs, 2H), 3.96 (d, 2H), 2.17 (m, 1H), 0.88 (d, 6H) ppm 4-[(3/5)-(5-Chloro-2-thienyl)-1-isopropyl-1H-pyrazol-4-yl]pyridin-2-amine To a mixture of 4-[(3/5)-(5-chloro-2-thienyl)-1-isopropyl-1H-pyrazol-4-yl]-N-(diphenylmethylene)pyridin-2-amine (1 eq, 9.1 mmol) in 70 mL tetrahydrofurane was added dropwise 10 mL of a HCl 10% solution. The resulting mixture was diluted with a saturated solution of sodium carbonate and extracted three times with ethyl acetate. The combined organic extracts were dried over MgSO4 filtered and concentrated. The residue was purified by chromatography on silica gel (dichloromethane:methanol 20:1 to 10:1) to afford 2.8 g of 4-[(3/5)-(5-chloro-2-thienyl)-1-isopropyl-1H-pyrazol-4-yl]pyridin-2-amine (85% yield) as a 86:14 mixture of isomers.

logP (pH2.7): 1.78 (1.72 minor isomer)
MS (ESI): 319 ([M+H]+)
1H-NMR (400 MHz, d6-DMSO): δ=8.05 (s, 1H$^{major}$), 7.89 (d, 1H$^{major}$), 7.04 (d, 1H$^{major}$), 6.89 (d, 1H$^{major}$), 6.47 (m, 2H$^{major}$), 5.93 (bs, 2H$^{major}$), 4.52 (m, 1H$^{major}$), 1.47 (d, 6H$^{major}$), 1.38 (d, 6H$^{minor}$) ppm Preparation of Compound of the Formula (Ice)

N-{4-[3-(5-chloro-2-thienyl)-1-isobutyl-1H-pyrazol-4-yl]pyridin-2-yl}-N-(cyclopropylcarbonyl)cyclopropanecarboxamide A mixture of 2-amino-4-[1-isobutyl-(3/5)-(5-chloro-2-thienyl)-1H-pyrazol-4-yl]pyridine (0.081 mmol), triethylamine (0.089 mmol) and cyclopropanecarbonyl chloride (0.089 mmol) in 1 mL of dichloromethane was stirred at room temperature for 2.5 h. Water was then added and the aqueous layer was extracted with dichloromethane. The organic layers were combined, dried over MgSO$_4$, filtered and concentrated. The residue was purified by chromatography on silica gel (dichloromethane:acetonitrile 1:0 to 97:3) to afford 15 mg of N-{4-[3-(5-chloro-2-thienyl)-1-isobutyl-1H-pyrazol-4-yl]pyridin-2-yl}-N-(cyclopropylcarbonyl)cyclopropanecarboxamide (36% yield).

logP (pH2.7): 4.75
MS (ESI): 469.2 ([M+H]$^+$)
$^1$H-NMR (400 MHz, CDCl$_3$): δ=8.56 (d, 1H), 7.55 (s, 1H), 7.34 (d, 1H), 7.33 's, 1H), 6.86 (d, 1H), 6.80 (d, 1H), 3.94 (d, 2H), 2.29 (m, 1H), 2.05 (m, 2H), 1.17 (m, 4H), 0.97 (d, 6H), 0.91 (m, 4H) ppm N-{4-[3-(5-chloro-2-thienyl)-1-isobutyl-1H-pyrazol-4-yl]-1-oxidopyridin-2-yl}acetamide A mixture of 2-amino-4-[1-isobutyl-(3/5)-(5-chloro-2-thienyl)-1H-pyrazol-4-yl]-1-oxidopyridine (0.14 mmol), triethylamine (0.19 mmol) and acetyl chloride (0.16 mmol) in 1 mL of dichloromethane was stirred at room temperature for 2 h30. Water was then added and the aqueous layer was extracted with dichloromethane. The organic layers were combined, dried over MgSO$_4$, filtered and concentrated. The residue was purified by chromatography on silica gel (dichloromethane:methanol 1:0 to 95:5) to afford 22 mg of N-{4-[3-(5-chloro-2-thienyl)-1-isobutyl-1H-pyrazol-4-yl]-1-oxidopyridin-2-yl}acetamide (37% yield).

logP (pH2.7): 2.86
MS (ESI): 391.1 ([M+H]$^+$)
$^1$H-NMR (400 MHz, CDCl$_3$): δ=9.92 (bs, 1H), 8.41 (d, 1H), 8.06 (d, 1H), 7.49 (s, 1H), 6.94 (dd, 1H), 6.78 (d, 1H), 6.75 (d, 1H), 3.86 (d, 2H), 2.25 (s, 3H), 2.20 (m, 1H), 0.90 (d, 6H) ppm N-Acetyl-N-{4-[3-(5-chloro-2-thienyl)-1-isopropyl-1H-pyrazol-4-yl]pyridin-2-yl}acetamide To a solution of 4-[3-(5-chloro-2-thienyl)-1-isopropyl-1H-pyrazol-4-yl]pyridin-2-amine (1 eq, 0.31 mmol) and triethylamine (4 eq, 1.3 mmol) in 3 mL THF was added acetyl chloride (2.1 eq, 0.66 mmol). The mixture was then stirred at room temperature for 30 min. Acetyl chloride (1 eq, 0.31 mmol) and triethylamine (2 eq, 0.62 mmol) were then added and the mixture was stirred for 1 h. The solvent was evaporated and the residue was purified by chromatography on silica gel (heptane:ethyl acetate 5:1 to 1:2) to afford 114 mg of N-acetyl-N-{4-[3-(5-chloro-2-thienyl)-1-isopropyl-1H-pyrazol-4-yl]pyridin-2-yl}acetamide (81% yield).

logP (pH2.7): 3.33
MS (ESI): 403 ([M+H]$^+$)
1H-NMR (400 MHz, d6-DMSO): δ=8.55 (d, 1H), 8.32 (s, 1H), 7.50 (m, 2H), 7.06 (d, 1H), 6.89 (d, 1H), 4.55 (m, 1H), 2.19 (s, 6H), 1.48 (d, 6H) ppm N-{4-[(3/5)-(5-Chloro-2-thienyl)-1-isopropyl-1H-pyrazol-4-yl]pyridin-2-yl}acetamide To a solution of 4-[(3/5)-(5-chloro-2-thienyl)-1-isopropyl-1H-pyrazol-4-yl]pyridin-2-amine (1 eq, 0.3 mmol) and triethylamine (4 eq, 1.2 mmol) in 5 mL THF was added acetyl chloride (2 eq, 0.6 mmol). The mixture was then stirred at room temperature overnight and the solvent was evaporated. The residue was dissolved in 2.5 mL of a 7M solution of ammonia in methanol and stirred overnight at room temperature. The solvent was evaporated and the residue was partitioned between water and dichloromethane. The layers were separated and the aqueous layer was extracted two times with dichloromethane. The combined organic extracts were dried over MgSO4 filtered and concentrated. The residue was purified by preparative HPLC (SunFire C18 OBD 5 μm 30×150, water/acetonitrile/formic acid) to afford 42 mg of N-{4-[(3/5)-(5-chloro-2-thienyl)-1-isopropyl-1H-pyrazol-4-yl]pyridin-2-yl}acetamide (42% yield, mixture of isomers 90:10).

logP (pH2.7): 2.45 (2.22 minor isomer)
MS (ESI): 361 ([M+H]$^+$)

Ethyl {4-[3-(5-chloro-2-thienyl)-1-isopropyl-1H-pyrazol-4-yl]pyridin-2-yl}carbamate To a solution of 4-[(3/5)-(5-chloro-2-thienyl)-1-isopropyl-1H-pyrazol-4-yl]pyridin-2-amine (1 eq, 0.3 mmol) and triethylamine (4 eq, 1.2 mmol) in 5 mL THF was added ethylcarbamoyl chloride (2 eq, 0.6 mmol). The mixture was then stirred at room temperature overnight and the solvent was evaporated. The residue was dissolved in 2.5 mL of a 7M solution of ammonia in methanol and stirred overnight at room temperature. The solvent was evaporated and the residue was partitioned between water and dichloromethane. The layers were separated and the aqueous layer was extracted two times with dichloromethane. The combined organic extracts were dried over MgSO4 filtered and concentrated. The residue was purified by preparative HPLC (SunFire C18 OBD 5 μm 30×150, water/acetonitrile/formic acid) to afford 57 mg of ethyl {4-[3-(5-chloro-2-thienyl)-1-isopropyl-1H-pyrazol-4-yl]pyridin-2-yl}carbamate (49% yield, mixture of isomers 87:13).

logP (pH2.7): 3.55 (3.23 minor isomer)
MS (ESI): 391 ([M+H]$^+$)

N-{4-[3-(5-Chloro-2-thienyl)-1-isopropyl-1H-pyrazol-4-yl]pyridin-2-yl}thiophene-2-carboxamide To a solution of 4-[(3/5)-(5-chloro-2-thienyl)-1-isopropyl-1H-pyrazol-4-yl]pyridin-2-amine (1 eq, 0.3 mmol) and triethylamine (4 eq, 1.2 mmol) in 5 mL THF was added thiophene-2-carbonyl chloride (2 eq, 0.6 mmol). The mixture was then stirred at room temperature overnight and the solvent was evaporated. The residue was dissolved in 2.5 mL of a 7M solution of ammonia in methanol and stirred overnight at room temperature. The solvent was evaporated and the residue was partitioned between water and dichloromethane. The layers were separated and the aqueous layer was extracted two times with dichloromethane. The combined organic extracts were dried over MgSO4 filtered and concentrated. The residue was purified by preparative HPLC (SunFire C18 OBD 5 μm 30×150, water/acetonitrile/formic acid) to afford 63 mg of N-{4-[3-(5-chloro-2-thienyl)-1-isopropyl-1H-pyrazol-4-yl]pyridin-2-yl}thiophene-2-carboxamide (49% yield, mixture of isomers 63:11).

logP (pH2.7): 4.09 (3.83 minor isomer)
MS (ESI): 429 ([M+H]$^+$)

N-{4-[3-(5-Chloro-2-thienyl)-1-isopropyl-1H-pyrazol-4-yl]pyridin-2-yl}propanamide To a solution of 4-[(3/5)-(5-chloro-2-thienyl)-1-isopropyl-1H-pyrazol-4-yl]pyridin-2-amine (1 eq, 0.3 mmol) and triethylamine (4 eq, 1.2 mmol) in 5 mL THF was added propionyl chloride (2 eq, 0.6 mmol). The mixture was then stirred at room temperature overnight and the solvent was evaporated. The residue was dissolved in 2.5 mL of a 7M solution of ammonia in methanol and stirred overnight at room temperature. The solvent was evaporated and the residue was partitioned between water and dichloromethane. The layers were separated and the aqueous layer was extracted two times with dichloromethane. The combined organic extracts were dried over MgSO4 filtered and concentrated. The residue was purified by preparative HPLC (SunFire C18 OBD 5 μm 30×150, water/acetonitrile/formic acid) to afford 50 mg of N-{4-[3-(5-chloro-2-thienyl)-1-isopropyl-1H-pyrazol-4-yl]pyridin-2-yl}propanamide (43% yield, mixture of isomers 63:11).

logP (pH2.7): 2.88 (2.61 minor isomer)
MS (ESI): 375 ([M+H]$^+$)

N-{4-[3-(5-Chloro-2-thienyl)-1-isopropyl-1H-pyrazol-4-yl]pyridin-2-yl}cyclopropane carboxamide To a solution of 4-[(3/5)-(5-chloro-2-thienyl)-1-isopropyl-1H-pyrazol-4-yl]pyridin-2-amine (1 eq, 0.3 mmol) and triethylamine (4 eq, 1.2 mmol) in 5 mL THF was added cyclopropylcarbonyl chloride (2 eq, 0.6 mmol). The mixture was then stirred at room temperature overnight and the solvent was evaporated. The residue was dissolved in 2.5 mL of a 7M solution of ammonia in methanol and stirred overnight at room temperature. The solvent was evaporated and the residue was partitioned between water and dichloromethane. The layers were separated and the aqueous layer was extracted two times with dichloromethane. The combined organic extracts were dried over MgSO4 filtered and concentrated. The residue was purified by preparative HPLC (SunFire C18 OBD 5 μm 30×150, water/acetonitrile/formic acid) to afford 62 mg of N-{4-[3-(5-Chloro-2-thienyl)-1-isopropyl-1H-pyrazol-4-yl]pyridin-2-yl}cyclopropane carboxamide (53% yield, mixture of isomers 71:12).

logP (pH2.7): 3.02 (2.751 minor isomer)
MS (ESI): 387 ([M+H]$^+$)

N-Acetyl-N-{4-[3-(5-chloro-2-thienyl)-1-isopropyl-1H-pyrazol-4-yl]pyrimidin-2-yl}acetamide and N-{4-[3-(5-chloro-2-thienyl)-1-isopropyl-1H-pyrazol-4-yl]pyrimidin-2-yl}acetamide To a solution of 4-[3-(5-chloro-2-thienyl)-1-isopropyl-1H-pyrazol-4-yl]pyrimidin-2-amine (1 eq, 1.9 mmol) and triethylamine (4 eq, 7.5 mmol) in 10 mL THF was added acetyl chloride (2 eq, 3.8 mmol). The mixture was then stirred at room temperature overnight and the solvent was evaporated. The residue was purified by chromatography on silica gel (heptane:ethyl acetate) to afford 220 mg of N-acetyl-N-{4-[3-(5-chloro-2-thienyl)-1-isopropyl-1H-pyrazol-4-yl]pyrimidin-2-yl}acetamide (27% yield).

N-Acetyl-N-{4-[3-(5-chloro-2-thienyl)-1-isopropyl-1H-pyrazol-4-yl]pyrimidin-2-yl}acetamide logP (pH2.7): 3.33
MS (ESI): 404 ([M+H]$^+$)
1H-NMR (400 MHz, d6-DMSO): δ=8.89 (d, 1H), 8.72 (s, 1H), 7.78 (d, 1H), 7.55 (d, 1H), 7.08 (d, 1H), 4.59 (m, 1H), 2.23 (s, 6H), 1.49 (d, 6H) ppm This compound (150 mg) was dissolved in 6 mL of a 7M solution of ammonia in methanol and stirred for 3 h. The precipitate was filtered and dried to afford 63 mg of N-{4-[3-(5-chloro-2-thienyl)-1-isopropyl-1H-pyrazol-4-yl]pyrimidin-2-yl}acetamide (47% yield)

N-{4-[3-(5-Chloro-2-thienyl)-1-isopropyl-1H-pyrazol-4-yl]pyrimidin-2-yl}acetamide logP (pH2.7): 2.59
MS (ESI): 362 ([M+H]$^+$)
1H-NMR (400 MHz, d6-DMSO): δ=10.48 (bs, 1H), 8.58 (d, 1H), 8.49 (s, 1H), 7.91 (d, 1H), 7.31 (d, 1H), 7.04 (d, 1H), 4.57 (m, 1H), 2.18 (s, 3H), 1.48 (d, 6H) ppm Preparation of Compound of the Formula (Ig)

4-[1-sec-Butyl-3-(5-chloro-2-thienyl)-1H-pyrazol-4-yl]-2-(cyclopropylethynyl)pyridine To a solution of 2-bromo-4-[1-sec-butyl-3-(5-chloro-2-thienyl)-1H-pyrazol-4-yl]pyridine (0.18 mmol) in 2 mL of tetrahydrofurane was added cyclopropylacetylene (0.71 mmol), copper iodide (0.053 mmol), dichlorobis(triphenylphosphine)palladium (II) (0.053 mmol) and N,N-diisopropylethlamine (0.88 mmol). The resulting mixture was stirred in the microwave at 120° C. for 3 min. The solvent was then evaporated and the residue was purified by chromatography on silica gel (hepthane:ethyl acetate 5:1 to 2:1) to afford 35 mg of 4-[1-sec-butyl-3-(5-chloro-2-thienyl)-1H-pyrazol-4-yl]-2-(cyclopropylethynyl)pyridine (51% yield).

logP (pH2.7): 4.56
MS (ESI): 382.2 ([M+H]$^+$)
1H-NMR (400 MHz, d$_6$-DMSO): δ=8.45 (bs, 1H), 8.30 (s, 1H), 7.45 (d, 1H), 7.32 (s, 1H), 7.08 (d, 1H), 6.88 (d, 1H), 4.30 (m, 1H), 1.84 (m, 1H), 1.77 (m, 1H), 1.46 (d, 3H), 1.58 (m, 1H), 0.94 (m, 2H), 0.78 (m, 5H) ppm 2-Cyano-4-[1-sec-butyl-3-(5-chloro-2-thienyl)-1H-pyrazol-4-yl]pyridine To a solution of 2-chloro-4-[1-sec-butyl-3-(5-chloro-2-thienyl)-1H-pyrazol-4-yl]pyridine (0.28 mmol) in 1 mL of N,N-dimethylformamide was added zinc cyanide (0.14 mmol) and tetrakistriphenylphosphine palladium (O) (0.057 mmol). The resulting mixture was stirred in the microwave for 10 min at 120° C. After cooling to room temperature, the mixture was filtered and purified by preparative HPLC (column: Waters Sunfire C18, eluent:water/methanol/0.1% formic acid) to afford 56.7 mg of 2-cyano-4-[1-sec-butyl-3-(5-chloro-2-thienyl)-1H-pyrazol-4-yl]pyridine (55% yield).

logP (pH2.7): 4.41
MS (ESI): 343.1 ([M+H]$^+$)
1H-NMR (400 MHz, CDCl$_3$): δ=8.69 (d, 1H), 8.41 (s, 1H), 8.09 (s, 1H), 7.72 (d, 1H), 7.10 (d, 1H), 6.95 (d, 1H), 4.33 (m, 1H), 1.86 (m, 1H), 1.80 (m, 1H), 1.46 (d, 3H), 0.81 (t, 3H) ppm 4-[1-sec-Butyl-3-(5-chloro-2-thienyl)-1H-pyrazol-4-yl]-N-isopropylpyridine-2-carboxamide To a solution of 2-chloro-4-[1-sec-butyl-3-(5-chloro-2-thienyl)-1H-pyrazol-4-yl]pyridine (0.28 mmol) in 2 mL of N,N-dimethylformamide was added molybdenum hexacarbonyl (0.28 mmol), tetrakistriphenylphosphine palladium (0) (0.028 mmol), isopropylamine (0.85 mmol), and 1,8-diazabicyclo(5-4-0)undece-7-ene (0.85 mmol). The mixture was stirred at 80° C. overnight. The solvent was then evaporated and the residue was purified by chromatography on silica gel (hepthane:ethyl acetate 5:1 to 2:1) to afford 30 mg of 4-[1-sec-butyl-3-(5-chloro-2-thienyl)-1H-pyrazol-4-yl]-N-isopropylpyridine-2-carboxamide (26% yield).

logP (pH2.7): 4.82
MS (ESI): 403.2 ([M+H]$^+$)
1H-NMR (400 MHz, d$_6$-DMSO): δ=8.58 (d, 1H), 8.458 (d, 1H), 8.38 (s, 1H), 8.06 (d, 1H), 7.59 (dd, 1H), 7.08 (d, 1H), 6.89 (d, 1H), 4.32 (m, 1H), 4.13 (m, 1H), 1.88 (m, 1H), 1.80 (m, 1H), 1.48 (d, 3H), 1.20 (d, 6H), 0.80 (t, 3H) ppm Preparation of Compound of the Formula (Ih)

4-[5-Bromo-3-(5-chloro-2-thienyl)-1H-pyrazol-4-yl]pyridine

N-Bromosuccinimide (1 eq, 0.38 mmol) was added to a solution of 4-[3-(5-chloro-2-thienyl)-1H-pyrazol-4-yl]pyridine (1 eq, 0.38 mmol) in 2 mL of N,N-dimethylformamide. The mixture was then stirred at 80° C. for 2 h. Further N-Bromosuccinimide (0.3 eq, 0.12 mmol) was added and the mixture was stirred for one more hour. After cooling to room temperature, ethyl acetate was added and the organic layer was washed with water, dried over MgSO4, filtered and evaporated. The residue was suspended in diisopropylether and dichloropethane, filtered and dried in a vacuum oven at 50° C. to afford 0.16 g of 4-[5-bromo-3-(5-chloro-2-thienyl)-1H-pyrazol-4-yl]pyridine.

logP (pH2.7): 1.40
MS (ESI): 339.9 ([M+H]$^+$)
1H-NMR (400 MHz, d$_6$-DMSO): δ=14.03 (bs, 1H), 8.66 (d, 2H), 7.38 (d, 2H), 7.20 (bs, 2H) ppm

4-[5-Bromo-3-(5-chloro-2-thienyl)-1-(4-methoxybenzyl)-1H-pyrazol-4-yl]pyridine and 4-[3-bromo-5-(5-chloro-2-thienyl)-1-(4-methoxybenzyl)-1H-pyrazol-4-yl]pyridine To a solution of 4-[5-bromo-3-(5-chloro-2-thienyl)-1H-pyrazol-4-yl]pyridine (14.7 mmol) in 80 mL of N,N-dimethylformamide was added slowly at 0° C. sodium hydride (16.1 mmol). The mixture was stirred 30 min at room temperature prior to dropwise addition of 4-methoxybenzyl chloride (16.1 mmol). The mixture was then stirred for further 5 hours. The mixture was then poured on water and ethyl acetate was added. The aqueous layer was extracted with ethyl acetate and the combined organic extracts were washed with brine, dried over MgSO$_4$, filtered and concentrated. The residue was purified by chromatography on silica gel (heptane/ethyl acetate 4:1 to 1:1) to afford 5.7 g of 4-[5-bromo-3-(5-chloro-2-thienyl)-1-(4-methoxybenzyl)-1H-pyrazol-4-yl]pyridine and 4-[3-bromo-5-(5-chloro-2-thienyl)-1-(4-methoxybenzyl)-1H-pyrazol-4-yl]pyridine (80% yield) as a mixture 2:1 which was used as such in the following step.

Minor Isomer:
logP (pH2.7): 3.0
MS (ESI): 460.0 ([M+H]$^+$)

Major Isomer:
logP (pH2.7): 3.53
MS (ESI): 460.0 ([M+H]$^+$)

4-[5-(5-Chloro-2-thienyl)-3-methyl-1H-pyrazol-4-yl]pyridine

To a mixture of sodium hydrogen carbonate (2.0 mmol) and PdCl$_2$dppf:CH$_2$Cl$_2$ 1:1 (0.03 mmol) under argon, was added a degassed solution of 4-[5-bromo-3-(5-chloro-2-thienyl)-1-(4-methoxybenzyl)-1H-pyrazol-4-yl]pyridine and 4-[3-bromo-5-(5-chloro-2-thienyl)-1-(4-methoxybenzyl)-1H-pyrazol-4-yl]pyridine (mixture of isomers 2:1, 0.65 mmol) in 10.5 mL dimethoxyethane and 3 mL of water. Trimethylboroxin (50% solution in THF, 1.3 mmol) was then added and the mixture was stirred at 90° C. for 3 h. After cooling to room temperature, water and ethyl acetate were added. The aqueous layer was extracted with ethyl acetate and the combined organic extracts were washed with brine, dried over MgSO$_4$, filtered and concentrated. The residue was dissolved in 3 mL of trifluoroacetic acid and stirred at 65° C. for 2 h. Water and ethyl acetate were added. And the aqueous layer was extracted with ethyl acetate. The combined organic extracts were washed with a saturated solution of sodium hydrogen carbonate, dried over MgSO$_4$, filtered and concentrated. The residue was purified by chromatography on silica gel (dichloromethane/methanol 20:1 to 10:1) to afford 57 mg of 4-[5-(5-chloro-2-thienyl)-3-methyl-1H-pyrazol-4-yl]pyridine (30% yield).

logP (pH2.7): 1.07
MS (ESI): 276.1 ([M+H]$^+$)
$^1$H-NMR (400 MHz, d$_6$-DMSO): δ=13.09 (s, 1H), 8.59 (d, 2H), 7.32 (m, 2H), 6.98 (d, 1H), 6.62 (d, 1H), 2.21 (s, 3H) ppm

3-(5-Chloro-2-thienyl)-4-(pyridin-4-yl)-1H-pyrazole-5-carbonitrile

To 4-[5-bromo-3-(5-chloro-2-thienyl)-1-(4-methoxybenzyl)-1H-pyrazol-4-yl]pyridine and 4-[3-bromo-5-(5-chloro-2-thienyl)-1-(4-methoxybenzyl)-1H-pyrazol-4-yl]pyridine (mixture of isomers 2:1, 1 eq, 0.435 mmol) in 1 mL of N,N-dimethylformamide, were added zinc cyanide (0.65 mmol) and Tetrakis(triphenylphosphine)palladium(0) (0.09 mmol). The mixture was stirred for 5 mins at 160° C. in the microwave. After cooling to room temperature, the reaction mixture was diluted with water and ethyl acetate was added. The aqueous layer was extracted with ethyl acetate and the combined organic extracts were dried over MgSO$_4$, filtered and concentrated. The residue was dissolved in 1 mL of trifluoroacetic acid and stirred at 65° C. for 2 h. Water and ethyl acetate were added. And the aqueous layer was extracted with ethyl acetate. The combined organic extracts were washed with a saturated solution of sodium hydrogen carbonate, dried over MgSO$_4$, filtered and concentrated. The residue was purified by chromatography on silica gel (dichloromethane/methanol 20:1 to 10:1) to afford 19 mg of 3-(5-chloro-2-thienyl)-4-(pyridin-4-yl)-1H-pyrazole-5-carbonitrile (15% yield).

logP (pH2.7): 1.53
MS (ESI): 287.1 ([M+H]$^+$)
$^1$H-NMR (400 MHz, d$_6$-DMSO): δ=8.69 (d, 2H), 7.45 (d, 2H), 7.20 (bs, 2H) ppm

4-[3-(5-Chloro-2-thienyl)-5-cyclopropyl-1H-pyrazol-4-yl]pyridine

To a mixture of sodium hydrogen carbonate (2.0 mmol) and PdCl$_2$dppf:CH$_2$Cl$_2$ 1:1 (0.05 eq, 0.03 mmol) under argon, was added a degassed solution of 4-[5-bromo-3-(5-chloro-2-thienyl)-1-(4-methoxybenzyl)-1H-pyrazol-4-yl]pyridine and 4-[3-bromo-5-(5-chloro-2-thienyl)-1-(4-methoxybenzyl)-1H-pyrazol-4-yl]pyridine (mixture of isomers 2:1, 0.65 mmol) in 10.5 mL dimethoxyethane and 3 mL of water. Cyclopropylboronic acid (1.3 mmol) was then added and the mixture was stirred at 90° C. for 3 h. Further cyclopropylboronic acid was then added (1.3 mmol), and the mixture was stirred overnight at 65° C. After cooling to room temperature, water and ethyl acetate were added. The aqueous layer was extracted with ethyl acetate and the combined organic extracts were washed with brine, dried over MgSO$_4$, filtered and concentrated. The residue was dissolved in 3 mL of trifluoroacetic acid and stirred at 65° C. for 2 h. Water and ethyl acetate were added. And the aqueous layer was extracted with ethyl acetate. The combined organic extracts were washed with a saturated solution of sodium hydrogen carbonate, dried over MgSO$_4$, filtered and concentrated. The residue was purified by preparative HPLC (Column WATERS Sunfire C18.5 μm 50*150 mm, eluent:water/methanol/0.1% formic acid) to afford 49 mg of 4-[3-(5-chloro-2-thienyl)-5-cyclopropyl-1H-pyrazol-4-yl]pyridine (25% yield).

logP (pH2.7): 1.29
MS (ESI): 302.1 ([M+H]$^+$)

4-[5-Cyclopropyl-1-isopropyl-3-(5-chloro-2-thienyl)-1H-pyrazol-4-yl]pyridine and 4-[3-cyclopropyl-1-isopropyl-5-(5-chloro-2-thienyl)-1H-pyrazol-4-yl]pyridine To a solution of 4-[5-cyclopropyl-3-(5-chloro-2-thienyl)-1H-pyrazol-4-yl]pyridine (1 eq, 0.32 mmol) in 2 mL N,N-dimethylformamide were added 2-iodopropane (1.5 eq, 0.48 mmol) and cesium carbonate (2 eq, 0.64 mmol). The reaction mixture was stirred overnight at room temperature, diluted with water and extracted three times with ethyl acetate. The combined organic extracts were dried over MgSO4, filtered and concentrated. The residue was purified by chromatography on silica gel (heptane:ethyl acetate 5:1 to 1:1) to afford 28.8 mg of 4-[5-cyclopropyl-1-isopropyl-3-(5-chloro-2-thienyl)-1H-pyrazol-4-yl]pyridine (26% yield) and 30.2 mg of 4-[3-cyclopropyl-1-isopropyl-5-(5-chloro-2-thienyl)-1H-pyrazol-4-yl]pyridine (28% yield).

4-[5-Cyclopropyl-1-isopropyl-3-(5-chloro-2-thienyl)-1H-pyrazol-4-yl]pyridine logP (pH2.7): 2.44
MS (ESI): 344 ([M+H]$^+$)
1H-NMR (400 MHz, CDCl$_3$): δ=8.59 (d, 2H), 7.26 (dd, 2H), 6.70 (d, 1H), 6.57 (d, 1H), 4.90 (m, 1H), 1.73 (m, 1H), 1.55 (d, 6H), 0.88 (m, 2H), 0.30 (m, 2H) ppm

4-[3-Cyclopropyl-1-isopropyl-5-(5-chloro-2-thienyl)-1H-pyrazol-4-yl]pyridine logP (pH2.7): 2.44
MS (ESI): 344 ([M+H]$^+$)
1H-NMR (400 MHz, CDCl$_3$): δ=8.52 (d, 2H), 7.24 (dd, 2H), 6.93 (d, 1H), 6.77 (d, 1H), 4.48 (m, 1H), 1.85 (m, 1H), 1.45 (d, 6H), 0.98 (m, 2H), 0.92 (m, 2H) ppm

4-[3-(5-Chloro-2-thienyl)-5-(prop-1-yn-1-yl)-1H-pyrazol-4-yl]pyridine and 4-[(3/5)-(5-chloro-2-thienyl)-1-(4-methoxybenzyl)-5-(prop-1-yn-1-yl)-1H-pyrazol-4-yl]pyridine Tetrakis(triphenylphosphine)palladium (0) (0.055 eq, 0.036 mmol) was added to a degassed solution of 4-[5-bromo-1-(4-methoxybenzyl)-(3/5)-(5-chloro-2-thienyl)-1H-pyrazol-4-yl]pyridine (1 eq, 0.65 mmol) and tributyl-1-propynylstannane (1.1 eq, 0.72 mmol) in 8 mL of acetonitrile. The mixture was then heated in the microwave at 150° C. for 30 min. The mixture was filtered and evaporated. The residue was purified by chromatography on silica gel (heptane:ethyl acetate 3:1 to 1:1) to afford 170 mg of 4-[(3/5)-(5-chloro-2-thienyl)-1-(4-methoxybenzyl)-5-(prop-1-yn-1-yl)-1H-pyrazol-4-yl]pyridine (62% yield, mixture of isomers 64:22).

4-[(3/5)-(5-chloro-2-thienyl)-1-(4-methoxybenzyl)-5-(prop-1-yn-1-yl)-1H-pyrazol-4-yl]pyridine logP (pH2.7): 3.11 (2.61 minor isomer)
MS (ESI): 420 ([M+H]$^+$)
148 mg of 4-[(3/5)-(5-chloro-2-thienyl)-1-(4-methoxybenzyl)-5-(prop-1-yn-1-yl)-1H-pyrazol-4-yl]pyridine were dissolved in 1.5 mL of a 1:1 mixture of trifluoroacetic acid:dichloromethane and the mixture was heated at 120° C. in the microwave for 10 min. The solvent was then evaporated to afford 97 mg of 4-[3-(5-chloro-2-thienyl)-5-(prop-1-yn-1-yl)-1H-pyrazol-4-yl]pyridine (100% yield).

4-[3-(5-Chloro-2-thienyl)-5-(prop-1-yn-1-yl)-1H-pyrazol-4-yl]pyridine logP (pH2.7): 1.44
MS (ESI): 300 ([M+H]$^+$)
1H-NMR (400 MHz, d6-DMSO): δ=13.90 (bs, 1H), 8.64 (d, 2H), 7.45 (d, 2H), 7.02 (d, 1H), 6.75 (d, 1H), 2.07 (s, 3H) ppm

4-[(3/5)-(5-Chloro-2-thienyl)-1-isopropyl-5-(prop-1-yn-1-yl)-1H-pyrazol-4-yl]pyridine To a solution of 4-[3-(5-chloro-2-thienyl)-5-(prop-1-yn-1-yl)-1H-pyrazol-4-yl]pyridine (1 eq, 0.24 mmol) in 2 mL N,N-dimethylformamide were added 2-iodopropane (1.5 eq, 0.35 mmol) and cesium carbonate (2 eq, 0.47 mmol). The reaction mixture was stirred overnight at room temperature, diluted with water and extracted three times with ethyl acetate. The combined organic extracts were dried over MgSO4, filtered and concentrated to afford 46.6 mg of 4-[(3/5)-(5-chloro-2-thienyl)-1-isopropyl-5-(prop-1-yn-1-yl)-1H-pyrazol-4-yl]pyridine (52% yield, mixture of isomers 86:14).

logP (pH2.7): 2.78 (2.21 minor isomer)
MS (ESI): 342 ([M+H]$^+$)
1H-NMR (400 MHz, d6-DMSO): δ=8.63 (d, M$^{major}$), 7.42 (d, M$^{major}$), 7.02 (d, 1H$^{major}$), 6.74 (d, 1H$^{major}$), 4.82 (m, 1H$^{major}$), 2.13 (s, 3H$^{major}$), 2.09 (s, 3H$^{minor}$), 1.47 (d, 6H$^{minor}$), 1.39 (d, 6H$^{major}$) ppm

4-[5-Bromo-1-secbutyl-(3/5)-(5-chloro-2-thienyl)-1H-pyrazol-4-yl]pyridine

To a solution of 4-[5-bromo-3-(5-chloro-2-thienyl)-1H-pyrazol-4-yl]pyridine (1 eq, 5.9 mmol) in 40 mL N,N-dimethylformamide were added 2-iodobutane (1.5 eq, 8.8 mmol) and cesium carbonate (1.1 eq, 6.5 mmol). The reaction mixture was stirred overnight at room temperature and the solvent was then evaporated. The residue was diluted with water and extracted three times with diethyl ether. The combined organic extracts were dried over MgSO4, filtered and concentrated. The residue was purified by chromatography on silica gel (heptane:ethyl acetate 10:1 to 2:1) to afford 2.23 g of 4-[5-bromo-1-secbutyl-(3/5)-(5-chloro-2-thienyl)-1H-pyrazol-4-yl]pyridine (91% yield, mixture of isomers 77:23).

logP (pH2.7): 3.69
MS (ESI): 397 ([M+H]$^+$)
1H-NMR (400 MHz, d6-DMSO): δ=8.67 (d, 2H$^{major}$), 8.55 (d, 2H$^{minor}$), 7.41 (d, 2H$^{major}$), 7.28 (d, 2H$^{minor}$), 7.00 (d, 1H$^{major}$), 6.65 (d, 1H$^{major}$), 4.55 (m, 1H$^{major}$), 4.22 (m, 1H$^{minor}$), 1.91 (m, 1H H$^{major}$), 1.82 (m, 1H$^{major}$), 1.46 (d, 3H$^{major}$), 1.42 (d, 3H$^{minor}$), 0.81 (t, 3H$^{major}$), 0.69 (t, 3H$^{minor}$) ppm

4-[5-Chloro-1-secbutyl-3-(5-chloro-2-thienyl)-1H-pyrazol-4-yl]pyridine

To a solution of 4-[5-bromo-1-secbutyl-(3/5)-(5-chloro-2-thienyl)-1H-pyrazol-4-yl]pyridine (1 eq, 0.38 mmol) in 5 mL of anhydrous tetrahydrofurane was added nbutyllithium (1.1 eq, 0.42 mmol, 1.6 M solution) dropwise under nitrogen at −78° C. The resulting mixture was stirred for 30 min at −78° C. A solution of hexachloroethane (2 eq, 0.76 mmol) in 0.5 mL of tetrahydrofurane was the added dropwise and the reaction was allowed to warm up to room temperature and stirred 2 h. The mixture was diluted with water and extracted three times with ethyl acetater. The combined organic extracts were washed with brine, dried over MgSO4, filtered and concentrated. The residue was purified by chromatography on silica gel (heptane:ethyl acetate 10:1 to 2:1) to afford 66 mg of 4-[5-chloro-1-secbutyl-3-(5-chloro-2-thienyl)-1H-pyrazol-4-yl]pyridine (45% yield).

logP (pH2.7): 3.44
MS (ESI): 353 ([M+H]$^+$)
1H-NMR (400 MHz, d6-DMSO): δ=8.57 (dd, 2H), 7.43 (dd, 2H), 7.01 (d, 1H), 6.70 (d, 1H), 4.54 (m, 1H), 1.90 (m, 1H), 1.83 (m, 1H), 1.47 (d, 3H), 0.81 (t, 3H) ppm

4-[3-(5-Chloro-2-thienyl)-5-methylsulfanyl-1-secbutyl-1H-pyrazol-4-yl]pyridine To a solution of 4-[5-bromo-1-secbutyl-(3/5)-(5-chloro-2-thienyl)-1H-pyrazol-4-yl]pyridine (1 eq, 0.38 mmol) in 5 mL of anhydrous tetrahydrofurane was added nbutyllithium (1.1 eq, 0.42 mmol, 1.6 M solution) dropwise under nitrogen at −78° C. The resulting mixture was stirred for 30 min at −78° C. Dimethyldisulfide (1.2 eq, 0.3 mmol) was then added dropwise and the reaction was allowed to warm up to room temperature and stirred 2 h. The mixture was diluted with a 1 M solution of sodium thiosulfate and extracted three times with ethyl acetater. The combined organic extracts were washed with brine, dried over MgSO4, filtered and concentrated. The residue was purified by chromatography on silica gel (heptane:ethyl acetate 10:1 to 2:1) to afford 58 mg of 4-[3-(5-chloro-2-thienyl)-5-methylsulfanyl-1-secbutyl-1H-pyrazol-4-yl]pyridine (60% yield).

logP (pH2.7): 3.35
MS (ESI): 364 ([M+H]$^+$)
1H-NMR (400 MHz, d6-DMSO): δ=8.66 (d, 2H), 7.43 (d, 2H), 6.98 (d, 1H), 6.61 (d, 1H), 4.82 (m, 1H), 2.21 (s, MH), 1.91 (m, 1H), 1.83 (m, 1H), 1.46 (d, 3H), 0.79 (t, 3H) ppm

4-[3-(5-Chloro-2-thienyl)-5-fluoro-1-secbutyl-1H-pyrazol-4-yl]pyridine

To a solution of 4-[5-bromo-1-secbutyl-(3/5)-(5-chloro-2-thienyl)-1H-pyrazol-4-yl]pyridine (1 eq, 0.38 mmol) in 5 mL of anhydrous tetrahydrofurane was added nbutyllithium (1.1 eq, 0.42 mmol, 1.6 M solution) dropwise under nitrogen at −78° C. The resulting mixture was stirred for 30 min at −78° C. A solution of N-fluorobenzenesulfonimide (2 eq, 0.76 mmol) in 0.5 mL of tetrahydrofurane was the added dropwise and the reaction was allowed to warm up to room temperature and stirred 2 h. The mixture was diluted with water and extracted three times with ethyl acetater. The combined organic extracts were washed with brine, dried over MgSO4, filtered and concentrated. The residue was purified by chromatography on silica gel (heptane:ethyl acetate 10:1 to 2:1) to afford 31 mg of 4-[3-(5-chloro-2-thienyl)-5-fluoro-1-secbutyl-1H-pyrazol-4-yl]pyridine (20% yield).

logP (pH2.7): 2.61
MS (ESI): 336 ([M+H]$^+$)
1H-NMR (400 MHz, d6-DMSO): δ=8.63 (d, 2H), 7.40 (d, 2H), 7.07 (d, 1H), 6.85 (d, 1H), 4.39 (m, 1H), 1.83 (m, 2H), 1.'-(d, 3H), 0.82 (t, 3H) ppm Preparation of Starting Materials of the Formula (Im)

4-[1-Isobutyl-3-(5-cyano-2-thienyl)-1H-pyrazol-4-yl]pyridine

To a solution of 4-[1-isobutyl-3-(5-bromo-2-thienyl)-1H-pyrazol-4-yl]pyridine (1 eq, 0.28 mmol) in N,N-dimethylformamide (1 mL) were added zinc cyanide (0.5 eq, 0.14 mmol) and tetrakis(triphenylphosphine)palladium (0) (0.2 eq, 0.055 mmol). The resulting mixture was stirred at 120° C. in the microwave for 10 min. Water was added and the aqueous layer was extracted three times with ethyl acetate. The combined organic extracts were washed with brine, dried over MgSO4, filtered and concentrated. The residue was purified by preparative HPLC (SunFire 50×150 mm 5 µm, eau/methanol/formic acid) to afford 44 mg of 4-[1-isobutyl-3-(5-cyano-2-thienyl)-1H-pyrazol-4-yl]pyridine (49% yield).

logP (pH2.7): 1.74
MS (ESI): 309 ([M+H]$^+$)
1H-NMR (400 MHz, d6-DMSO): δ=8.62 (d, 2H), 8.27 (s, 1H), 7.89 (d, 1H), 7.47 (d, 2H), 7.12 (d, 1H), 4.02 (d, 2H), 2.18 (m, 1H), 0.91 (d, 6H) ppm

4-[1-Isopropyl-(3/5)-(2-thienyl)-1H-pyrazol-4-yl]pyridine

To a solution of 4-[1-isopropyl-(3/5)-(5-bromo-2-thienyl)-1H-pyrazol-4-yl]pyridine (1 eq, 0.57 mmol) in 6 mL of anhydrous tetrahydrofurane was added dropwise at 0° C. isopropylmagnesium chloride (1.1 eq, 0.63 mmol, 2M solution). The mixture was stirred for 1 h at 0° C. and water was then added dropwise. The mixture was extracted three times with ethyl acetate. The combined organic extracts were washed with brine, dried over MgSO4, filtered and concentrated. The residue was purified by chromatography on silica gel (heptane:ethyl acetate 10:1 to 1:1) to afford 89 mg of 4-[1-isopropyl-(3/5)-(2-thienyl)-1H-pyrazol-4-yl]pyridine (55% yield, mixture of isomers 74:26).

logP (pH2.7): 1.27 (1.33 minor isomer)
MS (ESI): 270 ([M+H]$^+$)
1H-NMR (400 MHz, d6-DMSO): δ=8.52 (dd, 2H$^{major}$), 8.25 (s, 1H$^{major}$), 8.11 (s, 1H$_{minor}$), 7.54 (m, 1H$^{major}$), 7.36 (dd, 2H$^{major}$), 7.17 (dd, 2H$^{minor}$), 7.05 (m, 2H$^{major}$), 4.55 (m, 1H$^{major}$), 1.49 (d, 6H$^{major}$), 1.39 (d, 6H$^{minor}$) ppm

4-[1-Isopropyl-3-(5-methylsulfanyl-2-thienyl)-1H-pyrazol-4-yl]pyridine and 4-[1-isopropyl-5-(5-methylsulfanyl-2-thienyl)-1H-pyrazol-4-yl]pyridine To a solution of 4-[1-isopropyl-(3/5)-(5-bromo-2-thienyl)-1H-pyrazol-4-yl]pyridine (1 eq, 0.43 mmol) in 5 mL of anhydrous tetrahydrofurane was added dropwise at −78° C. butyllithium (1.1 eq, 0.47 mmol, 1.6M solution). The mixture was stirred for 30 min at −78° C. and dimethyldisulfide (1.2 eq, 0.52 mmol) was then added dropwise. The solution was allowed to warm up to room temperature and stirred for 2 h. The mixture was diluted with a 1M solution of sodium thiosulfate and extracted three times with ethyl acetate. The combined organic extracts were washed with brine, dried over MgSO4, filtered and concentrated. The residue was purified by chromatography on silica gel (heptane:ethyl acetate 10:1 to 2:1) to afford 60 mg of 4-[1-isopropyl-3-(5-methylsulfanyl-2-thienyl)-1H-pyrazol-4-yl]pyridine (42% yield) and 19 mg of 4-[1-isopropyl-5-(5-methylsulfanyl-2-thienyl)-1H-pyrazol-4-yl]pyridine (13% yield).

4-[1-Isopropyl-3-(5-methylsulfanyl-2-thienyl)-1H-pyrazol-4-yl]pyridine logP (pH2.7): 1.79
MS (ESI): 316 ([M+H]$^+$)
1H-NMR (400 MHz, d6-DMSO): δ=8.54 (d, 2H), 8.23 (s, 1H), 7.39 (d, 2H), 7.02 (d, 1H), 6.89 (d, 1H), 4.54 (m, 1H), 1.48 (d, 6H) ppm

4-[1-Isopropyl-5-(5-methylsulfanyl-2-thienyl)-1H-pyrazol-4-yl]pyridine logP (pH2.7): 1.78
MS (ESI): 316 ([M+H]$^+$)
1H-NMR (400 MHz, d6-DMSO): δ=8.44 (d, 2H), 8.10 (s, 1H), 7.24 (m, 4H), 4.42 (m, 1H), 1.39 (d, 6H) ppm Preparation of Starting Materials of the Formula (X)

3-(5-Chloro-2-thienyl)-1H-pyrazole

A mixture of 5-chlorothiophene-2-methylketone (1 eq, 0.032 mol), N,N-dimethylformamide dimethyl acetal (4.8 g) and hydrazine hydrate (2 eq, 0.064 mol) was heated at 80° C. for 6 h. After completion of reaction monitoring by TLC, the reaction mixture was poured in to ice water and extracted with ethyl acetate. The combined organic layers were washed with water and brine and dried over anhydrous Na2SO4, filtered and evaporated to afford 5.3 g of 3-(5-chloro-2-thienyl)-1H-pyrazole (89% yield).

1H NMR (CDCl$_3$, 400 MHz): δ=10.2-10.8 (1H, br), 7.5 (1H, d), 7.0 (1H, d), 6.8 (1H, d), 6.4 (1H, d).

3-(Dimethylamino)-1-(2-thienyl)prop-2-en-1-one

A mixture of 2-acetylthiophene (198 mmol) and N,N-dimethylformamide dimethyl acetal (297 mmol) was refluxed overnight and then allowed to cool to room temperature. The reaction mixture was concentrated under reduced pressure and dried in vacuo to afford 36 g (100% yield) of 3-(dimethylamino)-1-(2-thienyl)prop-2-en-1-one which was used in the next step without further purification.

logP (pH2.7): 1.33
MS (ESI): 182.1 ([M+H]$^+$)
1H-NMR (400 MHz, d$_6$-DMSO): δ=7.76 (d, 1H), 7.73 (d, 1H), 7.66 (d, 1H), 7.14 (m, 1H), 5.76 (d, 1H), 3.13 (s, 3H), 2.90 (s, 3H) ppm

3-(2-Thienyl)-1H-pyrazole

A mixture of 3-(dimethylamino)-1-(2-thienyl)prop-2-en-1-one (193 mmol) and hydrazine hydrate (396 mmol) in 50 mL ethanol was refluxed for 18 h and then allowed to cool to room temperature. The solvent was evaporated under reduced pressure and the residue was partitioned between ethyl acetate and water. The organic phase was successively washed with saturated aqueous ammonium chloride solution, saturated aqueous sodium bicarbonate solution and brine, dried over MgSO$_4$, filtered and concentrated. The residue was recrystallized (dichloromethane/cyclohexane) to afford 26.0 g 3-(2-thienyl)-1H-pyrazole (90% yield).

logP (pH2.7): 1.30
MS (ESI): 151.0 ([M+H]$^+$)
$^1$H-NMR (400 MHz, d$_6$-DMSO): δ=12.81 (bs, 1H), 7.76 (bs, 1H), 7.38 (m, 2H), 7.07 (m, 1H), 6.59 (bs, 1H) ppm

1-(4-Chloro-2-thienyl)-3-(dimethylamino)prop-2-en-1-one

A mixture of 1-(4-chloro-2-thienyl)ethanone (32.1 mmol) and N,N-dimethylformamide dimethyl acetal (112.2 mmol) was refluxed for 3 h and then allowed to cool to room temperature whereupon crystallization occurred. The reaction mixture was stored in a freezer at −18° C. for 2 h. The supernatant liquid was decanted, the crystals were dried in vacuum to afford 5.3 g (77% yield) of 1-(4-chloro-2-thienyl)-3-(dimethylamino)prop-2-en-1-one which was used in the next step without further purification.

logP (pH2.7): 1.86
MS (ESI): 216.0 ([M+H]$^+$)
$^1$H-NMR (400 MHz, d$_6$-DMSO): δ=7.81 (d, 1H), 7.74 (d, 1H), 7.69 (d, 1H), 5.80 (d, 1H), 3.15 (s, 3H), 2.92 (s, 3H) ppm

3-(4-Chloro-2-thienyl)-1H-pyrazole

A mixture of 1-(4-chloro-2-thienyl)-3-(dimethylamino) prop-2-en-1-one (24.6 mmol) and hydrazine hydrate (49.2 mmol) in 25 mL ethanol was refluxed for 15 h and then allowed to cool to room temperature. The solvent was evaporated under reduced pressure and dried in vacuum to afford 4.5 g (99% yield) 3-(4-chloro-2-thienyl)-1H-pyrazole which was used in the next step without further purification.

logP (pH2.7): 1.91
MS (ESI): 185.0 ([M+H]$^+$)
$^1$H-NMR (400 MHz, d$_6$-DMSO): δ=12.95 (bs, 1H), 7.79 (bs, 1H), 7.46 (bs, 1H), 7.38 (d, 1H), 6.67 (bs, 1H) ppm

1-(4-Bromo-2-thienyl)-3-(dimethylamino)prop-2-en-1-one

A mixture of 1-(4-bromo-2-thienyl)ethanone (48.8 mmol) and N,N-dimethylformamide dimethyl acetal (73.1 mmol) was refluxed overnight and then allowed to cool to room temperature. The reaction mixture was concentrated under reduced pressure and dried in vacuo to afford 12.6 g (99% yield) of 1-(4-bromo-2-thienyl)-3-(dimethylamino)prop-2-en-1-one which was used in the next step without further purification.

logP (pH2.7): 1.94
MS (ESI): 259.9 ([M+H]$^+$)
$^1$H-NMR (400 MHz, d$_6$-DMSO): δ=7.84 (m, 2H), 7.69 (d, 1H), 5.82 (d, 1H), 3.15 (s, 3H), 2.92 (s, 3H) ppm

3-(4-Bromo-2-thienyl)-1H-pyrazole

A mixture of 1-(4-bromo-2-thienyl)-3-(dimethylamino) prop-2-en-1-one (43.5 mmol) and hydrazine hydrate (86.9 mmol) in 50 mL ethanol was refluxed for 18 h and then allowed to cool to room temperature. The solvent was evaporated under reduced pressure and the residue was partitioned between ethyl acetate and water. The organic phase was successively washed with saturated aqueous ammonium chloride solution, saturated aqueous sodium bicarbonate solution and brine, dried over MgSO$_4$, filtered and concentrated to afford 9.74 g (94% yield) 3-(4-bromo-2-thienyl)-1H-pyrazole which was used in the next step without further purification.

logP (pH2.7): 1.99
MS (ESI): 228.9 ([M+H]$^+$)
$^1$H-NMR (400 MHz, d$_6$-DMSO): δ=12.94 (m, 1H), 7.78 (bs, 1H), 7.53 (d, 1H), 7.41 (d, 1H), 6.67 (m, 1H) ppm

3-(Dimethylamino)-1-(4-methyl-2-thienyl)prop-2-en-1-one

A mixture of 1-(4-methyl-2-thienyl)ethanone (70.8 mmol) and N,N-dimethylformamide dimethyl acetal (105.1 mmol) was refluxed overnight and then allowed to cool to room temperature. The reaction mixture was concentrated under reduced pressure and dried in vacuo to afford 13.8 g (100% yield) of 3-(dimethylamino)-1-(4-methyl-2-thienyl)prop-2-en-1-one which was used in the next step without further purification.

logP (pH2.7): 1.65
MS (ESI): 196.1 ([M+H]$^+$)
$^1$H-NMR (400 MHz, d$_6$-DMSO): δ=7.63 (d, 1H), 7.58 (d, 1H), 7.30 (d, 1H), 5.72 (d, 1H), 3.12 (s, 3H), 2.89 (s, 3H), 2.22 (s, 3H) ppm

3-(4-Methyl-2-thienyl)-1H-pyrazole

A mixture of 3-(dimethylamino)-1-(4-methyl-2-thienyl) prop-2-en-1-one (72 mmol) and hydrazine hydrate (144 mmol) in 80 mL ethanol was refluxed for 18 h and then allowed to cool to room temperature. The solvent was evaporated under reduced pressure and the residue was partitioned between ethyl acetate and water. The organic phase was successively washed with saturated aqueous ammonium chloride solution, saturated aqueous sodium bicarbonate solution and brine, dried over MgSO$_4$, filtered and concentrated to afford 11.58 g (98% yield) 3-(4-methyl-2-thienyl)-1H-pyrazole which was used in the next step without further purification.

logP (pH2.7): 1.72
MS (ESI): 165.0 ([M+H]$^+$)
$^1$H-NMR (400 MHz, d$_6$-DMSO): δ=12.94 (bs, 1H), 7.75 (d, 1H), 7.19 (d, 1H), 6.97 (s, 1H), 6.55 (m, 1H), 2.21 (s, 3H) ppm 1-(4,5-Dibromo-2-thienyl)-3-(dimethylamino)prop-2-en-1-one A mixture of 1-(4,5-dibromo-2-thienyl)ethanone (9.7 mmol) and N,N-dimethylformamide dimethyl acetal (44.8 mmol) was refluxed for 3 h and then allowed to cool to room temperature. The reaction mixture was concentrated under reduced pressure and dried in vacuo to afford 3.24 g (94% yield) of 1-(4,5-dibromo-2-thienyl)-3-(dimethylamino)prop-2-en-1-one which was used in the next step without further purification.

logP (pH2.7): 2.68
MS (ESI): 337.9 ([M+H]$^+$)
$^1$H-NMR (400 MHz, d$_6$-DMSO): δ=7.87 (s, 1H), 7.70 (d, 1H), 5.80 (d, 1H), 3.15 (s, 3H), 2.93 (s, 3H) ppm 3-(4,5-Dibromo-2-thienyl)-1H-pyrazole A mixture of 1-(4,5-dibromo-2-thienyl)-3-(dimethylamino)prop-2-en-1-one (9.6 mmol) and hydrazine hydrate (14.3 mmol) in 22 mL ethanol was refluxed for 15 h and then allowed to cool to room temperature. The solvent was evaporated under reduced pressure and dried in vacuum to afford 2.94 g (100% yield) 3-(4,5-dibromo-2-thienyl)-1H-pyrazole which was used in the next step without further purification.

logP (pH2.7): 2.74
MS (ESI): 306.9 ([M+H]$^+$)
$^1$H-NMR (400 MHz, d$_6$-DMSO): δ=13.02 (bs, 1H), 7.80 (bs, 1H), 7.44 (s, 1H), 6.70 (bs, 1H) ppm 3-(5-Chloro-2-thienyl)-5-methyl-1H-pyrazole A mixture of 2-acetyl-5-chlorothiophene (156 mmol) and N,N-dimethylacetamide dimethyl acetal (171 mmol) in 200 mL N,N-dimethylacetamide was heated to 90° C. for 4 h and then allowed to cool to room temperature. The reaction mixture was concentrated under reduced pressure and the residue was dissolved in 200 mL absolute ethanol. Hydrazine monohydrate (234 mmol) was added and the mixture was stirred at room temperature for 24 h. The solvent was removed under vacuum. Petroleum ether was added and the precipitate formed was filtered then washed to afford 22 g (71% yield) 3-(5-chloro-2-thienyl)-5-methyl-1H-pyrazole.
$^1$H-NMR (400 MHz, CDCl$_3$): δ=7.03 (d, 1H), 6.85 (d, 1H), 6.22 (s, 1H), 2.34 (s, 3H) ppm Preparation of Starting Materials of the Formula (IX)

3-(5-Chloro-2-thienyl)-1-isobutyl-1H-pyrazole

To a solution of 3-(5-chloro-2-thienyl)-1H-pyrazole (1 eq, 0.023 mol) and cesium carbonate (1.2 eq, 0.028 mol) in dry N,N-dimethylformamide (50 mL) was added 1-bromo-2-methylpropane (1.1 eq, 0.025 mol) slowly and the mixture was stirred at room temperature for 3 h. After completion of the reaction monitored by TLC, the reaction mixture was poured into ice cold water and extracted with ethyl acetate. The combined organic layers were washed with water, brine, dried over anhydrous Na2SO4, filtered and evaporated. The crude compound was purified by column-chromatography to afford 4.3 g of 3-(5-chloro-2-thienyl)-1-isobutyl-1H-pyrazole (76% yield).

1H NMR (CDCl$_3$, 400 MHz): δ=7.3 (1H, d), 7.0 (1H, d), 6.8 (1H, d), 6.3 (1H, d), 3.8 (2H, d), 2.2 (1H, m), 0.9 (6H, d).

1-Isopropyl-3-(2-thienyl)-1H-pyrazole and 1-isopropyl-5-(2-thienyl)-1H-pyrazole 3-(2-thienyl)-1H-pyrazole (31.6 mmol) was dissolved in 150 mL dry N,N-dimethylformamide and cooled to 0° C. under argon atmosphere. Sodium hydride (37.9 mmol, 60% dispersion in mineral oil) was added in portions at 0° C. The reaction mixture was allowed to warm to room temperature and was stirred at room temperature for 15 min. After cooling to 0° C. again, isopropyl iodide (47.4 mmol) was added dropwise at 0° C. The reaction mixture was stirred at room temperature for 14 h. Isopropyl iodide (5.9 mmol) was added and the mixture was stirred at room temperature overnight. Water and MTBE were added to the reaction mixture. The phases were separated and the aqueous phase was extracted with MTBE. The combined organic extracts were successively washed with water and brine, dried over MgSO$_4$, filtered and concentrated. The residue was purified by chromatography on silica gel (toluene:ethyl acetate 100:0 to 0:100) to afford 5.40 g 1-isopropyl-3-(2-thienyl)-1H-pyrazole (88% yield) and 50 mg of 1-isopropyl-5-(2-thienyl)-1H-pyrazole (1% yield).

1-Isopropyl-3-(2-thienyl)-1H-pyrazole logP (pH2.7): 2.66
MS (ESI): 193.0 ([M+H]$^+$)
$^1$H-NMR (400 MHz, d$_6$-DMSO): δ=7.78 (d, 1H), 7.40 (dd, 1H), 7.34 (dd, 1H), 7.06 (dd, 1H), 6.55 (d, 1H), 4.49 (sept, 1H), 1.43 (t, 6H) ppm 1-Isopropyl-5-(2-thienyl)-1H-pyrazole logP (pH2.7): 2.69
MS (ESI): 193.1 ([M+H]$^+$)
$^1$H-NMR (400 MHz, d$_6$-DMSO): δ=7.71 (dd, 1H), 7.51 (d, 1H), 7.27 (dd, 1H), 7.20 (m, 1H), 6.39 (d, 1H), 4.70 (sept, 1H), 1.40 (t, 6H) ppm 1-Ethyl-3-(2-thienyl)-1H-pyrazole and 1-ethyl-5-(2-thienyl)-1H-pyrazole 3-(2-thienyl)-1H-pyrazole (31.6 mmol) was dissolved in 150 mL N,N-dimethylformamide and cooled to 0° C. under argon atmosphere. Sodium hydride (37.9 mmol, 60% dispersion in mineral oil) was added in portions at 0° C. The reaction mixture was allowed to warm to room temperature and was stirred at room temperature for 15 min. After cooling to 0° C. again, ethyl iodide (47.4 mmol) was added dropwise at 0° C. The reaction mixture was stirred at room temperature for 14 h. Water and MTBE were added to the reaction mixture. The phases were separated and the aqueous phase was extracted with MTBE. The combined organic extracts were successively washed with water and brine, dried over MgSO$_4$, filtered and concentrated. The residue was purified by chromatography on silica gel (toluene:ethyl acetate 100:0 to 0:100) to afford 2.50 g 1-ethyl-3-(2-thienyl)-1H-pyrazole (44% yield) and 50 mg of 1-ethyl-5-(2-thienyl)-1H-pyrazole (1% yield).

1-Ethyl-3-(2-thienyl)-1H-pyrazole logP (pH2.7): 2.14
MS (ESI): 179.1 ([M+H]$^+$)
$^1$H-NMR (400 MHz, d$_6$-DMSO): δ=7.75 (d, 1H), 7.41 (dd, 1H), 7.34 (dd, 1H), 7.06 (dd, 1H), 6.55 (d, 1H), 4.13 (q, 2H), 1.38 (t, 3H) ppm

1-Ethyl-5-(2-thienyl)-1H-pyrazole logP (pH2.7): 2.18
MS (ESI): 179.1 ([M+H]$^+$)
$^1$H-NMR (400 MHz, d$_6$-DMSO): δ=7.70 (dd, 1H), 7.48 (d, 1H), 7.32 (m, 1H), 7.20 (m, 1H), 6.44 (d, 1H), 4.24 (q, 2H), 1.33 (t, 3H) ppm

1-Propyl-3-(2-thienyl)-1H-pyrazole and 1-propyl-5-(2-thienyl)-1H-pyrazole 3-(2-thienyl)-1H-pyrazole (33.3 mmol) was dissolved in 100 mL dry N,N-dimethylformamide and cooled to 0° C. under argon atmosphere. Sodium hydride (39.9 mmol, 60% dispersion in mineral oil) was added in portions at 0° C. The reaction mixture was allowed to warm to room temperature and was stirred at room temperature for 15 min. After cooling to 0° C. again, propyl iodide (49.9 mmol) was added dropwise at 0° C. The reaction mixture was stirred at room temperature for 14 h. Water and MTBE were added to the reaction mixture. The phases were separated and the aqueous phase was extracted with MTBE. The combined organic extracts were successively washed with water and brine, dried over MgSO$_4$, filtered and concentrated. 6.50 g of a mixture of 1-propyl-3-(2-thienyl)-1H-pyrazole and 1-propyl-5-(2-thienyl)-1H-pyrazole (81:19; 99% yield) were obtained. 1.0 g of this mixture was used as such in the next step. 5.50 g of the mixture were purified again by chromatography on silica gel (toluene:ethyl acetate 100:0 to 0:100) to afford 4.35 g of 1-propyl-3-(2-thienyl)-1H-pyrazole and 1-propyl-5-(2-thienyl)-1H-pyrazole (67% yield) and 0.40 g of 1-propyl-5-(2-thienyl)-1H-pyrazole (6% yield).

1-Propyl-3-(2-thienyl)-1H-pyrazole logP (pH2.7): 2.58
MS (ESI): 193.1 ([M+H]$^+$)
$^1$H-NMR (400 MHz, d$_6$-DMSO): δ=7.74 (d, 1H), 7.41 (dd, 1H), 7.35 (dd, 1H), 7.06 (dd, 1H), 6.55 (d, 1H), 4.05 (t, 2H), 1.79 (m, 2H), 0.85 (t, 3H) ppm

1-Propyl-5-(2-thienyl)-1H-pyrazole logP (pH2.7): 2.64
MS (ESI): 193.1 ([M+H]$^+$)
$^1$H-NMR (400 MHz, d$_6$-DMSO): δ=7.70 (dd, 1H), 7.48 (d, 1H), 7.31 (m, 1H), 7.19 (m, 1H), 6.44 (d, 1H), 4.16 (t, 2H), 1.74 (m, 2H), 0.81 (t, 3H) ppm

1-sec-Butyl-3-(2-thienyl)-1H-pyrazole and 1-sec-Butyl-5-(2-thienyl)-1H-pyrazole 3-(2-thienyl)-1H-pyrazole (23.2 mmol) was dissolved in 100 mL dry N,N-dimethylformamide and cooled to 0° C. under argon atmosphere. Sodium hydride (28.0 mmol, 60% dispersion in mineral oil) was added in portions at 0° C. The reaction mixture was allowed to warm to room temperature and was stirred at room temperature for 15 min. After cooling to 0° C. again, 2-iodobutane (35.0 mmol) was added dropwise at 0° C. The reaction mixture was stirred at room temperature for 14 h. Water and MTBE were added to the reaction mixture. The phases were separated and the aqueous phase was extracted with MTBE. The combined organic extracts were successively washed with water and brine, dried over MgSO$_4$, filtered and concentrated. 650 mg of a mixture of 1-sec-butyl-3-(2-thienyl)-1H-pyrazole and 1-sec-butyl-5-(2-thienyl)-1H-pyrazole (82:18; 13% yield) were obtained.

1-sec-Butyl-3-(2-thienyl)-1H-pyrazole logP (pH2.7): 3.10
MS (ESI): 207.1 ([M+H]$^+$)
$^1$H-NMR (400 MHz, d$_6$-DMSO): δ=7.77 (d, 1H), 7.40 (dd, 1H), 7.35 (m, 1H), 7.06 (m, 1H), 6.55 (d, 1H), 4.25 (m, 1H), 1.76 (m, 2H), 1.41 (d, 3H), 0.74 (t, 3H) ppm

1-sec-Butyl-5-(2-thienyl)-1H-pyrazole logP (pH2.7): 2.97
MS (ESI): 207.1 ([M+H]$^+$)
$^1$H-NMR (400 MHz, d$_6$-DMSO): δ=7.72 (dd, 1H), 7.54 (d, 1H), 7.24 (dd, 1H), 7.20 (m, 1H), 6.39 (d, 1H), 4.41 (m, 1H), 1.82 (m, 2H), 1.40 (d, 3H), 0.61 (t, 3H) ppm

3-(4-Bromo-2-thienyl)-1-ethyl-1H-pyrazole and 5-(4-bromo-2-thienyl)-1-ethyl-1H-pyrazole 3-(4-Bromo-2-thienyl)-1H-pyrazole (10.0 mmol) was dissolved in 25 mL dry N,N-dimethylformamide and cooled to 0° C. under argon atmosphere. Sodium hydride (15.0 mmol, 60% dispersion in mineral oil) was added in portions at 0° C. The reaction mixture was allowed to warm to room temperature and was stirred at room temperature for 15 min. After cooling to 0° C. again, ethyl iodide (20.0 mmol) was added dropwise at 0° C. The reaction mixture was stirred at room temperature overnight. Water and MTBE were added to the reaction mixture. The phases were separated and the aqueous phase was extracted with MTBE. The combined organic extracts were successively washed with water and brine, dried over MgSO$_4$, filtered and concentrated. The residue was purified by chromatography on silica gel (toluene:ethyl acetate 100:0 to 0:100) to afford 1.76 g 3-(4-bromo-2-thienyl)-1-ethyl-1H-pyrazole (68% yield) and 403 mg of 5-(4-bromo-2-thienyl)-1-ethyl-1H-pyrazole (15% yield).

3-(4-Bromo-2-thienyl)-1-ethyl-1H-pyrazole logP (pH2.7): 3.04
MS (ESI): 256.9 ([M+H]$^+$)
$^1$H-NMR (400 MHz, d$_6$-DMSO): δ=7.79 (d, 1H), 7.54 (d, 1H), 7.40 (d, 1H), 6.66 (d, 1H), 4.14 (q, 2H), 1.38 (t, 3H) ppm

5-(4-Bromo-2-thienyl)-1-ethyl-1H-pyrazole logP (pH2.7): 2.92
MS (ESI): 256.9 ([M+H]$^+$)
$^1$H-NMR (400 MHz, d$_6$-DMSO): δ=7.84 (d, 1H), 7.51 (d, 1H), 7.39 (d, 1H), 6.51 (d, 1H), 4.24 (q, 2H), 1.33 (t, 3H) ppm

3-(4-Bromo-2-thienyl)-1-isopropyl-1H-pyrazole and 5-(4-bromo-2-thienyl)-1-isopropyl-1H-pyrazole 3-(4-bromo-2-thienyl)-1H-pyrazole (8.7 mmol) was dissolved in 20 mL dry N,N-dimethylformamide under argon atmosphere. Sodium hydride (10.5 mmol, 60% dispersion in mineral oil) was added in portions at room temperature. The reaction mixture was stirred at room temperature for 15 min. Isopropyl iodide (13.1 mmol) was added dropwise and the reaction mixture was stirred at room temperature for 14 h. Water and MTBE were added to the reaction mixture. The phases were separated and the aqueous phase was extracted with MTBE. The combined organic extracts were successively washed with water and brine, dried over $MgSO_4$, filtered and concentrated. The residue was purified by chromatography on silica gel (cyclohexane:ethyl acetate 100:0 to 0:100) to afford 1.90 g 3-(4-bromo-2-thienyl)-1-isopropyl-1H-pyrazole (71% yield). Traces of the minor regioisomer 5-(4-bromo-2-thienyl)-1-isopropyl-1H-pyrazole were collected and analyzed as well.

3-(4-Bromo-2-thienyl)-1-isopropyl-1H-pyrazole logP (pH2.7): 3.61
MS (ESI): 271.0 ([M+H]$^+$)
$^1$H-NMR (400 MHz, $d_6$-DMSO): δ=7.81 (d, 1H), 7.53 (d, 1H), 7.39 (d, 1H), 6.64 (d, 1H), 4.50 (sept, 1H), 1.42 (d, 6H) ppm 5-(4-Bromo-2-thienyl)-1-isopropyl-1H-pyrazole logP (pH2.7): 3.44
MS (ESI): 271.0 ([M+H]$^+$)
$^1$H-NMR (400 MHz, $d_6$-DMSO): δ=7.86 (d, 1H), 7.54 (m, 1H), 7.34 (d, 1H), 6.46 (d, 1H), 4.69 (sept, 1H), 1.39 (d, 6H) ppm 1-Methyl-3-(4-methyl-2-thienyl)-1H-pyrazole and 1-methyl-5-(4-methyl-2-thienyl)-1H-pyrazole 3-(4-methyl-2-thienyl)-1H-pyrazole (9.0 mmol) was dissolved in 20 mL dry N,N-dimethylformamide and cooled to 0° C. under argon atmosphere. Sodium hydride (13.5 mmol, 60% dispersion in mineral oil) was added in portions at 0° C. The reaction mixture was allowed to warm to room temperature and was stirred at room temperature for 15 min. After cooling to 0° C. again, methyl iodide (18.0 mmol) was added dropwise at 0° C. The reaction mixture was stirred at room temperature for 14 h. Water and MTBE were added to the reaction mixture. The phases were separated and the aqueous phase was extracted with MTBE. The combined organic extracts were successively washed with water and brine, dried over $MgSO_4$, filtered and concentrated. The residue was purified by chromatography on silica gel (dichloromethane: MTBE 100:0 to 90:10) to afford 864 mg 1-methyl-3-(4-methyl-2-thienyl)-1H-pyrazole (54% yield) and 480 mg of 1-methyl-5-(4-methyl-2-thienyl)-1H-pyrazole (30% yield).

1-Methyl-3-(4-methyl-2-thienyl)-1H-pyrazole logP (pH2.7): 2.14
MS (ESI): 179.1 ([M+H]$^+$)
$^1$H-NMR (600 MHz, $d_6$-DMSO): δ=7.69 (d, 1H), 7.17 (d, 1H), 6.98 (m, 1H), 6.52 (d, 1H), 3.82 (s, 3H), 2.20 (s, 3H) ppm 1-Methyl-5-(4-methyl-2-thienyl)-1H-pyrazole logP (pH2.7): 2.26
MS (ESI): 179.1 ([M+H]$^+$)
$^1$H-NMR (600 MHz, $d_6$-DMSO): δ=7.43 (d, 1H), 7.26 (m, 1H), 7.22 (d, 1H), 6.43 (d, 1H), 3.92 (s, 3H), 2.26 (s, 3H) ppm 1-Ethyl-3-(4-methyl-2-thienyl)-1H-pyrazole and 1-ethyl-5-(4-methyl-2-thienyl)-1H-pyrazole 3-(4-methyl-2-thienyl)-1H-pyrazole (9.3 mmol) was dissolved in 20 mL dry N,N-dimethylformamide and cooled to 0° C. under argon atmosphere. Sodium hydride (14.0 mmol, 60% dispersion in mineral oil) was added in portions at 0° C. The reaction mixture was allowed to warm to room temperature and was stirred at room temperature for 15 min. After cooling to 0° C. again, ethyl iodide (18.6 mmol) was added dropwise at 0° C. The reaction mixture was stirred at room temperature for 14 h. Water and MTBE were added to the reaction mixture. The phases were separated and the aqueous phase was extracted with MTBE. The combined organic extracts were successively washed with water and brine, dried over $MgSO_4$, filtered and concentrated. The residue was purified by chromatography on silica gel (dichloromethane: MTBE 100:0 to 90:10) to afford 1.21 g 1-ethyl-3-(4-methyl-2-thienyl)-1H-pyrazole (68% yield) and 406 mg of 1-ethyl-5-(4-methyl-2-thienyl)-1H-pyrazole (23% yield).

1-Ethyl-3-(4-methyl-2-thienyl)-1H-pyrazole logP (pH2.7): 2.64
MS (ESI): 193.0 ([M+H]$^+$)
$^1$H-NMR (600 MHz, $d_6$-DMSO): δ=7.74 (d, 1H), 7.17 (d, 1H), 6.98 (m, 1H), 6.52 (d, 1H), 4.12 (q, 2H), 2.20 (s, 3H), 1.37 (t, 3H) ppm 1-Ethyl-5-(4-methyl-2-thienyl)-1H-pyrazole logP (pH2.7): 2.68
MS (ESI): 193.1 ([M+H]$^+$)
$^1$H-NMR (600 MHz, $d_6$-DMSO): δ=7.47 (d, 1H), 7.27 (m, 1H), 7.15 (d, 1H), 6.40 (d, 1H), 4.23 (q, 2H), 2.26 (s, 3H), 1.33 (t, 3H) ppm 3-(4-Methyl-2-thienyl)-1-propyl-1H-pyrazole and 5-(4-methyl-2-thienyl)-1-propyl-1H-pyrazole 3-(4-methyl-2-thienyl)-1H-pyrazole (9.1 mmol) was dissolved in 20 mL dry N,N-dimethylformamide and cooled to 0° C. under argon atmosphere. Sodium hydride (13.7 mmol, 60% dispersion in mineral oil) was added in portions at 0° C. The reaction mixture was allowed to warm to room temperature and was stirred at room temperature for 15 min. After cooling to 0° C. again, propyl iodide (18.3 mmol) was added dropwise at 0° C. The reaction mixture was stirred at room temperature for 14 h. Water and MTBE were added to the reaction mixture. The phases were separated and the aqueous phase was extracted with MTBE. The combined organic extracts were successively washed with water and brine, dried over $MgSO_4$, filtered and concentrated. The residue was purified by chromatography on silica gel (dichloromethane: MTBE 100:0 to 90:10) to afford 1.39 g 3-(4-methyl-2-thienyl)-1-propyl-1H-pyrazole (74% yield) and 341 mg of 5-(4-methyl-2-thienyl)-1-propyl-1H-pyrazole (18% yield).

3-(4-Methyl-2-thienyl)-1-propyl-1H-pyrazole logP (pH2.7): 3.07
MS (ESI): 207.2 ([M+H]$^+$)
$^1$H-NMR (600 MHz, $d_6$-DMSO): δ=7.73 (d, 1H), 7.17 (d, 1H), 6.98 (m, 1H), 6.52 (d, 1H), 4.04 (t, 2H), 2.20 (s, 3H), 1.79 (m, 2H), 0.83 (t, 3H) ppm

5-(4-Methyl-2-thienyl)-1-propyl-1H-pyrazole logP (pH2.7): 3.10
MS (ESI): 207.0 ([M+H]$^+$)
$^1$H-NMR (600 MHz, d$_6$-DMSO): δ=7.47 (d, 1H), 7.27 (m, 1H), 7.14 (d, 1H), 6.41 (d, 1H), 4.16 (t, 2H), 2.26 (s, 3H), 1.75 (m, 2H), 0.81 (t, 3H) ppm

1-Isopropyl-3-(4-methyl-2-thienyl)-1H-pyrazole and 1-isopropyl-5-(4-methyl-2-thienyl)-1H-pyrazole 3-(4-methyl-2-thienyl)-1H-pyrazole (9.0 mmol) was dissolved in 20 mL dry N,N-dimethylformamide and cooled to 0° C. under argon atmosphere. Sodium hydride (13.5 mmol, 60% dispersion in mineral oil) was added in portions at 0° C. The reaction mixture was allowed to warm to room temperature and was stirred at room temperature for 15 min. After cooling to 0° C. again, 2-iodopropane (18.0 mmol) was added dropwise at 0° C. The reaction mixture was stirred at room temperature for 14 h. Water and MTBE were added to the reaction mixture. The phases were separated and the aqueous phase was extracted with MTBE. The combined organic extracts were successively washed with water and brine, dried over MgSO$_4$, filtered and concentrated. The residue was purified by chromatography on silica gel (cyclohexane:dichloromethane 100:0 to 0:100, then cyclohexane:ethyl acetate 100:0 to 0:100) to afford 1.15 g 1-isopropyl-3-(4-methyl-2-thienyl)-1H-pyrazole (62% yield) and 305 mg of 1-isopropyl-5-(4-methyl-2-thienyl)-1H-pyrazole (16% yield).

1-Isopropyl-3-(4-methyl-2-thienyl)-1H-pyrazole logP (pH2.7): 3.14
MS (ESI): 207.1 ([M+H]$^+$)
$^1$H-NMR (600 MHz, d$_6$-DMSO): δ=7.77 (d, 1H), 7.17 (d, 1H), 6.98 (m, 1H), 6.51 (d, 1H), 4.48 (sept, 1H), 2.02 (s, 3H), 1.42 (d, 6H) ppm

1-Isopropyl-5-(4-methyl-2-thienyl)-1H-pyrazole logP (pH2.7): 3.18
MS (ESI): 207.1 ([M+H]$^+$)
$^1$H-NMR (600 MHz, d$_6$-DMSO): δ=7.50 (m, 1H), 7.28 (m, 1H), 7.10 (d, 1H), 6.35 (d, 1H), 4.73 (sept, 1H), 2.26 (s, 3H), 1.39 (d, 6H) ppm

1-sec-Butyl-3-(4-methyl-2-thienyl)-1H-pyrazole and 1-sec-butyl-5-(4-methyl-2-thienyl)-1H-pyrazole 3-(4-Methyl-2-thienyl)-1H-pyrazole (9.1 mmol) was dissolved in 20 mL dry N,N-dimethylformamide and cooled to 0° C. under argon atmosphere. Sodium hydride (13.7 mmol, 60% dispersion in mineral oil) was added in portions at 0° C. The reaction mixture was allowed to warm to room temperature and was stirred at room temperature for 15 min. After cooling to 0° C. again, 2-iodobutane (18.3 mmol) was added dropwise at 0° C. The reaction mixture was stirred at room temperature for 14 h. Water and MTBE were added to the reaction mixture. The phases were separated and the aqueous phase was extracted with MTBE. The combined organic extracts were successively washed with water and brine, dried over MgSO$_4$, filtered and concentrated. The residue was purified by chromatography on silica gel (cyclohexane:dichloromethane 100:0 to 0:100, then cyclohexane:ethyl acetate 100:0 to 0:100) to afford 1.08 g 1-sec-butyl-3-(4-methyl-2-thienyl)-1H-pyrazole (54% yield) and 362 mg of 1-sec-butyl-5-(4-methyl-2-thienyl)-1H-pyrazole (18% yield).

1-sec-Butyl-3-(4-methyl-2-thienyl)-1H-pyrazole logP (pH2.7): 3.63
MS (ESI): 221.1 ([M+H]$^+$)
$^1$H-NMR (600 MHz, d$_6$-DMSO): δ=7.76 (d, 1H), 7.17 (d, 1H), 6.97 (m, 1H), 6.51 (d, 1H), 4.24 (m, 1H), 2.20 (s, 3H), 1.76 (m, 2H), 1.40 (d, 3H), 0.73 (t, 3H) ppm

1-sec-Butyl-5-(4-methyl-2-thienyl)-1H-pyrazole logP (pH2.7): 3.65
MS (ESI): 221.0 ([M+H]$^+$)
$^1$H-NMR (600 MHz, d$_6$-DMSO): δ=7.52 (d, 1H), 7.28 (m, 1H), 7.06 (d, 1H), 6.35 (d, 1H), 4.44 (m, 1H), 2.26 (s, 3H), 1.88 (m, 1H), 1.70 (m, 1H), 1.39 (d, 3H), 0.61 (t, 3H) ppm

3-(4,5-Dibromo-2-thienyl)-1-isopropyl-1H-pyrazole and 5-(4,5-dibromo-2-thienyl)-1-isopropyl-1H-pyrazole 3-(4,5-dibromo-2-thienyl)-1H-pyrazole (9.4 mmol) was dissolved in 20 mL dry N,N-dimethylformamide under argon atmosphere. Sodium hydride (11.3 mmol, 60% dispersion in mineral oil) was added in portions at room temperature. The reaction mixture was stirred at room temperature for 15 min. Isopropyl iodide (14.1 mmol) was added dropwise and the reaction mixture was stirred at room temperature for 14 h. Water and MTBE were added to the reaction mixture. The phases were separated and the aqueous phase was extracted with MTBE. The combined organic extracts were successively washed with water and brine, dried over MgSO4, filtered and concentrated. The residue was purified by chromatography on silica gel (toluene:ethyl acetate 100:0 to 0:100) to afford 2.67 g 3-(4,5-dibromo-2-thienyl)-1-isopropyl-1H-pyrazole (81% yield) and 238 mg of 5-(4,5-dibromo-2-thienyl)-1-isopropyl-1H-pyrazole (7% yield).

3-(4,5-Dibromo-2-thienyl)-1-isopropyl-1H-pyrazole logP (pH2.7): 4.64
MS (ESI): 348.9 ([M+H]$^+$)
$^1$H-NMR (400 MHz, d$_6$-DMSO): δ=7.85 (d, 1H), 7.43 (s, 1H), 6.69 (d, 1H), 4.50 (sept, 1H), 1.42 (s, 6H) ppm

5-(4,5-Dibromo-2-thienyl)-1-isopropyl-1H-pyrazole logP (pH2.7): 4.44
MS (ESI): 348.9 ([M+H]$^+$)
$^1$H-NMR (400 MHz, d$_6$-DMSO): δ=7.54 (d, 1H), 7.35 (s, 1H), 6.48 (d, 1H), 4.68 (sept, 1H), 1.39 (d, 6H) ppm

1-Methyl-5-propyl-3-(2-thienyl)-1H-pyrazole and 1-methyl-3-propyl-5-(2-thienyl)-1H-pyrazole Dry THF was degassed by purging the solvent with a continuous flow of argon for 15 min. In a microwave vial (10-20 mL of reaction volume), bis(triphenylphosphine)palladium(II) chloride (0.08 mmol) and copper(I) iodide (0.16 mmol) were dissolved in 12 mL of degassed dry THF. 1-Pentyne (4.0 mmol), dry triethylamine (4.2 mmol) and thiophene-2-carbonyl chloride (4.0 mmol) were added to this solution successively while the reaction temperature was regulated by immersing the vial in a water bath. The reaction mixture was purged with argon and stirred for 1 h at room temperature under argon atmosphere. 1.5 mL Methanol, 1.5 mL acetic acid and methylhydrazine (4.4 mmol) were added to the reaction mixture. The microwave vial was capped with a septum and transferred to a laboratory microwave oven. The reaction mixture was irradiated to a reaction temperature of 150° C. for 10 min (irradiation power: 50 to 230 W, pressure: 7-8 bar). After cooling to room temperature, the reaction mixture was concentrated under reduced pressure and dried in vacuum overnight. The residue was partitioned between ethyl acetate and water. The aqueous phase was extracted with ethyl acetate and the combined organic layers were successively washed with saturated aqueous ammonium chloride solution, saturated aqueous sodium bicarbonate solution and with brine, dried over $MgSO_4$, filtered and concentrated to afford 864 mg of a mixture of 1-methyl-5-propyl-3-(2-thienyl)-1H-pyrazole and 1-methyl-3-propyl-5-(2-thienyl)-1H-pyrazole (90:10) with some phosphine and phosphinoxide impurities. The crude product was purified by chromatography on silica gel (dichloromethane:MTBE 100:0 to 90:10) to afford 533 mg 1-methyl-5-propyl-3-(2-thienyl)-1H-pyrazole (63% yield) and 61 mg of 1-methyl-3-propyl-5-(2-thienyl)-1H-pyrazole (6% yield).

1-Methyl-5-propyl-3-(2-thienyl)-1H-pyrazole logP (pH2.7): 2.90
MS (ESI): 207.1 ([M+H]$^+$)
$^1$H-NMR (600 MHz, $d_6$-DMSO): δ=7.39 (dd, 1H), 7.31 (dd, 1H), 7.04 (dd, 1H), 6.38 (s, 1H), 3.72 (s, 3H), 2.56 (t, 2H), 1.63 (m, 2H), 0.97 (t, 3H) ppm 1-Methyl-3-propyl-5-(2-thienyl)-1H-pyrazole logP (pH2.7): 2.90
MS (ESI): 207.1 ([M+H]$^+$)
$^1$H-NMR (600 MHz, $d_6$-DMSO): δ=7.67 (dd, 1H), 7.35 (dd, 1H), 7.19 (dd, 1H), 6.27 (s, 1H), 3.85 (s, 3H), 2.47 (t, 2H), 1.60 (m, 2H), 0.92 (t, 3H) ppm 1-Methyl-3-(3-methyl-2-thienyl)-5-propyl-1H-pyrazole and 1-Methyl-5-(3-methyl-2-thienyl)-3-propyl-1H-pyrazole Dry THF was degassed by purging the solvent with a continuous flow of argon for 15 min. In a microwave vial (10-20 mL of reaction volume), bis(triphenylphosphine)palladium(II) chloride (0.08 mmol) and copper(I) iodide (0.16 mmol) were dissolved in 12 mL of degassed dry THF. 1-Pentyne (4.0 mmol), dry triethylamine (4.2 mmol) and 3-methylthiophene-2-carbonyl chloride (4.0 mmol) were added to this solution successively while the reaction temperature was regulated by immersing the vial in a water bath. The reaction mixture was purged with argon and stirred for 2 h at room temperature under argon atmosphere. 1.5 mL Methanol, 1.5 mL acetic acid and methylhydrazine (4.4 mmol) were added to the reaction mixture. The microwave vial was capped with a septum and transferred to a laboratory microwave oven. The reaction mixture was irradiated to a reaction temperature of 150° C. for 10 min (irradiation power: 50 to 230 W, pressure: 7-8 bar). After cooling to room temperature, the reaction mixture was concentrated under reduced pressure and dried in vacuum overnight. The residue was partitioned between MTBE and aqueous saturated sodium carbonate solution. The aqueous phase was extracted with MTBE and the combined organic layers were washed with brine, dried over $MgSO_4$, filtered and concentrated to afford 1.01 g of a mixture of 1-methyl-3-(3-methyl-2-thienyl)-5-propyl-1H-pyrazole and 1-methyl-5-(3-methyl-2-thienyl)-3-propyl-1H-pyrazole (83:17) with some phosphine and phosphinoxide impurities. The crude product was used in the next step without further purification.

1-Methyl-3-(3-methyl-2-thienyl)-5-propyl-1H-pyrazole logP (pH2.7): 3.34
MS (ESI): 221.1 ([M+H]$^+$)
$^1$H-NMR (400 MHz, $d_6$-DMSO): δ=7.28 (d, 1H), 6.69 (d, 1H), 6.24 (s, 1H), 3.74 (s, 3H), 2.61 (t, 2H), 2.33 (s, 3H), 1.63 (m, 2H), 0.97 (t, 3H) ppm 1-Methyl-5-(3-methyl-2-thienyl)-3-propyl-1H-pyrazole logP (pH2.7): 3.34
MS (ESI): 221.1 ([M+H]$^+$)

Preparation of Starting Materials of the Formula (VIII)

4-Bromo-3-(5-chloro-2-thienyl)-1-isobutyl-1H-pyrazole

To a solution of 3-(5-chloro-2-thienyl)-1-isobutyl-1H-pyrazole (1 eq, 0.045 mol) in dry N,N-dimethylformamide (130 mL) was added N-bromosuccinimide (1.1 eq, 0.05 mol) slowly and the resulting mixture was stirred at room temperature for 3 h. After completion reaction monitored by TLC, the reaction mixture was poured into ice cold water and extracted with ethyl acetate. The combined organics layer were washed with water, brine, dried over anhydrous Na2SO4, filtered and evaporated to afford 12 g of 4-bromo-3-(5-chloro-2-thienyl)-1-isobutyl-1H-pyrazole (82% yield).
1H NMR ($CDCl_3$, 400 MHz): δ=7.44 (1H, d), 7.4 (1H, s), 6.8 (1H, d), 3.8 (2H, d), 2.2 (1H, m), 0.9 (6H, d).

4-Iodo-3-(2-thienyl)-1H-pyrazole 3-(2-thienyl)-1H-pyrazole (2.9 mmol) was dissolved in 8 mL N,N-dimethylformamide under argon atmosphere. N-Iodosuccinimide (3.1 mmol) was added in small portions. The reaction mixture was stirred at room temperature overnight. 5% aqueous sodium thiosulfate solution and saturated aqueous sodium carbonate solution were added and the mixture was stirred at room temperature for 1 h. The white precipitate was filtered, washed with little cold MTBE and dried in vacuum to afford 540 mg of 4-iodo-3-(2-thienyl)-1H-pyrazole (66% yield). The filtrate was extracted with ethyl acetate. The combined organic layers were successively washed with water and brine, dried over $MgSO_4$, filtered and concentrated to afford 303 mg of 4-iodo-3-(2-thienyl)-1H-pyrazole (34% yield) that was used without further purification.
logP (pH2.7): 2.10
MS (ESI): 276.8 ([M+H]$^+$)
$^1$H-NMR (400 MHz, $d_6$-DMSO): δ=7.94 (s, 1H), 7.66 (m, 1H), 7.57 (m, 1H), 7.15 (m, 1H) ppm 1-sec-Butyl-4-iodo-3-(2-thienyl)-1H-pyrazole and 1-sec-butyl-4-iodo-5-(2-thienyl)-1H-pyrazole To a solution of 4-iodo-3-(2-thienyl)-1H-pyrazole (7.1 mmol) in 57 mL dry N,N-dimethylformamide under argon atmosphere at 0° C. was added sodium hydride (8.5 mmol, 60% dispersion in mineral oil) in portions. The reaction mixture was stirred at 0° C. for 15 min, then 2-iodobutane (10.6 mmol) was added dropwise. After 14 h at room temperature, water and MTBE were added to the reaction mixture. The phases were separated and the aqueous phase was extracted with MTBE. The combined organic extracts were successively washed with water and brine, dried over MgSO$_4$, filtered and concentrated to afford 2.7 g of a mixture of 1-sec-butyl-4-iodo-3-(2-thienyl)-1H-pyrazole and 1-sec-butyl-4-iodo-5-(2-thienyl)-1H-pyrazole (80:20; 88% yield). The mixture was purified by chromatography on silica gel (toluene:ethyl acetate 100:0 to 0:100 and cyclohexane:toluene 100:0 to 0:100) to afford 1.16 g 1-sec-butyl-4-iodo-3-(2-thienyl)-1H-pyrazole (48% yield) and 71 mg of 1-sec-butyl-4-iodo-5-(2-thienyl)-1H-pyrazole (3% yield).

1-sec-Butyl-4-iodo-3-(2-thienyl)-1H-pyrazole logP (pH2.7): 4.12
MS (ESI): 333.0 ([M+H]$^+$)
$^1$H-NMR (600 MHz, d$_6$-DMSO): δ=8.08 (s, 1H), 7.67 (m, 1H), 7.52 (m, 1H), 7.13 (m, 1H), 4.27 (m, 1H), 1.77 (m, 2H), 1.40 (d, 3H), 0.74 (t, 3H) ppm 1-sec-Butyl-4-iodo-5-(2-thienyl)-1H-pyrazole logP (pH2.7): 4.12
MS (ESI): 332.9 ([M+H]$^+$)
$^1$H-NMR (600 MHz, d$_6$-DMSO): δ=7.86 (m, 1H), 7.70 (s, 1H), 7.26 (m, 1H), 7.23 (m, 1H), 4.21 (m, 1H), 1.83 (m, 1H), 1.65 (m, 1H), 1.34 (d, 3H), 0.59 (t, 3H) ppm 4-Iodo-1-isopropyl-3-(2-thienyl)-1H-pyrazole and 4-iodo-1-isopropyl-5-(2-thienyl)-1H-pyrazole To a solution of 4-iodo-3-(2-thienyl)-1H-pyrazole (1.1 mmol) in 3 mL dry N,N-dimethylformamide under argon atmosphere was added sodium hydride (1.3 mmol, 60% dispersion in mineral oil) in portions. The reaction mixture was stirred at room temperature, then isopropyl iodide (1.7 mmol) was added dropwise. After 2 h at room temperature, water and MTBE were added to the reaction mixture. The phases were separated and the aqueous phase was extracted with MTBE. The combined organic extracts were successively washed with water and brine, dried over MgSO$_4$, filtered and concentrated to afford 350 mg of a mixture of 4-iodo-1-isopropyl-3-(2-thienyl)-1H-pyrazole and 4-iodo-1-isopropyl-5-(2-thienyl)-1H-pyrazole (75:25; 99% yield). The mixture was purified by chromatography on silica gel (cyclohexane:ethyl acetate 100:0 to 0:100) to afford 151 mg 4-iodo-1-isopropyl-3-(2-thienyl)-1H-pyrazole (42% yield) and 42 mg of 4-iodo-1-isopropyl-5-(2-thienyl)-1H-pyrazole (11% yield).

4-Iodo-1-isopropyl-3-(2-thienyl)-1H-pyrazole logP (pH2.7): 3.71
MS (ESI): 319.0 ([M+H]$^+$)
$^1$H-NMR (400 MHz, d$_6$-DMSO): δ=8.08 (s, 1H), 7.66 (m, 1H), 7.53 (m, 1H), 7.13 (m, 1H), 4.52 (sept, 1H), 1.43 (t, 6H) ppm 4-Iodo-1-isopropyl-5-(2-thienyl)-1H-pyrazole logP (pH2.7): 3.66
MS (ESI): 319.0 ([M+H]$^+$)
$^1$H-NMR (400 MHz, d$_6$-DMSO): δ=7.86 (m, 1H), 7.68 (s, 1H), 7.27 (m, 2H), 4.51 (sept, 1H), 1.34 (t, 6H) ppm 4-Iodo-1-isopropyl-3-(2-thienyl)-1H-pyrazole (alternative synthesis)

To a solution of 1-isopropyl-3-(2-thienyl)-1H-pyrazole (27.5 mmol) in 98 mL dry N,N-dimethylformamide under argon atmosphere was added N-iodosuccinimide (28.9 mmol) in small portions. The reaction mixture was stirred overnight at room temperature. N-Iodosuccinimide (4.4 mmol) was added and stirring was continued for 24 h. 5% aqueous sodium thiosulfate solution and saturated aqueous sodium carbonate solution were added and the mixture was stirred at room temperature for 1 h, then extracted with ethyl acetate. The combined organic extracts were successively washed with water and brine, dried over MgSO$_4$, filtered and concentrated. The residue was purified by chromatography on silica gel (toluene:ethyl acetate 100:0 to 0:100) to afford 3.70 g 4-iodo-1-isopropyl-3-(2-thienyl)-1H-pyrazole (38% yield).

logP (pH2.7): 3.71
MS (ESI): 319.0 ([M+H]$^+$)
$^1$H-NMR (400 MHz, d$_6$-DMSO): δ=8.08 (s, 1H), 7.66 (m, 1H), 7.53 (m, 1H), 7.13 (m, 1H), 4.52 (sept, 1H), 1.43 (t, 6H) ppm 1-Ethyl-4-iodo-3-(2-thienyl)-1H-pyrazole To a solution of 1-ethyl-3-(2-thienyl)-1H-pyrazole (13.5 mmol) in 45 mL dry N,N-dimethylformamide under argon atmosphere was added N-iodosuccinimide (14.1 mmol) in small portions. The reaction mixture was stirred overnight at room temperature. N-Iodosuccinimide (4.4 mmol) was added and stirring was continued for 24 h. 5% aqueous sodium thiosulfate solution and saturated aqueous sodium carbonate solution were added and the mixture was stirred at room temperature for 1 h, then extracted with ethyl acetate. The combined organic extracts were successively washed with water and brine, dried over MgSO$_4$, filtered and concentrated. The residue was purified by chromatography on silica gel (toluene:ethyl acetate 100:0 to 0:100) to afford 2.10 g 1-ethyl-4-iodo-3-(2-thienyl)-1H-pyrazole (51% yield).

logP (pH2.7): 3.13
MS (ESI): 305.0 ([M+H]$^+$)
$^1$H-NMR (400 MHz, d$_6$-DMSO): δ=8.03 (s, 1H), 7.66 (m, 1H), 7.52 (m, 1H), 7.13 (m, 1H), 4.14 (q, 2H), 1.38 (t, 3H) ppm 4-Iodo-1-propyl-3-(2-thienyl)-1H-pyrazole To a mixture of 1-propyl-3-(2-thienyl)-1H-pyrazole and 1-propyl-5-(2-thienyl)-1H-pyrazole (80:20, 5.0 mmol) in 18 mL dry N,N-dimethylformamide under argon atmosphere was added N-iodosuccinimide (5.2 mmol) in small portions. The reaction mixture was stirred overnight at room temperature. 5% aqueous sodium thiosulfate solution and saturated aqueous sodium carbonate solution were added and the mixture was stirred at room temperature for 1 h, then extracted with ethyl acetate. The combined organic extracts were successively washed with water and brine, dried over MgSO$_4$, filtered and concentrated. The residue was purified by chromatography on silica gel (toluene:ethyl acetate 100:0 to 0:100) to afford 180 mg 4-iodo-1-propyl-3-(2-thienyl)-1H-pyrazole (11% yield).

logP (pH2.7): 3.65
MS (ESI): 318.9 ([M+H]$^+$)
$^1$H-NMR (400 MHz, d$_6$-DMSO): δ=8.02 (s, 1H), 7.67 (m, 1H), 7.52 (m, 1H), 7.13 (m, 1H), 4.08 (t, 2H), 1.79 (m, 2H), 0.84 (t, 3H) ppm

3-(4-chloro-2-thienyl)-4-iodo-1H-pyrazole 3-(4-chloro-2-thienyl)-1H-pyrazole (24.0 mmol) was dissolved in 50 mL N,N-dimethylformamide under argon atmosphere. N-Iodosuccinimide (25.1 mmol) was added in small portions. The reaction mixture was stirred at room temperature overnight. 5% aqueous sodium thiosulfate solution and saturated aqueous sodium carbonate solution were added and the mixture was stirred at room temperature for 1 h. The white precipitate was filtered, washed thoroughly with water and dried in vacuum to afford 6.80 g of 3-(4-chloro-2-thienyl)-4-iodo-1H-pyrazole (91% yield) that was used without further purification.

logP (pH2.7): 2.68
MS (ESI): 310.9 ([M+H]$^+$)
$^1$H-NMR (400 MHz, d$_6$-DMSO): δ=8.07 (m, 1H), 7.57 (m, 2H) ppm

3-(4-chloro-2-thienyl)-1-ethyl-4-iodo-1H-pyrazole and 5-(4-chloro-2-thienyl)-1-ethyl-4-iodo-1H-pyrazole To a solution of 4-iodo-3-(2-thienyl)-1H-pyrazole (4.8 mmol) in 15 mL dry N,N-dimethylformamide under argon atmosphere was added sodium hydride (5.8 mmol, 60% dispersion in mineral oil) in portions at 0° C. The reaction mixture was allowed to warm to room temperature and was stirred for 15 min. After cooling to 0° C., ethyliodide (7.2 mmol) was added dropwise. The reaction mixture was stirred at room temperature overnight. Sodium hydride (1.2 mmol) and ethyliodide (2.5 mmol) were added and stirring was continued for 24 h. Water and MTBE were added to the reaction mixture. The phases were separated and the aqueous phase was extracted with MTBE. The combined organic extracts were successively washed with water and brine, dried over MgSO$_4$, filtered and concentrated to afford 1.71 g of a mixture of 3-(4-chloro-2-thienyl)-1-ethyl-4-iodo-1H-pyrazole and 5-(4-chloro-2-thienyl)-1-ethyl-4-iodo-1H-pyrazole (80:20; 84% yield). The mixture was purified by chromatography on silica gel (toluene:ethyl acetate 100:0 to 0:100) to afford 1.27 g 3-(4-chloro-2-thienyl)-1-ethyl-4-iodo-1H-pyrazole (78% yield) and 92 mg of 5-(4-chloro-2-thienyl)-1-ethyl-4-iodo-1H-pyrazole (6% yield).

3-(4-Chloro-2-thienyl)-1-ethyl-4-iodo-1H-pyrazole logP (pH2.7): 4.02
MS (ESI): 338.9 ([M+H]$^+$)
$^1$H-NMR (600 MHz, d$_6$-DMSO): δ=8.08 (s, 1H), 7.59 (d, 1H), 7.56 (d, 1H), 4.16 (q, 2H), 1.38 (t, 3H) ppm

5-(4-Chloro-2-thienyl)-1-ethyl-4-iodo-1H-pyrazole logP (pH2.7): 3.76
MS (ESI): 338.9 ([M+H]$^+$)
$^1$H-NMR (600 MHz, d$_6$-DMSO): δ=7.90 (d, 1H), 7.69 (s, 1H), 7.38 (d, 1H), 4.14 (q, 2H), 1.26 (t, 3H) ppm

1-sec-Butyl-3-(4-chloro-2-thienyl)-4-iodo-1H-pyrazole and 1-sec-butyl-5-(4-chloro-2-thienyl)-4-iodo-1H-pyrazole To a solution of 4-iodo-3-(4-chloro-2-thienyl)-1H-pyrazole (3.3 mmol) in 10 mL dry N,N-dimethylformamide under argon atmosphere was added sodium hydride (3.9 mmol, 60% dispersion in mineral oil) in portions. The reaction mixture was stirred at room temperature for 15 min, then 2-iodobutane (4.9 mmol) was added dropwise. After 2 days at room temperature, water and MTBE were added to the reaction mixture. The phases were separated and the aqueous phase was extracted with MTBE. The combined organic extracts were successively washed with water and brine, dried over MgSO$_4$, filtered and concentrated to afford 1.2 g of a mixture of 1-sec-butyl-3-(4-chloro-2-thienyl)-4-iodo-1H-pyrazole and 1-sec-butyl-5-(4-chloro-2-thienyl)-4-iodo-1H-pyrazole (88:12; 100% yield). The mixture was purified by chromatography on silica gel (toluene:ethyl acetate 100:0 to 0:100) to afford 923 mg 1-sec-butyl-3-(4-chloro-2-thienyl)-4-iodo-1H-pyrazole (74% yield) and 150 mg of 1-sec-butyl-5-(4-chloro-2-thienyl)-4-iodo-1H-pyrazole (11% yield).

1-sec-Butyl-3-(4-chloro-2-thienyl)-4-iodo-1H-pyrazole logP (pH2.7): 5.01
MS (ESI): 367.0 ([M+H]$^+$)
$^1$H-NMR (400 MHz, d$_6$-DMSO): δ=8.10 (s, 1H), 7.56 (m, 2H), 4.28 (m, 1H), 1.76 (m, 2H), 1.41 (d, 3H), 0.74 (t, 3H) ppm

1-sec-Butyl-5-(4-chloro-2-thienyl)-4-iodo-1H-pyrazole logP (pH2.7): 4.72
MS (ESI): 366.9 ([M+H]$^+$)
$^1$H-NMR (400 MHz, d$_6$-DMSO): δ=7.90 (d, 1H), 7.72 (s, 1H), 7.28 (d, 1H), 4.22 (m, 1H), 1.83 (m, 1H), 1.68 (m, 1H), 1.35 (d, 3H), 0.60 (t, 3H) ppm

4-Bromo-3-(5-chloro-2-thienyl)-5-methyl-1H-pyrazole 3-(5-chloro-2-thienyl)-5-methyl-1H-pyrazole (111 mmol) was dissolved in 200 mL dry 1V, N-dim ethyl formamide and cooled to 0° C. under nitrogen atmosphere. N-Bromosuccinimide (118 mmol) was added in small portions at 0° C. The reaction mixture was allowed to warm to room temperature and was stirred overnight. The solution was poured into a mixture of saturated aqueous sodium thiosulfate solution and saturated aqueous sodium carbonate solution (1:1) at room temperature. The precipitate was filtered, washed thoroughly with water, dissolved in ethyl acetate, dried over MgSO$_4$, filtered and evaporated to afford 19.5 g of 4-bromo-3-(5-chloro-2-thienyl)-5-methyl-1H-pyrazole (64% yield) that was used without further purification.

$^1$H-NMR (400 MHz, CDCl$_3$): δ=10.65 (bs, 1H), 7.44 (d, 1H), 6.90 (d, 1H), 2.29 (s, 3H) ppm

4-Bromo-3-(5-chloro-2-thienyl)-1,5-dimethyl-1H-pyrazole

4-Bromo-3-(5-chloro-2-thienyl)-5-methyl-1H-pyrazole (35.3 mmol) was dissolved in 30 mL dry N,N-dimethylformamide and cooled to 0° C. under nitrogen atmosphere. Sodium hydride (37.1 mmol, 60% dispersion in mineral oil) was added in portions at 0° C. After stirring for 30 min, iodomethane (42.4 mmol) was added dropwise. The reaction mixture was allowed to warm to room temperature and was stirred overnight. The solution was poured into saturated aqueous ammonium chloride solution and extracted with diethyl ether, dried over MgSO$_4$, filtered and evaporated. The crude product was purified by chromatography on silica gel (100% dichloromethane) to afford 5.6 g 4-bromo-3-(5-chloro-2-thienyl)-1,5-dimethyl-1H-pyrazole (54% yield)

logP (pH2.7): 3.92
MS (ESI): 290.8 ([M+H]$^+$)
$^1$H-NMR (400 MHz, d$_6$-DMSO): δ=7.44 (d, 1H), 7.13 (d, 1H), 3.80 (s, 3H), 2.27 (s, 3H) ppm 4-Bromo-3-(5-chloro-2-thienyl)-1-ethyl-5-methyl-1H-pyrazole 4-Bromo-3-(5-chloro-2-thienyl)-5-methyl-1H-pyrazole (36.0 mmol) was dissolved in 30 mL dry N,N-dimethylformamide and cooled to 0° C. under nitrogen atmosphere. Sodium hydride (37.8 mmol, 60% dispersion in mineral oil) was added in portions at 0° C. After stirring for 30 min, iodoethane (43.2 mmol) was added dropwise. The reaction mixture was allowed to warm to room temperature and was stirred overnight. The solution was poured into saturated aqueous ammonium chloride solution and extracted with diethyl ether, dried over MgSO$_4$, filtered and evaporated. The crude product was purified by chromatography on silica gel (100% dichloromethane) to afford 7.0 g 4-bromo-3-(5-chloro-2-thienyl)-1-ethyl-5-methyl-1H-pyrazole (64% yield)
logP (pH2.7): 4.54
MS (ESI): 304.9 ([M+H]$^+$)
$^1$H-NMR (400 MHz, d$_6$-DMSO): δ=7.45 (d, 1H), 7.13 (d, 1H), 4.13 (q, 2H), 2.29 (s, 3H), 1.31 (t, 3H) ppm 4-Bromo-3-(5-chloro-2-thienyl)-1-isopropyl-5-methyl-1H-pyrazole 4-Bromo-3-(5-chloro-2-thienyl)-5-methyl-1H-pyrazole (36.0 mmol) was dissolved in 30 mL dry N,N-dimethylformamide and cooled to 0° C. under nitrogen atmosphere. Sodium hydride (37.8 mmol, 60% dispersion in mineral oil) was added in portions at 0° C. After stirring for 30 min, 2-iodopropane (43.2 mmol) was added dropwise. The reaction mixture was allowed to warm to room temperature and was stirred overnight. The solution was poured into saturated aqueous ammonium chloride solution and extracted with diethyl ether, dried over MgSO$_4$, filtered and evaporated. The crude product was purified by chromatography on silica gel (cyclohexane:dichloromethane 50:50) to afford 10.0 g 4-bromo-3-(5-chloro-2-thienyl)-1-isopropyl-5-methyl-1H-pyrazole (87% yield)
logP (pH2.7): 5.35
MS (ESI): 318.9 ([M+H]$^+$)
$^1$H-NMR (400 MHz, d$_6$-DMSO): δ=7.43 (d, 1H), 7.13 (d, 1H), 4.58 (sept, 1H), 2.30 (s, 3H), 1.39 (d, 6H) ppm 3-(5-Chloro-2-thienyl)-4-iodo-5-methyl-1H-pyrazole 3-(5-Chloro-2-thienyl)-5-methyl-1H-pyrazole (40.3 mmol) was dissolved in 70 mL dry N,N-dimethylformamide and cooled to 0° C. under nitrogen atmosphere. N-Iodosuccinimide (42.7 mmol) was added in small portions at 0° C. The reaction mixture was allowed to warm to room temperature and was stirred overnight. The solution was poured into a mixture of saturated aqueous sodium thiosulfate solution and saturated aqueous sodium carbonate solution (1:1) at room temperature. The precipitate was filtered, washed thoroughly with water, dissolved in ethyl acetate, dried over MgSO$_4$, filtered and evaporated to afford 9.9 g of 3-(5-chloro-2-thienyl)-4-iodo-5-methyl-1H-pyrazole (76% yield) that was used without further purification.
$^1$H-NMR (400 MHz, CDCl$_3$): δ=10.67 (bs, 1H), 7.49 (d, 1H), 6.91 (d, 1H), 2.32 (s, 3H) ppm 3-(5-Chloro-2-thienyl)-4-iodo-1-isopropyl-5-methyl-1H-pyrazole 3-(5-Chloro-2-thienyl)-4-iodo-5-methyl-1H-pyrazole (31.9 mmol) was dissolved in 30 mL dry N,N-dimethylformamide and cooled to 0° C. under nitrogen atmosphere. Sodium hydride (33.5 mmol, 60% dispersion in mineral oil) was added in portions at 0° C. After stirring for 30 min, 2-iodopropane (38.5 mmol) was added dropwise. The reaction mixture was allowed to warm to room temperature and was stirred overnight. The solution was poured into saturated aqueous ammonium chloride solution and extracted with diethyl ether, dried over MgSO$_4$, filtered and evaporated. The crude product was purified by chromatography on silica gel (cyclohexane:dichloromethane 90:10) to afford 7.5 g 3-(5-chloro-2-thienyl)-4-iodo-1-isopropyl-5-methyl-1H-pyrazole (67% yield)
$^1$H-NMR (400 MHz, CDCl$_3$): δ=7.48 (d, 1H), 6.87 (d, 1H), 4.47 (sept, 1H), 2.34 (s, 3H), 1.47 (d, 6H) ppm 4-Iodo-1-methyl-3-(4-methyl-2-thienyl)-1H-pyrazole To a solution of 1-methyl-3-(4-methyl-2-thienyl)-1H-pyrazole (4.7 mmol) in 14 mL dry 1V,N-dimethylformamide under argon atmosphere was added N-iodosuccinimide (5.0 mmol) in small portions at 0° C. The reaction mixture was allowed to warm to room temperature and was stirred overnight. 5% aqueous sodium thiosulfate solution and saturated aqueous sodium carbonate solution were added and the mixture was stirred at room temperature for 1 h, then extracted with MTBE. The combined organic extracts were successively washed with water and brine, dried over MgSO$_4$, filtered and concentrated. The residue was purified by chromatography on silica gel (cyclohexane:dichloromethane 100:0 to 0:100) to afford 1.26 g 4-iodo-1-methyl-3-(4-methyl-2-thienyl)-1H-pyrazole (84% yield).
logP (pH2.7): 3.18
MS (ESI): 305.0 ([M+H]$^+$)
$^1$H-NMR (600 MHz, d$_6$-DMSO): δ=7.71 (d, 1H), 7.11 (s, 1H), 6.53 (d, 1H), 3.82 (s, 3H), 2.14 (s, 3H) ppm 1-Ethyl-4-iodo-3-(4-methyl-2-thienyl)-1H-pyrazole To a solution of 1-ethyl-3-(4-methyl-2-thienyl)-1H-pyrazole (6.2 mmol) in 20 mL dry N,N-dimethylformamide under argon atmosphere was added N-iodosuccinimide (6.6 mmol) in small portions at 0° C. The reaction mixture was allowed to warm to room temperature and was stirred overnight. 5% aqueous sodium thiosulfate solution and saturated aqueous sodium carbonate solution were added and the mixture was stirred at room temperature for 1 h, then extracted with MTBE. The combined organic extracts were successively washed with water and brine, dried over MgSO$_4$, filtered and concentrated. The residue was purified by chromatography on silica gel (cyclohexane:dichloromethane 100:0 to 0:100) to afford 1.56 g 1-ethyl-4-iodo-3-(4-methyl-2-thienyl)-1H-pyrazole (76% yield).
logP (pH2.7): 3.70
MS (ESI): 319.0 ([M+H]$^+$)
$^1$H-NMR (600 MHz, d$_6$-DMSO): δ=7.76 (d, 1H), 7.11 (s, 1H), 6.53 (d, 1H), 4.11 (q, 2H), 2.14 (s, 3H), 1.37 (t, 3H) ppm 4-Iodo-3-(4-methyl-2-thienyl)-1-propyl-1H-pyrazole To a solution of 3-(4-methyl-2-thienyl)-1-propyl-1H-pyrazole (6.2 mmol) in 16 mL dry N,N-dimethylformamide under argon atmosphere was added N-iodosuccinimide (6.6 mmol)

in small portions at 0° C. The reaction mixture was allowed to warm to room temperature and was stirred overnight. 5% aqueous sodium thiosulfate solution and saturated aqueous sodium carbonate solution were added and the mixture was stirred at room temperature for 1 h, then extracted with MTBE. The combined organic extracts were successively washed with water and brine, dried over MgSO$_4$, filtered and concentrated. The residue was purified by chromatography on silica gel (cyclohexane:dichloromethane 100:0 to 0:100) to afford 1.77 g 4-iodo-3-(4-methyl-2-thienyl)-1-propyl-1H-pyrazole (85% yield).

logP (pH2.7): 4.20
MS (ESI): 333.0 ([M+H]$^+$)
$^1$H-NMR (600 MHz, d$_6$-DMSO): δ=7.75 (d, 1H), 7.11 (s, 1H), 6.53 (d, 1H), 4.04 (t, 2H), 2.14 (s, 3H), 1.77 (m, 2H), 0.83 (t, 3H) ppm 4-Iodo-1-isopropyl-3-(4-methyl-2-thienyl)-1H-pyrazole To a solution of 1-isopropyl-3-(4-methyl-2-thienyl)-1H-pyrazole (5.6 mmol) in 16 mL dry N,N-dimethylformamide under argon atmosphere was added N-iodosuccinimide (5.8 mmol) in small portions at 0° C. The reaction mixture was allowed to warm to room temperature and was stirred overnight. 5% aqueous sodium thiosulfate solution and saturated aqueous sodium carbonate solution were added and the mixture was stirred at room temperature for 1 h, then extracted with MTBE. The combined organic extracts were successively washed with water and brine, dried over MgSO$_4$, filtered and concentrated. The residue was purified by chromatography on silica gel (cyclohexane:dichloromethane 100:0 to 0:100) to afford 1.54 g 4-iodo-1-isopropyl-3-(4-methyl-2-thienyl)-1H-pyrazole (82% yield).

logP (pH2.7): 4.26
MS (ESI): 333.0 ([M+H]$^+$)
$^1$H-NMR (600 MHz, d$_6$-DMSO): δ=7.79 (d, 1H), 7.10 (s, 1H), 6.52 (d, 1H), 4.48 (sept, 1H), 2.14 (s, 3H), 1.42 (d, 6H) ppm 1-sec-Butyl-4-iodo-3-(4-methyl-2-thienyl)-1H-pyrazole To a solution of 1-sec-butyl-3-(4-methyl-2-thienyl)-1H-pyrazole (4.9 mmol) in 14 mL dry 1V,N-dimethylformamide under argon atmosphere was added N-iodosuccinimide (5.1 mmol) in small portions at 0° C. The reaction mixture was allowed to warm to room temperature and was stirred overnight. 5% aqueous sodium thiosulfate solution and saturated aqueous sodium carbonate solution were added and the mixture was stirred at room temperature for 1 h, then extracted with MTBE. The combined organic extracts were successively washed with water and brine, dried over MgSO$_4$, filtered and concentrated. The residue was purified by chromatography on silica gel (cyclohexane:dichloromethane 100:0 to 0:100) to afford 1.36 g 1-sec-butyl-4-iodo-3-(4-methyl-2-thienyl)-1H-pyrazole (78% yield).

logP (pH2.7): 4.79
MS (ESI): 346.9 ([M+H]$^+$)
$^1$H-NMR (600 MHz, d$_6$-DMSO): δ=7.78 (d, 1H), 7.10 (s, 1H), 6.52 (d, 1H), 4.23 (m, 1H), 2.14 (s, 3H), 1.75 (m, 2H), 1.40 (d, 3H), 0.72 (t, 3H) ppm 4-Iodo-1-methyl-5-propyl-3-(2-thienyl)-1H-pyrazole To a solution of 1-methyl-5-propyl-3-(2-thienyl)-1H-pyrazole (2.5 mmol) in 7 mL dry N,N-dimethylformamide under argon atmosphere was added N-iodosuccinimide (2.6 mmol) in small portions at 0° C. The reaction mixture was allowed to warm to room temperature and stirred overnight. 5% aqueous sodium thiosulfate solution and saturated aqueous sodium carbonate solution were added and the mixture was stirred at room temperature for 1 h, then extracted with MTBE. The combined organic extracts were successively washed with water and brine, dried over MgSO$_4$, filtered and concentrated to afford 720 mg of 4-iodo-1-methyl-5-propyl-3-(2-thienyl)-1H-pyrazole (88% yield) that was used in the next step without further purification.

logP (pH2.7): 3.92
MS (ESI): 332.9 ([M+H]$^+$)
$^1$H-NMR (600 MHz, d$_6$-DMSO): δ=7.69 (dd, 1H), 7.52 (dd, 1H), 7.13 (dd, 1H), 3.86 (s, 3H), 2.69 (t, 2H), 1.56 (m, 2H), 0.95 (t, 3H) ppm 4-Iodo-1-methyl-3-(3-methyl-2-thienyl)-5-propyl-1H-pyrazole and 4-iodo-1-methyl-5-(3-methyl-2-thienyl)-3-propyl-1H-pyrazole To a mixture of 1-methyl-3-(3-methyl-2-thienyl)-5-propyl-1H-pyrazole and 1-methyl-5-(3-methyl-2-thienyl)-3-propyl-1H-pyrazole (85:15, 3.7 mmol) in 10 mL dry N,N-dimethylformamide under argon atmosphere was added N-iodosuccinimide (4.6 mmol) in small portions. The reaction mixture was stirred at room temperature overnight. 5% aqueous sodium thiosulfate solution and saturated aqueous sodium carbonate solution were added and the mixture was stirred at room temperature for 1 h, then extracted with MTBE. The combined organic extracts were successively washed with water and brine, dried over MgSO$_4$, filtered and concentrated. The residue was purified by chromatography on silica gel (toluene:ethyl acetate 100:0 to 0:100) to afford 928 mg of a mixture of 4-iodo-1-methyl-3-(3-methyl-2-thienyl)-5-propyl-1H-pyrazole and 4-iodo-1-methyl-5-(3-methyl-2-thienyl)-3-propyl-1H-pyrazole (85:15; 61% yield) that was used in the next step without further purification.

4-Iodo-1-methyl-3-(3-methyl-2-thienyl)-5-propyl-1H-pyrazole logP (pH2.7): 4.03
MS (ESI): 347.0 ([M+H]$^+$)
$^1$H-NMR (400 MHz, d$_6$-DMSO): δ=7.47 (d, 1H), 6.98 (d, 1H), 3.87 (s, 3H), 2.69 (t, 2H), 2.21 (s, 3H), 1.57 (m, 2H), 0.95 (t, 3H) ppm 4-Iodo-1-methyl-5-(3-methyl-2-thienyl)-3-propyl-1H-pyrazole logP (pH2.7): 4.27
MS (ESI): 347.0 ([M+H]$^+$)
$^1$H-NMR (400 MHz, d$_6$-DMSO): δ=7.71 (d, 1H), 7.10 (d, 1H), 3.63 (s, 3H), 2.69 (t, 2H), 2.04 (s, 3H), 1.58 (m, 2H), 0.95 (t, 3H) ppm Preparation of Starting Materials of the Formula (VII)

3-(5-Chloro-2-thienyl)-1-isobutyl-4-(4,4,5,5-tetramethyl-1,3,2-dioxaborolan-2-yl)-1H-pyrazole To a solution of 4-bromo-3-(5-chloro-2-thienyl)-1-isobutyl-1H-pyrazole (1 eq, 0.015 mol), triethylamine (8.15 eq, 0.128 mol) and 1,1'-bis(diphenylphosphino)ferrocenepalladium(II)dichloride (767 mg) in dry acetonitrile (60 mL) was added pinacol diborane (3 eq, 0.046 mol) drop wise at room temperature. The resulting mixture was heated at 80° C. for 12 h. After completion reaction monited by TLC, the reaction mixture was cooled to room temperature, poured into ice cold water and extracted with diethyl ether. The combined organic layers were washed with water, brine, dried over anhydrous Na2SO4, filtered and evaporated. The residue was purified by column chromatography to afford 3 g of 3-(5-chloro-2-thienyl)-1-isobutyl-4-(4,4,5,5-tetramethyl-1,3,2-dioxaborolan-2-yl)-1H-pyrazole (82% yield).

1H NMR (CDCl$_3$, 300 MHz): δ=7.7 (1H, d), 7.5 (1H, s), 6.8 (1H, d), 3.8 (2H, d), 2.2 (1H, m), 1.3 (12H, s), 0.9 (6H, d).

3-(5-Chloro-2-thienyl)-1-isopropyl-5-methyl-4-(4,5,5-tetramethyl-1,3,2-dioxaborolan-2-yl)-1H-pyrazole To a solution of 3-(5-chloro-2-thienyl)-4-iodo-1-isopropyl-5-methyl-1H-pyrazole (11.3 mmol), dry triethylamine (96.1 mmol) and 1,1'-bis(diphenylphosphino)ferrocene-palladium(II)dichloride dichloromethane complex (0.79 mmol) in 75 mL of dry acetonitrile was added pinacolborane (33.9 mmol) dropwise at room temperature. The reaction mixture was stirred at 80° C. overnight. After cooling to room temperature, the reaction mixture was poured into cold water and extracted with ethyl acetate. The combined organic extracts were washed with brine, dried over MgSO$_4$, filtered and concentrated. The residue was purified by triturating in petroleum ether to afford 2.2 g 3-(5-chloro-2-thienyl)-1-isopropyl-5-methyl-4-(4,4,5,5-tetramethyl-1,3,2-dioxaborolan-2-yl)-1H-pyrazole (55% yield).

$^1$H-NMR (400 MHz, CDCl$_3$): δ=7.61 (d, 1H), 6.81 (d, 1H), 4.41 (sept, 1H), 2.46 (s, 3H), 1.46 (d, 6H), 1.33 (s, 12H) ppm

Preparation of Starting Materials of the Formula (XII)

N-[4-(4,4,5,5-Tetramethyl-1,3,2-dioxaborolan-2-yl)pyridin-2-yl]acetamide

To a solution of 4-bromo-2-aminopyridine (87 mmol) and pyridine (130 mol) in 200 mL dichloromethane was added dropwise acetyl chloride (117 mmol). The reaction mixture was stirred at room temperature for 4 h. Water was added and the reaction mixture was extracted with dichloromethane. The combined organic layers were washed with brine, dried over Na$_2$SO$_4$ and concentrated. The residue was washed with hexane to afford 13.5 g of N-(4-bromopyridin-2-yl)acetamide (72% yield).

$^1$H-NMR (400 MHz, CDCl$_3$): δ=8.46 (s, 1H), 8.44 (bs, 1H), 8.07 (d, 1H), 7.20 (dd, 1H), 2.20 (s, 3H) ppm A mixture of N-(4-bromopyridin-2-yl)acetamide (63 mmol), bis(pinacolato)diboron (75 mmol), potassium acetate (188 mmol) and [1,1'-bis(diphenylphosphino)ferrocene]dichloropalladium(II) (3.1 mmol) in 500 mL dry dioxane was stirred under argon atmosphere at 80° C. for 3 h. The reaction mixture was filtered and washed with dichloromethane. The filtrate was concentrated and washed with diethyl ether to afford 7.80 g of N-[4-(4,4,5,5-tetramethyl-1,3,2-dioxaborolan-2-yl)pyridin-2-yl]acetamide (47% yield).

$^1$H-NMR (400 MHz, CDCl$_3$): δ=8.50 (bs, 1H), 8.27 (d, 1H), 8.19 (bs, 1H), 7.37 (d, 1H), 2.21 (s, 3H), 1.34 (s, 12H) ppm

N-[4-(4,4,5,5-Tetramethyl-1,3,2-dioxaborolan-2-yl)pyridin-2-yl]propanamide

To a solution of 4-bromo-2-aminopyridine (580 mmol) in 1.5 L dichloromethane was added pyridine (1.16 mol). The mixture was stirred for 20 min. Propionyl chloride (669 mmol) was added dropwise. The reaction mixture was stirred at room temperature for 5 h. Water was added and the reaction mixture was extracted with dichloromethane. The combined organic layer was washed with brine, dried and concentrated. The residue was recrystallized from hexane/ethyl acetate (6:1) to afford 112 g of N-(4-bromopyridin-2-yl)propanamide (85% yield).

$^1$H-NMR (300 MHz, CDCl$_3$): δ=8.50 (d, 1H), 8.46 (bs, 1H), 8.06 (d, 1H), 7.19 (dd, 1H), 2.42 (q, 2H), 1.23 (t, 3H) ppm $^1$H-NMR (400 MHz, d$_6$-DMSO): δ=10.65 (bs, 1H), 8.30 (d, 1H), 8.19 (d, 1H), 7.33 (dd, 1H), 2.38 (q, 2H), 1.04 (t, 3H) ppm A mixture of N-(4-bromopyridin-2-yl)propionamide (262 mmol), bis(pinacolato)diboron (340 mmol), potassium acetate (785 mmol) and [1,1'-bis(diphenylphosphino)ferrocene]dichloropalladium(II) (13.1 mmol) in 2.0 L dry dioxane was stirred under argon atmosphere at 80° C. for 4 h. The reaction mixture was filtered and washed with dichloromethane. The filtrate was concentrated. The residue was recrystallized in hexane/ethyl acetate (8:1) to afford 50 g of N-[4-(4,4,5,5-tetramethyl-1,3,2-dioxaborolan-2-yl)pyridin-2-yl]propanamide (69% yield).

$^1$H-NMR (400 MHz, CDCl$_3$): δ=8.55 (bs, 1H), 8.43 (bs, 1H), 8.26 (m, 1H), 7.35 (m, 1H), 2.42 (q, 2H), 1.33 (s, 12H), 1.24 (t, 3H) ppm $^1$H-NMR (300 MHz, d$_6$-DMSO): δ=10.40 (bs, 1H), 8.36 (bs, 1H), 8.32 (m, 1H), 7.24 (m, 1H), 2.39 (q, 2H), 1.31 (s, 12H), 1.06 (t, 3H) ppm

2-Methoxy-N-[4-(4,4,5,5-tetramethyl-1,3,2-dioxaborolan-2-yl)pyridin-2-yl]acetamide To a solution of 4-bromo-2-aminopyridine (173 mmol) and pyridine (347 mol) in 250 mL dichloromethane was added dropwise 2-methoxyacetyl chloride (208 mmol). The reaction mixture was stirred at room temperature for 3 h. Water was added and the reaction mixture was extracted with dichloromethane. The combined organic layers were washed with brine, dried over Na$_2$SO$_4$ and concentrated. The residue was washed with hexane to afford 35.0 g of N-(4-bromopyridin-2-yl)-2-methoxyacetamide (82% yield).

$^1$H-NMR (300 MHz, CDCl$_3$): δ=8.89 (bs, 1H), 8.49 (d, 1H), 8.11 (d, 1H), 7.22 (dd, 1H), 4.03 (s, 2H), 3.49 (s, 3H) ppm A mixture of N-(4-bromopyridin-2-yl)-2-methoxyacetamide (143 mmol), bis(pinacolato)diboron (186 mmol), potassium acetate (428 mmol) and [1,1'-bis(diphenylphosphino)ferrocene]dichloropalladium(II) (7.1 mmol) in 500 mL dry dioxane was stirred under argon atmosphere at 80° C. for 3 h. Water was added to the reaction mixture. After extraction with ethyl acetate, the combined organic layers were washed with brine, dried over Na$_2$SO$_4$ and concentrated. The residue was washed with hexane/diethyl ether (4:1) to afford 15.8 g 2-methoxy-N-[4-(4,4,5,5-tetramethyl-1,3,2-dioxaborolan-2-yl)pyridin-2-yl]acetamide (38% yield).

$^1$H-NMR (400 MHz, CDCl$_3$): δ=8.82 (bs, 1H), 8.53 (s, 1H), 8.31 (dd, 1H), 7.39 (dd, 1H), 4.03 (s, 2H), 3.49 (s, 3H), 1.33 (s, 12H) ppm

2-Cyclopropyl-N-[4-(4,4,5,5-tetramethyl-1,3,2-dioxaborolan-2-yl)pyridin-2-yl]acetamide To a solution of 2-cyclopropylacetic acid (250 mmol) in DCM was added 1 mL of DMF. Oxalyl chloride (312 mmol) was added dropwise and the reaction mixture was stirred overnight at room temperature. The reaction mixture was concentrated to afford 30.3 g of the crude acid chloride that was added dropwise to a solution of 4-bromo-2-aminopyridine (202 mmol) and pyridine (506 mol) in 500 mL dichloromethane. The reaction mixture was stirred at room temperature for 4 h. Water was added and the reaction mixture was extracted with dichloromethane. The combined organic layers were washed with brine, dried and concentrated. The residue was purified by chromatography on silica gel to afford 26.0 g of N-(4-bromopyridin-2-yl)-2-cyclopropylacetamide (50% yield).

$^1$H-NMR (400 MHz, CDCl$_3$): δ=8.51 (d, 1H), 8.39 (bs, 1H), 8.07 (m, 1H), 7.20 (m, 1H), 2.35 (d, 2H), 1.07 (m, 1H), 0.71 (m, 2H), 0.28 (m, 2H) ppm A mixture of N-(4-bromopyridin-2-yl)-2-cyclopropylacetamide (102 mmol), bis(pinacolato)diboron (133 mmol), potassium acetate (306 mmol) and [1,1'-bis(diphenylphosphino)ferrocene]dichloropalladium(II) (5.1 mmol) in 500 mL dry dioxane was stirred under argon atmosphere at 80° C. for 3.5 h. The reaction mixture was filtered and washed with dichloromethane. The filtrate was concentrated and washed with diethyl ether to afford 17.2 g 2-cyclopropyl-N-[4-(4,4,5,5-tetramethyl-1,3,2-dioxaborolan-2-yl)pyridin-2-yl]acetamide (56% yield).

$^1$H-NMR (300 MHz, CDCl$_3$): δ=8.57 (bs, 1H), 8.28 (m, 2H), 7.37 (d, 1H), 2.35 (d, 2H), 1.34 (s, 12H), 1.11 (m, 1H), 0.70 (m, 2H), 0.27 (m, 2H) ppm tert-Butyl[4-(4,4,5,5-tetramethyl-1,3,2-dioxaborolan-2-yl)pyridin-2-yl]carbamate To a solution of 4-bromo-2-aminopyridine (54.9 mmol) in 150 mL dioxane was added di-tert-butyl dicarbonate (71.4 mmol). The reaction mixture was refluxed for 4 h. The mixture was concentrated and the residue was purified by chromatography on silica gel (hexane:ethyl acetate 30:1 to 20:1) to afford 8.21 g of N-tert-butyl (4-bromopyridin-2-yl)carbamate (55% yield).

$^1$H-NMR (300 MHz, d$_6$-DMSO): δ=10.08 (bs, 1H), 8.14 (d, 1H), 8.04 (d, 1H), 7.27 (dd, 1H), 1.47 (s, 9H) ppm A mixture of N-tert-butyl (4-bromopyridin-2-yl)carbamate (36.6 mmol), bis(pinacolato)diboron (42.1 mmol), potassium acetate (110 mmol) and [1,1'-bis(diphenylphosphino)ferrocene]dichloropalladium(II) (1.6 mmol) in 150 mL dry dioxane was stirred under argon atmosphere at 80° C. for 1.5 h. Water was added and the reaction mixture was extracted with ethyl acetate. The combined organic layers were washed with brine, dried and concentrated. The residue was washed with hexane and diethyl ether to afford 8.1 g of the crude product. Recrystallization (ethyl acetate/diethyl ether) afforded 5.01 g of pure tert-butyl[4-(4,4,5,5-tetramethyl-1,3,2-dioxaborolan-2-yl)pyridin-2-yl]carbamate (43% yield).

$^1$H-NMR (400 MHz, d$_6$-DMSO): δ=9.79 (bs, 1H), 8.26 (dd, 1H), 8.09 (s, 1H), 7.17 (dd, 1H), 1.47 (s, 9H), 1.31 (s, 12H) ppm Preparation of Compound of the Formula (Iz)

4-[3-(5-chloro-2-thienyl)-1-isobutyl-1H-pyrazol-4-yl]quinoline

To a degassed solution of acetonitrile (4 mL) and water (1 mL) were added potassium carbonate (4 eq, 2.8 mmol), 3-(5-chloro-2-thienyl)-1-isobutyl-4-(4,4,5,5-tetramethyl-1,3,2-dioxaborolan-2-yl)-1H-pyrazole (1 eq, 0.7 mmol), 4-bromoquinoline (1 eq, 0.7 mmol) and 1,1'-bis(diphenylphosphinoferrocene)palladium(II)dichloride (0.1 eq, 0.07 mmol). The mixture was stirred at 130° C. in the microwave for 60 min. The solvent was evaporated and water and dichloromethane were added. The aqueous layer was extracted two times with dichloromethane. The combined organic extracts were dried over MgSO4 filtered and concentrated. The residue was purified by chromatography on silica gel (dichloromethane:methanol 1:0 to 9:1) to afford 45 mg of 4-[3-(5-chloro-2-thienyl)-1-isobutyl-1H-pyrazol-4-yl]quinoline (15% yield).

logP (pH2.7): 3.69

MS (ESI): 368 ([M+H]$^+$)

1H-NMR (400 MHz, CDCl$_3$): δ=8.96 (d, 1H), 8.27 (d, 1H), 7.83 (m, 2H), 7.52 (m, 2H), 7.44 (d, 1H), 6.58 (d, 1H), 6.33 (d, 1H), 4.04 (d, 2H), 2.38 (m, 1H), 1.05 (d, 6H) ppm 6-[3-(5-chloro-2-thienyl)-1-isobutyl-1H-pyrazol-4-yl]pyrimidin-4-amine To a degassed solution of acetonitrile (4 mL) and water (1 mL) were added potassium carbonate (4 eq, 2.8 mmol), 3-(5-chloro-2-thienyl)-1-isobutyl-4-(4,4,5,5-tetramethyl-1,3,2-dioxaborolan-2-yl)-1H-pyrazole (1 eq, 0.7 mmol), 4-amino-6-chloropyrimidine (1.1 eq, 0.77 mmol) and 1,1'-bis(diphenylphosphinoferrocene)palladium(II)dichloride (0.1 eq, 0.07 mmol). The mixture was stirred at 130° C. in the microwave for 60 min. At room temperature, the mixture was filtered over celite and the filtrate was evaporated. The residue was purified by chromatography on silica gel (dichloromethane:methanol 1:0 to 9:1) to afford 12 mg of 6-[3-(5-chloro-2-thienyl)-1-isobutyl-1H-pyrazol-4-yl]pyrimidin-4-amine (5% yield).

logP (pH2.7): 1.97

MS (ESI): 334 ([M+H]$^+$)

1H-NMR (400 MHz, CDCl$_3$): δ=8.58 (s, 1H), 7.90 (s, 1H), 7.14 (d, 1H), 6.87 (d, 1H), 6.53 (s, 1H), 4.95 (bs, 2H), 3.94 (d, 2H), 2.28 (m, 1H), 0.97 (d, 6H) ppm 4-[1-Ethyl-3-(2-thienyl)-1H-pyrazol-4-yl]pyridine 4-(4,4,5,5-Tetramethyl-1,3,2-dioxaborolan-2-yl)pyridine (0.60 mmol) and bis(tricyclohexylphosphine)palladium(II) chloride (0.05 mmol) were weighed into a microwave vial (reaction volume 2-5 mL). A solution of 1-ethyl-4-iodo-3-(2-thienyl)-1H-pyrazole (0.50 mmol) in 3.3 mL degassed dioxane and 1.1 mL of a degassed 2 M aqueous sodium carbonate solution were added. The reaction mixture was purged with argon, the microwave vial was capped with a septum and transferred to a laboratory microwave oven. The reaction mixture was irradiated to a reaction temperature of 120° C. for 15 min. After cooling to room temperature, the reaction mixture was diluted with water and extracted with dichloromethane. The combined organic phases were washed with brine, dried over MgSO$_4$, filtered and concentrated. The residue was purified by chromatography on silica gel (cyclohexane:ethyl acetate 95:5 to 0:100) to afford 105 mg 4-[1-ethyl-3-(2-thienyl)-1H-pyrazol-4-yl]pyridine (82% yield).

logP (pH2.7): 0.75

MS (ESI): 256.0 ([M+H]$^+$)

$^1$H-NMR (600 MHz, d$_6$-DMSO): δ=8.52 (dd, 2H), 8.20 (s, 1H), 7.54 (dd, 1H), 7.35 (dd, 2H), 7.05 (m, 1H), 7.02 (m, 1H), 4.19 (q, 2H), 1.44 (t, 3H) ppm N-{4-[1-Ethyl-3-(2-thienyl)-1H-pyrazol-4-yl]pyridin-2-yl}propanamide N-[4-(4,4,5,5-Tetramethyl-1,3,2-dioxaborolan-2-yl)pyridin-2-yl]propanamide (0.60 mmol) and bis(tricyclohexylphosphine)palladium(II) chloride (0.05 mmol) were weighed into a microwave vial (reaction volume 2-5 mL). A solution of 1-ethyl-4-iodo-3-(2-thienyl)-1H-pyrazole (0.50 mmol) in 3.3 mL degassed dioxane and 1.1 mL of a degassed 2 M aqueous sodium carbonate solution were added. The reaction mixture was purged with argon, the microwave vial was capped with a septum and transferred to a laboratory microwave oven. The reaction mixture was irradiated to a reaction temperature of 120° C. for 15 min. After cooling to room temperature, the reaction mixture was diluted with water and extracted with dichloromethane. The combined organic phases were washed with brine, dried over $MgSO_4$, filtered and concentrated. The residue was purified by chromatography on silica gel (cyclohexane:ethyl acetate 95:5 to 0:100) to afford 152 mg N-{4-[1-ethyl-3-(2-thienyl)-1H-pyrazol-4-yl]pyridin-2-yl}propanamide (93% yield).

logP (pH2.7): 1.65

MS (ESI): 327.1 ([M+H]$^+$)

$^1$H-NMR (600 MHz, d$_6$-DMSO): δ=10.45 (s, 1H), 8.24 (dd, 1H), 8.17 (s, 1H), 8.12 (s, 1H), 7.50 (dd, 1H), 7.05 (m, 1H), 7.01 (m, 2H), 4.19 (q, 2H), 2.38 (q, 2H), 1.44 (t, 3H), 1.05 (t, 3H) ppm 4-[1-sec-Butyl-3-(4-chloro-2-thienyl)-1H-pyrazol-4-yl]pyridine 4-(4,4,5,5-Tetramethyl-1,3,2-dioxaborolan-2-yl)pyridine (0.48 mmol) and bis(tricyclohexylphosphine)palladium(II) chloride (0.04 mmol) were weighed into a microwave vial (reaction volume 2-5 mL). A solution of 1-sec-butyl-3-(4-chloro-2-thienyl)-4-iodo-1H-pyrazole (0.40 mmol) in 3.0 mL degassed dioxane and 1.0 mL of a degassed 2 M aqueous sodium carbonate solution were added. The reaction mixture was purged with argon, the microwave vial was capped with a septum and transferred to a laboratory microwave oven. The reaction mixture was irradiated to a reaction temperature of 120° C. for 12 min. After cooling to room temperature, the reaction mixture was diluted with dioxane and filtered through a short pad of silica. The filtered solid was washed thoroughly with dioxane, ethyl acetate and dichloromethane. The combined filtrates were concentrated in vacuum. The residue was purified by chromatography on silica gel (cyclohexane:ethyl acetate 97:3 to 0:100) to afford 34 mg 4-[1-sec-butyl-3-(4-chloro-2-thienyl)-1H-pyrazol-4-yl]pyridine (27% yield).

logP (pH2.7): 1.83

MS (ESI): 318.1 ([M+H]$^+$)

$^1$H-NMR (400 MHz, d$_6$-DMSO): δ=8.55 (dd, 2H), 8.24 (s, 1H), 7.56 (d, 1H), 7.38 (dd, 2H), 6.94 (d, 1H), 4.33 (m, 1H), 1.81 (m, 2H), 1.46 (d, 3H), 0.81 (t, 3H) ppm N-{4-[1-sec-Butyl-3-(4-chloro-2-thienyl)-1H-pyrazol-4-yl]pyridin-2-yl}propanamide N-[4-(4,4,5,5-Tetramethyl-1,3,2-dioxaborolan-2-yl)pyridin-2-yl]propanamide (0.48 mmol) and bis(tricyclohexylphosphine)palladium(II) chloride (0.04 mmol) were weighed into a microwave vial (reaction volume 2-5 mL). A solution of 1-sec-butyl-3-(4-chloro-2-thienyl)-4-iodo-1H-pyrazole (0.40 mmol) in 3.0 mL degassed dioxane and 1.0 mL of a degassed 2 M aqueous sodium carbonate solution were added. The reaction mixture was purged with argon, the microwave vial was capped with a septum and transferred to a laboratory microwave oven. The reaction mixture was irradiated to a reaction temperature of 120° C. for 12 min. After cooling to room temperature, the reaction mixture was diluted with dioxane and filtered through a short pad of silica. The filtered solid was washed thoroughly with dioxane, ethyl acetate and dichloromethane. The combined filtrates were concentrated in vacuum. The residue was purified by chromatography on silica gel (cyclohexane:ethyl acetate 97:3 to 0:100) to afford 155 mg N-{4-[1-sec-butyl-3-(4-chloro-2-thienyl)-1H-pyrazol-4-yl]pyridin-2-yl}propanamide (99% yield).

logP (pH2.7): 1.65

MS (ESI): 327.1 ([M+H]$^+$)

$^1$H-NMR (600 MHz, d$_6$-DMSO): δ=10.45 (s, 1H), 8.24 (dd, 1H), 8.17 (s, 1H), 8.12 (s, 1H), 7.50 (dd, 1H), 7.05 (m, 1H), 7.01 (m, 2H), 4.19 (q, 2H), 2.38 (q, 2H), 1.44 (t, 3H), 1.05 (t, 3H) ppm Preparation of Starting Materials of the Formula (XIV)

4-[1-(tetrahydro-2H-pyran-2-yl)-1H-pyrazol-4-yl]pyridine

A mixture of tetrakis(triphenylphosphine)palladium(0) (0.025 eq, 4.22 mmol), 4-bromo-1-(tetrahydro-2H-pyran-2-yl)-1H-pyrazole (1 eq, 0.17 mol, synthesis described in US2009/203705), sodium carbonate (675 mL, 2.0 M solution in water, 1.35 mol) and 4-pyridine boronic acid (1.2 eq, 0.21 mol) in dioxane (2000 mL) was heated under argon 41 h at 80° C. After that time, the reaction mixture was diluted with water (50 mL) and the volatiles were reduced in vacuo to a quarter of the volume. The crude was extracted with ethyl acetate and the combined organic fractions were washed with brine, dried over MgSO4 and evaporated. The obtained crude material was purified by bulb-to-bulb distillation (bp 130-135° C. at 0.02 mm Hg) and 26.37 g (68%) 4-[1-(tetrahydro-2H-pyran-2-yl)-1H-pyrazol-4-yl]pyridine were obtained as slightly yellow viscous oil.

1H-NMR (400 MHz, CD$_3$CN): δ=8.50-8.49 (m, 2H), 8.20 (s, 1H), 7.94 (s, 1H), 7.54-7.48 (m, 2H), 5.41-5.39 (dd, 1H), 4.02-3.98 (m, 1H), 3.72-3.66 (m, 1H), 2.17-2.10 (m, 1H), 2.00-1.90 (m, 1H), 1.75-1.55 (m, 4H) ppm logP (pH2.7): 0.38

MS (ESI): 230.1 ([M+H]+)

4-[1-(tetrahydro-2H-pyran-2-yl)-5-(tributylstannyl)-1H-pyrazol-4-yl]pyridine

A solution of n-butyllithium in hexane (13.5 mL; 2.5M) was added to a solution of 4-[1-(tetrahydro-2H-pyran-2-yl)-1H-pyrazol-4-yl]pyridine (7 g) in THF (200 mL), during 3 min at −70° C. under nitrogen atmosphere and stirring was continued at this temperature for addition 1 hour. Then Bu$_3$SnCl (9.5 g) was added and the reaction mixture was allowed to warm to room temperature and stirred at this temperature for 15 min.

All of volatile materials were evaporated in vacuo and the residue was distilled under reduced pressure (0.1 Torr) collecting the fraction with b.p.≥130° C. This crude product was purified again by column chromatography (hexane/ether=1:4 eluent; 9–Rf=0.43 in ether) giving target compound 4-[1-(tetrahydro-2H-pyran-2-yl)-5-(tributylstannyl)-1H-pyrazol-4-yl]pyridine (7.5 g; 45%).

logP (pH2.7): 4.89

MS (ESI): 520.2 ([M+H]+)

1H-NMR (400 MHz, CD3CN): d=8.53-8.52 (m, 2H), 7.66 (s, 1H), 7.26-7.25 (m, 2H), 5.28-5.26 (m, 1H), 3.92-3.90 (m, 1H), 3.68-3.64 (m, 1H), 2.40-2.38 (m, 1H), 2.05-2.00 (m, 2H), 1.70-1.55 (m, 3H), 1.45-1.35 (m, 6H), 1.25-1.20 (m, 6H), 1.02 (m, 6H), 0.81 (t, 9H) ppm Preparation of Compound of the Formula (I)

N-Butyl-5-[4-(pyridin-4-yl)-1H-pyrazol-3-yl]thiophene-2-carboxamide hydrochloride To a solution of 51 mg (0.10 mmol) 4-[1-(tetrahydro-2H-pyran-2-yl)-5-(tributylstannyl)-1H-pyrazol-4-yl]pyridine and 31 mg (0.15 mmol) 5-bromothiophene-2-carboxamide (synthesis described in WO2007/131991) in 1 mL N,N-dimethylformamide in a microwave vial is added 2 mg (0.01 mmol) Copper(I) iodide, 30 mg (0.2 mmol) cesium fluoride and 17 mg (0.015 mmol) Tetrakis(triphenylphosphin)palladium(0). The mixture is purged with nitrogen for 5 min and the vial is sealed. The reaction mixture is heated for 20 min at 150° C. in the microwave (CEM Explorer). After cooling, the crude mixture is filtered through a pad of celite and the volatiles are removed in vacuo. The crude product is purified by preparative HPLC (Phenomenex Axia, Gemini 5 µm, 50×21 mm; Gradient: 0-1.5 min 95% water, 5% aqueous 10% NaHCO3, 1.5-8.0 min linear gradient to 25% water, 70% acetonitrile, 5% aqueous 10% NaHCO3, 8.0-12.0 min 25% water, 70% acetonitrile, 5% aqueous 10% NaHCO3). The obtained material is treated with 500 µL 4M HCl in dioxane and stirred overnight at room temperature. After removal of the volatiles and trituration of the solid with diethyl ether 8.5 mg (15%) N-butyl-5-[4-(pyridin-4-yl)-1H-pyrazol-3-yl]thiophene-2-carboxamide hydrochloride are obtained.

logP (pH2.7): 1.47

MS (ESI): 321.0 ([M+H]+)

1-{5-[4-(pyridin-4-yl)-1H-pyrazol-3-yl]-2-thienyl}ethanone hydrochloride

To a solution of 51 mg (0.10 mmol) 4-[1-(tetrahydro-2H-pyran-2-yl)-5-(tributylstannyl)-1H-pyrazol-4-yl]pyridine and 31 mg (0.15 mmol) 1-(5-bromo-2-thienyl)ethanone (synthesis described in U.S. Pat. No. 4,839,365) in 1 mL N,N-dimethylformamide in a microwave vial is added 2 mg (0.01 mmol) Copper(I) iodide, 30 mg (0.2 mmol) cesium fluoride and 17 mg (0.015 mmol) Tetrakis(triphenylphosphin)palladium(0). The mixture is purged with nitrogen for 5 min and the vial is sealed. The reaction mixture is heated for 20 min at 150° C. in the microwave (CEM Explorer). After cooling, the crude mixture is filtered through a pad of celite and the volatiles are removed in vacuo. The crude product is purified by preparative HPLC (Phenomenex Axia, Gemini 5 µm, 50×21 mm; Gradient: 0-1.5 min 95% water, 5% aqueous 10% NaHCO3, 1.5-8.0 min linear gradient to 25% water, 70% acetonitrile, 5% aqueous 10% NaHCO3, 8.0-12.0 min 25% water, 70% acetonitrile, 5% aqueous 10% NaHCO3). The obtained material is treated with 500 µL 4M HCl in dioxane and stirred overnight at room temperature. After removal of the volatiles and trituration of the solid with diethyl ether 19.2 mg (63%) 1-{5-[4-(pyridin-4-yl)-1H-pyrazol-3-yl]-2-thienyl}ethanone hydrochloride are obtained.

logP (pH2.7): 0.62

MS (ESI): 270.2 ([M+H]+)

4-[3-(5-trifluoromethyl-2-thienyl)-1H-pyrazol-4-yl]pyridine hydrochloride and 4-[1-(2-tetrahydropyrannyl)-5-(5-trifluoromethyl-2-thienyl)-1H-pyrazol-4-yl]pyridine To a solution of 4-[1-(tetrahydro-2H-pyran-2-yl)-5-(tributylstannyl)-1H-pyrazol-4-yl]pyridine (1 eq, 0.55 mmol) and 31 mg (0.15 mmol) 2-bromo-5-trifluoromethylthiophene (synthesis described in Journal of Fluorine Chemistry, 2010, vol. 131(1), 98) in 2 mL degassed toluene in a microwave vial was added potassium iodide (0.1 eq, 0.055 mmol), cesium fluoride (2 eq, 1.1 mmol) and tetrakis(triphenylphosphin)palladium(0) (0.15, 0.083 mmol). The mixture is purged with nitrogen for 5 min and the vial is sealed. The reaction mixture is heated for 30 min at 140° C. in the microwave. After cooling, the crude mixture was filtered through a pad of celite. Water was then added to the filtrate and the aqueous layer was extracted three times with ethyl acetate. The combined organic extracts were dried over MgSO4, filtered and concentrated. The residue was purified by chromatography on silica gel (heptane:ethyl acetate 8:2 to 3:7) to afford 150 mg of 4-[1-(2-tetrahydropyrannyl)-5-(5-trifluoromethyl-2-thienyl)-1H-pyrazol-4-yl]pyridine (68% yield).

logP (pH2.7): 1.96

MS (ESI): 380 ([M+H]+)

1H-NMR (400 MHz, CDCl$_3$): δ=8.51 (d, 2H), 7.88 (s, 1H), 7.51 (m, 1H), 7.15 (m, 3H), 5.18 (dd, 1H), 4.08 (m, 1H), 3.59 (m, 1H), 2.54 (m, 2H), 2.10 (m, 1H), 1.95 (m, 1H), 1.63 (m, 2H) ppm The solid is treated with 4 mL of 4M hydrochloric acid in dioxane and stirred overnight at room temperature. The resulting precipitate was filtered and dried to afford 100 mg of 4-[3-(5-trifluoromethyl-2-thienyl)-1H-pyrazol-4-yl]pyridine hydrochloride (49% yield).

logP (pH2.7): 1.34

MS (ESI): 296 ([M+H]+)

4-[1-isopropyl-(3/5)-(5-trifluoromethyl-2-thienyl)-1H-pyrazol-4-yl]pyridine

To a solution of 4-[3-(5-trifluoromethyl-2-thienyl)-1H-pyrazol-4-yl]pyridine hydrochloride (1 eq, 0.19 mmol) in 0.5 mL N,N-dimethylformamide were added 2-iodopropane (1.5 eq, 0.29 mmol) and cesium carbonate (2.5 eq, 0.48 mmol). The reaction mixture was stirred overnight at room temperature and the solvent was then evaporated. The residue was diluted with water and extracted three times with dichloromethane. The combined organic extracts were dried over MgSO4 filtered and concentrated. The residue was purified by chromatography on silica gel (heptane:ethyl acetate 8:2 to 3:7) to afford 26 mg of 44-[1-isopropyl-(3/5)-(5-trifluoromethyl-2-thienyl)-1H-pyrazol-4-yl]pyridine (36% yield, mixture of isomer 90:10).

logP (pH2.7): 2.20 (2.08 minor isomer)

MS (ESI): 338 ([M+H]$^+$)

$^1$H-NMR (400 MHz, CDCl$_3$): δ=8.48 (d, 2H$^{major}$), 7.51 (s, 1H$^{major}$), 7.21 (m, 3H$^{major}$), 6.84 (m, 1H$^{major}$), 4.45 (m, 1H$^{major}$), 1.48 (d, 6H$^{major}$), 1.41 (d, 6H$^{minor}$) ppm

EXAMPLES
The compounds of the formula (I) listed in Table 1 can be obtained analogously to the methods given above.
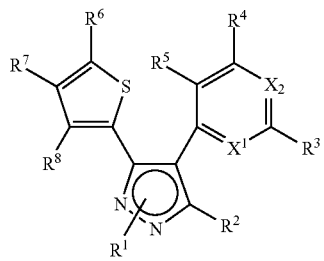
(I)
With $R^4$=H and $R^5$=H the following types result:
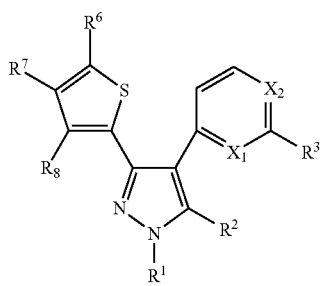
(IA)
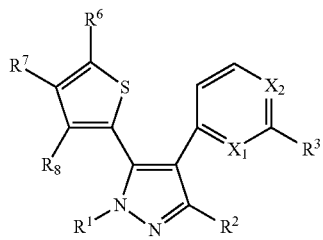
(IB)
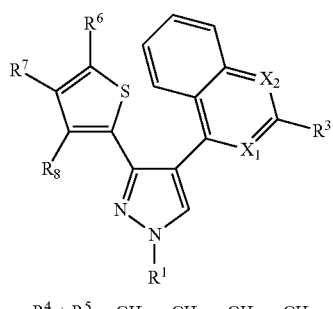
(IC)
$R^4 + R^5$ = CH=CH—CH=CH
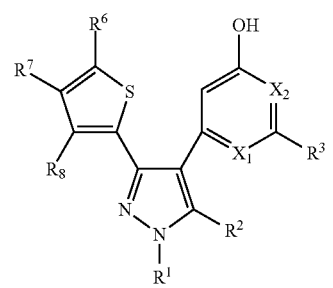
(ID)
$R^4$ = OH, $R^5$ = H
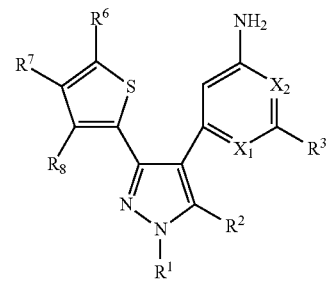
(IE)
$R^4$ = $NH_2$, $R^5$ = H

TABLE I

| Exa-No. | Type | $X_1$ | $X_2$ | $R^1$ | $R^2$ | $R^3$ | $R^6$ | $R^7$ | $R^8$ | log p | MW measured | Isomer ratio[d] |
|---|---|---|---|---|---|---|---|---|---|---|---|---|
| 1 | (IA) | CH | N | H | H | H | chloro | H | H | 0.96[b] | 262 | — |
| 2 | (IA) | CH | N | H | H | H | chloro | chloro | chloro | 1.52[b] | 331 | — |
| 3 | (IA) | N | N | H | H | H | chloro | H | H | 1.82[a]; 1.74[b] | 263 | — |
| 4 | (IA) | N | N | acetyl | H | H | chloro | H | H | 2.92[b] | 305 | — |
| 5 | (IA) | N | N | benzyl | H | H | chloro | H | H | 3.41[b] | 353 | 90:10 (3.17) |
| 6 | (IB) | CH | N | 2-methylpropyl | H | H | chloro | H | H | 2.2[a] | 318 | — |
| 7 | (IA) | CH | N | 3-methylbut-2-en-1-yl | H | H | chloro | H | H | 2.25[b] | 330 | — |
| 8 | (IB) | CH | N | butan-2-yl | H | H | chloro | H | H | 2.1[b] | 318 | — |
| 9 | (IA) | CH | N | butan-2-yl | H | H | chloro | H | H | 1.91[b] | 318 | — |
| 10 | (IB) | CH | N | tert-butyl | H | H | chloro | H | H | 1.95[b] | 318 | — |
| 11 | (IA) | CH | N | cyclohexyl | H | H | chloro | H | H | 2.54[b] | 344 | — |
| 12 | (IB) | CH | N | cyclohexyl | H | H | chloro | H | H | 2.26[b] | 344 | — |
| 13 | (IB) | CH | N | 4-methylpentan-2-yl | H | H | chloro | H | H | 2.7[b] | 346 | — |
| 14 | (IA) | CH | N | 4-methylpentan-2-yl | H | H | chloro | H | H | 2.42[b] | 346 | — |
| 15 | (IA) | CH | N | cyclopentyl | H | H | chloro | H | H | 2.25[b] | 330 | — |
| 16 | (IB) | CH | N | cyclopentyl | H | H | chloro | H | H | 2.13[b] | 330 | — |
| 17 | (IA) | CH | N | 3-methylbutyl | H | H | chloro | H | H | 2.45[b] | 332 | — |
| 18 | (IA) | CH | N | cyclobutyl | H | H | chloro | H | H | 2.04[b] | 316 | — |
| 19 | (IB) | CH | N | 3,3-dimethylbutan-2-yl | H | H | chloro | H | H | 2.47[b] | 346 | — |
| 20 | (IB) | CH | N | 3-methylbutan-2-yl | H | H | chloro | H | H | 2.1[b] | 332 | — |
| 21 | (IA) | CH | N | 2-methylpropyl | H | H | chloro | H | H | 2.08[b] | 318 | — |
| 22 | (IB) | CH | N | phenyl | H | H | chloro | H | H | 2.63[b] | 338 | — |
| 23 | (IA) | CH | N | phenyl | H | H | chloro | H | H | 1.88[b] | 338 | — |
| 24 | (IB) | CH | N | 2,2-dimethylpropyl | H | H | chloro | H | H | 2.39[b] | 332 | — |
| 25 | (IA) | CH | N | 2,2-dimethylpropyl | H | H | chloro | H | H | 2.17[b] | 332 | — |
| 26 | (IB) | N | N | 2-methylpropyl | H | H | chloro | H | H | 3.31[b] | 319 | — |
| 27 | (IB) | CH | N | 3-methylbutyl | H | H | chloro | H | H | 3.8[b] | 333 | — |
| 28 | (IB) | CH | N | 4-methylpentan-2-yl | H | H | chloro | H | H | 4.29[b] | 347 | — |
| 29 | (IB) | CH | N | 3-methylbut-2-en-1-yl | H | H | chloro | H | H | 3.44[b] | 331 | — |
| 30 | (IB) | CH | N | propan-2-yl | H | H | chloro | H | H | 2.94[b] | 305 | — |
| 31 | (IB) | CH | N | butan-2-yl | H | H | chloro | H | H | 3.34[b] | 319 | — |
| 32 | (IB) | CH | N | 3-methylbutan-2-yl | H | H | chloro | H | H | 3.8[b] | 333 | — |
| 33 | (IB) | CH | N | 3,3-dimethylbutan-2-yl | H | H | chloro | H | H | 4.46[b] | 347 | — |
| 34 | (IB) | CH | N | 2,2-dimethylpropyl | H | H | chloro | H | H | 3.82[b] | 333 | — |
| 35 | (IB) | CH | N | H | H | H | $CH_3$ | H | H | 0.77[b] | 242 | — |
| 36 | (IB) | CH | N | H | H | H | acetyl | H | H | 0.62[b] | 270 | — |
| 37 | (IB) | CH | N | H | H | H | butylcarbamoyl | H | H | 0.0[b] | 328 | — |
| 38 | (IA) | CH | N | propan-2-yl | H | H | chloro | H | H | 1.63[a]; 1.88[b] | 304 | — |
| 39 | (IB) | CH | N | propan-2-yl | H | H | H | H | H | 1.63[a]; 1.7[b] | 304 | — |
| 40 | (IA) | CH | N | H | H | chloro | chloro | H | H | 2.75[b] | 297 | — |
| 41 | (IB) | CH | N | pentan-3-yl | H | H | chloro | H | H | 2.08[b] | 332 | — |
| 42 | (IB) | CH | N | benzyl | H | H | chloro | H | H | 1.94[a] | 352 | — |
| 43 | (IB) | CH | N | benzyl | H | H | chloro | H | H | 2.35[b] | 352 | — |
| 44 | (IA) | CH | N | H | bromo | H | chloro | H | H | 1.4[b] | 341 | — |

TABLE I-continued

| Exa-No. | Type | $X_1$ | $X_2$ | $R^1$ | $R^2$ | $R^3$ | $R^6$ | $R^7$ | $R^8$ | log p | MW measured | Isomer ratio[d] |
|---|---|---|---|---|---|---|---|---|---|---|---|---|
| 45 | (IA) | CH | N | tetrahydro-2H-pyran-2-yl | H | H | chloro | H | H | 1.91[b] | 346 | — |
| 46 | (IA) | CH | N | CH$_3$ | H | H | chloro | H | H | 1.26[b] | 276 | 63:21 (1.17) |
| 47 | (IA) | CH | N | prop-2-yn-1-yl | H | H | chloro | H | H | 1.54[b] | 300 | 73:10 (1.36) |
| 48 | (IA) | CH | N | prop-2-en-1-yl | H | H | chloro | H | H | 1.65[b] | 302 | 81:11 (1.50) |
| 49 | (IA) | CH | N | 2-methoxyethyl | H | H | chloro | H | H | 1.42[b] | 320 | 83:17 (1.29) |
| 50 | (IA) | CH | N | 3,3-dichloroprop-2-en-1-yl | H | H | chloro | H | H | 2.3[b] | 371 | 85:14 (2.07) |
| 51 | (IA) | CH | N | but-2-yn-1-yl | H | H | chloro | H | H | 1.81[b] | 314 | 85:15 (1.60) |
| 52 | (IA) | CH | N | methoxymethyl | H | H | chloro | H | H | 1.38[b] | 306 | 86:11 (1.10) |
| 53 | (IA) | CH | N | cyanomethyl | H | H | chloro | H | H | 1.4[b] | 301 | |
| 54 | (IA) | CH | N | 2,2,2-trifluoroethyl | H | H | chloro | H | H | 1.88[b] | 344 | 80:17 (1.50) |
| 55 | (IA) | CH | N | 2-chloroethyl | H | H | chloro | H | H | 1.65[b] | 325 | |
| 56 | (IA) | CH | N | tetrahydrofuran-2-ylmethyl | H | H | chloro | H | H | 1.6[b] | 346 | 86:13 (1.44) |
| 57 | (IA) | CH | N | ethyl | H | H | chloro | H | H | 1.5[b] | 290 | 77:17 (1.42) |
| 58 | (IA) | CH | N | 2-phenylethyl | H | H | chloro | H | H | 2.3[b] | 366 | — |
| 59 | (IA) | CH | N$^+$—O$^-$ | H | H | chloro | chloro | H | H | 1.57[c] | 312 | — |
| 60 | (IA) | CH | N | 2-(morpholin-4-yl)ethyl | H | H | chloro | H | H | 0.52[b] | 375 | — |
| 61 | (IA) | CH | N | but-3-en-2-yl | H | H | chloro | H | H | 1.91[b] | 316 | 87:10 (1.76) |
| 62 | (IA) | CH | N | 2-fluoroethyl | H | H | chloro | H | H | 1.39[b] | 308 | 83:16 (1.25) |
| 63 | (IA) | CH | N | 2-ethoxy-2-oxoethyl | H | H | chloro | H | H | 1.67[b] | 347 | — |
| 64 | (IA) | CH | N | pentan-3-yl | H | H | chloro | H | H | 2.18[b] | 332 | — |
| 65 | (IA) | N | N | H | H | propylamino | chloro | H | H | 1.75[a] | 320 | — |
| 66 | (IA) | CH | N | cyclopropyl | H | H | chloro | H | H | 1.62[b] | 302 | — |
| 67 | (IA) | CH | N | H | cyclopropyl | H | chloro | H | H | 1.36[b] | 302 | — |
| 68 | (IA) | CH | N | H | CH$_3$ | H | chloro | H | H | 1.07[b] | 275 | — |
| 69 | (IA) | N | N | H | H | methoxy | chloro | H | H | 2.23[a] | 293 | — |
| 70 | (IA) | CH | N | 2-methylpropyl | H | chloro | chloro | H | H | 4.85[a] | 353 | — |
| 71 | (IA) | CH | N$^+$—O$^-$ | H | H | propylamino | chloro | H | H | 1.9[a] | 335 | — |
| 72 | (IB) | CH | N | 2-methylpropyl | H | chloro | chloro | H | H | 4.65[a] | 353 | — |
| 73 | (IA) | CH | N$^+$—O$^-$ | 2-methylpropyl | H | benzylamino | chloro | H | H | 3.73[a] | 439 | — |
| 74 | (IA) | CH | N$^+$—O$^-$ | 2-methylpropyl | H | chloro | chloro | H | H | 3.04[a] | 369 | — |
| 75 | (IB) | CH | N$^+$—O$^-$ | 2-methylpropyl | H | benzylamino | chloro | H | H | 3.48[a] | 439 | 80:20 (2.82) |
| 76 | (IA) | CH | N | 2-methylpropyl | H | amino | chloro | H | H | 2.04[a] | 333 | 76:20 (1.93) |
| 77 | (IA) | CH | N | 2-methylpropyl | H | amino | chloro | H | H | 2.39[a] | 349 | 70:19 (2.21) |
| 78 | (IA) | N | N | H | H | hydrazinyl | chloro | H | H | 2.26[a] | 293 | — |
| 79 | (IA) | N | N | H | H | dimethylamino | chloro | H | H | 1.69[a] | 306 | — |

| Exa-No. | Type | X₁ | X₂ | R¹ | R² | R³ | R⁶ | R⁷ | R⁸ | log p | MW measured | Isomer ratio[d] |
|---|---|---|---|---|---|---|---|---|---|---|---|---|
| 80 | (IA) | CH | N⁺—O⁻ | 2-methylpropyl | H | acetylamino | chloro | H | H | 2.86[a] | 391 | — |
| 81 | (IA) | N | N | H | H | chloro | chloro | H | H | 2.64[a] | 298 | — |
| 82 | (IA) | CH | N⁺—O⁻ | 2-methylpropyl | H | bis(cyclopropylcarbonyl)amino | chloro | H | H | 4.75[a] | 470 | — |
| 83 | (IB) | CH | N⁺—O⁻ | 2-methylpropyl | H | prop-2-yn-1-ylamino | chloro | H | H | 2.7[a] | 388 | — |
| 84 | (IA) | CH | N⁺—O⁻ | 2-methylpropyl | H | prop-2-yn-1-ylamino | chloro | H | H | 2.92[a] | 388 | — |
| 85 | (IA) | CH | N | H | cyano | H | chloro | H | H | 1.53[a] | 287 | — |
| 86 | (IA) | CH | N | acetyl | H | H | chloro | H | H | 2.04[a] | 304 | — |
| 87 | (IA) | CH | N | ethoxycarbonyl | H | H | chloro | H | H | 1.97[a] | 334 | — |
| 88 | (IA) | CH | N | methylsulfonyl | H | H | chloro | H | H | 1.78[a] | 340 | — |
| 89 | (IA) | CH | N | propan-2-ylcarbamoyl | H | H | chloro | H | H | 2.26[a] | 347 | — |
| 90 | (IA) | N | N | H | H | benzylamino | chloro | H | H | 2.37[a] | 368 | — |
| 91 | (IA) | CH | N | 3-dimethylamino)-2-methylpropyl | H | chloro | chloro | H | H | 1.84[a] | 396 | 87:12 (1.74) |
| 92 | (IA) | CH | N⁺—O⁻ | butan-2-yl | H | H | chloro | H | H | 2.56[b] | 334 | — |
| 93 | (IA) | N | N | 2-methylpropyl | H | benzylamino | chloro | H | H | 4.31[a] | 425 | — |
| 94 | (IA) | N | N | 2-methylpropyl | H | benzyl(2-methylpropanoyl)amino | chloro | H | H | 5.88[a] | 495 | — |
| 95 | (IA) | N | N | 2-methylpropyl | H | amino | chloro | H | H | 2.35[a] | 334 | — |
| 96 | (IB) | N | N | 2-methylpropyl | H | benzylamino | chloro | H | H | 3.96[a] | 424 | — |
| 97 | (IA) | N | N | butan-2-yl | H | cyano | chloro | H | H | 4.41[b] | 343 | — |
| 98 | (IA) | N | N | 2-methylpropyl | H | (2-methylpropanoyl)amino | chloro | H | H | 3.67[a] | 404 | — |
| 99 | (IA) | N | N | butan-2-yl | H | propan-2-ylcarbamoyl | chloro | H | H | 4.82[b] | 402 | — |
| 100 | (IA) | CH | N | butan-2-yl | H | bromo | chloro | H | H | 5.03[b] | 395 | — |
| 101 | (IA) | CH | N | butan-2-yl | cyclopropyl | H | chloro | H | H | 2.69[a] | 422 | — |
| 102 | (IA) | CH | N | 4-methoxybenzyl | trimethylsilyl | H | chloro | H | H | 4.84[b] | 454 | — |
| 103 | (IA) | CH | N | 4-methoxybenzyl | methylsulfanyl | H | chloro | H | H | 3.78[b] | 428 | — |
| 104 | (IA) | CH | N | 4-methoxybenzyl | H | H | fluoro | H | H | 2.74[b] | 382 | — |
| 105 | (IA) | CH | N | H | H | H | fluoro | H | H | 0.57[b] | 246 | — |
| 106 | (IA) | CH | N | butan-2-yl | H | H | fluoro | H | H | 1.78[b] | 302 | — |
| 107 | (IB) | CH | N | butan-2-yl | H | H | fluoro | H | H | 1.69[b] | 302 | — |
| 108 | (IA) | CH | N | propan-2-yl | H | H | fluoro | H | H | 1.53[b] | 288 | — |
| 109 | (IB) | CH | N | propan-2-yl | H | H | fluoro | H | H | 1.51[b] | 288 | — |
| 110 | (IA) | CH | N | butan-2-yl | H | acetylamino | chloro | H | H | 2.94[b] | 375 | — |
| 111 | (IA) | CH | N | butan-2-yl | H | cyclopropylethynyl | chloro | H | H | 4.56[b] | 382 | — |
| 112 | (IA) | CH | N | 2-methylpropyl | H | prop-2-yn-1-ylamino | chloro | H | H | 2.30[b] | 371 | — |
| 113 | (IA) | CH | N | 2-fluorobenzyl | H | H | H | chloro | chloro | 1.74[b] | 370 | 55:45 (1.76) |
| 114 | (IA) | CH | N | propan-2-yl | H | H | H | chloro | H | 1.6[b] | 304 | 83:15 (1.74) |
| 115 | (IA) | N | N | methoxymethyl | H | propan-2-ylamino | chloro | H | H | 2.39[b] | 364 | 70:30 (2.39) |
| 116 | (IA) | N | N | pentan-3-yl | H | propan-2-ylamino | chloro | H | H | 3.57[b] | 390 | 90:10 (3.37) |
| 117 | (IA) | N | N | prop-2-yn-1-yl | H | propan-2-ylamino | chloro | H | H | 2.52[b] | 358 | 90:10 (3.13) |
| 118 | (IA) | N | N | 3-methylbut-2-en-1-yl | H | propan-2-ylamino | chloro | H | H | 3.44[b] | 388 | 90:10 (3.00) |
| 119 | (IA) | N | N | 2-chloroethyl | H | propan-2-ylamino | chloro | H | H | 2.63[b] | 382 | 90:10 (2.35) |
| 120 | (IA) | N | N | 2-ethoxyethyl | H | propan-2-ylamino | chloro | H | H | 2.56[b] | 392 | 90:10 (2.33) |

TABLE I-continued

| Exa-No. | Type | $X_1$ | $X_2$ | $R^1$ | $R^2$ | $R^3$ | $R^6$ | $R^7$ | $R^8$ | log p | MW measured | Isomer ratio[d] |
|---|---|---|---|---|---|---|---|---|---|---|---|---|
| 121 | (IA) | N | N | 2-fluorobenzyl | H | propan-2-ylamino | chloro | H | H | 3.39[b] | 428 | 95:5 (3.02) |
| 122 | (IA) | N | N | cyanomethyl | H | propan-2-ylamino | chloro | H | H | 2.4[b] | 359 | — |
| 123 | (IA) | N | N | but-3-en-2-yl | H | propan-2-ylamino | chloro | H | H | 3.02[b] | 374 | 95:5 (2.73) |
| 124 | (IA) | N | N | 2,2,2-trifluoroethyl | H | propan-2-ylamino | chloro | H | H | 3.11[b] | 402 | 76:20 (1.05) |
| 125 | (IA) | CH | N | $CH_3$ | H | H | H | chloro | H | 1.11[b] | 276 | |
| 126 | (IA) | CH | N | 2-cyanoethyl | H | H | H | chloro | H | 1.16[b] | 315 | 65:35 (1.17) |
| 127 | (IA) | CH | N | 2,2-difluoroethyl | H | H | H | H | chloro | 1.14[b] | 326 | |
| 128 | (IA) | CH | N | 2-phenylethyl | H | H | H | H | chloro | 1.88[b] | 366 | 40:60 (1.84) |
| 129 | (IA) | CH | N | methoxymethyl | H | H | H | H | chloro | 0.95[b] | 306 | 55:45 (1.88) |
| 130 | (IA) | CH | N | pentan-3-yl | H | H | H | H | chloro | 1.78[b] | 332 | |
| 131 | (IA) | CH | N | prop-2-yn-1-yl | H | H | H | H | chloro | 1.11[b] | 300 | 85:15 (1.10) |
| 132 | (IA) | CH | N | sec-butyl | H | H | H | H | chloro | 1.56[b] | 318 | 60:40 (1.67) |
| 133 | (IA) | CH | N | 3-methylbut-2-en-1-yl | H | H | H | H | chloro | 1.74[b] | 330 | 84:14 (1.29) |
| 134 | (IA) | CH | N | 2-chloroethyl | H | H | H | H | chloro | 1.22[b] | 324 | |
| 135 | (IA) | CH | N | 2-ethoxyethyl | H | H | H | H | chloro | 1.23[b] | 334 | 67:33 (1.28) |
| 136 | (IA) | CH | N | prop-2-en-1-yl | H | H | H | H | chloro | 1.22[b] | 302 | |
| 137 | (IA) | CH | N | cyanomethyl | H | H | H | H | chloro | 0.93[b] | 301 | 70:30 (0.78) |
| 138 | (IA) | CH | N | 2,2,2-trifluoroethyl | H | H | H | H | chloro | 1.39[b] | 344 | |
| 139 | (IA) | N | N | $CH_3$ | H | propan-2-ylamino | chloro | H | H | 2.07[b] | 334 | 80:20 (1.93) |
| 140 | (IA) | N | N | 2-cyanoethyl | H | propan-2-ylamino | chloro | H | H | 2.15[b] | 373 | 90:10 (2.20) |
| 141 | (IA) | N | N | ethyl | H | propan-2-ylamino | chloro | H | H | 2.39[b] | 348 | |
| 142 | (IA) | CH | N | $CH_3$ | H | H | H | H | chloro | 0.78[b] | 276 | 50:50 (0.88) |
| 143 | (IA) | CH | N | 2-cyanoethyl | H | H | H | H | chloro | 0.86[b] | 315 | — |
| 144 | (IA) | N | N | propan-2-yl | H | formylamino | chloro | H | H | 3.81[c], 1.61[b] | 348 | — |
| 145 | (IA) | CH | N | propan-2-yl | $CH_3$ | H | chloro | H | H | 3.8[c], 2.07[b] | 318 | — |
| 146 | (IA) | CH | N | ethyl | $CH_3$ | H | chloro | H | H | 3.08[c], 1.61[b] | 304 | — |
| 147 | (IA) | CH | N | $CH_3$ | $CH_3$ | H | chloro | H | H | 2.62[c], 1.29[b] | 290 | — |
| 148 | (IA) | CH | N | ethyl | H | H | H | H | H | 2.06[c], 0.75[b] | 256 | — |
| 149 | (IA) | CH | N | ethyl | H | propanoylamino | H | H | H | 2.26[c], 1.65[b] | 327 | — |
| 150 | (IA) | N | N | butan-2-yl | H | diacetylamino | chloro | H | H | 3.72[a] | 418 | — |
| 151 | (IA) | N | N | butan-2-yl | H | acetylamino | chloro | H | H | 3[a] | 376 | — |
| 152 | (IA) | CH | N | isobutyl | H | H | H | chloro | H | 1.87[b] | 318 | 80:20 |

TABLE I-continued

| Exa-No. | Type | $X_1$ | $X_2$ | $R^1$ | $R^2$ | $R^3$ | $R^6$ | $R^7$ | $R^8$ | log p | MW measured | Isomer ratio[d] |
|---|---|---|---|---|---|---|---|---|---|---|---|---|
| 153 | (IA) | N | N | 2-phenylethyl | H | propan-2-ylamino | chloro | H | H | 3.63[b] | 424 | 90:10 |
| 154 | (IA) | N | N | cyclopentyl | H | propan-2-ylamino | chloro | H | H | 3.61[b] | 388 | 90:10 |
| 155 | (IA) | N | N | prop-2-en-1-yl | H | propan-2-ylamino | chloro | H | H | 2.68[b] | 360 | 90:10 |
| 156 | (IA) | CH | N | ethyl | H | H | H | chloro | H | 1.34[b] | 290 | 80:20 |
| 157 | (IA) | CH | N | 2,2-difluoroethyl | H | H | H | chloro | H | 1.42[b] | 326 | 80:20 |
| 158 | (IA) | CH | N | propan-2-yl | H | H | H | H | chloro | 1.38[b] | 304 | 65:35 |
| 159 | (IA) | CH | N | isobutyl | H | H | H | H | chloro | 1.62[b] | 318 | 60:40 |
| 160 | (IA) | CH | N | cyclopentyl | H | H | H | H | chloro | 1.76[b] | 330 | 65:35 |
| 161 | (IA) | CH | N | but-3-en-2-yl | H | H | H | H | chloro | 1.51[b] | 316 | 65:35 |
| 162 | (IA) | N | N | 2,2-difluoroethyl | H | propan-2-ylamino | chloro | H | H | 2.66[b] | 384 | 90:10 |
| 163 | (IA) | CH | N | ethyl | H | H | H | H | chloro | 1.14[b] | 290 | 60:40 |
| 164 | (IA) | CH | N | butan-2-yl | H | propanoylamino | H | chloro | H | 3.59[c]; 3.07[b] | 389 | — |
| 165 | (IA) | CH | N | $CH_3$ | propyl | H | H | H | $CH_3$ | 2.59[c]; 1.31[b] | 298 | 85:15 (2.79[c]; 1.46[b]) |
| 166 | (IA) | CH | N | $CH_3$ | propyl | propanoylamino | H | H | $CH_3$ | 2.71[c]; 2.29[b] | 369 | 85:15 (2.84[c]; 2.39[b]) |
| 167 | (IA) | CH | N | sec-butyl | H | H | H | chloro | H | 1.86[b] | 318 | 79:21 (1.76) |
| 168 | (IA) | N | N | propan-2-yl | $CH_3$ | propanoylamino | chloro | H | H | 3.76[c]; 3.34[b] | 389 | — |
| 169 | (IA) | N | N | ethyl | $CH_3$ | propanoylamino | chloro | H | H | 3.1[c]; 2.71[b] | 375 | — |
| 170 | (IA) | N | N | $CH_3$ | $CH_3$ | propanoylamino | chloro | H | H | 2.68[c]; 2.32[b] | 361 | — |
| 171 | (IA) | N | N | propan-2-yl | H | diacetylamino | chloro | H | H | 3.33[a] | 404 | — |
| 172 | (IA) | N | N | propan-2-yl | H | propanoylamino | chloro | H | H | 3.04[a] | 376 | — |
| 173 | (IA) | N | N | butan-2-yl | H | (2-methylpropanoyl)amino | chloro | H | H | 3.72[a] | 404 | — |
| 174 | (IA) | N | N | propan-2-yl | H | (2-methylpropanoyl)amino | chloro | H | H | 3.29[a] | 390 | — |
| 175 | (IA) | N | N | propan-2-yl | H | propanoylamino | H | H | H | 2.61[c]; 2.01[b] | 341 | — |
| 176 | (IA) | N | N | propan-2-yl | H | acetylamino | chloro | H | H | 2.59[a] | 362 | — |
| 177 | (IA) | N | N | propan-2-yl | H | cyclopropylamino | chloro | H | H | 2.59[a] | 360 | — |
| 178 | (IA) | N | N | propan-2-yl | H | (1-methoxypropan-2-yl)amino | chloro | H | H | 2.82[a] | 392 | — |
| 179 | (IA) | N | N | propan-2-yl | H | oxetan-3-ylamino | chloro | H | H | 2.7[a] | 376 | — |
| 180 | (IA) | N | N | butan-2-yl | H | prop-2-yn-1-ylamino | chloro | H | H | 3.25[a] | 358 | — |
| 181 | (IA) | N | N | propan-2-yl | H | propan-2-ylamino | chloro | H | H | 2.82[a] | 362 | — |
| 182 | (IA) | N | N | propan-2-yl | H | butan-2-ylamino | chloro | H | H | 3.15[a] | 376 | — |
| 183 | (IA) | N | N | propan-2-yl | H | (cyclopropylmethyl)amino | chloro | H | H | 3.02[a] | 374 | — |
| 184 | (IA) | N | N | propan-2-yl | H | prop-2-en-1-ylamino | chloro | H | H | 3[a] | 360 | — |
| 185 | (IA) | N | N | propan-2-yl | H | amino | chloro | H | H | 2.01[a] | 320 | — |
| 186 | (IA) | N | N | butan-2-yl | H | (1-methoxypropan-2-yl)amino | chloro | H | H | 3.21[a] | 406 | — |
| 187 | (IA) | N | N | butan-2-yl | H | (cyclopropylmethlyl)amino | chloro | H | H | 3.41[a] | 388 | — |
| 188 | (IA) | N | N | butan-2-yl | H | prop-2-yn-1-ylamino | chloro | H | H | 3.68[a] | 372 | — |
| 189 | (IA) | N | N | butan-2-yl | H | propan-2-ylamino | chloro | H | H | 3.25[a] | 376 | — |
| 190 | (IA) | N | N | butan-2-yl | H | propanoylamino | chloro | H | H | 3.37[a] | 390 | — |
| 191 | (IA) | CH | N | H | H | H | H | chloro | H | n.d | 262 | — |
| 192 | (IA) | N | N | propan-2-yl | H | chloro | chloro | H | H | 4.31[a] | 340 | 91:9 |
| 193 | (IA) | N | N | butan-2-yl | H | amino | chloro | H | H | 2.3[a] | 334 | — |

TABLE I-continued

| Exa-No. | Type | X₁ | X₂ | R¹ | R² | R³ | R⁶ | R⁷ | R⁸ | log p | MW measured | Isomer ratio[d] |
|---|---|---|---|---|---|---|---|---|---|---|---|---|
| 194 | (IA) | N | N | butan-2-yl | H | oxetan-3-ylamino | chloro | H | H | 3.09[a] | 390 | — |
| 195 | (IA) | N | N | butan-2-yl | H | cyclopropylamino | chloro | H | H | 2.9[a] | 374 | — |
| 196 | (IA) | N | N | butan-2-yl | H | prop-2-en-1-ylamino | chloro | H | H | 3.39[a] | 374 | — |
| 197 | (IA) | N | N | butan-2-yl | H | butan-2-ylamino | chloro | H | H | 3.48[a] | 390 | — |
| 198 | (IA) | N | N | propan-2-yl | H | benzylamino | chloro | H | H | 3.81[a] | 411 | — |
| 199 | (IA) | N | CH | propan-2-yl | H | H | CH₃ | H | H | 1.5[a] | 284 | — |
| 200 | (IA) | N | N | butan-2-yl | H | benzylamino | chloro | H | H | 4.27[a] | 424 | — |
| 201 | (IA) | N | N | butan-2-yl | chloro | H | chloro | H | H | 3.44[a] | 352 | — |
| 202 | (IA) | N | N | butan-2-yl | H | methylsulfonyl | chloro | H | H | 3.52[a] | 398 | — |
| 203 | (IA) | N | N | propan-2-yl | H | methylsulfonyl | chloro | H | H | 3.15[a] | 383 | — |
| 204 | (IA) | N | N | butan-2-yl | H | [(2S)-2-hydroxypropanoyl]amino | chloro | H | H | 3.13[b] | 405 | 83:17 |
| 205 | (IA) | N | N | propan-2-yl | H | [(2S)-2-hydroxypropanoyl]amino | chloro | H | H | 2.75[b] | 391 | 86:14 |
| 206 | (IA) | N | CH | ethyl | H | [(2S)-2-hydroxypropanoyl]amino | chloro | H | H | 2.37[b] | 377 | 93:7 |
| 207 | (IA) | N | CH | CH₃ | H | [(2S)-2-hydroxypropanoyl]amino | chloro | H | H | 2.11[b] | 363 | 91:9 |
| 208 | (IA) | N | CH | CH₃ | H | [(2S)-2-hydroxy-2-methylpropanoyl]amino | chloro | H | H | 2.26[b] | 377 | 93:7 |
| 209 | (IB) | N | N | butan-2-yl | H | methylsulfanyl | chloro | H | H | 4.76[a] | 365 | 90:10 |
| 210 | (IB) | N | CH | butan-2-yl | H | (2-hydroxy-2-methylpropanoyl)amino | chloro | H | H | 4.24[a] | 419 | 77:23 |
| 211 | (IA) | CH | N | propan-2-yl | H | (2-hydroxy-2-methylpropanoyl)amino | chloro | H | H | 3.17[b] | 405 | 89:11 |
| 212 | (IA) | CH | N | ethyl | H | (2-hydroxy-2-methylpropanoyl)amino | chloro | H | H | 2.73[b] | 391 | 82:18 |
| 213 | (IA) | CH | CH | butan-2-yl | fluoro | H | chloro | H | H | 2.61[b] | 336 | — |
| 214 | (IA) | CH | CH | propan-2-yl | H | H | iodo | H | H | 1.89[b] | 395 | — |
| 215 | (IB) | CH | CH | propan-2-yl | H | H | iodo | H | H | 1.78[b] | 395 | — |
| 216 | (IA) | CH | CH | CH₃ | H | acetylamino | acetylamino | H | H | 0.76[b] | 356 | — |
| 217 | (IA) | CH | CH | butan-2-yl | H | (dimethylsulfamoyl)amino | chloro | H | H | 3.35[b] | 440 | 82:18 |
| 218 | (IA) | CH | CH | propan-2-yl | H | (dimethylsulfamoyl)amino | chloro | H | H | 3[b] | 426 | 88:12 |
| 219 | (IA) | CH | CH | ethyl | H | (dimethylcarbamoyl)amino | chloro | H | H | 2.59[b] | 412 | 82:18 |
| 220 | (IA) | CH | CH | CH₃ | H | (dimethylsulfamoyl)amino | chloro | H | H | 2.19[b] | 398 | 84:16 |
| 221 | (IA) | CH | N | butan-2-yl | H | methylsulfanyl | chloro | H | H | 4.88[a] | 366 | — |
| 222 | (IA) | CH | CH | propan-2-yl | H | methylsulfanyl | chloro | H | H | 4.44[a] | 351 | — |
| 223 | (IA) | CH | CH | butan-2-yl | H | (methoxyacetyl)amino | chloro | H | H | 3.68[b] | 405 | 82:18 |
| 224 | (IA) | CH | CH | butan-2-yl | H | (phenylacetyl)amino | chloro | H | H | 4.35[b] | 451 | 82:18 |
| 225 | (IA) | CH | CH | butan-2-yl | H | propanoylamino | chloro | H | H | 3.19[b] | 389 | 89:11 |
| 226 | (IA) | CH | CH | butan-2-yl | H | (cyclopropylcarbonyl)amino | chloro | H | H | 3.35[b] | 401 | 87:13 |
| 227 | (IA) | CH | CH | propan-2-yl | H | (dimethylcarbamoyl)amino | chloro | H | H | 2.19[b] | 404 | 81:19 |
| 228 | (IA) | CH | CH | butan-2-yl | H | (2-methylbutanoyl)amino | chloro | H | H | 4.05[b] | 417 | 92:8 |
| 229 | (IA) | CH | CH | butan-2-yl | H | (cyclopropylacetyl)amino | chloro | H | H | 3.81[b] | 415 | 92:8 |
| 230 | (IA) | CH | CH | butan-2-yl | H | (3-thienyl)carbonyl)amino | chloro | H | H | 4.21[b] | 443 | 79:21 |
| 231 | (IA) | CH | CH | butan-2-yl | H | (2,2-dimethylpropanoyl)amino | chloro | H | H | 4.35[b] | 417 | 82:18 |
| 232 | (IA) | CH | CH | propan-2-yl | H | (3-thienylcarbonyl)amino | chloro | H | H | 3.79[b] | 429 | 82:18 |
| 233 | (IA) | CH | CH | propan-2-yl | H | (2,2-dimethylpropanoyl)amino | chloro | H | H | 3.87[b] | 403 | 83:17 |
| 234 | (IA) | CH | CH | butan-2-yl | H | (2-methylpropanoyl)amino | chloro | H | H | 3.63[b] | 403 | 93:7 |
| 235 | (IA) | CH | CH | butan-2-yl | H | (3-methylbutanoyl)amino | chloro | H | H | 4.08[b] | 417 | 91:9 |
| 236 | (IA) | CH | CH | butan-2-yl | H | (ethoxycarbonyl)amino | chloro | H | H | 3.92[b] | 405 | 82:18 |
| 237 | (IA) | CH | CH | butan-2-yl | H | (phenylcarbonyl)amino | chloro | H | H | 4.46[b] | 437 | 84:16 |
| 238 | (IA) | CH | CH | butan-2-yl | H | (thiophen-2-ylcarbonyl)amino | chloro | H | H | 4.37[b] | 443 | 81:19 |
| 239 | (IA) | CH | CH | butan-2-yl | H | (isopropoxycarbonyl)amino | chloro | H | H | 4.33[b] | 419 | 85:15 |
| 240 | (IA) | CH | CH | butan-2-yl | H | (cyclobutylcarbonyl)amino | chloro | H | H | 3.81[b] | 415 | 88:12 |

TABLE I-continued

| Exa-No. | Type | X₁ | X₂ | R¹ | R² | R³ | R⁶ | R⁷ | R⁸ | log p | MW measured | Isomer ratio[a] |
|---|---|---|---|---|---|---|---|---|---|---|---|---|
| 241 | (IA) | CH | N | propan-2-yl | H | (thiophen-2-ylcarbonyl)amino | chloro | H | H | 3.96[b] | 429 | 92:8 |
| 242 | (IA) | CH | N | propan-2-yl | H | (isopropoxycarbonyl)amino | chloro | H | H | 3.85[b] | 405 | 86:14 |
| 243 | (IA) | CH | N | propan-2-yl | H | (cyclobutylcarbonyl)amino | chloro | H | H | 3.37[b] | 401 | 95:5 |
| 244 | (IA) | CH | N | propan-2-yl | H | (methoxyacetyl)amino | chloro | H | H | 3.25[b] | 391 | 75:25 |
| 245 | (IA) | CH | N | propan-2-yl | H | (phenylacetyl)amino | chloro | H | H | 3.94[b] | 437 | 86:14 |
| 246 | (IA) | CH | N | propan-2-yl | H | propanoylamino | chloro | H | H | 2.78[b] | 375 | 92:8 |
| 247 | (IA) | CH | N | propan-2-yl | H | (cyclopropylcarbonyl)amino | chloro | H | H | 2.94[b] | 387 | 90:10 |
| 248 | (IA) | CH | N | propan-2-yl | H | (dimethylcarbamoyl)amino | chloro | H | H | 1.97[b] | 390 | n.d. |
| 249 | (IA) | CH | N | propan-2-yl | H | (2-methylbutanoyl)amino | chloro | H | H | 3.61[b] | 403 | 93:7 |
| 250 | (IA) | CH | N | propan-2-yl | H | (cyclopropylacetyl)amino | chloro | H | H | 3.37[b] | 401 | 92:8 |
| 251 | (IA) | CH | N | ethyl | H | (dimethylcarbamoyl)amino | chloro | H | H | 1.72[b] | 376 | — |
| 252 | (IA) | CH | N | ethyl | H | (2-methylbutanoyl)amino | chloro | H | H | 3.13[b] | 389 | 91:9 |
| 253 | (IA) | CH | N | ethyl | H | (cyclopropylacetyl)amino | chloro | H | H | 2.94[b] | 387 | 90:10 |
| 254 | (IA) | CH | N | ethyl | H | (3-thienylcarbonyl)amino | chloro | H | H | 3.29[b] | 415 | 87:13 |
| 255 | (IA) | CH | N | ethyl | H | (2,2-dimethylpropanoyl)amino | chloro | H | H | 3.37[b] | 389 | 92:8 |
| 256 | (IA) | CH | N | propan-2-yl | H | acetylamino | chloro | H | H | 2.45[b] | 361 | 90:10 |
| 257 | (IA) | CH | N | propan-2-yl | H | (2-methylpropanoyl)amino | chloro | H | H | 3.21[b] | 389 | 91:9 |
| 258 | (IA) | CH | N | propan-2-yl | H | (3-methylbutanoyl)amino | chloro | H | H | 3.63[b] | 403 | 92:8 |
| 259 | (IA) | CH | N | propan-2-yl | H | (ethoxycarbonyl)amino | chloro | H | H | 3.46[b] | 391 | 87:13 |
| 260 | (IA) | CH | N | propan-2-yl | H | (phenylcarbonyl)amino | chloro | H | H | 4.03[b] | 423 | 91:9 |
| 261 | (IA) | CH | N | ethyl | H | (methoxyacetyl)amino | chloro | H | H | 2.78[b] | 377 | 80:20 |
| 262 | (IA) | CH | N | ethyl | H | (phenylacetyl)amino | chloro | H | H | 3.48[b] | 423 | 90:10 |
| 263 | (IA) | CH | N | ethyl | H | propanoylamino | chloro | H | H | 2.4[b] | 361 | 87:13 |
| 264 | (IA) | CH | N | ethyl | H | (cyclopropylcarbonyl)amino | chloro | H | H | 2.52[b] | 373 | 93:7 |
| 265 | (IA) | CH | N | ethyl | H | (ethoxycarbonyl)amino | chloro | H | H | 3[b] | 377 | 82:18 |
| 266 | (IA) | CH | N | ethyl | H | (phenylcarbonyl)amino | chloro | H | H | 3.55[b] | 409 | 87:13 |
| 267 | (IA) | CH | N | ethyl | H | (thiophen-2-ylcarbonyl)amino | chloro | H | H | 3.48[b] | 415 | 88:12 |
| 268 | (IA) | CH | N | ethyl | H | (isopropoxycarbonyl)amino | chloro | H | H | 3.35[b] | 391 | 84:16 |
| 269 | (IA) | CH | N | ethyl | H | (cyclobutylcarbonyl)amino | chloro | H | H | 2.92[b] | 387 | 86:14 |
| 270 | (IA) | CH | N | ethyl | H | (3-methylbutanoyl)amino | chloro | H | H | 2.75[b] | 375 | 86:14 |
| 271 | (IA) | CH | N | ethyl | H | (ethoxycarbonyl)amino | chloro | H | H | 2.56[b] | 363 | 78:22 |
| 272 | (IA) | CH | N | ethyl | H | (phenylcarbonyl)amino | chloro | H | H | 3.09[b] | 395 | 86:14 |
| 273 | (IA) | CH | N | ethyl | H | (thiophen-2-ylcarbonyl)amino | chloro | H | H | 3.04[b] | 401 | 88:12 |
| 274 | (IA) | CH | N | ethyl | H | (isopropoxycarbonyl)amino | chloro | H | H | 2.9[b] | 377 | 82:18 |
| 275 | (IA) | CH | N | ethyl | H | (cyclobutylcarbonyl)amino | chloro | H | H | 2.52[b] | 373 | 84:16 |
| 276 | (IA) | CH | N | ethyl | H | (methoxyacetyl)amino | chloro | H | H | 2.4[b] | 363 | 91:9 |
| 277 | (IA) | CH | N | CH₃ | H | (phenylacetyl)amino | chloro | H | H | 3.06[b] | 409 | 91:9 |
| 278 | (IA) | CH | N | CH₃ | H | propanoylamino | chloro | H | H | 2.05[b] | 347 | 94:6 |
| 279 | (IA) | CH | N | CH₃ | H | (cyclopropylcarbonyl)amino | chloro | H | H | 2.16[b] | 359 | 93:7 |
| 280 | (IA) | CH | N | CH₃ | H | (2-methylbutanoyl)amino | chloro | H | H | 2.71[b] | 375 | 90:10 |
| 281 | (IA) | CH | N | CH₃ | H | (cyclopropylacetyl)amino | chloro | H | H | 2.54[b] | 373 | 88:12 |
| 282 | (IA) | CH | N | CH₃ | H | (3-thienylcarbonyl)amino | chloro | H | H | 2.88[b] | 401 | 85:15 |
| 283 | (IA) | CH | N | CH₃ | H | (2,2-dimethylpropanoyl)amino | chloro | H | H | 2.92[b] | 375 | 87:13 |
| 284 | (IA) | CH | N | ethyl | H | acetylamino | chloro | H | H | 2.1[b] | 347 | 89:11 |
| 285 | (IA) | CH | N | ethyl | H | (2-methylpropanoyl)amino | chloro | H | H | 2.77[b] | 375 | 89:11 |
| 286 | (IA) | CH | N | ethyl | H | (3-methylbutanoyl)amino | chloro | H | H | 3.15[b] | 389 | 90:10 |
| 287 | (IA) | CH | N | CH₃ | H | acetylamino | chloro | H | H | 1.79[b] | 333 | 89:11 |
| 288 | (IA) | CH | N | CH₃ | H | (2-methylpropanoyl)amino | chloro | H | H | 2.39[b] | 361 | 87:13 |
| 289 | (IA) | CH | N | CH₃ | H | diacetylamino | diacetylamino | H | H | 1.84[b] | 440 | — |
| 290 | (IA) | CH | N | CH₃ | H | diacetylamino | acetylamino | H | H | 1.39[b] | 398 | 50:36 (1.47) |

TABLE I-continued

| Exa-No. | Type | X$_1$ | X$_2$ | R$^1$ | R$^2$ | R$^3$ | R$^6$ | R$^7$ | R$^8$ | log p | MW measured | Isomer ratio[d] |
|---|---|---|---|---|---|---|---|---|---|---|---|---|
| 291 | (IB) | CH | N | (E)-2-fluorovinyl | H | diacetylamino | chloro | H | H | 3.39[b] | 405 | — |
| 292 | (IB) | CH | N | (E)-2-fluorovinyl | H | acetylamino | chloro | H | H | 2.84[b] | 363 | — |
| 293 | (IA) | CH | N | (E)-2-fluorovinyl | H | acetylamino | chloro | H | H | 2.52[b] | 363 | — |
| 294 | (IA) | CH | N | propan-2-yl | H | H | methylsulfanyl | H | H | 1.79[b] | 316 | — |
| 295 | (IB) | CH | N | propan-2-yl | H | H | methylsulfanyl | H | H | 1.78[b] | 316 | 93:7 |
| 296 | (IA) | CH | N | 2-fluoroethyl | H | amino | chloro | H | H | 1.46[b] | 323 | — |
| 297 | (IA) | CH | N | (E)-2-fluorovinyl | H | diacetylamino | chloro | H | H | 3.09[b] | 405 | — |
| 298 | (IA) | CH | N | butan-2-yl | methylsulfanyl | H | chloro | H | H | 3.35[b] | 364 | — |
| 299 | (IA) | CH | N | CH$_3$ | H | amino | amino | H | H | 1.34[b] | 291 | 60:40 |
| 300 | (IA) | CH | N | propan-2-yl | H | H | H | H | H | 1.27[b] | 270 | 80:20 |
| 301 | (IA) | CH | N | (E)-2-fluorovinyl | H | amino | chloro | H | H | 1.59[b] | 321 | 78:22 |
| 302 | (IA) | CH | N | CH$_3$ | H | (diphenylmethylene)amino | chloro | H | H | 4.67[b] | 485 | 78:22 |
| 303 | (IA) | CH | N | propan-2-yl | H | diacetylamino | chloro | H | H | 2.52[b] | 375 | 82:18 |
| 304 | (IA) | CH | N | CH$_3$ | H | diacetylamino | chloro | H | H | 3.33[b] | 403 | 83:17 |
| 305 | (IA) | CH | N | CH$_3$ | H | amino | chloro | H | H | 1.34[b] | 291 | 79:21 |
| 306 | (IA) | CH | N | propan-2-yl | H | amino | chloro | H | H | 1.78[b] | 319 | 86:14 |
| 307 | (IA) | CH | N | ethyl | H | amino | chloro | H | H | 1.54[b] | 305 | 80:20 |
| 308 | (IA) | CH | N | butan-2-yl | H | (diphenylmethylene)amino | chloro | H | H | 6.5[c] | 497 | 84:16 |
| 309 | (IA) | CH | N | CH$_3$ | H | (diphenylmethylene)amino | chloro | H | H | 4.67[b] | — | 79:21 |
| 310 | (IA) | CH | N | propan-2-yl | H | (diphenylmethylene)amino | chloro | H | H | 4.46[b] | 483 | 80:20 |
| 311 | (IA) | CH | N | ethyl | H | (diphenylmethylene)amino | chloro | H | H | 3.99[b] | 469 | 79:21 |
| 312 | (IA) | N | CH | H | H | propan-2-ylamino | chloro | H | H | 1.79[a] | 320 | — |
| 313 | (IA) | CH | N | CH$_3$ | H | chloro | chloro | H | H | 3.37[b] | 310 | 72:28 |
| 314 | (IA) | CH | N | 2,2-difluoroethyl | H | chloro | chloro | H | H | 3.71[b] | 360 | 86:14 |
| 315 | (IA) | CH | N | propan-2-yl | H | chloro | chloro | H | H | 4.44[b] | 338 | 80:20 (4.25) |
| 316 | (IA) | CH | N | ethyl | H | chloro | chloro | H | H | 3.89[b] | 324 | 79:21 |
| 317 | (IA) | CH | N | butan-2-yl | H | amino | chloro | H | H | 3.31[c] | 333 | 83:17 |
| 318 | (IA) | CH | N | butan-2-yl | H | chloro | chloro | H | H | 4.89[b] | 352 | 80:20 |
| 319 | (IA) | CH | N | 2-methylpropyl | H | [(propan-2-yloxy)carbonyl]amino | chloro | H | H | 5.15[a] | 419 | — |
| 320 | (IA) | CH | N | 2-methylpropyl | H | (thiophen-2-ylcarbonyl)amino | chloro | H | H | 4.62[a] | 443 | — |
| 321 | (IA) | CH | N | 2-methylpropyl | H | (ethylcarbamoyl)amino | chloro | H | H | 3.18[a] | 404 | — |
| 322 | (IA) | CH | N | 2-cyanoethyl | H | H | chloro | H | H | 0.98[b] | 315 | — |
| 323 | (IA) | CH | N | (5-chloro-2-thienyl)methyl | H | H | chloro | H | H | 2.64[b] | 392 | — |
| 324 | (IA) | CH | N | (2,2-dichloro-1-methylcyclopropyl)methyl | H | H | chloro | H | H | 2.71[b] | 398 | — |
| 325 | (IA) | CH | N | 2,3-difluorobenzyl | H | H | chloro | H | H | 2.39[b] | 388 | — |
| 326 | (IA) | CH | N | (2,2-dichloro-1-methylcyclopropyl)methyl | H | H | S—CH=CH | | H | 2.62[b] | 420 | 88:11 (2.46) |
| 327 | (IA) | CH | N | 2,3-difluorobenzyl | H | H | S—CH=CH | | H | 1.75[b] | 410 | — |
| 328 | (IA) | CH | N | butan-2-yl | H | H | S—CH=CH | | H | 2.07[b] | 340 | 95:5 (2.02) |
| 329 | (IA) | CH | N | ethyl | H | H | S—CH=CH | | H | 1.57[b] | 312 | 81:18 (1.54) |
| 330 | (IA) | CH | N | 2,2,2-trifluoroethyl | H | H | S—CH=CH | | H | 1.91[b] | 366 | 91:8 (1.76) |
| 331 | (IA) | CH | N | 3-methylbut-2-en-1-yl | H | H | S—CH=CH | | H | 1.69[b] | 352 | — |
| 332 | (IA) | CH | N | cyclopentyl | H | H | S—CH=CH | | H | 2.25[b] | 352 | — |
| 333 | (IA) | CH | N | pentan-3-yl | H | H | S—CH=CH | | H | 2.3[b] | 354 | — |

TABLE I-continued

| Exa-No. | Type | $X_1$ | $X_2$ | $R^1$ | $R^2$ | $R^3$ | $R^6$ | $R^7$ | $R^8$ | log p | MW measured | Isomer ratio[d] |
|---|---|---|---|---|---|---|---|---|---|---|---|---|
| 334 | (IA) | CH | N | 2,2-dimethylpropyl | H | H | S—CH=CH | | | 2.35[b] | 354 | 74:26 (2.23) |
| 335 | (IA) | CH | N | 3,3-dichloroprop-2-en-1-yl | H | H | S—CH=CH | | | 1.67[b] | 392 | — |
| 336 | (IA) | CH | N | cyanomethyl | H | H | S—CH=CH | | | 1.48[b] | 323 | — |
| 337 | (IA) | CH | N | 2-ethoxyethyl | H | H | S—CH=CH | | | 1.7[b] | 356 | — |
| 338 | (IA) | CH | N | 2-cyanoethyl | H | H | S—CH=CH | | | 1.07[b] | 337 | 83:17 (1.40) |
| 339 | (IA) | CH | N | (5-chloro-2-thienyl)methyl | H | H | S—CH=CH | | | 2.57[b] | 414 | 89:6 (2.35) |
| 340 | (IA) | CH | N | 2-cyanoethyl | H | H | fluoro | H | H | 1.12[b] | 299 | — |
| 341 | (IA) | CH | N | (5-chloro-2-thienyl)methyl | H | H | fluoro | H | H | 2.34[b] | 376 | — |
| 342 | (IA) | CH | N | (2,2-dichloro-1-methylcyclopropyl)methyl | H | H | fluoro | H | H | 2.39[b] | 382 | — |
| 343 | (IA) | CH | N | 3-methylbut-2-en-1-yl | H | H | fluoro | H | H | 1.45[b] | 314 | — |
| 344 | (IA) | CH | N | cyclopentyl | H | H | fluoro | H | H | 2.02[b] | 314 | 89:9 (1.94) |
| 345 | (IA) | CH | N | 2,2-dimethylpropyl | H | H | fluoro | H | H | 2.11[b] | 316 | 90:10 (1.99) |
| 346 | (IA) | CH | N | 3,3-dichloroprop-2-en-1-yl | H | H | fluoro | H | H | 1.43[b] | 354 | — |
| 347 | (IA) | CH | N | 2,2-dimethylpropyl | H | H | bromo | H | H | 2.46[b] | 376 | 80:17 (2.25) |
| 348 | (IA) | CH | N | cyanomethyl | H | H | bromo | H | H | 1.51[b] | 345 | — |
| 349 | (IA) | CH | N | 2-ethoxyethyl | H | H | bromo | H | H | 1.75[b] | 378 | — |
| 350 | (IA) | CH | N | 2-cyanoethyl | H | H | bromo | H | H | 1.42[b] | 359 | — |
| 351 | (IA) | CH | N | (5-chloro-2-thienyl)methyl | H | H | bromo | H | H | 2.69[b] | 436 | — |
| 352 | (IA) | CH | N | 2-cyanobenzyl | H | H | bromo | H | H | 2.13[b] | 421 | — |
| 353 | (IA) | CH | N | 2,3-difluorobenzyl | H | H | bromo | H | H | 2.44[b] | 432 | — |
| 354 | (IA) | CH | N | sec-butyl | H | H | bromo | H | H | 2.15[b] | 362 | 90:10 (2.02) |
| 355 | (IA) | CH | N | 3-methylbut-2-en-1-yl | H | H | bromo | H | H | 2.35[b] | 374 | 76:18 (2.11) |
| 356 | (IA) | CH | N | cyclopentyl | H | H | bromo | H | H | 2.37[b] | 374 | 86:14 (2.21) |
| 357 | (IA) | CH | N | H | H | H | H | H | chloro | n.d | 262 | — |
| 358 | (IA) | CH | N | 2-methylpropyl | H | acetylamino | chloro | H | H | 2.96[a] | 375 | — |
| 359 | (IA) | CH | N | 2-methylpropyl | H | (cyclopropylcarbonyl)amino | chloro | H | H | 3.48[a] | 401 | — |
| 360 | (IA) | CH | N | 2-methylpropyl | H | (methoxyacetyl)amino | chloro | H | H | 3.78[a] | 405 | — |
| 361 | (IA) | CH | N | 2-methylpropyl | H | (cyclobutylcarbonyl)amino | chloro | H | H | 3.96[a] | 415 | — |
| 362 | (IA) | CH | N | 2-methylpropyl | H | (methylsulfonyl)amino | chloro | H | H | 3.04[a] | 411 | — |
| 363 | (IA) | CH | N | 2,2-difluoroethyl | H | H | chloro | H | H | 1.61[b] | 326 | 78:14 (1.45) |
| 364 | (IA) | CH | N | 2-ethoxyethyl | H | H | chloro | H | H | 1.69[b] | 334 | 68:15 (1.57) |
| 365 | (IA) | CH | N | 2-oxotetrahydrofuran-3-yl | H | H | chloro | H | H | 1.48[b] | 346 | 85:4 (1.64) |
| 366 | (IA) | CH | N | propan-2-yl | H | H | S—CH=CH | | | 1.79[b] | 326 | — |
| 367 | (IA) | CH | N | 2-fluoroethyl | H | H | S—CH=CH | | | 1.45[b] | 330 | 78:22 (1.37) |

TABLE I-continued

| Exa-No. | Type | $X_1$ | $X_2$ | $R^1$ | $R^2$ | $R^3$ | $R^6$ | $R^7$ | $R^8$ | log p | MW measured | Isomer ratio[a] |
|---|---|---|---|---|---|---|---|---|---|---|---|---|
| 368 | (IA) | CH | N | but-3-en-2-yl | H | H | S—CH=CH | | | 1.94[b] | 338 | 86:14 (1.86) |
| 369 | (IA) | CH | N | isobutyl | H | H | S—CH=CH | | | 2.04[b] | 340 | 76:24 (1.97) |
| 370 | (IA) | CH | N | 2-chloroethyl | H | H | S—CH=CH | | | 1.7[b] | 346 | 69:24 (1.63) |
| 371 | (IA) | CH | N | 2,2-difluoroethyl | H | H | S—CH=CH | | | 1.63[b] | 348 | 74:18 (1.52) |
| 372 | (IA) | CH | N | 2-oxotetrahydrofuran-3-yl | H | H | S—CH=CH | | | 1.49[b] | 368 | — |
| 373 | (IA) | CH | N | 2,2-difluoroethyl | H | H | fluoro | H | H | 1.34[b] | 310 | 71:15 (1.22) |
| 374 | (IA) | CH | N | 2-ethoxyethyl | H | H | fluoro | H | H | 1.43[b] | 318 | 62:17 (1.34) |
| 375 | (IA) | CH | N | 2-fluoroethyl | H | H | fluoro | H | H | 1.16[b] | 292 | 77:17 (1.05) |
| 376 | (IA) | CH | N | but-3-en-2-yl | H | H | fluoro | H | H | 1.73[b] | 300 | 49:37 (1.70) |
| 377 | (IA) | CH | N | ethyl | H | H | fluoro | H | H | 1.28[b] | 274 | 48:10 (1.22) |
| 378 | (IA) | CH | N | 2,2,2-trifluoroethyl | H | H | fluoro | H | H | 1.64[b] | 328 | 88:6 (1.46) |
| 379 | (IA) | CH | N | isobutyl | H | H | fluoro | H | H | 1.82[b] | 302 | 74:19 (1.72) |
| 380 | (IA) | CH | N | pentan-3-yl | H | H | fluoro | H | H | 2.04[b] | 316 | 67:17 (1.95) |
| 381 | (IA) | CH | N | 2-chloroethyl | H | H | fluoro | H | H | 1.45[b] | 308 | 74:23 (1.34) |
| 382 | (IA) | CH | N | prop-2-en-1-yl | H | H | fluoro | H | H | 1.54[b] | 286 | 75:13 (1.48) |
| 383 | (IA) | CH | N | prop-2-en-1-yl | H | H | bromo | H | H | 1.82[b] | 346 | 83:12 (1.73) |
| 384 | (IA) | CH | N | 2,2-difluoroethyl | H | H | bromo | H | H | 1.67[b] | 370 | 80:15 (1.51) |
| 385 | (IA) | CH | N | 2-oxotetrahydrofuran-3-yl | H | H | bromo | H | H | 1.52[b] | 390 | — |
| 386 | (IA) | CH | N | (2,2-dichloro-1-methylcyclopropyl)methyl | H | H | bromo | H | H | 2.75[b] | 442 | 86:8 (2.50) |
| 387 | (IA) | CH | N | propan-2-yl | H | H | bromo | H | H | 1.88[b] | 348 | 82:18 (1.34) |
| 388 | (IA) | CH | N | 2-fluoroethyl | H | H | bromo | H | H | 1.49[b] | 352 | 82:16 |
| 389 | (IA) | CH | N | but-3-en-2-yl | H | H | bromo | H | H | 2.03[b] | 360 | 87:11 (1.88) |
| 390 | (IA) | CH | N | ethyl | H | H | bromo | H | H | 1.6[b] | 334 | 79:20 (1.49) |
| 391 | (IA) | CH | N | 2,2,2-trifluoroethyl | H | H | bromo | H | H | 1.98[b] | 388 | — |
| 392 | (IA) | CH | N | pentan-3-yl | H | H | bromo | H | H | 2.39[b] | 376 | 77:15 (2.22) |
| 393 | (IA) | CH | N | 2-chloroethyl | H | H | bromo | H | H | 1.78[b] | 368 | 80:20 (1.61) |
| 394 | (IA) | CH | N | butan-2-yl | bromo | H | chloro | H | H | 3.69[b] | 396 | 70:30 |

TABLE I-continued

| Exa-No. | Type | $X_1$ | $X_2$ | $R^1$ | $R^2$ | $R^3$ | $R^6$ | $R^7$ | $R^8$ | log p | MW measured | Isomer ratio[d] |
|---|---|---|---|---|---|---|---|---|---|---|---|---|
| 395 | (IA) | CH | N | 2-methylpropyl | bromo | H | chloro | H | H | 3.58[b] | 397 | 65:45 |
| 396 | (IA) | CH | N | 2-methylpropyl | H | propanoylamino | chloro | H | H | 3.33[a] | 389 | — |
| 397 | (IA) | CH | N | 2-methylpropyl | H | (2-methylpropanoyl)amino | chloro | H | H | 3.83[a] | 404 | — |
| 398 | (IA) | N | N | 2-methylpropyl | H | hydroxy | chloro | H | H | 2.62[a] | 335 | — |
| 399 | (IA) | CH | N | 2-methylpropyl | H | 4-methyl-1H-imidazol-1-yl | chloro | H | H | 2.56[a] | 398 | — |
| 400 | (IA) | CH | N | butan-2-yl | H | H | trifluoromethyl | H | H | 2.58[a] | 351 | 9:1 |
| 401 | (IA) | CH | N | propan-2-yl | H | H | trifluoromethyl | H | H | 2.2[a] | 338 | 9:1 |
| 402 | (IA) | CH | N | H | H | H | trifluoromethyl | H | H | 1.25[a] | 332 | — |
| 403 | (IB) | CH | N | tetrahydro-2H-pyran-2-yl | H | H | trifluoromethyl | H | H | 1.94[a] | 380 | — |
| 404 | (IA) | CH | N | 2-methylpropyl | H | H | cyano | H | H | 1.74[b] | 309 | — |
| 405 | (IA) | CH | N | 2-methylpropyl | H | H | bromo | H | H | 2.1[b] | 362 | 79:19 (1.98) |
| 406 | (IB) | CH | N | 2-methylpropyl | H | H | bromo | H | H | 1.91[b] | 362 | 86:14 |
| 407 | (IA) | CH | N | 2-methylpropyl | H | H | H | H | H | 1.5[b] | 284 | 80:20 |
| 408 | (IA) | CH | N | H | H | H | bromo | H | H | 0.94[a] | 307 | — |
| 409 | (IA) | CH | N | H | H | H | S—CH=CH | H | H | 1.13[a] | 284 | — |
| 410 | (IA) | N | N | 2-methylpropyl | H | acetylamino | chloro | H | H | 3.04[a] | 376 | — |
| 411 | (IA) | N | N | 2-methylpropyl | H | propan-2-ylamino | chloro | H | H | 4.34[a] | 376 | — |
| 412 | (IA) | CH | N | propan-2-yl | prop-1-yn-1-yl | H | chloro | H | H | 2.78[a] | 342 | 84:12 |
| 413 | (IB) | CH | N | 2-methylpropyl | cyclopropyl | H | chloro | H | H | 2.61[a] | 358 | — |
| 414 | (IA) | CH | N | 2-methylpropyl | cyclopropyl | H | chloro | H | H | 2.7[a] | 358 | — |
| 415 | (IB) | CH | N | butan-2-yl | cyclopropyl | H | chloro | H | H | 2.73[a] | 358 | — |
| 416 | (IA) | CH | N | butan-2-yl | cyclopropyl | H | chloro | H | H | 2.75[a] | 358 | — |
| 417 | (IB) | CH | N | propan-2-yl | cyclopropyl | H | chloro | H | H | 2.44[a] | 344 | — |
| 418 | (IA) | CH | N | propan-2-yl | cyclopropyl | H | chloro | H | H | 2.44[a] | 344 | — |
| 419 | (IA) | CH | N | H | prop-1-yn-1-yl | H | chloro | H | H | 1.44[a] | 300 | — |
| 420 | (IA) | CH | N | 4-methoxybenzyl | H | (2E)-But-2-en-1,4-diyl | chloro | H | H | 3.02[a] | 420 | 64:22 (2.53) |
| 421 | (IC) | CH | N | 2-methylpropyl | H | H | chloro | H | H | 3.69[a] | 368 | — |
| 422 | (ID) | N | N | 2-methylpropyl | H | H | chloro | H | H | 2.84[a] | 335 | — |
| 423 | (IE) | N | N | 2-methylpropyl | H | H | chloro | H | H | 1.97[a] | 334 | — |

Measurement of logP values was performed according EEC directive 79/831 Annex V.A8 by HPLC (High Performance Liquid Chromatography) on reversed phase columns with the following methods:
[a]Measurement was done at pH 2.3 with 0.1% phosphoric acid and acetonitrile as eluent.
[b]Measurement of LC-MS was done at pH 2.7 with 0.1% formic acid in water and with acetonitrile (contains 0.1% formic acid) as eluent with a linear gradient from 10% acetonitrile to 95% acetonitrile.
[c]Measurement with LC-MS was done at pH 7.8 with 0.001 molar ammonium hydrogen carbonate solution in water as eluent with a linear gradient from 10% acetonitrile to 95% acetonitrile.
Calibration was done with not branched alkan2-ones (with 3 to 16 carbon atoms) with known logP-values (measurement of logP values using retention times with linear interpolation between successive alkanones) . . . lambda-maX-values were determined using UV-spectra from 200 nm to 400 nm and the peak values of the chromatographic signals.
[d]Between parenthesis is the logP value of the minor isomer.

In table 1, M + H (or M H) means the molecular ion peak, plus or minus 1 a.m.u. (atomic mass unit) respectively, as observed in mass spectroscopy and M (ApcI+) means the molecular ion peak as it was found via positive atmospheric pressure chemical ionisation in mass spectroscopy.
In all examples of table 1 the M + 1 peak was measured.

In table 1, M+H (or M H) means the molecular ion peak, plus or minus 1 a.m.u. (atomic mass unit) respectively, as observed in mass spectroscopy and M (ApcI+) means the molecular ion peak as it was found via positive atmospheric pressure chemical ionisation in mass spectroscopy.
In all examples of table 1 the M+1 peak was measured.

1H-NMR data of selected examples of table 1 are written in form of 1H-NMR-peak lists in the following NMR peak list table. To each signal peak are listed the δ-value in ppm and the signal intensity in the form "$delta_1$ (intensity$_1$); $delta_2$ (intensity$_2$); ... $delta_n$(intensity$_n$)":

| NMR peak list table |
|---|
| Example 110<br>Solvent: DMSO |
| 10.4977 (2.06); 8.2771 (2.53); 8.2757 (2.44); 8.2643 (2.56); 8.2627 (2.49); 8.1753 (0.42); 8.1607 (6.94); 8.1424 (2.02); 8.0119 (0.7); 7.3038 (0.42); 7.2942 (0.5); 7.1874 (0.48); 7.1778 (0.41); 7.0933 (2.23); 7.0894 (2.16); 7.0804 (2.17); 7.0765 (2.14); 7.0239 (4.06); 7.0141 (4.72); 6.9062 (4.8); 6.8964 (4.21); 4.3348 (0.51); 4.3189 (0.82); 4.3027 (0.78); 4.2993 (0.82); 4.283 (0.53); 3.3529 (53.1); 3.3478 (43.64); 3.345 (41.63); 3.3359 (71.22); 2.8914 (1.12); 2.7327 (0.89); 2.5126 (12.05); 2.5081 (23.97); 2.5035 (31.7); 2.4989 (22.83); 2.4944 (10.89); 2.0808 (16); 2.046 (1.89); 1.8964 (0.41); 1.8776 (0.6); 1.8618 (0.88); 1.8427 (1.02); 1.8232 (0.74); 1.8002 (0.68); 1.7851 (0.84); 1.7818 (0.8); 1.7667 (0.99); 1.7477 (0.56); 1.7326 (0.35); 1.4623 (7.46); 1.4455 (7.38); 1.3901 (0.81); 1.3736 (0.8); 0.8097 (3.58); 0.7913 (7.85); 0.7728 (3.38); 0.6711 (0.38); 0.6527 (0.85); 0.6344 (0.39); 0.0079 (0.36); −0.0002 (10.23); −0.0084 (0.4) |
| Example 145<br>Solvent: DMSO |
| 8.6185 (3.19); 8.6159 (2.03); 8.6111 (2.05); 8.6085 (3.3); 7.325 (3.57); 7.3223 (2.21); 7.3177 (2.19); 7.315 (3.54); 6.9668 (4.07); 6.9603 (4.12); 6.5998 (4.12); 6.5932 (4.1); 5.766 (0.36); 4.6365 (0.36); 4.6256 (0.96); 4.6147 (1.33); 4.6037 (0.97); 4.5928 (0.36); 3.4171 (0.46); 3.4105 (0.47); 3.3891 (469.34); 3.3662 (2.42); 2.5339 (0.33); 2.5308 (0.43); 2.5277 (0.42); 2.5189 (11.25); 2.5159 (25.09); 2.5128 (35.62); 2.5098 (25.83); 2.5068 (11.74); 2.2343 (16); 1.4405 (14.34); 1.4295 (14.39); 1.4213 (0.35) |
| Example 146<br>Solvent: DMSO |
| 8.7354 (0.78); 8.7326 (0.49); 8.728 (0.49); 8.7252 (0.81); 8.6183 (3.36); 8.6156 (2.08); 8.611 (2.1); 8.6083 (3.47); 7.8447 (0.87); 7.8419 (0.54); 7.8373 (0.54); 7.8345 (0.84); 7.3199 (3.49); 7.3172 (2.18); 7.3126 (2.14); 7.3099 (3.46); 6.9626 (3.89); 6.956 (4.01); 6.5943 (3.93); 6.5877 (3.88); 4.1657 (1.03); 4.1537 (3.4); 4.1417 (3.44); 4.1296 (1.05); 3.3616 (194.71); 3.3383 (2.07); 2.5258 (0.35); 2.5227 (0.44); 2.5196 (0.41); 2.5108 (9.77); 2.5078 (21.58); 2.5047 (30.37); 2.5017 (21.91); 2.4987 (9.92); 2.2214 (16); 1.9086 (0.41); 1.3746 (3.9); 1.3625 (8.99); 1.3505 (3.96) |
| Example 147<br>Solvent: DMSO |
| 8.6305 (2.15); 8.6209 (2.17); 7.8536 (0.34); 7.8435 (0.33); 7.3201 (2.22); 7.3104 (2.17); 6.9705 (2.77); 6.964 (2.84); 6.5999 (2.94); 6.5934 (2.88); 3.8466 (0.39); 3.8204 (16); 3.3673 (97.05); 3.344 (1.45); 2.5338 (0.39); 2.5307 (0.51); 2.5276 (0.56); 2.5188 (10.31); 2.5158 (22.03); 2.5128 (30.49); 2.5097 (22.15); 2.5068 (10.16); 2.3077 (0.34); 2.2121 (13.1) |
| Example 148<br>Solvent: DMSO |
| 8.5267 (5.97); 8.5241 (3.8); 8.5193 (3.74); 8.5166 (6.13); 8.1982 (10.32); 7.5421 (3.02); 7.5402 (3.2); 7.5337 (3.24); 7.5318 (3.21); 7.3549 (7.48); 7.3522 (4.52); 7.3475 (4.36); 7.3448 (7.37); 7.0598 (2.76); 7.0538 (3.88); 7.0514 (2.67); 7.0454 (3.9); 7.027 (3.89); 7.0251 (4.19); 7.0211 (2.83); 7.0192 (2.67); 4.2082 (2.06); 4.196 (6.45); 4.1839 (6.5); 4.1718 (2.1); 3.353 (85.63); 3.3296 (0.37); 2.5191 (0.34); 2.5103 (6.29); 2.5074 (13.29); 2.5044 (18.19); 2.5013 (13.23); 2.4984 (6.06); 1.9114 (0.39); 1.4546 (7.49); 1.4424 (16); 1.4303 (7.43); −0.0002 (3.01) |
| Example 149<br>Solvent: DMSO |
| 10.445 (2.66); 8.2444 (3.3); 8.2433 (3.4); 8.2359 (3.55); 8.2347 (3.56); 8.168 (2.4); 8.1186 (10.13); 7.5048 (3.35); 7.5029 (3.79); 7.4964 (3.47); 7.4945 (3.71); 7.0552 (2.78); 7.0533 (3.17); 7.0493 (4.6); 7.0473 (4.13); 7.029 (4.55); 7.023 (3.06); 7.0207 (6.79); 7.0183 (3.26); 7.0146 (3.21); 7.0124 (3.29); 7.0098 (3.35); 5.7619 (0.34); 4.2089 (1.62); 4.1967 (5.2); 4.1846 (5.25); 4.1725 (1.65); 3.9547 (0.7); 3.3854 (0.44); 3.3587 (140.07); 3.3354 (1.06); 2.5259 (0.43); 2.5228 (0.53); 2.5197 (0.58); 2.5109 (9.24); 2.5079 (20.18); 2.5048 (27.65); 2.5018 (20.02); 2.4987 (8.74); 2.4039 (1.52); 2.3914 (5.12); 2.386 (0.42); 2.3789 (5.2); 2.3663 (1.62); 1.4505 (6.87); 1.4384 (15.53); 1.4263 (6.98); 1.0695 (4.99); 1.0612 (7.07); 1.0487 (16); 1.0361 (7); −0.0002 (1.01) |
| Example 164<br>Solvent: DMSO |
| 10.422 (1.18); 8.276 (1.24); 8.2632 (1.26); 8.1723 (4.57); 7.5267 (1.66); 7.5231 (1.65); 7.0643 (1.02); 7.0604 (1); 7.0514 (1); 7.0475 (0.98); 6.9776 (2.03); 6.9739 (1.97); 5.7478 (2.74); 4.3341 (0.45); 4.3152 (0.45); 3.9026 (1.61); 3.3037 (69.23); 2.5095 (5.87); 2.5054 (10.48); 2.501 (13.3); 2.4968 (9.39); 2.4171 (0.65); 2.3982 (2.02); 2.3794 (2.07); 2.3606 (0.68); 1.9091 (0.37); 1.8751 (0.44); 1.856 (0.53); 1.8368 (0.38); 1.8111 (0.35); 1.7959 (0.45); 1.7775 (0.51); 1.4731 (3.67); 1.4563 (3.61); 1.0766 (3.59); 1.0714 (16); 1.0582 (4.83); 1.0393 (2.15); 0.8162 (1.83); 0.7978 (3.84); 0.7794 (1.68); −0.0002 (2.01) |

NMR peak list table

Example 165
Solvent: DMSO 8.4969 (3.95); 8.4822 (3.72); 8.4435 (0.59); 8.4287 (0.56); 7.6753 (0.36); 7.6625 (0.37);
7.4098 (2.52); 7.3971 (2.6); 7.0807 (4.52); 7.0689 (3.41); 7.0658 (4.11); 7.0534 (0.77); 7.038 (0.97);
7.0245 (0.4); 6.8597 (2.79); 6.847 (2.63); 5.7471 (0.56); 3.9061 (0.79); 3.8678 (16);
3.6342 (2.31); 3.3102 (152.75); 2.7203 (2.03); 2.701 (2.63); 2.6808 (2.35); 2.661 (0.63); 2.6408 (0.41);
2.501 (24.47); 1.8925 (2.23); 1.7606 (15.3); 1.6 (0.47); 1.5811 (0.46); 1.5745 (0.39);
1.5556 (1.14); 1.5368 (1.9); 1.5173 (1.92); 1.4985 (1.1); 1.0714 (6.47); 0.9032 (0.7); 0.8848 (1.43);
0.8695 (4.13); 0.8513 (7.55); 0.833 (3.31); −0.0002 (2.35)

Example 166
Solvent: DMSO 10.361 (2.64); 10.3046 (0.36); 8.1555 (2.75); 8.1426 (2.74); 8.1129 (0.43); 8.1001 (0.41);
8.0181 (3.26); 7.6527 (0.38); 7.6398 (0.42); 7.3968 (2.87); 7.3841 (2.94); 7.027 (0.43); 7.0143 (0.42);
6.8579 (3.12); 6.8452 (2.92); 6.6459 (2.29); 6.6424 (1.96); 6.6331 (2.43); 6.6297 (1.83);
5.7468 (0.46); 3.8653 (16); 3.6205 (2.31); 3.4413 (0.36); 3.3129 (274.79); 2.7187 (1.81); 2.6993 (2.38);
2.6793 (1.97); 2.6475 (0.6); 2.6278 (0.44); 2.505 (36.51); 2.501 (42.58); 2.4068 (1.38);
2.3881 (4.18); 2.3693 (4.56); 2.3509 (1.88); 2.3323 (0.43); 1.9272 (2.26); 1.8116 (15.66); 1.615 (0.63);
1.5978 (1.35); 1.5788 (1.94); 1.5597 (1.83); 1.541 (1.02); 1.2369 (0.59); 1.0832 (0.7);
1.0709 (8.84); 1.0676 (5.7); 1.0486 (9.66); 1.0432 (2.39); 1.0298 (4.35); 0.9066 (4); 0.8884 (7.92);
0.8701 (3.43); −0.0002 (4.49)

Example 167
Solvent: DMSO 8.5591 (8.62); 8.5551 (5.57); 8.5478 (5.7); 8.5438 (8.53); 8.2406 (13.04); 7.5637 (6.34);
7.5601 (6.14); 7.3881 (9.5); 7.384 (6.09); 7.3769 (5.98); 7.3728 (8.94); 6.9457 (7.42); 6.942 (7.12);
4.3567 (0.41); 4.3416 (1.13); 4.3254 (1.83); 4.3063 (1.84); 4.2899 (1.14); 3.3018 (254.84);
2.848 (0.46); 2.6738 (0.48); 2.6697 (0.62); 2.5089 (32.76); 2.5048 (58.87); 2.5004 (74.75);
2.4961 (52.69); 2.4517 (0.38); 2.3269 (0.49); 2.3229 (0.35); 2.0701 (0.64); 1.9079 (0.82); 1.8889 (1.25);
1.8731 (1.83); 1.8542 (2.27); 1.8349 (1.72); 1.8134 (1.57); 1.7981 (1.8); 1.7951 (1.73);
1.7795 (2.07); 1.7608 (1.16); 1.7454 (0.7); 1.473 (15.58); 1.4562 (15.31); 1.2362 (0.95); 1.1596 (0.43);
1.0708 (2.96); 0.823 (7.64); 0.8046 (16); 0.7861 (7); 0.0079 (0.73); −0.0002 (12.46)

Example 168
Solvent: DMSO 10.4715 (2.11); 8.3209 (2.11); 8.3195 (2.09); 8.3082 (2.18); 8.3067 (2.1); 8.0286 (2.43);
6.9887 (1.86); 6.9849 (1.82); 6.976 (1.82); 6.9722 (1.77); 6.9424 (3.42); 6.9325 (3.55); 6.6573 (3.6);
6.6475 (3.38); 5.7475 (0.39); 4.6275 (0.33); 4.611 (0.9); 4.5947 (1.23); 4.5783 (0.88);
4.5617 (0.34); 3.9023 (1.14); 3.303 (246.12); 2.509 (17.53); 2.5047 (32); 2.5003 (41.33); 2.4959 (28.96);
2.4916 (14.18); 2.4242 (1.15); 2.416 (0.5); 2.4054 (3.5); 2.3971 (0.89); 2.3866 (3.57);
2.3783 (0.84); 2.3677 (1.19); 2.3273 (0.35); 2.2207 (13.57); 2.0698 (0.43); 1.4404 (12.53); 1.424 (12.38);
1.1593 (0.65); 1.0833 (0.89); 1.0706 (16); 1.0502 (8.54); 1.0313 (3.82); −0.0002 (3.16)

Example 169
Solvent: DMSO 10.476 (1.62); 8.3266 (1.66); 8.314 (1.69); 8.0352 (1.92); 6.9889 (1.42); 6.9852 (1.36);
6.9763 (1.38); 6.9725 (1.3); 6.9462 (2.44); 6.9364 (2.57); 6.665 (2.6); 6.6552 (2.45); 5.7476 (3.12);
4.1685 (0.74); 4.1506 (2.24); 4.1325 (2.28); 4.1144 (0.72); 3.9027 (1.82); 3.3032 (161.17);
3.2808 (1.74); 2.5391 (0.45); 2.5091 (13.64); 2.5049 (24.16); 2.5005 (30.49); 2.4962 (21.14);
2.4252 (0.88); 2.4162 (0.41); 2.4064 (2.69); 2.3972 (0.71); 2.3875 (2.76); 2.3784 (0.64); 2.3687 (0.92);
2.2153 (10.59); 2.0699 (0.39); 1.9036 (0.91); 1.3857 (2.63); 1.3676 (5.83); 1.3496 (2.54);
1.1593 (0.4); 1.0834 (0.86); 1.0706 (16); 1.0506 (6.46); 1.0318 (2.9); −0.0002 (4.3)

Example 170
Solvent: DMSO 10.477 (2.82); 8.3296 (2.82); 8.3169 (2.83); 8.0376 (3.46); 6.9798 (2.35); 6.9769 (2.08);
6.9671 (2.29); 6.9643 (1.99); 6.9454 (3.38); 6.9355 (3.52); 6.6667 (3.56); 6.657 (3.31); 5.748 (3.28);
3.9029 (1.36); 3.8407 (0.33); 3.8081 (16); 3.3041 (103.72); 3.2814 (1.32); 2.5014 (22.43);
2.4261 (1.39); 2.4072 (4.11); 2.3884 (4.18); 2.3697 (1.39); 2.1988 (15.78); 1.9089 (0.71); 1.2364 (0.41);
1.1599 (0.88); 1.0714 (12.66); 1.0516 (9.17); 1.0329 (4.24); −0.0002 (2.88)

Example 175
Solvent: DMSO 10.3834 (1.97); 8.2363 (2.13); 8.2235 (2.17); 8.2223 (2.14); 8.156 (2.48); 8.1284 (6.1);
7.4941 (1.77); 7.4912 (1.84); 7.4815 (1.91); 7.4786 (1.87); 7.0565 (1.52); 7.0535 (1.72); 7.0475 (2.74);
7.0446 (2.47); 7.0276 (3.66); 7.0228 (2.22); 7.0189 (1.97); 7.0151 (3.22); 7.0099 (2.08);
7.0064 (1.67); 4.5869 (0.42); 4.5703 (1.06); 4.5536 (1.44); 4.537 (1.08); 4.5203 (0.42); 3.3151 (138.01);
2.5104 (5.78); 2.5062 (10.54); 2.5017 (13.57); 2.4974 (9.5); 2.4932 (4.64); 2.4122 (1.13);
2.3934 (3.63); 2.3745 (3.72); 2.3557 (1.21); 1.4917 (16); 1.475 (15.78); 1.0718 (5.97); 1.052 (8.72);
1.0332 (3.93); −0.0002 (0.51)

-continued

NMR peak list table

Example 185
Solvent: DMSO 8.3719 (6.38); 8.1952 (3.31); 8.1823 (3.39); 7.8197 (3.63); 7.8097 (3.71); 7.0428 (3.82);
7.0329 (3.65); 6.7483 (3.5); 6.7354 (3.46); 6.6158 (3.22); 5.7637 (0.33); 4.5685 (0.41); 4.5519 (1.05);
4.5352 (1.43); 4.5186 (1.07); 4.5019 (0.42); 4.0417 (0.9); 4.0239 (0.9); 3.3364 (16.88);
2.5289 (0.6); 2.5156 (6.26); 2.5112 (12.71); 2.5066 (17.04); 2.5021 (12.09); 2.4977 (5.47); 1.9936 (3.9);
1.4768 (16); 1.4602 (15.76); 1.1962 (1.05); 1.1784 (2.08); 1.1606 (1.01)

Example 186
Solvent: DMSO 8.3719 (9.69); 8.2234 (3.84); 8.2106 (3.87); 7.5992 (0.7); 7.0496 (7.57); 7.0398 (7.15);
6.8706 (2.42); 6.8493 (2.47); 6.7232 (8.28); 6.7104 (8.18); 4.33 (1.13); 4.314 (1.82); 4.2946 (1.77);
4.2783 (1.12); 4.2259 (0.71); 4.2096 (1.5); 4.1933 (1.67); 4.1888 (1.61); 4.1724 (1.47);
4.1561 (0.71); 3.4057 (0.94); 3.3849 (1.5); 3.3688 (1.2); 3.3547 (0.82); 3.3365 (56.99); 3.3128 (0.84);
3.2624 (3.03); 3.2481 (24.51); 3.2237 (1.63); 3.1942 (0.45); 2.6758 (0.35); 2.5462 (0.51);
2.5291 (1.97); 2.5158 (21.32); 2.5114 (43.48); 2.5069 (58.59); 2.5024 (41.89); 2.498 (19.14);
2.3337 (0.36); 1.891 (0.72); 1.8723 (1.2); 1.8562 (1.77); 1.8371 (2.19); 1.818 (1.76); 1.8012 (1.66);
1.7864 (1.84); 1.7832 (1.74); 1.768 (2.11); 1.7523 (1.11); 1.749 (1.16); 1.7338 (0.7); 1.4617 (16);
1.4449 (15.7); 1.2358 (0.76); 1.1309 (7.72); 1.1145 (7.54); 1.0076 (0.35); 0.992 (0.34);
0.7987 (7.13); 0.7804 (15.05); 0.762 (6.58)

Example 187
Solvent: DMSO 8.3851 (8.96); 8.2185 (3.82); 8.2058 (3.85); 7.6518 (0.42); 7.1628 (1.58); 7.1482 (2.97);
7.1334 (1.52); 7.0557 (8.49); 7.0459 (8.06); 6.7262 (7.49); 6.7134 (7.36); 5.7641 (3.7); 4.3295 (1.18);
4.3137 (1.94); 4.2942 (1.89); 4.2778 (1.18); 4.0414 (0.35); 4.0236 (0.34); 3.3364 (19.61);
3.3127 (1.75); 3.162 (3.55); 2.5457 (0.52); 2.5152 (15.96); 2.5066 (40.48); 2.5022 (29.1);
2.4982 (13.72); 1.9935 (1.43); 1.8927 (0.76); 1.874 (1.26); 1.8579 (1.86); 1.839 (2.3);
1.8197 (1.91); 1.8017 (1.79); 1.7868 (1.94); 1.7839 (1.82); 1.7684 (2.19); 1.7499 (1.2); 1.7343 (0.7);
1.4628 (16); 1.446 (15.65); 1.196 (0.41); 1.1782 (0.78); 1.1604 (0.4); 1.0486 (1); 1.0078 (0.57);
0.9922 (0.39); 0.7992 (7.37); 0.7808 (15.29); 0.7624 (6.69); 0.4254 (1.63); 0.4146 (4.86);
0.4106 (5.06); 0.4006 (2.69); 0.3945 (4.82); 0.3907 (4.6); 0.3807 (1.73); 0.2001 (3.79)

Example 188
Solvent: DMSO 8.4334 (14.96); 8.2924 (3.29); 8.2796 (3.26); 7.7731 (1.33); 7.4991 (1.83); 7.4838 (3.76);
7.4686 (1.74); 7.0537 (8.74); 7.0439 (8.26); 6.8417 (6.2); 6.8288 (6.11); 5.7651 (4.23); 4.3334 (1.16);
4.3177 (1.86); 4.2982 (1.84); 4.2819 (1.11); 4.0859 (4.58); 4.0804 (4.87); 4.0709 (4.71);
4.0654 (4.27); 3.3367 (58.86); 3.313 (2.46); 3.0598 (2.62); 2.6803 (0.45); 2.6756 (0.6); 2.6713 (0.42);
2.5459 (1.14); 2.5155 (37.71); 2.5111 (74.32); 2.5066 (98.1); 2.5021 (69.62); 2.4978 (31.61);
2.3382 (0.46); 2.3336 (0.58); 2.3291 (0.43); 1.8968 (0.73); 1.8782 (1.2); 1.8621 (1.83);
1.8431 (2.23); 1.8239 (1.82); 1.8067 (1.72); 1.792 (1.86); 1.7888 (1.73); 1.7735 (2.1); 1.7548 (1.15);
1.7392 (0.66); 1.4674 (16); 1.4506 (15.62); 0.8034 (7.33); 0.7851 (15.41); 0.7667 (6.62)

Example 189
Solvent: DMSO 8.3798 (0.65); 8.3626 (5.89); 8.2138 (2.93); 8.2011 (2.88); 7.6137 (0.81); 7.0664 (6.87);
7.0566 (6.44); 6.9105 (2); 6.89 (2.01); 6.7212 (0.34); 6.7083 (0.51); 6.6983 (6.08); 6.6855 (5.95);
4.3291 (0.97); 4.3132 (1.58); 4.2937 (1.52); 4.2773 (0.95); 4.1163 (0.34); 4.0998 (0.89); 4.0836 (1.36);
4.0672 (1.24); 4.0634 (1.27); 4.047 (0.91); 4.0419 (1.29); 4.0304 (0.37); 4.0241 (1.12);
4.0063 (0.36); 3.334 (30.6); 3.3103 (3); 2.5458 (0.32); 2.5154 (18.66); 2.5111 (36.71); 2.5066 (48.47);
2.5022 (34.61); 2.4979 (16.03); 1.9936 (4.48); 1.8908 (0.6); 1.872 (0.99); 1.856 (1.49);
1.837 (1.85); 1.8179 (1.51); 1.8006 (1.43); 1.7857 (1.56); 1.7828 (1.47); 1.7674 (1.78); 1.7486 (0.98);
1.7332 (0.57); 1.4613 (13.24); 1.4445 (12.97); 1.2358 (0.33); 1.1963 (1.34); 1.1786 (2.84);
1.154 (16); 1.1378 (15.76); 1.1046 (0.47); 1.0075 (0.55); 0.9919 (0.58); 0.7982 (6.03); 0.7798 (12.7);
0.7614 (5.56)

Example 190
Solvent: DMSO 10.4431 (4.59); 8.5825 (5.95); 8.5693 (6.13); 8.5044 (11.18); 7.9595 (5.24); 7.9496 (5.3);
7.3094 (6.07); 7.2962 (6.01); 7.0424 (6.7); 7.0325 (6.45); 4.4645 (0.4); 4.4113 (0.51); 4.4 (0.53);
4.3613 (0.9); 4.3452 (1.46); 4.3258 (1.45); 4.3096 (0.91); 4.0591 (0.58); 4.0413 (1.74); 4.0235 (1.76);
4.0058 (0.59); 3.3374 (37.76); 3.3139 (0.96); 2.6757 (0.32); 2.5457 (0.64); 2.5258 (4.57);
2.5153 (22.58); 2.511 (44.83); 2.5067 (62.15); 2.5022 (41.66); 2.4979 (19.85); 2.489 (7.98); 2.4703 (2.5);
2.3333 (0.4); 1.9937 (7.48); 1.9026 (0.64); 1.8838 (0.95); 1.8678 (1.46); 1.8488 (1.8);
1.8294 (1.4); 1.8168 (1.22); 1.8018 (1.51); 1.7988 (1.41); 1.7834 (1.65); 1.7648 (0.91); 1.7493 (0.53);
1.4767 (12.21); 1.4599 (12.01); 1.2357 (1.26); 1.1961 (2.15); 1.1783 (4.15); 1.1605 (2.16);
1.103 (0.36); 1.0867 (7.76); 1.068 (16); 1.0493 (7.37); 1.0067 (1.81); 0.9911 (1.75); 0.8557 (0.36);
0.8054 (6.12); 0.7871 (12.9); 0.7687 (5.65)

NMR peak list table

Example 192
Solvent: DMSO 8.7277 (6.16); 8.6927 (3.3); 8.6794 (3.41); 8.5964 (0.33); 8.5831 (0.35); 8.2934 (0.53); 7.7508 (3.57); 7.7409 (3.77); 7.7346 (3.53); 7.7212 (3.41); 7.3501 (0.42); 7.3055 (0.42); 7.2113 (0.36); 7.198 (0.37); 7.1491 (3.68); 7.1391 (3.5); 4.6139 (0.4); 4.5972 (1.03); 4.5805 (1.43); 4.5639 (1.09); 4.5472 (0.46); 3.3282 (19.25); 3.3044 (0.41); 3.0959 (1.11); 2.5289 (0.91); 2.5157 (10.5); 2.5112 (21.6); 2.5067 (29.19); 2.5022 (20.82); 2.4977 (9.58); 1.5183 (0.36); 1.5012 (16); 1.4845 (15.92); 1.4648 (0.78); 1.4088 (1.33); 1.3923 (1.37); 1.2336 (0.57)

Example 193
Solvent: DMSO 8.3698 (14.47); 8.1948 (7.58); 8.1818 (7.73); 7.8157 (8.33); 7.8057 (8.44); 7.0418 (8.76); 7.0319 (8.33); 6.7416 (8); 6.7287 (7.89); 6.6176 (7.8); 4.3258 (1.05); 4.3102 (1.66); 4.2904 (1.64); 4.2741 (1.05); 3.3885 (0.38); 3.3422 (257.13); 3.3187 (1.15); 3.2917 (1.53); 2.6761 (0.44); 2.5463 (0.62); 2.516 (26.8); 2.5116 (54.36); 2.5071 (72.78); 2.5025 (51.56); 2.4981 (23.26); 2.4564 (0.45); 2.4519 (0.44); 2.3382 (0.35); 2.3339 (0.45); 1.9938 (1.08); 1.8888 (0.67); 1.8703 (1.09); 1.8541 (1.7); 1.8349 (2.09); 1.8156 (1.61); 1.8011 (1.47); 1.7864 (1.71); 1.783 (1.62); 1.7679 (1.95); 1.7491 (1.04); 1.7337 (0.62); 1.4623 (15.18); 1.4455 (14.9); 1.2378 (0.36); 1.1965 (0.33); 1.1787 (0.59); 1.0075 (0.95); 0.9918 (0.92); 0.792 (7.38); 0.7736 (16); 0.7552 (6.8)

Example 194
Solvent: DMSO 8.3851 (9.81); 8.3811 (11.93); 8.2554 (5); 8.251 (6.6); 8.2426 (5.23); 8.2382 (6.29); 7.8558 (4.06); 7.8411 (4.04); 7.5677 (0.46); 7.1042 (4.8); 6.7948 (6.29); 6.7821 (5.83); 5.7626 (0.53); 5.7578 (0.67); 4.9627 (1.47); 4.9464 (3); 4.929 (3.28); 4.9136 (1.93); 4.898 (0.58); 4.7138 (4.79); 4.5458 (5.05); 4.5318 (7.94); 4.5171 (4.11); 4.3325 (1.53); 4.3167 (2.94); 4.3001 (2.98); 4.2833 (1.61); 4.0407 (0.82); 4.0231 (0.82); 3.3235 (24.87); 3.3191 (31.86); 3.2973 (1.49); 2.6771 (0.57); 2.5431 (0.42); 2.5084 (90.14); 2.5042 (87.59); 2.3353 (0.59); 1.9956 (2.6); 1.991 (3.45); 1.8929 (0.83); 1.8763 (1.56); 1.8583 (2.49); 1.84 (2.84); 1.8215 (2.25); 1.8036 (2.11); 1.7885 (2.82); 1.7704 (2.63); 1.754 (1.72); 1.7368 (0.89); 1.4623 (16); 1.4456 (15.59); 1.2383 (0.58); 1.1949 (0.99); 1.1818 (1.44); 1.1771 (1.87); 1.1638 (0.77); 1.1592 (0.97); 0.8017 (8.02); 0.7832 (15.9); 0.7652 (7.48)

Example 195
Solvent: DMSO 8.4005 (7.07); 8.254 (3.62); 8.2413 (3.64); 7.9832 (0.61); 7.3267 (3.62); 7.3182 (3.59); 7.0564 (7.37); 7.0466 (7.1); 6.8048 (6.26); 6.792 (6.12); 5.7636 (7.01); 4.3269 (1.2); 4.3108 (2.01); 4.2919 (1.98); 4.2752 (1.21); 3.5051 (2.75); 3.3334 (37.34); 3.3096 (0.68); 2.7704 (0.41); 2.7614 (1.17); 2.7526 (1.84); 2.7439 (2.61); 2.7349 (2.61); 2.7261 (1.82); 2.7168 (1.34); 2.713 (3.03); 2.5462 (0.36); 2.5109 (38.5); 2.5068 (51.01); 2.5026 (37.08); 1.9938 (0.87); 1.8945 (0.74); 1.8758 (1.27); 1.8597 (1.88); 1.8408 (2.38); 1.8218 (1.93); 1.8042 (1.77); 1.7888 (1.96); 1.7709 (2.19); 1.7525 (1.24); 1.7369 (0.69); 1.465 (16); 1.4482 (15.76); 1.179 (0.44); 0.8023 (7.57); 0.784 (15.88); 0.7656 (7); 0.6948 (1.54); 0.6822 (4.64); 0.6772 (6.02); 0.6655 (5.96); 0.6597 (4.74); 0.6489 (1.98); 0.6266 (0.34); 0.5335 (2.12); 0.5232 (6.32); 0.5162 (5.96); 0.5077 (4.92); 0.4959 (1.44)

Example 196
Solvent: DMSO 8.3914 (13.48); 8.2362 (5.67); 8.2233 (5.77); 7.6853 (0.43); 7.2906 (1.77); 7.2757 (3.48); 7.2608 (1.75); 7.0473 (8.06); 7.0374 (7.68); 6.757 (7.47); 6.7442 (7.34); 5.9701 (0.62); 5.9576 (1.29); 5.9447 (1.24); 5.9319 (1.49); 5.9147 (1.6); 5.9018 (1.36); 5.889 (1.5); 5.8765 (0.71); 5.7634 (2.66); 5.1793 (2.44); 5.1759 (2.55); 5.1363 (2.19); 5.1329 (2.28); 5.0714 (3.17); 5.0671 (3.23); 5.0457 (2.97); 5.0415 (3); 4.3269 (1.21); 4.3105 (2); 4.2915 (1.99); 4.2751 (1.21); 3.9364 (4.41); 3.5055 (2.13); 3.3349 (23.54); 3.3111 (0.44); 2.7132 (2.15); 2.5464 (0.4); 2.5114 (24.03); 2.507 (32.89); 2.5027 (24.99); 1.9938 (1); 1.8925 (0.78); 1.8735 (1.31); 1.8575 (1.9); 1.8384 (2.42); 1.8195 (2); 1.8013 (1.84); 1.7837 (1.94); 1.7679 (2.18); 1.7494 (1.26); 1.734 (0.69); 1.462 (15.84); 1.4452 (15.61); 1.1787 (0.53); 0.8597 (0.41); 0.7993 (7.64); 0.781 (16); 0.7625 (7.07)

Example 197
Solvent: DMSO 8.35 (6.11); 8.2041 (3.33); 8.1914 (3.36); 7.5804 (0.48); 7.0543 (8.59); 7.0445 (8.09); 6.8663 (2.24); 6.8449 (2.28); 6.6825 (6.13); 6.6698 (6.01); 5.7633 (0.57); 4.3294 (1.03); 4.3134 (1.65); 4.2939 (1.62); 4.2775 (1.04); 3.9032 (0.81); 3.8866 (1); 3.8693 (0.78); 3.5048 (2.48); 3.3326 (35.2); 3.3088 (0.6); 2.7126 (2.51); 2.5459 (0.53); 2.5289 (1.57); 2.5156 (16.53); 2.5112 (33.63); 2.5066 (45.16); 2.5021 (32.03); 2.4977 (14.51); 1.9935 (1.15); 1.8921 (0.66); 1.8733 (1.06); 1.8574 (1.58); 1.8383 (1.95); 1.8191 (1.66); 1.8009 (1.61); 1.786 (1.67); 1.7828 (1.58); 1.7675 (1.93); 1.7487 (1.04); 1.7335 (0.63); 1.5359 (0.84); 1.5189 (0.89); 1.4949 (0.8); 1.4613 (16); 1.4445 (15.65); 1.427 (0.89); 1.409 (0.45); 1.2474 (0.51); 1.1963 (0.36); 1.1785 (0.66); 1.1608 (0.42); 1.1102 (5.74); 1.0945 (5.59); 0.8783 (4.31); 0.8602 (8.38); 0.8419 (3.82); 0.8007 (6.07); 0.7823 (12.58); 0.7639 (5.52)

| NMR peak list table |
|---|
| Example 198<br>Solvent: DMSO |
| 10.0267 (1.06); 8.3891 (3.96); 8.2443 (2.37); 8.2313 (2.37); 7.9343 (0.49); 7.9316 (0.56);<br>7.9145 (0.7); 7.9107 (0.57); 7.7446 (0.87); 7.7296 (1.53); 7.7133 (0.77); 7.7076 (0.53); 7.6351 (0.51);<br>7.6158 (0.72); 7.5974 (0.32); 7.477 (0.41); 7.4743 (0.4); 7.4307 (0.45); 7.4122 (0.36);<br>7.3103 (4.27); 7.2979 (5.27); 7.2361 (0.89); 7.2253 (1.05); 7.2146 (1.29); 7.2032 (0.7); 7.1932 (0.33);<br>6.7858 (3.52); 6.7728 (3.46); 5.7649 (1.09); 4.5645 (0.7); 4.5483 (3.26); 4.5319 (3.51);<br>4.515 (1.26); 4.4983 (0.51); 3.5075 (1.1); 2.7136 (1.05); 2.5154 (3.32); 2.511 (6.75); 2.5066 (9.04);<br>2.5021 (6.44); 2.4977 (2.94); 1.4708 (16); 1.4542 (15.66) |
| Example 199<br>Solvent: DMSO |
| 8.5186 (1.07); 8.2108 (6.03); 8.0905 (0.35); 7.4327 (0.33); 7.42 (0.36); 7.4173 (0.33);<br>7.3817 (2.39); 7.3678 (2.19); 7.2915 (0.42); 7.2775 (0.4); 6.8163 (2.46); 6.8076 (3); 6.7882 (0.35);<br>6.7856 (0.32); 6.7384 (1.74); 6.7358 (1.71); 6.7297 (1.41); 6.7271 (1.28); 4.5581 (0.42);<br>4.5415 (1.06); 4.5248 (1.43); 4.5082 (1.06); 4.4916 (0.42); 3.3353 (14.63); 2.5457 (0.43); 2.5323 (1.48);<br>2.5293 (1.4); 2.5155 (14.11); 2.5111 (28.04); 2.5067 (37.08); 2.5022 (26.23); 2.4979 (12.01);<br>2.462 (0.43); 2.4574 (0.52); 2.4449 (10.02); 2.243 (2.4); 1.4821 (16); 1.4654 (15.82); 1.453 (2.4);<br>1.4366 (2.3); 1.3899 (0.92); 1.3734 (0.9); 1.2382 (0.36) |
| Example 200<br>Solvent: DMSO |
| 8.5831 (0.71); 8.2923 (1.41); 8.2556 (0.47); 7.4277 (0.4); 7.4146 (0.42); 7.4093 (0.32);<br>7.395 (0.36); 7.3473 (1.73); 7.3281 (6.32); 7.3119 (8.07); 7.2647 (2); 7.25 (1.72); 7.2439 (2.32);<br>6.9508 (0.69); 5.7655 (3.98); 4.5765 (3.75); 4.5691 (3.77); 4.3438 (1.09); 4.3278 (1.73); 4.3086 (1.74);<br>4.2922 (1.12); 3.5065 (1.35); 3.0035 (0.61); 2.7129 (1.36); 2.5958 (0.58); 2.5292 (0.86);<br>2.5244 (1.19); 2.5157 (11.47); 2.5113 (24.31); 2.5067 (33.3); 2.5022 (24.12); 2.4978 (11.25);<br>2.4213 (0.91); 2.2851 (0.93); 1.89 (0.62); 1.8714 (1.06); 1.8552 (1.66); 1.8361 (2.11); 1.8251 (0.63);<br>1.8168 (1.61); 1.807 (1.44); 1.7921 (1.77); 1.7889 (1.68); 1.7737 (1.98); 1.7548 (1.05);<br>1.7395 (0.62); 1.4645 (14.18); 1.4477 (14.05); 0.7963 (7.28); 0.778 (16); 0.7595 (6.85) |
| Example 201<br>Solvent: DMSO |
| 8.6791 (9.25); 8.6745 (11.43); 8.6684 (10.08); 8.6641 (11.66); 8.5563 (0.65); 8.5463 (0.63);<br>7.506 (0.39); 7.4319 (9.59); 7.4274 (11.81); 7.4213 (10.3); 7.4169 (11.77); 7.2775 (0.91); 7.2677 (1.08);<br>7.2296 (0.5); 7.221 (0.51); 7.0243 (6.44); 7.0148 (7.98); 7.009 (5.34); 6.7112 (6.87);<br>6.7017 (7.82); 6.6958 (5.09); 4.5598 (1.79); 4.5447 (3.19); 4.5359 (2.42); 4.5283 (3.04); 4.5136 (1.55);<br>3.3885 (0.67); 3.3379 (53.79); 3.3323 (45.88); 3.3128 (5.41); 2.6739 (0.72); 2.5095 (96.24);<br>2.5056 (99.86); 2.4557 (0.44); 2.3334 (0.66); 1.967 (0.42); 1.9601 (0.63); 1.9424 (1.04);<br>1.9269 (1.89); 1.9083 (2.8); 1.8906 (3.02); 1.8713 (2.39); 1.8528 (2.45); 1.8339 (3.01); 1.8157 (2.63);<br>1.8005 (1.74); 1.781 (0.93); 1.7629 (0.38); 1.4746 (15.84); 1.4692 (15.93); 1.4582 (15.61);<br>1.4531 (14.55); 1.4221 (1.4); 1.4061 (1.27); 1.2401 (0.51); 0.8807 (0.38); 0.8298 (8.38); 0.8245 (8.85);<br>0.8118 (16); 0.8064 (15.37); 0.7932 (7.61); 0.7887 (7.03); 0.7669 (0.4); 0.7138 (0.74);<br>0.6957 (1.28); 0.6775 (0.65) |
| Example 202<br>Solvent: DMSO |
| 8.9722 (7.4); 8.9587 (7.66); 8.8899 (1.98); 8.8765 (2.05); 8.8159 (13.44); 8.7695 (3.59);<br>8.1515 (1.48); 8.1415 (1.5); 7.9708 (7.44); 7.9572 (7.35); 7.9306 (7.92); 7.9207 (8.09); 7.8168 (2.01);<br>7.8034 (1.97); 7.1005 (8.28); 7.0905 (7.94); 7.0732 (2.13); 7.0632 (2.04); 5.7633 (0.38);<br>4.3941 (1.05); 4.3784 (1.72); 4.3622 (1.69); 4.3588 (1.73); 4.3425 (1.1); 4.3342 (0.39); 3.37 (42.38);<br>3.3346 (27.18); 3.3109 (0.82); 2.8848 (11.2); 2.5158 (14.76); 2.5114 (29.86); 2.5068 (40.07);<br>2.5023 (28.42); 2.4979 (12.91); 1.9226 (0.72); 1.9039 (1.24); 1.8877 (1.87); 1.8684 (2.41);<br>1.8494 (1.84); 1.8395 (1.6); 1.8245 (1.89); 1.8213 (2.03); 1.806 (2.06); 1.787 (1.2); 1.7719 (0.64);<br>1.4968 (15.88); 1.48 (15.62); 0.8211 (7.47); 0.8027 (16); 0.7843 (6.94) |
| Example 203<br>Solvent: DMSO |
| 8.9742 (3.19); 8.9606 (3.29); 8.8917 (1.07); 8.8783 (1.11); 8.8121 (5.83); 8.7636 (1.97);<br>8.1426 (1.16); 8.1325 (1.17); 7.9795 (3.22); 7.9659 (3.16); 7.9268 (3.42); 7.9169 (3.48); 7.8246 (1.09);<br>7.8112 (1.07); 7.0993 (3.55); 7.0893 (3.43); 7.0719 (1.19); 7.0619 (1.15); 5.7627 (0.55);<br>4.6313 (0.39); 4.6147 (1.02); 4.6063 (0.47); 4.5981 (1.4); 4.5897 (0.58); 4.5815 (1.05); 4.5731 (0.41);<br>4.5649 (0.41); 3.3688 (18.2); 3.3375 (8.09); 2.8827 (6.06); 2.5158 (3.95); 2.5114 (8.04);<br>2.5069 (10.81); 2.5024 (7.7); 2.498 (3.51); 1.5126 (16); 1.496 (15.76) |
| Example 204<br>Solvent: DMSO |
| 9.6261 (4.09); 9.4903 (0.85); 8.2999 (4); 8.2984 (4.12); 8.287 (4.16); 8.2853 (4.31);<br>8.2015 (12.26); 8.1891 (1.25); 8.1877 (1.3); 8.1798 (4.92); 8.1779 (4.94); 8.1763 (4.19); 8.0652 (1.04);<br>8.0635 (0.95); 8.0444 (2.07); 7.9527 (1.06); 7.3086 (1.48); 7.299 (1.75); 7.2029 (1.7);<br>7.1932 (1.45); 7.1508 (3.72); 7.1469 (3.63); 7.1379 (3.61); 7.1339 (3.62); 7.0423 (0.34); 7.0302 (7.1);<br>7.0204 (8.15); 7.0024 (0.5); 7.0001 (0.61); 6.9984 (0.59); 6.9963 (0.5); 6.9892 (0.5);<br>6.9869 (0.57); 6.9854 (0.6); 6.983 (0.48); 6.9114 (8.49); 6.9016 (7.38); 5.9185 (4.13); 5.9048 (4.5);<br>5.8889 (0.84); 4.3406 (0.83); 4.3246 (1.31); 4.3088 (1.24); 4.3053 (1.33); 4.2888 (0.9);<br>4.2452 (0.49); 4.2284 (1.87); 4.2146 (2.1); 4.2114 (2.13); 4.1977 (2); 4.1801 (0.76); 4.1757 (0.52);<br>4.1619 (0.5); 3.4403 (0.41); 3.4218 (0.56); 3.3477 (347.1); 3.2922 (0.62); 2.8916 (8.86);<br>2.7329 (6.98); 2.7317 (7.12); 2.6729 (0.39); 2.5431 (0.34); 2.5262 (1.1); 2.513 (22.72); 2.5085 (46.4); |

| NMR peak list table |
|---|
| 2.5039 (62.14); 2.4993 (45.22); 2.4947 (22); 2.3306 (0.4); 1.9002 (0.73); 1.8899 (0.37); 1.8814 (0.99); 1.8656 (1.47); 1.8458 (1.68); 1.8268 (1.31); 1.8048 (1.15); 1.7898 (1.38); 1.7863 (1.3); 1.7713 (1.63); 1.7522 (0.96); 1.7452 (0.34); 1.7371 (0.63); 1.7333 (0.45); 1.4668 (12.4); 1.4499 (12.69); 1.434 (0.75); 1.3964 (2.55); 1.3799 (2.6); 1.3115 (13.96); 1.2946 (16); 1.2772 (2.48); 1.2407 (0.42); 1.2341 (0.39); 1.2236 (0.34); 0.811 (5.99); 0.7926 (13.21); 0.7804 (1.52); 0.7742 (5.64); 0.7626 (0.44); 0.6744 (1.2); 0.6561 (2.67); 0.6377 (1.17); −0.0002 (4.41)<br>Example 205<br>Solvent: DMSO |
| 10.7392 (2.18); 10.6041 (0.36); 8.2882 (2.21); 8.2748 (2.25); 8.187 (0.39); 8.1736 (0.39); 8.1463 (6.06); 8.1271 (2.38); 8.0326 (0.38); 7.9659 (0.95); 7.9521 (0.77); 7.3555 (0.37); 7.3493 (0.8); 7.3348 (10.08); 7.3293 (5.66); 7.3188 (5.08); 7.3042 (0.61); 7.2988 (0.9); 7.2817 (0.55); 7.2721 (0.82); 7.2644 (0.84); 7.2584 (1.03); 7.2509 (0.95); 7.2426 (1.17); 7.2337 (0.57); 7.2276 (0.53); 7.2209 (0.37); 7.2177 (0.71); 7.2081 (0.52); 7.0956 (1.88); 7.0917 (1.83); 7.0827 (1.85); 7.0788 (1.81); 7.0057 (3.35); 6.9959 (3.81); 6.9185 (0.33); 6.9145 (0.34); 6.881 (3.99); 6.8712 (3.48); 4.563 (0.42); 4.5464 (1.07); 4.5297 (1.47); 4.5131 (1.09); 4.4964 (0.41); 3.7149 (7.28); 3.6793 (1.33); 3.5153 (0.4); 3.4774 (0.61); 3.3901 (357.94); 3.3164 (1); 3.2812 (0.42); 2.8922 (6.04); 2.7334 (4.86); 2.5153 (11.92); 2.5109 (23.62); 2.5064 (31.1); 2.5018 (22.54); 2.4974 (10.91); 1.4627 (16); 1.446 (15.73); 1.3906 (2.17); 1.3741 (2.13); −0.0002 (6.02)<br>CHECK<br>Example 205<br>Solvent: DMSO |
| 9.6243 (2.52); 9.4927 (0.52); 8.2979 (1.99); 8.2851 (2.82); 8.2774 (1.75); 8.2036 (4.75); 8.1943 (3.2); 8.188 (2.08); 8.1716 (3.96); 8.0579 (0.86); 8.0129 (0.99); 8.004 (0.74); 7.9504 (0.92); 7.9007 (0.34); 7.8845 (0.35); 7.3106 (0.36); 7.3009 (0.64); 7.2506 (0.51); 7.2408 (0.66); 7.1433 (1.91); 7.1343 (2.37); 7.1305 (2.65); 7.0727 (0.34); 7.0631 (0.25); 7.0311 (2.38); 7.0213 (3.96); 7.0122 (2.11); 6.9944 (0.77); 6.9901 (0.8); 6.9812 (0.79); 6.9772 (0.8); 6.9421 (0.42); 6.9318 (0.43); 6.9046 (2.74); 6.8948 (3.88); 6.8861 (2.12); 6.8335 (0.39); 5.9096 (1.61); 5.8963 (2.45); 4.584 (0.35); 4.5682 (0.98); 4.5595 (0.78); 4.5518 (1.5); 4.5436 (1.11); 4.5353 (1.41); 4.519 (0.89); 4.4288 (0.36); 4.4134 (0.34); 4.2271 (0.98); 4.2109 (1.61); 4.1974 (1.55); 4.1809 (1.02); 3.3289 (90.78); 3.319 (54.57); 3.0589 (1.55); 3.0136 (1.19); 2.9372 (0.89); 2.9178 (0.75); 2.8904 (4.04); 2.8815 (2.82); 2.7309 (3.32); 2.7223 (2.29); 2.6667 (0.48); 2.5017 (33.4); 2.4976 (38.64); 2.4935 (35.86); 2.3249 (1.56); 2.2369 (1.01); 1.4821 (11.79); 1.4732 (9.14); 1.4656 (16); 1.4571 (10.52); 1.4031 (2.93); 1.3944 (2.56); 1.3869 (3.41); 1.3105 (6.45); 1.3018 (5.31); 1.2935 (8.89); 1.2855 (6.43); 1.2766 (4.25); 1.2337 (1.54); 1.1511 (0.9); 1.1342 (0.87); 1.0928 (0.69); −0.0002 (6.11); −0.0097 (3.88); −0.0162 (1.97)<br>Example 206<br>Solvent: DMSO |
| 9.6317 (3.36); 8.3039 (3.42); 8.3023 (3.48); 8.291 (3.54); 8.2894 (3.65); 8.1756 (4.45); 8.1737 (4.79); 8.1695 (10.6); 7.9909 (0.84); 7.9531 (0.43); 7.308 (0.37); 7.2984 (0.54); 7.2572 (0.52); 7.2475 (0.39); 7.1372 (3.2); 7.1332 (3.14); 7.1242 (3.15); 7.1203 (3.15); 7.0324 (6.05); 7.0225 (6.94); 6.9068 (7.17); 6.897 (6.31); 5.9113 (2.9); 5.8977 (3); 4.2461 (0.38); 4.2292 (1.46); 4.2164 (2.92); 4.2125 (1.93); 4.1988 (6.95); 4.1807 (6.01); 4.1624 (1.97); 4.0792 (0.39); 4.0612 (0.4); 3.3666 (0.49); 3.3334 (161.18); 2.891 (3.6); 2.7323 (2.79); 2.7312 (2.82); 2.5251 (0.68); 2.5119 (15.52); 2.5073 (31.42); 2.5027 (41.87); 2.4981 (30.21); 2.4936 (14.58); 1.451 (7.08); 1.4328 (16); 1.4145 (6.92); 1.3355 (0.53); 1.3173 (2.03); 1.3115 (12.17); 1.2945 (12.41); 1.2759 (1.01); 0.008 (0.67); −0.0002 (18.78); −0.0085 (0.68)<br>Example 207<br>Solvent: DMSO |
| 9.6369 (2.21); 8.307 (2.33); 8.3054 (2.36); 8.2941 (2.41); 8.2924 (2.43); 8.1744 (2.43); 8.1728 (2.78); 8.1709 (2.81); 8.1693 (2.36); 8.1093 (6); 7.9444 (0.73); 7.2975 (0.47); 7.2675 (0.46); 7.127 (2.2); 7.123 (2.16); 7.1141 (2.16); 7.1101 (2.16); 7.0313 (4.16); 7.0215 (4.75); 6.9057 (4.85); 6.8959 (4.28); 5.9114 (0.75); 5.8989 (0.79); 4.2273 (0.55); 4.2168 (0.64); 4.2112 (0.64); 4.2005 (0.59); 3.8995 (16); 3.7804 (1.56); 3.3375 (114.57); 2.8912 (1.07); 2.7325 (0.85); 2.7312 (0.84); 2.5254 (0.43); 2.5122 (10); 2.5076 (20.24); 2.503 (26.98); 2.4984 (19.43); 2.4939 (9.39); 1.3112 (8.24); 1.2942 (8.67); 1.2763 (0.83); 0.008 (0.34); −0.0002 (9.43); −0.0085 (0.35)<br>Example 208<br>Solvent: DMSO |
| 9.441 (1.3); 8.3023 (1.34); 8.3006 (1.39); 8.2894 (1.39); 8.2877 (1.44); 8.1775 (1.45); 8.1757 (1.66); 8.1737 (1.7); 8.1718 (1.46); 8.1203 (3.4); 7.9478 (0.39); 7.128 (1.28); 7.1241 (1.25); 7.1151 (1.25); 7.1111 (1.27); 7.0339 (2.48); 7.0241 (2.81); 6.9010 (1.2); 6.8914 (2.56); 6.0318 (1.52); 3.8986 (9.07); 3.7849 (0.81); 3.3321 (57.77); 2.8909 (0.81); 2.7324 (0.65); 2.731 (0.66); 2.5249 (0.33); 2.5117 (6.49); 2.5072 (13.18); 2.5026 (17.59); 2.498 (12.71); 2.4934 (6.12); 1.3581 (16); 1.3408 (1.44); 0.008 (0.56); −0.0002 (15.15); −0.0085 (0.55)<br>Example 209<br>Solvent: DMSO |
| 8.5958 (0.68); 8.573 (0.37); 8.5597 (0.41); 8.4723 (3.21); 8.4591 (3.31); 8.3255 (5.06); 7.5535 (0.39); 7.5436 (0.42); 7.3494 (0.38); 7.3361 (0.41); 7.3188 (3.16); 7.3092 (3.7); 7.2078 (3.66); 7.1982 (3.09); 7.1187 (3.41); 7.1056 (3.4); 5.7636 (4.67); 4.1516 (0.36); 4.1383 (0.49); 4.1283 (0.49); 4.1227 (0.49); 4.1153 (0.49); 4.0994 (0.37); 3.3319 (10.36); 2.5159 (8.24); 2.5115 (16.67); 2.507 (22.33); 2.5024 (15.8); 2.498 (7.14); 2.479 (1.87); 2.2433 (16); 1.9458 (0.34); 1.9276 (0.45); 1.9225 (0.38); 1.9113 (0.57); 1.9042 (0.46); 1.893 (0.56); 1.8883 (0.58); 1.87 (0.5); 1.7464 (0.45); 1.7337 (0.53); 1.7281 (0.52); 1.7152 (0.62); 1.6993 (0.41); 1.6938 (0.4); 1.6812 (0.32); |

|     |
| --- |
| NMR peak list table |
| 1.4779 (0.74); 1.4611 (0.72); 1.3929 (5.97); 1.3764 (5.85); 0.8105 (0.37); 0.7921 (0.77); 0.7737 (0.34); 0.6707 (2.93); 0.6524 (6.36); 0.6341 (2.69) |
| Example 210 Solvent: DMSO |
| 9.4371 (1.52); 9.3305 (0.44); 8.2951 (1.37); 8.2939 (1.36); 8.2821 (1.41); 8.2808 (1.39); 8.2075 (3.82); 8.1963 (0.52); 8.1837 (2.09); 8.1821 (2.18); 8.0746 (0.51); 8.0725 (0.51); 8.0478 (1.01); 7.9524 (0.47); 7.3063 (0.62); 7.2967 (0.74); 7.198 (0.72); 7.1884 (0.62); 7.1509 (1.19); 7.147 (1.16); 7.138 (1.17); 7.134 (1.17); 7.0325 (2.22); 7.0227 (2.55); 6.9776 (0.35); 6.9736 (0.35); 6.9644 (0.35); 6.9603 (0.35); 6.9068 (2.63); 6.897 (2.3); 6.0577 (1.98); 6.0144 (0.57); 4.3246 (0.46); 4.3051 (0.47); 3.4419 (1.03); 3.3887 (223.31); 3.3179 (0.51); 2.8933 (3.83); 2.7342 (3.09); 2.7334 (2.93); 2.5159 (7.17); 2.5115 (14.44); 2.5069 (19.24); 2.5023 (14); 2.4979 (6.83); 1.8815 (0.34); 1.8655 (0.5); 1.8463 (0.57); 1.8266 (0.45); 1.806 (0.41); 1.791 (0.47); 1.7876 (0.45); 1.7724 (0.55); 1.7535 (0.34); 1.4676 (4.18); 1.4507 (4.14); 1.3999 (1.18); 1.3834 (1.25); 1.3598 (16); 1.3421 (4.19); 0.8093 (2.05); 0.7909 (4.48); 0.7725 (1.91); 0.6739 (0.57); 0.6556 (1.27); 0.6373 (0.55); −0.0002 (4.65) |
| Example 211 Solvent: DMSO |
| 9.4486 (1.25); 8.2951 (1.37); 8.2935 (1.41); 8.2822 (1.42); 8.2805 (1.46); 8.2132 (3.99); 8.1818 (1.62); 8.18 (1.72); 8.178 (1.72); 8.1762 (1.45); 8.0196 (0.44); 7.9526 (0.47); 7.3003 (0.37); 7.2476 (0.36); 7.1488 (1.24); 7.1448 (1.21); 7.1358 (1.23); 7.1318 (1.31); 7.0342 (2.48); 7.0244 (2.96); 6.9017 (2.91); 6.8977 (0.39); 6.8919 (2.6); 4.5687 (0.67); 4.552 (0.93); 4.5354 (0.69); 3.357 (118.31); 2.8917 (3.95); 2.7331 (3.11); 2.7317 (3.19); 2.5134 (7.54); 2.5089 (15.46); 2.5043 (20.73); 2.4996 (15.04); 2.4951 (7.26); 2.0533 (0.77); 1.5646 (1.08); 1.4832 (11.01); 1.4664 (10.98); 1.4063 (1.14); 1.3898 (1.17); 1.3595 (16); 1.3413 (2.37); 0.0081 (0.32); −0.0002 (9.44); −0.0085 (0.35) |
| Example 212 Solvent: DMSO |
| 9.4379 (1.33); 8.2987 (1.34); 8.2972 (1.34); 8.2858 (1.38); 8.2842 (1.41); 8.1902 (0.45); 8.1887 (0.48); 8.1806 (5.29); 8.0764 (0.35); 8.0742 (0.35); 7.9947 (0.97); 7.3088 (0.43); 7.2991 (0.62); 7.2565 (0.6); 7.2469 (0.43); 7.1369 (1.23); 7.133 (1.2); 7.124 (1.2); 7.12 (1.21); 7.0351 (2.33); 7.0253 (2.67); 6.9024 (2.76); 6.8926 (2.45); 6.0317 (1.89); 5.9911 (0.39); 4.2162 (0.67); 4.198 (2.15); 4.1798 (2.18); 4.1615 (0.7); 4.0845 (0.46); 4.0664 (0.46); 3.3277 (49.19); 2.8909 (1.34); 2.7322 (1.05); 2.731 (1.05); 2.5248 (0.39); 2.5114 (7.84); 2.5069 (15.94); 2.5023 (21.32); 2.4977 (15.4); 2.4931 (7.44); 1.4509 (2.75); 1.4327 (6.23); 1.4145 (2.68); 1.3585 (16); 1.3401 (3.97); 1.3205 (1.3); 1.3024 (0.56); 0.008 (0.55); −0.0002 (15.55); −0.0085 (0.59) |
| Example 213 Solvent: DMSO |
| 8.6774 (0.36); 8.6626 (0.41); 8.6318 (6.86); 8.6171 (6.86); 7.8424 (0.42); 7.8235 (0.65); 7.8119 (0.45); 7.8083 (0.57); 7.6811 (0.36); 7.6722 (0.48); 7.6534 (0.51); 7.412 (8.22); 7.3974 (7.76); 7.0694 (7.51); 7.0596 (8.07); 6.8502 (8.08); 6.8404 (7.5); 5.764 (0.43); 4.4132 (1.05); 4.3968 (1.72); 4.377 (1.68); 4.3605 (1.05); 4.0713 (0.51); 4.0604 (0.37); 3.3377 (14.98); 2.6754 (0.48); 2.5619 (0.84); 2.5577 (0.84); 2.5525 (0.78); 2.5109 (59.79); 2.5066 (76.48); 2.5022 (54.59); 2.4669 (0.68); 2.4624 (0.7); 2.3379 (0.37); 2.3337 (0.48); 1.8861 (0.63); 1.8677 (1.06); 1.8511 (1.84); 1.8318 (2.5); 1.8158 (2.41); 1.8017 (2.18); 1.7983 (2.08); 1.7834 (2.15); 1.7652 (1.07); 1.7489 (0.53); 1.5033 (0.34); 1.4691 (16); 1.4525 (15.63); 1.2367 (0.34); 1.1758 (0.44); 1.1635 (0.96); 1.1473 (0.89); 0.8716 (0.32); 0.8383 (7.63); 0.82 (15.52); 0.8016 (6.93) |
| Example 214 Solvent: DMSO |
| 8.5427 (1.42); 8.5337 (1.43); 8.2343 (6.17); 7.3846 (2.84); 7.3698 (2.7); 7.2653 (3.49); 7.2559 (3.58); 6.7322 (3.49); 6.7229 (3.42); 4.5717 (0.41); 4.5551 (1.06); 4.5384 (1.44); 4.5218 (1.08); 4.5051 (0.41); 3.3359 (0.91); 3.17 (0.53); 2.5461 (0.46); 2.5156 (18.26); 2.5112 (37.06); 2.5067 (49.74); 2.5022 (35.78); 2.4978 (16.71); 1.9939 (0.47); 1.4828 (16); 1.4661 (15.77) |
| Example 215 Solvent: DMSO |
| 8.4443 (3.53); 8.1041 (5.76); 7.5384 (3.24); 7.5356 (3.29); 7.5295 (3.43); 7.2103 (5.2); 7.1988 (4.98); 7.1031 (3.41); 7.0969 (3.29); 4.4099 (0.53); 4.3929 (1.25); 4.3772 (1.69); 4.3611 (1.29); 4.345 (0.55); 3.3351 (9.57); 2.6738 (0.41); 2.5084 (59.83); 2.5047 (56.5); 2.3343 (0.4); 1.4856 (0.34); 1.4701 (0.37); 1.3905 (16); 1.3744 (15.98) |
| Example 216 Solvent: DMSO |
| 11.4225 (1.51); 11.1709 (2.79); 10.4799 (2.22); 10.3732 (1.11); 8.2454 (2.41); 8.2324 (2.45); 8.1393 (2.62); 8.125 (1.37); 8.0788 (0.85); 7.9974 (5.92); 7.8493 (3.68); 7.0516 (1.84); 7.042 (3.72); 7.0384 (2.07); 7.0292 (1.88); 7.0254 (1.86); 6.8673 (0.99); 6.8634 (0.96); 6.8542 (0.96); 6.8503 (0.95); 6.7795 (3.39); 6.7697 (3.62); 6.7162 (1.92); 6.7064 (1.86); 6.4942 (3.5); 6.4843 (3.26); 5.7634 (0.57); 3.8769 (14.46); 3.7395 (7.59); 3.3345 (18.62); 3.1799 (1.21); 3.1668 (1.17); 2.5461 (0.35); 2.5157 (14.18); 2.5113 (28.99); 2.5068 (39.24); 2.5023 (28.09); 2.4978 (12.89); 2.0843 (11.23); 2.0813 (16); 2.0641 (15.16); 2.0491 (7.63); 1.7723 (0.39); 1.7595 (13.39) |

-continued

NMR peak list table

Example 217
Solvent: DMSO 8.2175 (3.44); 8.0767 (0.48); 8.0636 (0.49); 8.0505 (1.03); 7.3185 (0.64); 7.3089 (0.74);
7.2022 (0.73); 7.1925 (0.63); 7.1314 (1.45); 7.0695 (2.95); 7.0596 (3.33); 7.0007 (0.39); 6.943 (0.59);
6.9336 (0.88); 6.927 (2.72); 6.9172 (2.26); 4.3358 (0.33); 4.3201 (0.56); 4.3003 (0.57);
4.2838 (0.4); 3.3707 (1.21); 3.3334 (98.74); 2.8908 (0.9); 2.732 (0.74); 2.7309 (0.77); 2.6892 (16);
2.6718 (0.64); 2.6448 (4.1); 2.5488 (0.41); 2.5419 (0.38); 2.5248 (0.57); 2.5116 (11.89);
2.5071 (23.99); 2.5025 (31.94); 2.4979 (23.1); 2.4933 (11.18); 1.8726 (0.45); 1.8569 (0.59);
1.8378 (0.67); 1.8184 (0.54); 1.7987 (0.51); 1.7835 (0.56); 1.7802 (0.55); 1.765 (0.65); 1.746 (0.38);
1.4582 (4.84); 1.4414 (4.83); 1.384 (1.14); 1.3675 (1.13); 0.8081 (2.35); 0.7995 (0.7);
0.7898 (5.19); 0.7814 (1.05); 0.7713 (2.21); 0.7632 (0.41); 0.663 (0.55); 0.6447 (1.22); 0.6263 (0.52);
0.008 (0.89); −0.0002 (24.47); −0.0085 (0.91)

Example 218
Solvent: DMSO 8.2329 (0.37); 8.2129 (3.35); 8.0779 (0.48); 8.0641 (0.5); 8.0194 (0.64); 7.3172 (0.39);
7.3076 (0.49); 7.245 (0.47); 7.2353 (0.38); 7.1273 (1.4); 7.0886 (0.47); 7.0788 (0.55); 7.0698 (2.36);
7.06 (2.71); 6.9693 (0.5); 6.9595 (0.45); 6.9394 (0.67); 6.9219 (2.53); 6.9121 (2.03); 4.5639 (0.71);
4.5473 (0.99); 4.5307 (0.74); 3.3807 (198.44); 3.2781 (0.61); 2.8922 (0.67); 2.7322 (0.56);
2.686 (16); 2.6682 (0.91); 2.6424 (2.97); 2.5507 (0.46); 2.5147 (10.39); 2.5102 (20.97); 2.5056 (27.8);
2.501 (20.09); 2.4965 (9.71); 1.4841 (1.03); 1.4751 (11.37); 1.4584 (11.18); 1.3921 (1.55);
1.3756 (1.53); 0.008 (0.52); −0.0002 (12.31); −0.0085 (0.39)

Example 219
Solvent: DMSO 8.1757 (3.51); 8.0841 (0.48); 8.071 (0.49); 7.9962 (1.2); 7.3176 (0.54); 7.3079 (0.73);
7.2568 (0.71); 7.2472 (0.53); 7.1246 (1.36); 7.0749 (0.43); 7.0697 (2.45); 7.0599 (2.72); 6.9948 (0.36);
6.9184 (2.7); 6.9085 (2.45); 4.2113 (0.7); 4.1932 (2.23); 4.175 (2.25); 4.1568 (0.72);
4.0617 (0.54); 4.0436 (0.54); 3.3708 (1.24); 3.3322 (50.3); 2.8908 (0.92); 2.732 (0.75); 2.7309 (0.76);
2.6939 (16); 2.6453 (4.09); 2.5956 (0.33); 2.5248 (0.42); 2.5115 (8.54); 2.507 (17.23);
2.5024 (22.93); 2.4978 (16.54); 2.4933 (7.98); 1.4432 (2.89); 1.425 (6.56); 1.4067 (2.84); 1.3213 (0.68);
1.3033 (1.57); 1.2852 (0.67); 0.008 (0.51); −0.0002 (13.91); −0.0085 (0.53)

Example 220
Solvent: DMSO 8.152 (0.67); 8.1115 (2.9); 8.0879 (0.53); 8.0744 (0.52); 7.9519 (1.01); 7.317 (0.46);
7.3073 (0.67); 7.2669 (0.65); 7.2572 (0.47); 7.1188 (1.4); 7.0947 (0.69); 7.0849 (0.79); 7.068 (2.22);
7.0582 (2.47); 7.0007 (0.34); 6.9742 (0.67); 6.9644 (0.59); 6.9139 (2.13); 6.9041 (2.34);
6.8927 (0.73); 6.7376 (0.33); 3.894 (10); 3.7691 (0.81); 3.7633 (2.31); 3.3722 (3.85); 3.3419 (57.55);
2.8912 (0.33); 2.6981 (16); 2.646 (3.89); 2.5986 (0.33); 2.5509 (0.48); 2.5423 (0.34);
2.5254 (0.48); 2.5206 (0.83); 2.5122 (9.55); 2.5077 (19.15); 2.5031 (25.45); 2.4985 (18.39); 2.494 (8.89);
0.008 (0.62); −0.0002 (16.35); −0.0085 (0.64)

Example 221
Solvent: DMSO 8.5937 (14); 8.5838 (0.46); 8.5723 (7.32); 8.5591 (7.45); 7.5528 (7.67); 7.5429 (7.92);
7.3484 (7.44); 7.3351 (7.36); 7.116 (8.05); 7.1062 (7.65); 5.763 (1.44); 4.3598 (1.06); 4.344 (1.72);
4.3245 (1.68); 4.308 (1.07); 3.3316 (14.39); 2.5456 (0.49); 2.5288 (1.51); 2.5155 (14.86);
2.5111 (29.29); 2.5066 (38.67); 2.5022 (27.41); 2.4978 (12.73); 2.479 (36.99); 1.9086 (0.71);
1.8899 (1.14); 1.8739 (1.75); 1.8549 (2.18); 1.8358 (1.76); 1.8185 (1.62); 1.8037 (1.74); 1.8005 (1.61);
1.7852 (1.99); 1.7665 (1.06); 1.7511 (0.64); 1.4771 (15.26); 1.4603 (14.94); 0.8099 (7.5);
0.7915 (16); 0.7731 (6.83)

Example 222
Solvent: DMSO 8.5894 (6.36); 8.5724 (3.36); 8.5591 (3.47); 7.5462 (3.59); 7.5363 (3.72); 7.3532 (3.45);
7.3399 (3.4); 7.1156 (3.8); 7.1057 (3.58); 5.7629 (0.46); 4.6018 (0.41); 4.5852 (1.05); 4.5685 (1.44);
4.5519 (1.07); 4.5353 (0.41); 3.334 (6.06); 2.5289 (0.4); 2.5156 (3.95); 2.5112 (7.93);
2.5067 (10.55); 2.5021 (7.49); 2.4977 (3.44); 2.4748 (16.76); 1.4933 (16); 1.4766 (15.64)

Example 223
Solvent: DMSO 10.0022 (3.63); 9.8463 (0.73); 8.2978 (3.87); 8.2968 (3.83); 8.2849 (3.96); 8.2838 (3.89);
8.2011 (1.3); 8.1946 (10.65); 8.1899 (1.51); 8.1479 (3.84); 8.0469 (2.04); 8.0298 (0.79); 7.3092 (1.21);
7.2996 (1.41); 7.2009 (1.41); 7.1913 (1.2); 7.1443 (3.33); 7.1404 (3.28); 7.1314 (3.26);
7.1275 (3.23); 7.0298 (5.99); 7.0199 (7.42); 7.0155 (1.08); 7.0061 (0.75); 7.002 (0.69); 6.9147 (7.32);
6.9049 (6.31); 4.3419 (0.8); 4.326 (1.3); 4.3065 (1.31); 4.2899 (0.85); 4.0589 (16); 4.0205 (3.44);
3.3948 (0.55); 3.3633 (43.54); 3.3533 (22.78); 3.3415 (292.45); 3.2911 (0.59); 3.2791 (0.37);
2.8915 (2.33); 2.7324 (1.84); 2.6726 (0.33); 2.5125 (19.76); 2.508 (38.99); 2.5034 (51.58);
2.4989 (37.63); 2.4944 (18.48); 2.3302 (0.32); 1.9011 (0.74); 1.8824 (1.01); 1.8664 (1.46); 1.8473 (1.65);
1.8278 (1.22); 1.8052 (1.1); 1.79 (1.34); 1.7867 (1.26); 1.7716 (1.59); 1.7526 (0.92);
1.7374 (0.61); 1.4669 (11.7); 1.4501 (11.84); 1.4338 (0.51); 1.3948 (2.33); 1.3784 (2.31); 0.8129 (5.76);
0.7945 (12.53); 0.7761 (5.39); 0.6749 (1.14); 0.6566 (2.53); 0.6383 (1.11); −0.0002 (5.52)

|  |
| --- |
| NMR peak list table |

Example 224
Solvent: DMSO 10.7451 (3.27); 10.6074 (0.71); 8.2882 (3.34); 8.2869 (3.37); 8.2754 (3.45); 8.2739 (3.53);
8.1858 (0.75); 8.1738 (0.79); 8.1725 (0.81); 8.1476 (9.65); 8.1335 (3.57); 8.0404 (0.72); 7.9946 (1.88);
7.9525 (1.09); 7.3544 (0.58); 7.3482 (1.26); 7.3333 (16); 7.3284 (8.5); 7.3171 (8); 7.3116 (1.54);
7.3025 (1.03); 7.297 (1.5); 7.2818 (1.23); 7.2722 (1.6); 7.2627 (1.35); 7.2568 (1.63);
7.2491 (1.43); 7.2409 (1.89); 7.2316 (0.84); 7.2259 (0.85); 7.2195 (0.49); 7.1735 (1.36); 7.1639 (1.16);
7.0973 (3.02); 7.0934 (2.93); 7.0844 (2.96); 7.0804 (2.94); 7.0052 (5.6); 6.9954 (6.42);
6.9332 (0.67); 6.9291 (0.67); 6.92 (0.67); 6.916 (0.69); 6.8853 (6.69); 6.8755 (5.88); 4.3166 (0.7);
4.3003 (1.11); 4.2847 (1.04); 4.281 (1.12); 4.2649 (0.72); 3.7152 (10.92); 3.6797 (2.45); 3.4349 (0.45);
3.3542 (361.79); 3.2919 (0.47); 3.2794 (0.38); 2.8912 (8.95); 2.7327 (7.06); 2.7318 (6.94);
2.6731 (0.36); 2.5432 (0.39); 2.5263 (1.09); 2.5131 (20.88); 2.5086 (41.71); 2.504 (55.27);
2.4994 (39.86); 2.4949 (19.21); 2.3307 (0.35); 1.8798 (0.56); 1.8613 (0.81); 1.8531 (0.36); 1.8453 (1.17);
1.8261 (1.38); 1.8065 (1.08); 1.7853 (0.96); 1.7703 (1.14); 1.7669 (1.06); 1.7518 (1.36);
1.7325 (0.86); 1.7179 (0.62); 1.7 (0.34); 1.4463 (10.24); 1.4295 (10.1); 1.3824 (2.09); 1.366 (2.07);
1.2339 (0.32); 0.7906 (5.05); 0.7722 (10.98); 0.7538 (4.61); 0.6595 (1.05); 0.6412 (2.29);
0.6229 (0.97); −0.0002 (3.62)

Example 225
Solvent: DMSO 10.4468 (3.1); 10.3157 (0.38); 8.271 (3.49); 8.2693 (3.59); 8.2581 (3.64); 8.2564 (3.76);
8.1704 (3.89); 8.1612 (10.74); 8.1537 (0.79); 8.1518 (0.78); 8.0789 (0.42); 8.0073 (1.1); 7.9531 (0.65);
7.3066 (0.79); 7.297 (0.93); 7.1923 (0.89); 7.1827 (0.76); 7.0805 (3.29); 7.0766 (3.19);
7.0677 (3.27); 7.0637 (3.27); 7.0264 (6.48); 7.0165 (7.47); 6.9082 (0.71); 6.9025 (7.73); 6.8927 (6.84);
4.3358 (0.69); 4.3196 (1.1); 4.316 (0.98); 4.304 (1.04); 4.3004 (1.12); 4.284 (0.75); 3.3509 (1.37);
3.3294 (138.29); 3.2994 (0.57); 2.891 (5.62); 2.7325 (4.45); 2.7311 (4.52); 2.5251 (0.71);
2.5118 (16.74); 2.5072 (34.54); 2.5026 (46.46); 2.498 (33.67); 2.4934 (16.41); 2.4168 (1.74);
2.398 (5.98); 2.3791 (6.35); 2.3606 (2.51); 2.3424 (0.83); 2.3293 (0.35); 2.3241 (0.4); 1.8986 (0.57);
1.8799 (0.82); 1.864 (1.21); 1.8447 (1.39); 1.8252 (1.07); 1.8058 (0.63); 1.802 (0.95);
1.7871 (1.16); 1.7836 (1.11); 1.7685 (1.39); 1.7493 (0.79); 1.7343 (0.52); 1.4642 (10.72); 1.4473 (10.78);
1.394 (1.26); 1.3775 (1.28); 1.0723 (7.12); 1.0616 (1.48); 1.0535 (16); 1.0429 (2.56);
1.0346 (7.03); 1.0241 (1.04); 0.8098 (5.16); 0.7914 (11.6); 0.7819 (0.98); 0.7729 (4.94); 0.6731 (0.62);
0.6548 (1.39); 0.6364 (0.6); 0.008 (0.53); −0.0002 (15.54); −0.0085 (0.58)

Example 226
Solvent: DMSO 10.8202 (3.49); 10.6893 (0.54); 8.2794 (4.18); 8.2778 (4.25); 8.2665 (4.27); 8.2648 (4.42);
8.1741 (0.73); 8.1725 (0.78); 8.1592 (1.37); 8.15 (16); 8.0514 (0.72); 8.0493 (0.7); 7.9944 (1.65);
7.9529 (1.58); 7.2917 (1.13); 7.2821 (1.35); 7.175 (1.28); 7.1654 (1.11); 7.0794 (3.68); 7.0755 (3.6);
7.0665 (3.62); 7.0625 (3.64); 7.0196 (7.52); 7.0098 (8.56); 6.9007 (0.7); 6.8966 (0.83);
6.89 (8.88); 6.8833 (1.32); 6.8801 (7.84); 4.328 (0.82); 4.3121 (1.28); 4.2962 (1.22); 4.2925 (1.29);
4.2762 (0.85); 3.3365 (200.51); 2.8912 (13.35); 2.7326 (10.6); 2.7312 (10.78); 2.672 (0.38);
2.5423 (0.33); 2.5252 (0.91); 2.5121 (21.33); 2.5076 (43.84); 2.503 (58.87); 2.4983 (42.61);
2.4938 (20.62); 2.3298 (0.38); 2.0386 (0.39); 2.023 (1.34); 2.0079 (1.77); 1.9926 (1.39);
1.9767 (0.58); 1.97 (0.35); 1.8907 (0.66); 1.8721 (0.94); 1.8561 (1.39); 1.8365 (1.62); 1.8173 (1.26);
1.7953 (1.15); 1.7804 (1.35); 1.7769 (1.3); 1.7618 (1.61); 1.7426 (0.95); 1.7277 (0.64);
1.4568 (12.56); 1.4399 (12.46); 1.3894 (1.89); 1.373 (1.87); 1.234 (0.39); 0.8046 (8.52); 0.8014 (9.6);
0.7916 (15.34); 0.7828 (15.15); 0.7643 (5.95); 0.6663 (0.93); 0.648 (2.06); 0.6296 (0.9);
0.008 (0.37); −0.0002 (11.1); −0.0085 (0.42)

Example 227
Solvent: DMSO 8.8605 (1.27); 8.7287 (0.34); 8.202 (1.14); 8.2008 (1.12); 8.1891 (1.16); 8.1878 (1.14);
8.1224 (3.37); 8.0747 (0.33); 7.9751 (0.85); 7.9649 (0.35); 7.9531 (0.37); 7.8689 (1.44); 7.8671 (1.42);
7.8066 (0.39); 7.8046 (0.38); 7.2992 (0.59); 7.2896 (0.68); 7.1821 (0.65); 7.1725 (0.57);
7.0301 (0.33); 7.025 (2.01); 7.0152 (2.36); 6.9725 (1.03); 6.9687 (0.99); 6.9596 (1); 6.9557 (0.98);
6.9229 (2.42); 6.9131 (2.05); 6.5263 (0.77); 4.3122 (0.39); 4.2961 (0.37); 4.2922 (0.39);
3.3357 (92.48); 2.9342 (16); 2.9182 (5.14); 2.891 (3.03); 2.7323 (2.39); 2.7312 (2.35); 2.5459 (0.59);
2.5251 (0.38); 2.5119 (8.22); 2.5074 (16.64); 2.5028 (22.17); 2.4982 (16.01); 2.4936 (7.75);
1.8763 (0.33); 1.8603 (0.45); 1.8413 (0.51); 1.8217 (0.38); 1.7984 (0.34); 1.7835 (0.41);
1.7801 (0.39); 1.765 (0.49); 1.4603 (3.66); 1.4435 (3.68); 1.4316 (0.42); 1.3917 (1.05); 1.3874 (0.59);
1.3753 (1.08); 1.371 (0.57); 0.8073 (1.8); 0.7976 (0.47); 0.7889 (3.98); 0.7798 (0.62);
0.7704 (1.7); 0.6709 (0.51); 0.6526 (1.13); 0.647 (0.57); 0.6343 (0.52); 0.008 (0.6); −0.0002 (17.1);
−0.0085 (0.67)

Example 228
Solvent: DMSO 10.4654 (3.77); 8.2737 (4.32); 8.2722 (4.44); 8.2608 (4.46); 8.2593 (4.6); 8.1982 (4.92);
8.1966 (4.97); 8.1867 (0.62); 8.1769 (12.16); 8.1607 (0.49); 8.015 (0.91); 7.9533 (0.72); 7.2928 (0.49);
7.2834 (0.58); 7.188 (0.54); 7.1785 (0.47); 7.0861 (3.78); 7.0821 (3.72); 7.0732 (3.74);
7.0692 (3.73); 7.0209 (7.31); 7.0111 (8.48); 6.9158 (0.4); 6.9072 (8.95); 6.8974 (7.63); 4.338 (0.88);
4.3222 (1.38); 4.3059 (1.29); 4.3023 (1.39); 4.286 (0.9); 3.3414 (258.27); 2.8916 (6);
2.7329 (4.73); 2.7317 (4.71); 2.6727 (0.35); 2.6089 (0.81); 2.5917 (1.36); 2.5735 (1.43); 2.5567 (0.93);
2.5429 (0.48); 2.5401 (0.36); 2.5259 (1.03); 2.5127 (20.46); 2.5082 (41.26); 2.5036 (55.06);
2.499 (39.97); 2.4944 (19.56); 2.3303 (0.36); 1.9007 (0.67); 1.8819 (1.01); 1.866 (1.47); 1.8469 (1.71);
1.8273 (1.28); 1.8034 (1.15); 1.7886 (1.43); 1.7853 (1.34); 1.7701 (1.69); 1.751 (0.96);
1.736 (0.64); 1.6229 (0.89); 1.6042 (1.25); 1.5895 (1.41); 1.5844 (1.12); 1.5704 (1.66); 1.5509 (1.15);

| NMR peak list table |
|---|
| 1.5322 (0.35); 1.4653 (13.03); 1.4484 (12.9); 1.4308 (0.44); 1.4122 (1.05); 1.4018 (0.98); 1.397 (1.78); 1.3943 (1.84); 1.3852 (1.05); 1.3786 (2.55); 1.3637 (1.1); 1.3603 (1.3); 1.3453 (0.92); 1.2341 (0.43); 1.0666 (14.18); 1.0495 (14.53); 1.0335 (1.02); 1.0304 (0.89); 0.8653 (7.24); 0.8468 (16); 0.8281 (7.18); 0.809 (6.83); 0.7907 (13.86); 0.7723 (5.89); 0.6779 (0.33); 0.6677 (0.37); 0.6596 (0.7); 0.6494 (0.7); 0.6412 (0.35); 0.6311 (0.35); 0.008 (0.6); −0.0002 (16.75); −0.0085 (0.67) <br> Example 229 <br> Solvent: DMSO |
| 10.3899 (4.76); 10.2573 (0.43); 8.274 (4.9); 8.2731 (4.96); 8.2612 (5); 8.2602 (5.09); 8.1877 (5.35); 8.1741 (13.99); 8.159 (0.59); 8.0918 (0.45); 8.0167 (1.17); 7.953 (0.66); 7.3053 (0.71); 7.2956 (0.84); 7.1965 (0.82); 7.1869 (0.71); 7.0905 (4.27); 7.0866 (4.23); 7.0776 (4.17); 7.0737 (4.19); 7.028 (7.84); 7.0182 (9.02); 6.9193 (0.55); 6.9152 (0.69); 6.9076 (9.48); 6.9022 (1.2); 6.8978 (8.13); 4.3386 (1.02); 4.3226 (1.62); 4.3069 (1.5); 4.3033 (1.63); 4.2869 (1.04); 3.398 (0.7); 3.34 (326.51); 3.3019 (0.99); 2.8914 (5.63); 2.7321 (4.38); 2.6724 (0.41); 2.5426 (0.38); 2.5256 (1.19); 2.5124 (23.38); 2.5079 (46.93); 2.5033 (62.62); 2.4988 (45.64); 2.4942 (22.41); 2.3302 (0.42); 2.3256 (0.32); 2.2845 (8.97); 2.2668 (9.21); 2.2498 (0.99); 2.2322 (0.88); 1.901 (0.79); 1.8822 (1.14); 1.8663 (1.7); 1.8471 (2); 1.8277 (1.49); 1.8042 (1.36); 1.7892 (1.65); 1.7859 (1.6); 1.7707 (1.99); 1.7516 (1.13); 1.7366 (0.7); 1.4664 (14.85); 1.4496 (14.76); 1.3965 (1.32); 1.38 (1.31); 1.2343 (0.41); 1.074 (0.41); 1.0678 (0.54); 1.0621 (0.42); 1.0559 (1.1); 1.0544 (1.1); 1.0483 (1.07); 1.0443 (0.93); 1.0363 (1.94); 1.0284 (0.94); 1.0241 (1.23); 1.0164 (1.22); 1.0042 (0.71); 0.9985 (0.46); 0.8113 (7.3); 0.7929 (16); 0.7744 (6.85); 0.6747 (0.67); 0.6564 (1.45); 0.6379 (0.63); 0.4851 (1.84); 0.4745 (4.91); 0.4702 (5.3); 0.4649 (2.79); 0.4602 (2.83); 0.4543 (5.25); 0.45 (5.07); 0.4401 (2.08); 0.4335 (0.37); 0.1993 (1.92); 0.1888 (5.31); 0.1854 (5.65); 0.177 (5.49); 0.1734 (5.74); 0.1625 (1.82); −0.0002 (7.71); −0.0084 (0.32) <br> Example 230 <br> Solvent: DMSO |
| 10.7023 (4.65); 10.5725 (1.22); 8.57 (3.79); 8.5668 (4.16); 8.5628 (4.11); 8.5596 (3.92); 8.5339 (1.02); 8.5306 (1.11); 8.5267 (1.1); 8.5234 (1.04); 8.3636 (4.27); 8.3622 (4.48); 8.3508 (4.42); 8.3493 (4.68); 8.2757 (5.41); 8.2739 (5.47); 8.2606 (1.28); 8.2593 (1.31); 8.2476 (1.22); 8.2461 (1.28); 8.2148 (12.23); 8.1691 (1.43); 8.167 (1.44); 8.0669 (3.02); 7.9594 (1.91); 7.7074 (3.22); 7.7042 (3.26); 7.6948 (4.85); 7.6916 (4.86); 7.6833 (0.97); 7.6801 (0.92); 7.6706 (1.4); 7.6674 (1.4); 7.6492 (4.58); 7.6419 (4.88); 7.6366 (3.42); 7.6331 (1.83); 7.6293 (3.33); 7.6204 (0.84); 7.3222 (1.9); 7.3126 (2.29); 7.2238 (2.2); 7.2141 (1.85); 7.1737 (3.82); 7.1698 (3.77); 7.1609 (3.75); 7.157 (3.81); 7.044 (7.16); 7.0342 (8.87); 6.9988 (1.05); 6.9948 (1.06); 6.9857 (1.07); 6.9817 (1.1); 6.962 (8.96); 6.9522 (7.29); 4.3508 (0.87); 4.3348 (1.42); 4.3151 (1.43); 4.2988 (0.93); 3.3327 (178.43); 3.2802 (0.5); 2.8909 (16); 2.7322 (12.42); 2.7312 (12.72); 2.6763 (0.35); 2.6718 (0.49); 2.6671 (0.36); 2.5419 (0.4); 2.525 (1.13); 2.5117 (27.98); 2.5072 (57.23); 2.5026 (76.69); 2.498 (55.83); 2.4935 (27.35); 2.3339 (0.37); 2.3294 (0.52); 2.3248 (0.38); 1.9306 (0.36); 1.9196 (0.38); 1.9118 (0.84); 1.893 (1.12); 1.8771 (1.63); 1.8575 (1.81); 1.8384 (1.3); 1.8137 (1.17); 1.7988 (1.45); 1.7955 (1.4); 1.7802 (1.74); 1.7611 (1.04); 1.754 (0.41); 1.7462 (0.69); 1.7414 (0.53); 1.7355 (0.38); 1.7223 (0.41); 1.4765 (13.19); 1.4596 (13.14); 1.406 (3.37); 1.3896 (3.34); 1.2332 (0.5); 0.8223 (6.45); 0.804 (14.24); 0.7855 (6.09); 0.6863 (1.65); 0.668 (3.66); 0.6496 (1.59); 0.008 (0.97); −0.0002 (27.5); −0.0085 (1.07) <br> Example 231 <br> Solvent: DMSO |
| 9.8081 (0.71); 8.2914 (0.71); 8.29 (0.71); 8.2786 (0.74); 8.277 (0.74); 8.1751 (2.14); 8.1241 (0.89); 8.1223 (0.89); 8.0257 (0.58); 7.1028 (0.64); 7.0989 (0.62); 7.09 (0.63); 7.086 (0.63); 7.0306 (1.21); 7.0208 (1.38); 6.9069 (1.53); 6.897 (1.33); 3.3353 (45.46); 2.8913 (1.06); 2.7326 (0.85); 2.7314 (0.83); 2.5121 (3.93); 2.5076 (7.97); 2.503 (10.62); 2.4984 (7.73); 2.4939 (3.8); 1.4659 (2.15); 1.449 (2.13); 1.3986 (0.48); 1.3821 (0.47); 1.234 (16); 1.2131 (4.05); 0.8096 (1.05); 0.7913 (2.31); 0.7728 (0.98); 0.6566 (0.51); −0.0002 (3.48) <br> Example 232 <br> Solvent: DMSO |
| 10.701 (2.23); 10.5741 (0.42); 8.5686 (1.88); 8.5654 (2.03); 8.5614 (2.01); 8.5581 (1.88); 8.5337 (0.36); 8.5304 (0.4); 8.5264 (0.39); 8.5232 (0.37); 8.3638 (2.14); 8.3625 (2.14); 8.351 (2.18); 8.3496 (2.22); 8.27 (2.65); 8.2684 (2.65); 8.2614 (0.59); 8.2482 (0.45); 8.2468 (0.45); 8.2161 (6.12); 8.1625 (0.49); 8.1603 (0.5); 8.0353 (1.07); 7.953 (1); 7.7071 (1.58); 7.7039 (1.58); 7.6944 (2.37); 7.6912 (2.33); 7.6838 (0.38); 7.6805 (0.34); 7.6711 (0.5); 7.6679 (0.49); 7.649 (2.22); 7.6417 (2.31); 7.6363 (1.61); 7.6327 (0.7); 7.629 (1.55); 7.3232 (0.61); 7.3136 (0.85); 7.2696 (0.83); 7.26 (0.61); 7.1715 (1.87); 7.1676 (1.83); 7.1587 (1.84); 7.1547 (1.83); 7.0453 (3.46); 7.0354 (4.23); 6.9936 (0.38); 6.9896 (0.36); 6.9805 (0.38); 6.9579 (4.28); 6.948 (3.52); 4.5955 (0.39); 4.5788 (1.04); 4.5622 (1.43); 4.5455 (1.06); 4.5289 (0.41); 3.3802 (0.38); 3.3368 (116.28); 2.891 (8.31); 2.7322 (6.57); 2.5251 (0.59); 2.5119 (12.54); 2.5074 (25.22); 2.5028 (33.49); 2.4982 (24.17); 2.4937 (11.72); 1.493 (16); 1.4763 (15.84); 1.4145 (2.44); 1.398 (2.44); −0.0002 (8.65) <br> Example 233 <br> Solvent: DMSO |
| 9.8114 (0.64); 8.2908 (0.7); 8.2893 (0.71); 8.278 (0.73); 8.2764 (0.74); 8.178 (2.04); 8.1203 (0.86); 8.1185 (0.86); 8.1168 (0.74); 7.0998 (0.62); 7.0959 (0.61); 7.0869 (0.61); 7.083 (0.61); 7.032 (1.2); 7.0222 (1.37); 6.9027 (1.45); 6.8929 (1.28); 4.5655 (0.34); 4.5488 (0.47); 4.5321 (0.35); 3.332 (30.15); 2.8909 (1.08); 2.7322 (0.82); 2.7311 (0.83); 2.5116 (3.43); 2.5071 (7.02); 2.5025 (9.41); 2.4979 (6.82); 2.4933 (3.31); 1.482 (5.36); 1.4653 (5.33); 1.3894 (0.35); 1.2341 (16); 1.2127 (1.35); −0.0002 (7.61) |

NMR peak list table

Example 234
Solvent: DMSO 10.4488 (1.99); 8.272 (2.21); 8.2707 (2.23); 8.2591 (2.26); 8.2577 (2.32); 8.1794 (2.65);
8.1777 (2.71); 8.1672 (6.51); 8.154 (0.32); 8.0069 (0.59); 7.9531 (0.45); 7.3035 (0.38); 7.2939 (0.44);
7.191 (0.43); 7.1814 (0.38); 7.0801 (1.94); 7.0762 (1.91); 7.0672 (1.91); 7.0633 (1.91);
7.0266 (3.69); 7.0168 (4.22); 6.8999 (4.37); 6.8901 (3.85); 6.8857 (0.39); 4.3357 (0.45); 4.3201 (0.71);
4.3039 (0.66); 4.3 (0.71); 4.2838 (0.46); 3.338 (131.26); 2.8914 (3.8); 2.7863 (0.33);
2.7693 (0.94); 2.7523 (1.33); 2.7327 (3.39); 2.7182 (0.45); 2.5255 (0.54); 2.5124 (10.68); 2.5079 (21.46);
2.5033 (28.62); 2.4987 (20.74); 2.4942 (10.1); 1.8988 (0.35); 1.8802 (0.51); 1.8643 (0.75);
1.8449 (0.88); 1.8255 (0.66); 1.8026 (0.61); 1.7877 (0.73); 1.7843 (0.69); 1.7692 (0.87); 1.7501 (0.5);
1.4646 (6.71); 1.4478 (6.65); 1.3973 (0.69); 1.3808 (0.68); 1.0857 (15.53); 1.0687 (16);
1.0535 (1.56); 0.8083 (3.31); 0.79 (7.23); 0.7715 (3.05); 0.6725 (0.33); 0.6542 (0.74); −0.0002 (5.36)

Example 235
Solvent: DMSO 10.4478 (1.83); 10.3082 (0.39); 8.2727 (2.07); 8.2713 (2.1); 8.2598 (2.12); 8.2583 (2.16);
8.177 (2.58); 8.1721 (6.09); 8.1635 (0.64); 8.162 (0.63); 8.0391 (0.46); 8.0184 (1.15); 7.9531 (0.36);
7.2892 (0.74); 7.2796 (0.89); 7.1863 (0.85); 7.1767 (0.73); 7.0891 (1.81); 7.0852 (1.77);
7.0762 (1.76); 7.0723 (1.75); 7.0172 (3.49); 7.0074 (4.09); 6.9541 (0.39); 6.9501 (0.39); 6.941 (0.4);
6.9369 (0.39); 6.9092 (4.25); 6.8993 (3.64); 4.3384 (0.42); 4.3228 (0.67); 4.3065 (0.62);
4.3027 (0.67); 4.2865 (0.43); 3.3997 (0.41); 3.3459 (154.12); 2.8916 (3.03); 2.7329 (2.4); 2.7317 (2.39);
2.5259 (0.57); 2.5129 (11.27); 2.5084 (22.7); 2.5038 (30.25); 2.4992 (21.85); 2.4946 (10.5);
2.2711 (3.53); 2.2532 (4.25); 2.2282 (0.76); 2.2103 (0.95); 2.0883 (0.42); 2.0714 (0.82);
2.0544 (1.04); 2.0373 (0.86); 2.0201 (0.48); 1.8999 (0.39); 1.8811 (0.51); 1.8652 (0.75); 1.846 (0.82);
1.8265 (0.61); 1.8024 (0.55); 1.7875 (0.68); 1.784 (0.65); 1.769 (0.81); 1.7498 (0.48);
1.4641 (6.28); 1.4473 (6.2); 1.395 (1.3); 1.3786 (1.28); 0.9238 (16); 0.9107 (5.72); 0.9072 (15.89);
0.8944 (3.56); 0.8099 (3.09); 0.7915 (6.78); 0.7731 (2.86); 0.6728 (0.64); 0.6545 (1.42);
0.6361 (0.6); −0.0002 (6.76)

Example 236
Solvent: DMSO 10.115 (2.8); 9.9793 (0.5); 8.2338 (2.74); 8.2323 (2.69); 8.2209 (2.85); 8.2193 (2.83);
8.167 (7.71); 8.1342 (0.52); 8.1327 (0.51); 8.1211 (0.53); 8.1195 (0.54); 8.0276 (1.26); 7.9529 (0.55);
7.8903 (3.37); 7.8887 (3.38); 7.7624 (0.61); 7.7605 (0.61); 7.3034 (0.82); 7.2937 (0.97);
7.187 (0.95); 7.1774 (0.81); 7.0525 (2.44); 7.0486 (2.4); 7.0396 (2.47); 7.0357 (2.54); 7.0292 (4.8);
7.0194 (5.36); 6.9176 (0.48); 6.9136 (0.5); 6.9022 (5.69); 6.8923 (4.88); 4.3346 (0.55);
4.3188 (0.88); 4.3026 (0.82); 4.299 (0.89); 4.2828 (0.58); 4.1469 (1.87); 4.1292 (5.84); 4.1148 (1.91);
4.1115 (5.95); 4.0974 (1.41); 4.0938 (1.95); 4.0799 (0.37); 3.4278 (0.37); 3.4161 (0.54);
3.352 (227.6); 2.8918 (4.49); 2.7331 (3.58); 2.7319 (3.5); 2.5265 (0.61); 2.5133 (13.91); 2.5088 (28.17);
2.5042 (37.58); 2.4996 (27.27); 2.4951 (13.29); 1.8976 (0.45); 1.8789 (0.65); 1.863 (0.96);
1.8438 (1.1); 1.8242 (0.83); 1.802 (0.75); 1.787 (0.91); 1.7836 (0.85); 1.7684 (1.08); 1.7493 (0.62);
1.7343 (0.41); 1.4637 (8.35); 1.4469 (8.17); 1.3937 (1.46); 1.3772 (1.45); 1.2422 (7.57);
1.2245 (16); 1.2068 (7.21); 0.8098 (4.02); 0.7914 (8.85); 0.773 (3.75); 0.6734 (0.71); 0.6551 (1.58);
0.6367 (0.68); 0.008 (0.77); −0.0002 (20.56); −0.0085 (0.79)

Example 237
Solvent: DMSO 10.8223 (5.06); 10.6861 (1.12); 8.3726 (4.87); 8.3711 (4.89); 8.3598 (5.04); 8.3581 (5.14);
8.2847 (5.3); 8.283 (6.04); 8.2812 (6.07); 8.2795 (5.07); 8.2713 (1.32); 8.2698 (1.27); 8.2582 (1.17);
8.2566 (1.2); 8.2294 (13.92); 8.1796 (1.2); 8.1781 (1.33); 8.1759 (1.34); 8.1743 (1.14);
8.0845 (2.75); 8.0366 (5.13); 8.034 (6.5); 8.0213 (2.08); 8.0145 (7.76); 8.0127 (6); 8.0084 (1.84);
8.0053 (1.77); 7.9926 (0.53); 7.9876 (1.78); 7.984 (1.35); 7.9532 (1.58); 7.6221 (0.75); 7.619 (1.4);
7.6159 (0.89); 7.6061 (1.21); 7.6008 (4); 7.5956 (1.52); 7.5906 (1.24); 7.5855 (2.15);
7.5823 (3.29); 7.579 (1.81); 7.5756 (0.69); 7.5722 (0.84); 7.5689 (0.47); 7.534 (5.37); 7.5305 (2.56);
7.5247 (1.85); 7.5178 (4.43); 7.5147 (7.87); 7.5054 (2.33); 7.5009 (1.79); 7.4967 (3.39);
7.4944 (2.26); 7.4875 (0.94); 7.4852 (0.63); 7.3264 (1.92); 7.3168 (2.25); 7.2304 (2.14); 7.2208 (1.83);
7.1876 (4.38); 7.1837 (4.29); 7.1748 (4.3); 7.1708 (4.33); 7.0489 (8.29); 7.0391 (10.35);
7.0233 (1.06); 7.0193 (1.01); 7.0102 (1.02); 7.0061 (1.01); 6.97 (10.48); 6.9601 (8.54); 4.3548 (0.97);
4.3391 (1.55); 4.3227 (1.46); 4.3191 (1.57); 4.3029 (1); 3.3297 (222.53); 2.8908 (13.42);
2.7323 (10.82); 2.731 (10.62); 2.6761 (0.37); 2.6715 (0.51); 2.667 (0.39); 2.5417 (0.43); 2.5248 (1.33);
2.5115 (28.97); 2.507 (58.68); 2.5024 (78.44); 2.4978 (56.77); 2.4932 (27.5); 2.3338 (0.36);
2.3292 (0.5); 2.3246 (0.36); 1.9338 (0.36); 1.923 (0.36); 1.9152 (0.93); 1.8964 (1.22);
1.8806 (1.79); 1.8613 (1.97); 1.8418 (1.42); 1.835 (0.47); 1.8164 (1.27); 1.8015 (1.59); 1.798 (1.53);
1.7829 (1.93); 1.7669 (0.97); 1.7637 (1.11); 1.7563 (0.4); 1.7487 (0.73); 1.744 (0.51);
1.7377 (0.35); 1.7248 (0.38); 1.4795 (14.8); 1.4627 (14.71); 1.4089 (3.11); 1.3924 (3.11); 1.2329 (0.46);
0.8253 (7.2); 0.8069 (16); 0.7885 (6.76); 0.6893 (1.53); 0.671 (3.43); 0.6526 (1.47); 0.008 (1.18);
−0.0002 (32.49); −0.0085 (1.2)

Example 238
Solvent: DMSO 10.9526 (4.45); 10.8196 (0.97); 8.3694 (4.16); 8.368 (4.2); 8.3566 (4.28); 8.3551 (4.38);
8.2658 (1.11); 8.2558 (3.88); 8.2533 (4.7); 8.2464 (3.79); 8.2438 (3.69); 8.2229 (5.69); 8.2212 (6.02);
8.2166 (12.8); 8.2053 (1.11); 8.2025 (0.92); 8.1224 (1.15); 8.1203 (1.18); 8.0724 (2.37);
7.953 (1.94); 7.8992 (3.69); 7.8966 (3.84); 7.8866 (4.46); 7.8841 (4.49); 7.8735 (0.96); 7.8709 (0.89);
7.3228 (1.53); 7.3132 (1.84); 7.2264 (3.99); 7.2223 (2.31); 7.2169 (4.1); 7.2138 (4.55);
7.2044 (3.92); 7.2016 (1.29); 7.1983 (1.05); 7.1888 (0.97); 7.1803 (3.68); 7.1764 (3.63); 7.1674 (3.61);
7.1635 (3.64); 7.0461 (6.94); 7.0363 (8.4); 7.0022 (0.86); 6.9982 (0.83); 6.9891 (0.85);

|  |
| --- |
| NMR peak list table |

6.9851 (0.85); 6.9556 (8.53); 6.9458 (7.18); 4.3492 (0.84); 4.3328 (1.35); 4.3171 (1.26); 4.3134 (1.39);
4.2973 (0.89); 3.4008 (0.4); 3.3417 (319.03); 3.2744 (0.37); 3.2639 (0.32); 2.8913 (16);
2.7327 (12.68); 2.7316 (12.6); 2.6725 (0.43); 2.5427 (0.34); 2.5257 (1.06); 2.5125 (25.02); 2.508 (50.73);
2.5034 (67.92); 2.4988 (49.34); 2.4943 (23.96); 2.3301 (0.44); 2.3255 (0.33); 1.9112 (0.81);
1.8925 (1.06); 1.8766 (1.56); 1.8573 (1.73); 1.8379 (1.25); 1.8137 (1.13); 1.7987 (1.4);
1.7954 (1.34); 1.7803 (1.68); 1.7612 (0.98); 1.7532 (0.34); 1.7461 (0.64); 1.7412 (0.44); 1.7217 (0.32);
1.476 (12.75); 1.4592 (12.64); 1.4053 (2.7); 1.3888 (2.68); 1.2328 (0.41); 0.8216 (6.23);
0.8032 (13.76); 0.7848 (5.85); 0.6852 (1.31); 0.6669 (2.94); 0.6484 (1.25); 0.008 (0.73); −0.0002 (20.13);
−0.0085 (0.78)
Example 239
Solvent: DMSO 10.0105 (1.82); 9.8754 (0.33); 8.2255 (1.73); 8.224 (1.75); 8.2127 (1.8); 8.211 (1.82);
8.1661 (4.98); 8.1261 (0.33); 8.1247 (0.34); 8.113 (0.34); 8.1115 (0.35); 8.0262 (0.83); 7.953 (0.41);
7.8879 (2.16); 7.8863 (2.16); 7.7594 (0.4); 7.7574 (0.39); 7.2993 (0.55); 7.2897 (0.64);
7.1845 (0.62); 7.1749 (0.53); 7.0428 (1.59); 7.039 (1.59); 7.0279 (3.74); 7.0181 (3.51); 6.9107 (0.34);
6.9066 (0.37); 6.8981 (3.71); 6.8936 (0.59); 6.8883 (3.11); 4.9104 (0.36); 4.8947 (1.01);
4.8791 (1.41); 4.8634 (1.05); 4.8477 (0.41); 4.3346 (0.35); 4.3184 (0.56); 4.3026 (0.52); 4.299 (0.57);
4.2827 (0.37); 3.3327 (88.81); 2.8912 (3.51); 2.7325 (2.74); 2.7314 (2.75); 2.5252 (0.48);
2.512 (9.81); 2.5075 (19.68); 2.5029 (26.13); 2.4982 (18.8); 2.4937 (9.07); 1.8792 (0.42); 1.8633 (0.61);
1.844 (0.71); 1.8245 (0.53); 1.8015 (0.48); 1.7867 (0.59); 1.7832 (0.55); 1.7681 (0.69);
1.7489 (0.41); 1.4634 (5.41); 1.4466 (5.3); 1.3939 (0.96); 1.3775 (0.95); 1.2449 (16); 1.2292 (15.91);
0.8097 (2.62); 0.7913 (5.74); 0.7729 (2.42); 0.6733 (0.46); 0.655 (1.03); 0.6366 (0.44);
0.008 (0.88); −0.0002 (22.42); −0.0085 (0.86)
Example 240
Solvent: DMSO 10.3253 (4.62); 10.1901 (0.65); 8.2622 (4.96); 8.2605 (5.03); 8.2493 (5.07); 8.2476 (5.21);
8.1971 (4.66); 8.1688 (14.34); 8.1577 (0.96); 8.1561 (0.86); 8.1443 (0.73); 8.1428 (0.74); 8.0985 (0.61);
8.0166 (1.75); 7.9531 (1.22); 7.3144 (1.2); 7.3048 (1.37); 7.196 (1.38); 7.1864 (1.16);
7.0768 (4.56); 7.0728 (4.46); 7.0639 (4.49); 7.0599 (4.45); 7.0319 (8.84); 7.0221 (10.03); 6.9054 (10.37);
6.8956 (9.28); 6.8847 (0.71); 6.8806 (0.66); 4.34 (0.99); 4.3241 (1.55); 4.3081 (1.45);
4.3045 (1.56); 4.288 (1.02); 3.4057 (0.69); 3.3846 (2.28); 3.3633 (5.78); 3.3386 (350.08); 3.3013 (0.98);
3.2867 (0.57); 2.8914 (10.4); 2.7327 (8.33); 2.7314 (8.18); 2.677 (0.33); 2.6724 (0.46);
2.6678 (0.33); 2.5425 (0.5); 2.5257 (1.5); 2.5124 (27.06); 2.5079 (54.16); 2.5032 (71.92); 2.4986 (51.63);
2.4941 (24.61); 2.3346 (0.34); 2.3299 (0.44); 2.3254 (0.32); 2.2424 (0.58); 2.2374 (0.39);
2.2192 (1.85); 2.2139 (1.64); 2.1902 (3.33); 2.174 (2.11); 2.169 (2.96); 2.1522 (0.8); 2.1464 (1);
2.1306 (0.86); 2.1212 (1.07); 2.1089 (2.06); 2.1005 (2.73); 2.0938 (1.89); 2.0916 (1.88); 2.0877 (2.01);
2.0787 (2.63); 2.0711 (1.65); 2.064 (0.99); 2.0585 (0.98); 2.0495 (0.73); 1.9762 (0.45);
1.9549 (0.95); 1.9497 (0.86); 1.9319 (1.58); 1.9281 (1.73); 1.9109 (1.19); 1.9052 (2.41); 1.8956 (0.69);
1.884 (2.22); 1.8679 (1.75); 1.8636 (1.29); 1.8488 (1.97); 1.8289 (1.89); 1.8098 (1.73);
1.8056 (2.3); 1.791 (2.64); 1.7876 (2.49); 1.7727 (2.58); 1.7534 (1.47); 1.7384 (0.78); 1.468 (14.84);
1.4512 (14.76); 1.4374 (0.56); 1.3989 (2); 1.3824 (2); 1.2338 (0.47); 0.8129 (7.22); 0.7945 (16);
0.776 (6.73); 0.6762 (0.98); 0.6579 (2.19); 0.6396 (0.95); 0.008 (0.66); −0.0002 (17.95);
−0.0085 (0.62)
Example 241
Solvent: DMSO 10.9525 (2.12); 8.3694 (2.04); 8.3679 (2.08); 8.3565 (2.1); 8.355 (2.16); 8.2554 (1.88);
8.2528 (2.04); 8.2459 (1.85); 8.2432 (1.79); 8.2185 (8.31); 8.0406 (0.48); 7.9529 (0.89); 7.8992 (1.82);
7.8966 (1.87); 7.8867 (2.07); 7.8841 (2.01); 7.3148 (0.38); 7.2688 (0.38); 7.2259 (1.95);
7.2164 (1.96); 7.2135 (1.95); 7.204 (1.9); 7.1775 (1.85); 7.1746 (1.79); 7.1646 (1.81); 7.1607 (1.8);
7.0472 (3.53); 7.0374 (4.23); 6.9512 (4.39); 6.9414 (3.69); 4.5938 (0.38); 4.5771 (1.02);
4.5605 (1.41); 4.5438 (1.05); 4.5271 (0.4); 3.3359 (88.46); 2.8908 (7.68); 2.7323 (5.85); 2.7311 (6.02);
2.5247 (0.54); 2.5117 (11.31); 2.5072 (22.94); 2.5026 (30.61); 2.498 (22.06); 2.4934 (10.61);
1.4924 (16); 1.4757 (15.88); 1.4134 (1.08); 1.397 (1.08); 0.008 (0.43); −0.0002 (12.14);
−0.0085 (0.45)
Example 242
Solvent: DMSO 10.0066 (1.97); 8.2256 (1.8); 8.2243 (1.73); 8.2128 (1.85); 8.2114 (1.79); 8.167 (5.08);
7.9951 (0.68); 7.8825 (2.21); 7.8809 (2.21); 7.7539 (0.32); 7.7521 (0.32); 7.3005 (0.4); 7.2909 (0.51);
7.231 (0.51); 7.2214 (0.39); 7.0402 (1.64); 7.0364 (1.65); 7.0287 (3.68); 7.0235 (1.86);
7.019 (3.47); 6.8997 (0.38); 6.8928 (3.44); 6.883 (3.03); 4.9104 (0.37); 4.8947 (1); 4.8791 (1.41);
4.8634 (1.06); 4.8478 (0.42); 4.58 (0.33); 4.5633 (0.86); 4.5467 (1.18); 4.53 (0.88); 4.5133 (0.34);
3.3344 (98.27); 3.2962 (0.36); 2.8913 (0.52); 2.7324 (0.41); 2.512 (8.87); 2.5075 (17.54);
2.5029 (23.22); 2.4983 (16.9); 2.4938 (8.3); 1.4797 (13.03); 1.463 (12.89); 1.402 (1.61); 1.3855 (1.61);
1.2443 (16); 1.2286 (15.93); 0.0079 (0.79); −0.0002 (17.57); −0.0085 (0.71)
Example 243
Solvent: DMSO 10.3226 (2.04); 8.2622 (2.1); 8.2607 (2.23); 8.2494 (2.16); 8.2478 (2.31); 8.1914 (2.07);
8.1693 (6.29); 7.9528 (0.6); 7.0741 (1.94); 7.0701 (1.9); 7.0612 (1.91); 7.0572 (1.92); 7.0329 (3.68);
7.0231 (4.16); 6.9006 (4.32); 6.8908 (3.88); 4.5853 (0.39); 4.5686 (1.04); 4.5519 (1.43);
4.5353 (1.07); 4.5186 (0.41); 3.4049 (0.37); 3.3839 (1.28); 3.3456 (160.77); 3.3013 (0.45); 2.8914 (4.98);
2.7327 (3.85); 2.7316 (3.93); 2.5259 (0.41); 2.5127 (9.68); 2.5082 (19.66); 2.5036 (26.25);
2.499 (19.1); 2.4945 (9.29); 2.2196 (0.81); 2.2144 (0.7); 2.1957 (1.15); 2.1907 (1.43); 2.1743 (0.92);
2.1694 (1.29); 2.1525 (0.33); 2.1469 (0.44); 2.1301 (0.36); 2.121 (0.47); 2.1086 (0.89);

|  |
|---|
| NMR peak list table |
| 2.1003 (1.19); 2.0938 (0.79); 2.0875 (0.82); 2.0786 (1.12); 2.0639 (0.37); 2.0579 (0.37); 2.0549 (0.37); 1.9548 (0.41); 1.9499 (0.37); 1.9318 (0.66); 1.9282 (0.7); 1.9108 (0.41); 1.9054 (0.91); 1.8841 (0.48); 1.8113 (0.36); 1.8013 (0.62); 1.7905 (0.42); 1.7875 (0.4); 1.7769 (0.48); 1.4843 (16); 1.4676 (15.9); 1.4568 (0.76); 1.4064 (0.65); 1.39 (0.65); −0.0002 (7.09)<br>Example 244<br>Solvent: DMSO |
| 9.9974 (1.97); 9.8462 (0.65); 8.2981 (2.09); 8.2852 (2.14); 8.2017 (0.91); 8.1947 (6.06); 8.1903 (1.16); 8.1426 (2.21); 8.0212 (0.79); 8.0155 (1.96); 7.9863 (0.32); 7.3096 (1.08); 7.3058 (0.38); 7.2999 (1.4); 7.2463 (1.4); 7.242 (0.39); 7.2367 (1.08); 7.1425 (1.84); 7.1386 (1.8); 7.1296 (1.8); 7.1257 (1.78); 7.0305 (3.39); 7.0207 (3.9); 7.0136 (0.71); 7.0096 (0.65); 7.0004 (0.63); 6.9964 (0.6); 6.9083 (4); 6.8985 (3.51); 6.5275 (0.39); 4.587 (0.4); 4.5703 (1.04); 4.5536 (1.42); 4.5369 (1.06); 4.5203 (0.41); 4.4246 (0.41); 4.0582 (8.94); 4.0196 (3.1); 3.4303 (0.34); 3.3632 (36.54); 3.3491 (281.96); 3.2907 (0.58); 3.2766 (0.41); 2.8916 (0.54); 2.7325 (0.43); 2.5127 (18.48); 2.5082 (36.79); 2.5036 (48.55); 2.4991 (35.16); 2.4946 (16.92); 1.483 (16); 1.4663 (15.83); 1.4031 (4.54); 1.3867 (4.48); 1.2345 (0.57); 0.008 (1.04); −0.0002 (26.01); −0.0085 (0.95)<br>Example 245<br>Solvent: DMSO |
| 10.7449 (1.96); 10.6093 (0.32); 8.2876 (2.08); 8.2861 (2.12); 8.2747 (2.14); 8.2732 (2.19); 8.187 (0.35); 8.1855 (0.36); 8.1738 (0.39); 8.1724 (0.39); 8.1509 (6.21); 8.1303 (2.14); 8.0371 (0.33); 7.9643 (0.94); 7.953 (0.75); 7.3546 (0.4); 7.3486 (0.81); 7.3333 (9.33); 7.3282 (5.45); 7.3183 (3.9); 7.3166 (4.67); 7.3114 (1); 7.302 (0.65); 7.2967 (0.98); 7.2847 (0.59); 7.2751 (0.82); 7.2618 (0.79); 7.2562 (1.01); 7.248 (0.82); 7.24 (1.12); 7.2325 (0.46); 7.2301 (0.48); 7.2224 (0.92); 7.2188 (0.36); 7.2127 (0.57); 7.093 (1.92); 7.0891 (1.87); 7.0801 (1.87); 7.0762 (1.88); 7.006 (3.64); 6.9962 (4.16); 6.9259 (0.32); 6.9218 (0.35); 6.9127 (0.34); 6.9087 (0.34); 6.8793 (4.32); 6.8695 (3.8); 4.5626 (0.38); 4.546 (1.03); 4.5293 (1.42); 4.5127 (1.06); 4.4961 (0.41); 3.7148 (6.7); 3.6792 (1.17); 3.3284 (79.98); 2.8903 (6.16); 2.7319 (4.81); 2.7307 (4.83); 2.5244 (0.54); 2.5112 (11.98); 2.5067 (24.21); 2.5021 (32.3); 2.4975 (23.32); 2.4929 (11.29); 1.4622 (16); 1.4455 (15.85); 1.3898 (2.08); 1.3734 (2.06); 0.008 (0.74); −0.0002 (19.39); −0.0085 (0.71)<br>Example 246<br>Solvent: DMSO |
| 10.4453 (1.98); 8.271 (2.22); 8.2581 (2.26); 8.2569 (2.18); 8.1623 (7.41); 8.1544 (0.46); 7.9773 (0.52); 7.953 (0.53); 7.3077 (0.32); 7.2981 (0.4); 7.2386 (0.39); 7.078 (1.93); 7.074 (1.85); 7.0651 (1.87); 7.0611 (1.83); 7.0273 (3.53); 7.0175 (3.99); 6.9036 (0.36); 6.8971 (4.13); 6.8872 (3.73); 4.5815 (0.4); 4.5649 (1.07); 4.5482 (1.47); 4.5315 (1.09); 4.5148 (0.42); 3.3339 (99.07); 2.8912 (4.22); 2.7322 (3.4); 2.5119 (10.4); 2.5074 (20.84); 2.5028 (27.61); 2.4983 (20.02); 2.4938 (9.78); 2.4168 (1.07); 2.398 (3.62); 2.3791 (3.81); 2.3605 (1.47); 2.3422 (0.39); 1.4804 (16); 1.4637 (15.91); 1.402 (1.21); 1.3856 (1.2); 1.0727 (4.21); 1.061 (0.85); 1.0538 (9.14); 1.0424 (1.23); 1.035 (4.13); 1.0236 (0.49); 0.008 (0.42); −0.0002 (11.37); −0.0085 (0.48)<br>Example 247<br>Solvent: DMSO |
| 10.8169 (1.77); 8.2793 (2.12); 8.2777 (2.1); 8.2664 (2.18); 8.2648 (2.16); 8.1595 (0.5); 8.1506 (6.5); 8.1471 (2.52); 8.1454 (2.6); 8.1437 (2.5); 7.9641 (0.64); 7.9526 (0.85); 7.2933 (0.37); 7.2837 (0.47); 7.2216 (0.46); 7.212 (0.36); 7.0761 (1.87); 7.0721 (1.82); 7.0632 (1.84); 7.0592 (1.82); 7.0204 (3.75); 7.0106 (4.21); 6.8919 (0.34); 6.8848 (4.32); 6.875 (3.77); 4.5733 (0.38); 4.5567 (1.03); 4.5401 (1.41); 4.5234 (1.05); 4.5067 (0.39); 3.3372 (167.53); 3.2951 (0.32); 2.8911 (7.18); 2.7323 (5.69); 2.7311 (5.49); 2.525 (0.7); 2.5119 (13.41); 2.5074 (26.94); 2.5028 (35.76); 2.4981 (25.67); 2.4936 (12.34); 2.0219 (0.69); 2.0068 (0.91); 1.9915 (0.71); 1.4728 (16); 1.4561 (15.83); 1.3968 (1.37); 1.3803 (1.37); 0.8051 (3.82); 0.7911 (7.21); 0.008 (0.94); −0.0002 (24.65); −0.0086 (0.92)<br>Example 248<br>Solvent: DMSO |
| 8.8613 (1.05); 8.2017 (1.12); 8.2002 (1.14); 8.1888 (1.15); 8.1873 (1.15); 8.1251 (3.56); 7.8654 (1.34); 7.8637 (1.33); 7.0261 (2); 7.0163 (2.35); 6.9702 (1.02); 6.9663 (1); 6.9573 (1); 6.9534 (1); 6.9238 (0.35); 6.9196 (2.47); 6.9142 (0.36); 6.9097 (2.11); 6.5242 (0.43); 4.5566 (0.59); 4.5399 (0.82); 4.5233 (0.62); 3.3299 (68.32); 2.9339 (16); 2.9174 (1.21); 2.8906 (2.65); 2.7318 (2); 2.7307 (2.08); 2.5415 (0.56); 2.5246 (0.42); 2.5112 (8.63); 2.5067 (17.67); 2.5021 (23.73); 2.4975 (17.25); 2.4929 (8.4); 1.4764 (9.07); 1.4667 (1.91); 1.4597 (9.08); 1.4501 (1.45); 1.3992 (0.53); 1.3941 (0.77); 1.3827 (0.56); 1.3777 (0.76); 0.008 (0.72); −0.0002 (21.03); −0.0085 (0.86)<br>Example 249<br>Solvent: DMSO |
| 10.4642 (1.87); 8.2735 (2.3); 8.2606 (2.34); 8.1913 (2.6); 8.1774 (6.18); 7.9863 (0.46); 7.9533 (0.45); 7.2851 (0.34); 7.2355 (0.34); 7.083 (1.83); 7.0791 (1.78); 7.0701 (1.8); 7.0662 (1.76); 7.0217 (3.46); 7.0119 (3.95); 6.9022 (4.05); 6.8924 (3.5); 4.5838 (0.39); 4.5671 (1.06); 4.5504 (1.47); 4.5338 (1.09); 4.5171 (0.42); 3.3422 (129.08); 2.8916 (3.79); 2.7324 (3.06); 2.6083 (0.41); 2.591 (0.7); 2.5725 (0.73); 2.5559 (0.51); 2.5494 (0.41); 2.5258 (0.55); 2.5126 (10.37); 2.5081 (20.68); 2.5035 (27.42); 2.4989 (19.9); 2.4944 (9.75); 1.6234 (0.47); 1.6046 (0.63); 1.5899 (0.71); 1.5851 (0.58); 1.5709 (0.86); 1.5516 (0.6); 1.4817 (16); 1.465 (15.88); 1.412 (0.66); 1.4089 (0.71); 1.401 (0.8); 1.3975 (0.96); 1.3933 (1.06); 1.3847 (0.78); 1.3791 (1.07); 1.3638 (0.57); 1.3606 (0.67); 1.3456 (0.45); 1.0668 (7.12); 1.0497 (7.36); 1.0314 (0.67); 0.8652 (3.67); 0.8467 (7.94); 0.8281 (3.47); 0.807 (0.33); −0.0002 (6.46) |

| NMR peak list table |
|---|
| Example 250<br>Solvent: DMSO |
| 10.388 (1.95); 8.2745 (2.11); 8.2729 (2.15); 8.2616 (2.17); 8.2599 (2.25); 8.182 (2.32);<br>8.1752 (6.46); 7.9871 (0.47); 7.9526 (0.37); 7.297 (0.38); 7.243 (0.37); 7.0878 (1.93); 7.0838 (1.89);<br>7.0749 (1.89); 7.0709 (1.9); 7.029 (3.71); 7.0192 (4.26); 6.9021 (4.55); 6.8922 (3.9);<br>4.5843 (0.38); 4.5676 (1.03); 4.551 (1.42); 4.5343 (1.05); 4.5176 (0.4); 3.3437 (140.89); 2.8913 (3.17);<br>2.7326 (2.47); 2.7314 (2.44); 2.5258 (0.46); 2.5125 (9.84); 2.508 (20.06); 2.5034 (26.88);<br>2.4988 (19.46); 2.4942 (9.37); 2.2844 (3.81); 2.2667 (3.91); 2.2494 (0.38); 2.2316 (0.35); 1.4826 (16);<br>1.4659 (15.85); 1.4041 (1.08); 1.3877 (1.07); 1.0569 (0.46); 1.0549 (0.45); 1.0491 (0.45);<br>1.045 (0.38); 1.0426 (0.36); 1.037 (0.83); 1.0316 (0.37); 1.0291 (0.38); 1.0247 (0.52); 1.0192 (0.47);<br>1.017 (0.51); 0.4855 (0.8); 0.4749 (2.07); 0.4707 (2.24); 0.4654 (1.15); 0.4606 (1.21);<br>0.4547 (2.23); 0.4504 (2.11); 0.4405 (0.92); 0.1997 (0.81); 0.1893 (2.24); 0.1858 (2.34); 0.1773 (2.26);<br>0.1737 (2.41); 0.1629 (0.81); −0.0002 (3.82) |
| Example 251<br>Solvent: DMSO |
| 8.8636 (1.21); 8.2049 (1.11); 8.193 (1.13); 8.192 (1.13); 8.0915 (3.33); 7.8709 (1.41);<br>7.8693 (1.41); 7.027 (1.94); 7.0171 (2.28); 6.9609 (0.99); 6.9571 (0.98); 6.9481 (0.98); 6.9442 (0.98);<br>6.9244 (2.38); 6.9145 (2.03); 6.5255 (0.63); 4.2052 (0.61); 4.187 (1.94); 4.1688 (1.99);<br>4.1507 (0.68); 3.3355 (72.79); 2.9341 (16); 2.8908 (1.36); 2.732 (1.07); 2.731 (1.05); 2.5451 (0.34);<br>2.5422 (0.33); 2.5116 (6.34); 2.5071 (12.8); 2.5025 (17.13); 2.4979 (12.51); 2.4934 (6.14);<br>1.4445 (2.4); 1.4338 (0.46); 1.4263 (5.43); 1.4159 (0.66); 1.4081 (2.39); 0.0079 (0.52); −0.0002 (13.71);<br>−0.0085 (0.55) |
| Example 252<br>Solvent: DMSO |
| 10.4681 (3.43); 10.335 (0.35); 8.2783 (3.85); 8.2767 (3.73); 8.2654 (3.94); 8.2638 (3.82);<br>8.1934 (4.55); 8.1919 (4.45); 8.183 (0.72); 8.1696 (0.47); 8.1681 (0.47); 8.1471 (9.89); 8.0713 (0.45);<br>7.9641 (1.23); 7.9531 (0.64); 7.2935 (0.54); 7.2839 (0.77); 7.2442 (0.76); 7.2346 (0.54);<br>7.0754 (3.27); 7.0715 (3.18); 7.0625 (3.22); 7.0586 (3.13); 7.0237 (5.95); 7.0139 (6.86); 6.9192 (0.45);<br>6.9152 (0.6); 6.9068 (7.26); 6.897 (6.08); 4.2136 (1.8); 4.1954 (5.65); 4.1772 (5.71); 4.159 (1.86);<br>4.0848 (0.56); 4.0667 (0.56); 3.4063 (0.42); 3.346 (252.22); 2.8917 (4.7); 2.7329 (3.93);<br>2.7318 (3.68); 2.6079 (0.75); 2.5909 (1.3); 2.5725 (1.34); 2.5558 (0.86); 2.5431 (0.42); 2.5127 (18.35);<br>2.5083 (34.98); 2.5038 (45.03); 2.4992 (33.01); 2.4948 (16.45); 1.6239 (0.72); 1.6051 (1.13);<br>1.5901 (1.32); 1.5713 (1.53); 1.5519 (1.04); 1.5334 (0.33); 1.449 (7.09); 1.4308 (16);<br>1.4126 (7.73); 1.3973 (1.4); 1.3788 (1.73); 1.3605 (1.15); 1.3453 (0.84); 1.3369 (0.8); 1.3269 (0.39);<br>1.3188 (1.56); 1.3008 (0.7); 1.2339 (0.33); 1.0669 (11.94); 1.0498 (12.47); 1.0313 (1.4);<br>0.8648 (6.12); 0.8463 (13.39); 0.8276 (6.26); 0.8076 (0.67); −0.0002 (6.46) |
| Example 253<br>Solvent: DMSO |
| 7.969 (0.56); 6.8563 (0.35); 6.8464 (0.4); 6.732 (0.42); 6.7222 (0.36); 3.1841 (16); 2.3387 (0.91);<br>2.3341 (1.86); 2.3295 (2.49); 2.3249 (1.81); 2.3204 (0.88); 2.1107 (0.37); 2.0931 (0.38);<br>1.2758 (0.41); 1.2576 (0.93); 1.2393 (0.4) |
| Example 254<br>Solvent: DMSO |
| 10.7054 (3.96); 10.5803 (0.57); 8.5676 (2.5); 8.5654 (2.93); 8.5613 (2.81); 8.5581 (2.85);<br>8.5332 (0.37); 8.531 (0.42); 8.5269 (0.42); 8.5238 (0.42); 8.3682 (3.74); 8.3667 (3.79); 8.3554 (3.86);<br>8.3538 (3.92); 8.2702 (4.86); 8.2562 (0.64); 8.2546 (0.63); 8.1804 (9.3); 8.1661 (0.7);<br>8.1642 (0.7); 8.0112 (1.93); 7.9528 (1.41); 7.7062 (2.46); 7.7032 (2.48); 7.6936 (3.73); 7.6905 (3.67);<br>7.6831 (0.5); 7.6799 (0.46); 7.6702 (0.59); 7.6672 (0.58); 7.6484 (3.86); 7.6411 (4.09);<br>7.6358 (2.76); 7.6329 (1.06); 7.6285 (2.71); 7.6201 (0.42); 7.3199 (0.68); 7.3102 (1.03); 7.2754 (0.94);<br>7.2658 (0.63); 7.161 (3.53); 7.157 (3.4); 7.1481 (3.44); 7.1442 (3.42); 7.0458 (6.05); 7.036 (7.35);<br>7.0009 (0.51); 6.9969 (0.5); 6.9878 (0.52); 6.9838 (0.52); 6.96 (7.69); 6.9502 (6.33);<br>4.2277 (1.79); 4.2095 (5.69); 4.1912 (5.76); 4.173 (1.85); 4.0915 (0.79); 4.0734 (0.8); 3.356 (85.28);<br>3.3527 (83.99); 3.3475 (81.87); 3.3393 (105.61); 2.8913 (12.06); 2.7326 (9.6); 2.7314 (9.4);<br>2.6725 (0.36); 2.5426 (0.35); 2.5257 (0.98); 2.5125 (20.16); 2.508 (40.89); 2.5034 (54.64);<br>2.4988 (39.47); 2.4942 (19.04); 2.3302 (0.35); 1.4612 (7.17); 1.443 (16); 1.4248 (7.01); 1.3464 (0.93);<br>1.3284 (2.12); 1.3103 (0.91); 0.0079 (1.05); −0.0002 (27.63); −0.0085 (1.13) |
| Example 255<br>Solvent: DMSO |
| 9.8199 (0.62); 8.2959 (0.72); 8.2945 (0.72); 8.2831 (0.74); 8.2815 (0.75); 8.1466 (2);<br>8.1229 (0.88); 8.1211 (0.88); 7.0937 (0.63); 7.0898 (0.62); 7.0808 (0.62); 7.0769 (0.62); 7.034 (1.21);<br>7.0242 (1.38); 6.9078 (1.44); 6.898 (1.27); 4.2135 (0.35); 4.1952 (1.12); 4.177 (1.14);<br>4.1588 (0.36); 3.3338 (22.27); 2.8911 (0.83); 2.7323 (0.65); 2.7313 (0.64); 2.5118 (3.18); 2.5073 (6.46);<br>2.5027 (8.61); 2.4981 (6.23); 2.4935 (3.03); 1.4501 (1.43); 1.4319 (3.24); 1.4137 (1.4);<br>1.2341 (16); 1.2135 (1.7); −0.0002 (3.27) |
| Example 256<br>Solvent: DMSO |
| 10.4976 (1.61); 8.2773 (2.08); 8.2757 (2.12); 8.2645 (2.14); 8.2628 (2.18); 8.1619 (6.29);<br>8.1372 (1.69); 7.98 (0.59); 7.9527 (0.6); 7.3046 (0.36); 7.295 (0.46); 7.2337 (0.45); 7.2241 (0.36);<br>7.0911 (1.96); 7.0871 (1.92); 7.0782 (1.88); 7.0742 (1.88); 7.0246 (3.65); 7.0147 (4.18); 6.8993 (4.4);<br>6.8894 (3.84); 4.5802 (0.39); 4.5636 (1.03); 4.5469 (1.41); 4.5302 (1.05); 4.5136 (0.4);<br>3.3729 (0.58); 3.3387 (130.35); 2.891 (5.19); 2.7324 (3.98); 2.7312 (4.07); 2.5253 (0.47); 2.5121 (10.05); |

| NMR peak list table |
| --- |
| 2.5076 (20.38); 2.503 (27.29); 2.4984 (19.76); 2.4938 (9.55); 2.0804 (13.84); 2.0452 (1.57); 1.4783 (16); 1.4616 (15.83); 1.3983 (1.36); 1.3819 (1.35); 0.008 (0.63); −0.0002 (17.25); −0.0085 (0.64)<br>Example 257<br>Solvent: DMSO |
| 10.4466 (1.82); 8.2721 (2.11); 8.2705 (2.15); 8.2592 (2.17); 8.2576 (2.23); 8.1732 (2.68); 8.1712 (2.92); 8.1679 (7.03); 7.9782 (0.52); 7.9528 (0.5); 7.2954 (0.41); 7.2376 (0.4); 7.077 (1.91); 7.0731 (1.86); 7.0642 (1.87); 7.0602 (1.87); 7.0276 (3.72); 7.0178 (4.21); 6.8951 (4.36); 6.8853 (3.87); 4.5812 (0.38); 4.5645 (1.02); 4.5479 (1.41); 4.5312 (1.05); 4.5145 (0.4); 3.384 (0.62); 3.3458 (153.87); 2.8915 (4.24); 2.7854 (0.33); 2.7684 (0.88); 2.7513 (1.26); 2.7328 (3.94); 2.7316 (3.66); 2.7173 (0.42); 2.5259 (0.47); 2.5127 (10.23); 2.5082 (20.68); 2.5036 (27.57); 2.499 (19.91); 2.4945 (9.61); 1.4807 (16); 1.464 (15.84); 1.4041 (1.19); 1.3877 (1.18); 1.0862 (14.95); 1.0692 (15.54); 1.0532 (1.62); −0.0002 (5.55)<br>Example 258<br>Solvent: DMSO |
| 10.4484 (1.8); 8.2732 (2.09); 8.2718 (2.09); 8.2603 (2.15); 8.2588 (2.17); 8.1723 (7.95); 7.989 (0.43); 7.9527 (0.4); 7.2806 (0.36); 7.2328 (0.35); 7.0879 (1.82); 7.084 (1.77); 7.075 (1.78); 7.0711 (1.77); 7.0182 (3.51); 7.0084 (4.09); 6.9039 (4.23); 6.894 (3.67); 4.5844 (0.38); 4.5677 (1.01); 4.551 (1.4); 4.5344 (1.04); 4.5177 (0.39); 3.3563 (158.63); 3.2904 (0.36); 2.8919 (3.43); 2.733 (2.69); 2.7319 (2.6); 2.5266 (0.54); 2.5135 (10.03); 2.5089 (20.12); 2.5043 (26.71); 2.4997 (19.22); 2.4952 (9.27); 2.2709 (3.57); 2.253 (4.29); 2.2099 (3.07); 2.0884 (0.42); 2.0715 (0.78); 2.0545 (0.94); 2.0375 (0.75); 2.0201 (0.41); 1.4806 (15.66); 1.4639 (15.49); 1.4028 (1.01); 1.3863 (1); 0.924 (16); 0.9074 (15.72); 0.8938 (1.56); −0.0002 (4.98)<br>Example 259<br>Solvent: DMSO |
| 10.113 (2.23); 9.978 (0.33); 8.2334 (2.1); 8.2319 (2.09); 8.2206 (2.18); 8.2189 (2.19); 8.1693 (6.21); 8.1339 (0.36); 8.1208 (0.32); 8.1192 (0.33); 7.9951 (0.8); 7.8864 (2.61); 7.8847 (2.66); 7.7588 (0.38); 7.7569 (0.38); 7.3054 (0.49); 7.2958 (0.64); 7.2349 (0.63); 7.2253 (0.48); 7.0485 (1.94); 7.0447 (1.91); 7.0356 (2.01); 7.03 (4.24); 7.0201 (4.25); 6.9079 (0.33); 6.904 (0.38); 6.8959 (4.48); 6.8909 (0.6); 6.8861 (3.88); 4.5798 (0.38); 4.5632 (1.02); 4.5465 (1.41); 4.5298 (1.05); 4.5132 (0.4); 4.1464 (1.36); 4.1286 (4.49); 4.1109 (4.59); 4.0965 (0.93); 4.0932 (1.5); 3.3268 (71.38); 3.3031 (0.93); 2.5246 (0.46); 2.5114 (10.11); 2.5069 (20.55); 2.5023 (27.42); 2.4977 (19.8); 2.4932 (9.57); 1.4797 (16); 1.463 (15.81); 1.4016 (1.86); 1.3851 (1.83); 1.2414 (5.63); 1.2339 (0.75); 1.2237 (11.8); 1.206 (5.35); 0.008 (0.79); −0.0002 (21.35); −0.0085 (0.79)<br>Example 260<br>Solvent: DMSO |
| 10.8235 (2.15); 8.3728 (2.09); 8.3713 (2.16); 8.3599 (2.16); 8.3584 (2.24); 8.277 (2.66); 8.2751 (2.68); 8.2735 (2.33); 8.2314 (6.05); 8.0537 (0.54); 8.0334 (2.85); 8.0206 (0.9); 8.0157 (3.33); 8.0121 (2.53); 7.953 (0.73); 7.6226 (0.33); 7.6194 (0.59); 7.6164 (0.37); 7.6065 (0.48); 7.6012 (1.72); 7.596 (0.6); 7.5859 (0.85); 7.5827 (1.39); 7.5795 (0.77); 7.5344 (2.34); 7.5245 (0.5); 7.5181 (1.9); 7.515 (3.39); 7.5055 (0.54); 7.5012 (0.66); 7.4971 (1.41); 7.4948 (0.95); 7.3178 (0.42); 7.2763 (0.39); 7.1863 (1.87); 7.1824 (1.83); 7.1735 (1.84); 7.1696 (1.84); 7.0503 (3.52); 7.0405 (4.31); 6.9656 (4.42); 6.9557 (3.63); 4.5997 (0.39); 4.583 (1.02); 4.5664 (1.42); 4.5497 (1.05); 4.533 (0.4); 3.336 (93.35); 2.8907 (6); 2.7322 (4.77); 2.7311 (4.79); 2.5117 (10.78); 2.5072 (21.76); 2.5026 (28.94); 2.498 (20.95); 2.4935 (10.15); 1.496 (16); 1.4793 (15.81); 1.4172 (1.15); 1.4007 (1.14); 0.008 (0.41); −0.0002 (11.27); −0.0085 (0.44)<br>Example 261<br>Solvent: DMSO |
| 10.0083 (3.2); 9.8583 (0.77); 8.3015 (3.56); 8.3002 (3.58); 8.2886 (3.65); 8.2872 (3.71); 8.21 (0.9); 8.2087 (0.9); 8.1968 (0.93); 8.1955 (0.94); 8.1623 (10.03); 8.1447 (3.57); 8.0281 (0.84); 7.9929 (2.79); 7.3084 (1.25); 7.2988 (1.74); 7.255 (1.73); 7.2453 (1.24); 7.1298 (3.19); 7.1259 (3.11); 7.1169 (3.11); 7.1129 (3.1); 7.0318 (5.8); 7.022 (6.68); 7.017 (1.07); 7.0129 (0.83); 7.0037 (0.77); 6.9997 (0.76); 6.9097 (7); 6.8999 (6.08); 4.2179 (1.8); 4.1997 (5.71); 4.1815 (5.78); 4.1634 (1.87); 4.094 (0.44); 4.0758 (1.54); 4.0598 (15.82); 4.0397 (0.52); 4.0211 (3.89); 3.363 (38.24); 3.352 (10.34); 3.3261 (97.34); 2.8908 (0.91); 2.7311 (0.71); 2.5245 (0.85); 2.5113 (17.29); 2.5068 (34.53); 2.5023 (45.69); 2.4977 (32.96); 2.4932 (15.72); 1.4512 (7.11); 1.433 (16); 1.4213 (0.95); 1.4148 (6.96); 1.3342 (1.56); 1.3161 (3.6); 1.2981 (1.55); 0.008 (0.79); −0.0002 (20.22); −0.0085 (0.71)<br>Example 262<br>Solvent: DMSO |
| 10.7499 (3.53); 10.6176 (0.35); 8.2919 (3.66); 8.2906 (3.74); 8.2791 (3.73); 8.2777 (3.85); 8.1936 (0.41); 8.1817 (0.41); 8.1312 (4.12); 8.1197 (10.35); 8.0415 (0.38); 7.9527 (1.12); 7.9417 (1.26); 7.3547 (0.81); 7.3489 (1.57); 7.3334 (15.32); 7.3284 (8.56); 7.3164 (7.45); 7.3113 (1.7); 7.3018 (1.12); 7.2966 (1.68); 7.2826 (0.65); 7.2729 (0.95); 7.2617 (1.32); 7.2561 (1.77); 7.2477 (1.34); 7.2399 (1.91); 7.2291 (1.34); 7.2244 (0.94); 7.219 (0.95); 7.0848 (3.32); 7.0809 (3.23); 7.0719 (3.22); 7.068 (3.23); 7.0075 (5.93); 6.9977 (6.75); 6.9327 (0.34); 6.9286 (0.33); 6.9195 (0.32); 6.9154 (0.34); 6.883 (7.01); 6.8732 (6.13); 4.1939 (1.83); 4.1757 (5.71); 4.1575 (5.75); 4.1393 (1.85); 4.064 (0.54); 4.0459 (0.56); 3.7155 (11.94); 3.6805 (1.31); 3.3879 (0.33); 3.3332 (182.28); 2.8904 (8.7); 2.731 (6.93); 2.6716 (0.33); 2.5114 (20.32); 2.507 (39.86); 2.5024 (52.53); 2.4978 (38.29); 2.4934 (18.85); 2.3292 (0.35); 1.4306 (7.21); 1.4208 (1.12); 1.4124 (16); 1.3942 (7.04); 1.3215 (0.67); 1.3034 (1.53); 1.2854 (0.67); 1.2336 (0.34); 0.0079 (0.81); −0.0002 (19.39); −0.0085 (0.82) |

| NMR peak list table |
| --- |
| Example 263<br>Solvent: DMSO |
| 10.4512 (2.98); 10.325 (0.45); 8.2752 (3.41); 8.2735 (3.52); 8.2623 (3.52); 8.2606 (3.64);<br>8.1676 (3.6); 8.1299 (9.99); 8.0768 (0.5); 7.9533 (2.47); 7.3053 (0.86); 7.2956 (1.13); 7.2458 (1.13);<br>7.2362 (0.83); 7.0683 (3.23); 7.0644 (3.16); 7.0555 (3.18); 7.0515 (3.17); 7.0286 (6.16);<br>7.0188 (7.04); 6.9105 (0.59); 6.9063 (0.71); 6.8999 (7.37); 6.8931 (1.15); 6.8901 (6.47); 4.2124 (1.71);<br>4.1942 (5.48); 4.176 (5.55); 4.1578 (1.78); 4.076 (0.8); 4.0578 (0.81); 3.3327 (145.08);<br>2.8909 (5.45); 2.7324 (4.18); 2.7312 (4.3); 2.5253 (0.62); 2.5119 (15.07); 2.5074 (30.95); 2.5027 (41.54);<br>2.4981 (30.14); 2.4936 (14.64); 2.4173 (1.73); 2.3985 (5.95); 2.3797 (6.29); 2.3612 (2.45);<br>2.3434 (0.99); 2.3296 (0.33); 2.3247 (0.5); 1.4484 (6.99); 1.4302 (16); 1.412 (6.92); 1.3337 (0.95);<br>1.3157 (2.23); 1.2976 (0.96); 1.0726 (7.06); 1.0605 (1.8); 1.0538 (15.61); 1.0418 (2.96);<br>1.0349 (6.95); 1.023 (1.16); 0.008 (0.54); −0.0002 (16.28); −0.0085 (0.61) |
| Example 264<br>Solvent: DMSO |
| 10.8246 (2.84); 8.2838 (3.43); 8.2822 (3.51); 8.2709 (3.54); 8.2692 (3.64); 8.1467 (3.85);<br>8.145 (3.86); 8.129 (0.33); 8.1197 (9.7); 7.9529 (1.17); 7.9413 (0.86); 7.2916 (0.37); 7.2819 (0.5);<br>7.2298 (0.5); 7.2201 (0.38); 7.0682 (3.08); 7.0643 (3.01); 7.0554 (3.04); 7.0514 (3.03);<br>7.0221 (6.08); 7.0123 (6.91); 6.8892 (7.31); 6.8793 (6.39); 4.2043 (1.68); 4.1861 (5.37); 4.1679 (5.45);<br>4.1497 (1.75); 4.0722 (0.35); 4.0541 (0.36); 3.3374 (125.28); 2.8911 (9.85); 2.7324 (7.81);<br>2.7312 (7.81); 2.5253 (0.56); 2.5121 (15.04); 2.5075 (30.72); 2.5029 (41.1); 2.4983 (29.68);<br>2.4938 (14.39); 2.0387 (0.34); 2.0229 (1.16); 2.0079 (1.49); 1.9924 (1.21); 1.9767 (0.44); 1.4408 (6.97);<br>1.4226 (16); 1.4044 (6.87); 1.3292 (0.43); 1.3112 (1); 1.2931 (0.44); 0.8063 (6.65);<br>0.7917 (11.58); 0.7784 (0.96); 0.008 (0.77); −0.0002 (22.74); −0.0085 (0.87) |
| Example 265<br>Solvent: DMSO |
| 10.1211 (3.13); 9.9866 (0.62); 8.2374 (2.98); 8.2358 (3.02); 8.2246 (3.1); 8.2229 (3.14);<br>8.1398 (1.07); 8.1352 (8.59); 8.1286 (0.89); 8.1269 (0.83); 7.9725 (2.05); 7.8862 (3.63); 7.8845 (3.7);<br>7.8828 (3.13); 7.7626 (0.72); 7.7606 (0.72); 7.3032 (0.94); 7.2935 (1.28); 7.2421 (1.25);<br>7.2324 (0.93); 7.038 (2.9); 7.0341 (3.1); 7.031 (5.67); 7.0251 (3.18); 7.0212 (8.57); 6.9141 (0.6);<br>6.9101 (0.61); 6.8982 (6.45); 6.8884 (5.47); 4.2114 (1.47); 4.1933 (4.67); 4.175 (4.71); 4.1568 (1.54);<br>4.1468 (2.02); 4.1291 (6.55); 4.1114 (6.82); 4.0938 (2.65); 4.0762 (1.05); 4.0578 (0.91);<br>3.3317 (140.4); 3.3078 (1.48); 2.525 (0.68); 2.5118 (14.21); 2.5073 (28.86); 2.5026 (38.53);<br>2.498 (27.78); 2.4935 (13.32); 1.4478 (5.99); 1.4296 (13.73); 1.4114 (5.86); 1.3331 (1.07); 1.315 (2.51);<br>1.297 (1.06); 1.2416 (7.63); 1.2239 (16); 1.2062 (7.28); 0.008 (1.18); −0.0002 (32.36);<br>−0.0085 (1.19) |
| Example 266<br>Solvent: DMSO |
| 10.8259 (3.6); 10.6937 (0.5); 8.3766 (3.17); 8.3755 (3.16); 8.3637 (3.27); 8.3625 (3.27);<br>8.2813 (4.34); 8.2795 (4.64); 8.266 (0.52); 8.1951 (9.88); 8.1765 (0.62); 8.1744 (0.62); 8.0328 (4.71);<br>8.0296 (3.91); 8.0201 (1.46); 8.0152 (5.49); 8.0115 (4.17); 7.9868 (0.79); 7.9832 (0.6);<br>7.953 (0.34); 7.6219 (0.53); 7.6189 (0.97); 7.6157 (0.61); 7.606 (0.8); 7.6007 (2.84); 7.5955 (1);<br>7.5908 (0.63); 7.5854 (1.45); 7.5822 (2.3); 7.5789 (1.24); 7.5723 (0.41); 7.5337 (3.81); 7.5301 (1.75);<br>7.5244 (0.95); 7.5174 (3.1); 7.5143 (5.58); 7.5052 (1.15); 7.5004 (1.11); 7.4963 (2.37);<br>7.494 (1.53); 7.4873 (0.44); 7.3246 (0.7); 7.3149 (1.09); 7.2824 (1.05); 7.2728 (0.69); 7.1743 (3.13);<br>7.1704 (3.07); 7.1614 (3.06); 7.1575 (3.05); 7.0509 (5.8); 7.0411 (7.14); 7.0237 (0.47);<br>7.0197 (0.45); 7.0106 (0.45); 7.0066 (0.45); 6.9675 (7.37); 6.9577 (6.04); 4.2315 (1.69); 4.2133 (5.45);<br>4.1951 (5.51); 4.1769 (1.76); 4.0946 (0.73); 4.0765 (0.72); 3.3723 (0.55); 3.3348 (181.11);<br>3.2905 (0.32); 2.8909 (2.77); 2.7323 (2.2); 2.7311 (2.14); 2.525 (0.74); 2.5119 (17.07); 2.5074 (34.55);<br>2.5028 (46.01); 2.4982 (33.13); 2.4936 (15.91); 1.4643 (7.04); 1.4461 (16); 1.4279 (6.91);<br>1.349 (0.87); 1.331 (2.04); 1.3129 (0.86); 0.0081 (0.65); −0.0002 (18.53); −0.0085 (0.65) |
| Example 267<br>Solvent: DMSO |
| 10.9561 (3.62); 10.8283 (0.46); 8.3741 (3.44); 8.3726 (3.47); 8.3612 (3.56); 8.3597 (3.63);<br>8.2755 (0.5); 8.2739 (0.51); 8.2606 (0.78); 8.2554 (2.98); 8.2527 (3.16); 8.2458 (3.15); 8.2432 (3.02);<br>8.2193 (4.37); 8.2175 (4.47); 8.2065 (0.56); 8.2038 (0.51); 8.1827 (9.8); 8.1195 (0.55);<br>8.1176 (0.59); 8.0163 (1.55); 7.953 (1.43); 7.8989 (3.07); 7.8963 (3.16); 7.8864 (1.66); 7.8838 (3.54);<br>7.8738 (0.52); 7.8712 (0.46); 7.3213 (0.68); 7.3117 (1); 7.2745 (0.98); 7.2649 (0.68);<br>7.2258 (3.24); 7.2163 (3.3); 7.2134 (3.28); 7.2038 (3.21); 7.1985 (0.6); 7.1889 (0.47); 7.1672 (3.12);<br>7.1634 (3.06); 7.1544 (3.09); 7.1505 (3.06); 7.0477 (5.89); 7.0379 (7.07); 7.0027 (0.45);<br>6.9987 (0.42); 6.9897 (0.43); 6.9856 (0.42); 6.9533 (7.25); 6.9434 (6.11); 4.2265 (1.7); 4.2083 (5.44);<br>4.1901 (5.5); 4.1719 (1.76); 4.0899 (0.68); 4.0718 (0.69); 3.3997 (0.41); 3.341 (213.31);<br>2.8912 (11.89); 2.7326 (9.24); 2.7314 (9.39); 2.5256 (0.83); 2.5123 (18.35); 2.5078 (37.23);<br>2.5032 (49.64); 2.4986 (35.93); 2.4941 (17.5); 2.33 (0.33); 1.4608 (7.02); 1.4426 (16); 1.4244 (6.91);<br>1.3455 (0.84); 1.3275 (1.92); 1.3095 (0.82); 1.2328 (0.34); 0.0079 (0.44); −0.0002 (11.95);<br>−0.0086 (0.45) |
| Example 268<br>Solvent: DMSO |
| 10.0145 (1.84); 9.8812 (0.32); 8.2298 (1.73); 8.2283 (1.71); 8.2169 (1.78); 8.2154 (1.77);<br>8.133 (5.09); 8.1211 (0.39); 7.9725 (1); 7.8823 (2.12); 7.8808 (2.13); 7.7578 (0.37); 7.756 (0.37);<br>7.2987 (0.45); 7.289 (0.61); 7.2388 (0.6); 7.2291 (0.45); 7.0301 (4.41); 7.0263 (1.77);<br>7.0203 (3.52); 7.0173 (1.81); 7.0134 (1.59); 6.9058 (0.33); 6.8956 (3.58); 6.8857 (3.03); 4.9108 (0.36);<br>4.8952 (0.99); 4.8795 (1.38); 4.8639 (1.03); 4.8596 (0.36); 4.8483 (0.39); 4.2115 (0.84); |

NMR peak list table 4.1933 (2.69); 4.1751 (2.72); 4.1568 (0.87); 4.0781 (0.45); 4.06 (0.45); 3.339 (98.81); 2.8913 (0.52);
2.7326 (0.41); 2.7315 (0.41); 2.5256 (0.36); 2.5123 (7.98); 2.5078 (16.11); 2.5032 (21.51);
2.4986 (15.58); 2.4941 (7.54); 1.4478 (3.43); 1.4296 (7.76); 1.4114 (3.35); 1.3334 (0.54); 1.3154 (1.26);
1.2973 (0.55); 1.2441 (16); 1.2284 (15.9); 0.008 (0.65); −0.0002 (17.63); −0.0085 (0.68)
Example 269
Solvent: DMSO 10.3298 (3.24); 10.2006 (0.54); 8.2669 (3.52); 8.2655 (3.66); 8.254 (3.63); 8.2526 (3.8);
8.1912 (3.45); 8.165 (0.67); 8.1532 (0.68); 8.1518 (0.72); 8.1375 (10.03); 8.0934 (0.55); 7.9637 (2.04);
7.9527 (0.95); 7.3131 (0.91); 7.3035 (1.22); 7.2497 (1.21); 7.24 (0.94); 7.0668 (3.16);
7.0628 (3.11); 7.0539 (3.13); 7.05 (3.16); 7.0344 (6.02); 7.0246 (6.9); 6.9043 (7.2); 6.8981 (1.16);
6.8945 (6.38); 6.8894 (0.81); 6.8853 (0.68); 4.2165 (1.74); 4.1983 (5.56); 4.1801 (5.63); 4.1619 (1.8);
4.083 (0.89); 4.0649 (0.91); 3.4313 (0.53); 3.4048 (1.39); 3.3545 (320.4); 3.3075 (0.87);
3.2859 (0.43); 2.8917 (7.7); 2.7329 (6.09); 2.7319 (5.98); 2.5265 (0.78); 2.5133 (17.61); 2.5088 (35.82);
2.5042 (47.83); 2.4996 (34.72); 2.4951 (16.88); 2.2431 (0.4); 2.22 (41.36); 2.2147 (1.2);
2.1962 (1.97); 2.1911 (2.46); 2.1748 (1.64); 2.1697 (2.22); 2.1575 (0.58); 2.1528 (0.66); 2.1473 (0.75);
2.1305 (0.64); 2.121 (0.78); 2.1088 (1.54); 2.1006 (2.05); 2.0937 (1.44); 2.0877 (1.52);
2.0789 (1.99); 2.0711 (1.28); 2.064 (0.77); 2.0586 (0.75); 2.0503 (0.56); 1.976 (0.32); 1.9547 (0.69);
1.9497 (0.61); 1.9317 (1.14); 1.928 (1.19); 1.9106 (0.71); 1.8915 (1.54); 1.8958 (0.39);
1.8838 (0.8); 1.8254 (0.55); 1.8107 (0.68); 1.8007 (1.15); 1.7903 (0.78); 1.7871 (0.73); 1.7764 (0.88);
1.7675 (0.48); 1.4523 (7.06); 1.4341 (16); 1.4159 (6.93); 1.3385 (1.06); 1.3204 (2.46);
1.3024 (1.04); −0.0002 (3.88)
Example 270
Solvent: DMSO 10.456 (1.76); 8.279 (2.07); 8.2775 (2.07); 8.2662 (2.12); 8.2645 (2.16); 8.1914 (0.4);
8.1898 (0.41); 8.1765 (2.39); 8.0845 (5.24); 8.056 (0.32); 7.9529 (0.52); 7.921 (1.13); 7.2908 (0.45);
7.2811 (0.75); 7.255 (0.74); 7.2453 (0.44); 7.0669 (1.84); 7.0629 (1.81); 7.054 (1.79);
7.0501 (1.81); 7.0194 (3.5); 7.0096 (4.09); 6.908 (4.19); 6.8982 (3.61); 3.8955 (13.84); 3.7794 (2.42);
3.3399 (106.68); 2.8912 (4.44); 2.7325 (3.45); 2.7314 (3.45); 2.5255 (0.38); 2.5123 (9.82);
2.5078 (20.11); 2.5032 (26.99); 2.4986 (19.53); 2.494 (9.45); 2.2717 (3.57); 2.2539 (4.32); 2.2312 (0.6);
2.2133 (0.72); 2.0885 (0.41); 2.0716 (0.78); 2.0546 (0.95); 2.0372 (0.77); 2.0198 (0.43);
0.9231 (16); 0.9099 (4.72); 0.9065 (15.82); 0.8938 (2.82); 0.008 (0.59); −0.0002 (16.99); −0.0085 (0.62)
Example 271
Solvent: DMSO 10.125 (2.48); 9.9966 (0.64); 8.2404 (2.36); 8.2388 (2.42); 8.2276 (2.44); 8.2259 (2.52);
8.1496 (0.63); 8.1481 (0.64); 8.1365 (0.64); 8.1349 (0.67); 8.0746 (6.07); 7.9255 (2.16); 7.8824 (2.92);
7.8808 (2.99); 7.879 (2.56); 7.773 (0.76); 7.7711 (0.77); 7.7695 (0.67); 7.3025 (0.92);
7.2929 (1.34); 7.2528 (1.32); 7.2431 (0.93); 7.0299 (4.47); 7.0278 (2.82); 7.0237 (2.54); 7.0201 (4.99);
7.0147 (2.3); 7.0108 (2.22); 6.9187 (0.6); 6.9148 (0.61); 6.9056 (0.69); 6.9016 (0.83);
6.8972 (4.78); 6.8874 (4.2); 4.1466 (1.57); 4.129 (5.29); 4.1113 (5.71); 4.0941 (2.28); 4.0773 (0.45);
3.8941 (16); 3.7768 (4.64); 3.339 (139.45); 3.3163 (1.88); 2.8911 (1.09); 2.7326 (0.84);
2.7314 (0.87); 2.5256 (0.47); 2.5123 (10.92); 2.5078 (22.22); 2.5032 (29.68); 2.4986 (21.53);
2.4941 (10.45); 1.2413 (5.98); 1.2328 (1.33); 1.2236 (12.46); 1.2059 (5.69); 0.008 (0.6); −0.0002 (17.13);
−0.0085 (0.65)
Example 272
Solvent: DMSO 10.8273 (2.45); 10.7017 (0.33); 8.3798 (2.3); 8.3782 (2.39); 8.367 (2.39); 8.3653 (2.49);
8.2853 (0.55); 8.2786 (2.89); 8.2767 (2.96); 8.2748 (2.68); 8.1852 (0.39); 8.1831 (0.4); 8.1331 (6.11);
8.0309 (3.15); 8.0181 (1); 8.0131 (3.81); 8.0095 (2.87); 7.9867 (0.58); 7.9821 (1.42);
7.6222 (0.36); 7.619 (0.68); 7.6159 (0.43); 7.6062 (0.55); 7.6008 (1.92); 7.5956 (0.68); 7.5917 (0.43);
7.5856 (0.97); 7.5823 (1.57); 7.579 (0.86); 7.5335 (2.6); 7.5299 (1.21); 7.5252 (0.64);
7.5173 (2.08); 7.5141 (3.8); 7.5059 (0.79); 7.5003 (0.73); 7.4961 (1.62); 7.4937 (1.06); 7.3226 (0.43);
7.3129 (0.79); 7.2911 (0.77); 7.2815 (0.43); 7.164 (2.21); 7.16 (2.17); 7.1511 (2.17);
7.1472 (2.16); 7.0497 (4.03); 7.0398 (5.01); 7.03 (0.38); 7.026 (0.35); 6.9678 (5.11); 6.9579 (4.18);
3.9139 (16); 3.7953 (2.4); 3.3467 (177.47); 3.3016 (0.48); 2.891 (1.14); 2.7326 (0.88);
2.7313 (0.91); 2.5259 (0.58); 2.5126 (11.54); 2.5081 (23.36); 2.5035 (31.13); 2.4989 (22.44);
2.4943 (10.79); 0.008 (0.68); −0.0002 (18.71); −0.0085 (0.71)
Example 273
Solvent: DMSO 10.961 (2.44); 10.8415 (0.32); 8.3778 (2.43); 8.3766 (2.36); 8.365 (2.5); 8.3637 (2.42);
8.2843 (0.35); 8.2712 (0.38); 8.2527 (2.03); 8.2501 (2.13); 8.2405 (2.14); 8.2135 (3.2);
8.1223 (6.51); 7.9699 (1.14); 7.9528 (1.24); 7.8993 (2.11); 7.8968 (2.13); 7.8869 (2.46);
7.8844 (2.32); 7.8754 (0.39); 7.8728 (0.34); 7.3199 (0.44); 7.3102 (0.74); 7.2838 (0.73); 7.2741 (0.43);
7.2263 (2.19); 7.2168 (2.26); 7.2138 (2.37); 7.2043 (2.29); 7.1909 (0.32); 7.1593 (2.14);
7.1555 (2.1); 7.1465 (2.09); 7.1426 (2.08); 7.0467 (3.86); 7.0368 (4.68); 6.9536 (4.76); 6.9438 (3.95);
3.9096 (16); 3.7914 (2.36); 3.4332 (0.39); 3.3578 (207.74); 2.8918 (10.31); 2.7329 (8.21);
2.732 (7.73); 2.5266 (0.61); 2.5135 (12.37); 2.509 (24.95); 2.5044 (33.22); 2.4998 (24.04);
2.4953 (11.74); −0.0002 (3.64)
Example 274
Solvent: DMSO 10.0197 (2.09); 9.892 (0.42); 8.232 (1.93); 8.2192 (2); 8.1413 (0.4); 8.1283 (0.42); 8.074 (4.56);
7.9248 (1.13); 7.8786 (2.52); 7.7695 (0.51); 7.2994 (0.47); 7.2897 (0.7); 7.2516 (0.7);
7.242 (0.48); 7.0292 (2.79); 7.0192 (4.49); 7.015 (1.82); 7.0058 (1.64); 7.0021 (1.55); 6.9116 (0.37);

| NMR peak list table |
|---|
| 6.9076 (0.37); 6.8943 (3.49); 6.8844 (2.83); 4.9111 (0.38); 4.8955 (1.03); 4.8798 (1.42); 4.8642 (1.09); 4.86 (0.45); 4.8486 (0.44); 3.8939 (12.17); 3.7782 (2.61); 3.3247 (47.32); 2.8909 (1.03); 2.7319 (0.85); 2.5111 (12.13); 2.5067 (23); 2.5022 (29.62); 2.4977 (21.85); 2.4934 (11.11); 1.2433 (16); 1.2277 (15.88); −0.0002 (3.76)<br>Example 275<br>Solvent: DMSO |
| 10.3319 (2.21); 10.2102 (0.4); 8.2694 (2.34); 8.268 (2.38); 8.2566 (2.42); 8.2551 (2.45); 8.1916 (2.3); 8.1739 (0.5); 8.1609 (0.47); 8.1595 (0.48); 8.1073 (0.41); 8.0796 (6.08); 7.9148 (1.48); 7.3129 (0.63); 7.3032 (0.92); 7.2627 (0.91); 7.253 (0.64); 7.0552 (2.15); 7.0513 (2.11); 7.0424 (2.17); 7.0384 (2.27); 7.0332 (4.16); 7.0234 (4.63); 6.9032 (4.86); 6.8933 (4.37); 6.8884 (0.57); 3.8986 (16); 3.7838 (3.18); 3.3849 (0.93); 3.3633 (1.68); 3.3325 (112.57); 2.8911 (1.99); 2.7323 (1.59); 2.7313 (1.54); 2.5251 (0.5); 2.5118 (11.83); 2.5074 (23.81); 2.5028 (31.63); 2.4982 (22.86); 2.4937 (11.12); 2.2201 (0.94); 2.2147 (0.82); 2.1961 (1.33); 2.1911 (1.66); 2.1749 (1.12); 2.1698 (1.5); 2.1573 (0.42); 2.1532 (0.46); 2.1473 (0.51); 2.1288 (0.43); 2.1194 (0.53); 2.1069 (1.07); 2.0985 (1.4); 2.0917 (1.01); 2.0857 (1.08); 2.0769 (1.37); 2.0698 (0.89); 2.062 (0.57); 2.0563 (0.51); 2.0476 (0.38); 1.9529 (0.47); 1.9481 (0.43); 1.9301 (0.77); 1.9264 (0.8); 1.9091 (0.48); 1.9036 (1.04); 1.8823 (0.54); 1.8229 (0.38); 1.8089 (0.46); 1.799 (0.78); 1.7888 (0.53); 1.7855 (0.5); 1.7747 (0.6); 1.7661 (0.33); 0.008 (0.66); −0.0002 (18.04); −0.0085 (0.68)<br>Example 276<br>Solvent: DMSO |
| 10.0096 (2.01); 8.3043 (2.28); 8.3029 (2.33); 8.2915 (2.35); 8.2899 (2.39); 8.1416 (2.23); 8.1012 (5.99); 7.9468 (0.77); 7.3068 (0.32); 7.2971 (0.48); 7.2641 (0.47); 7.1193 (2.16); 7.1153 (2.11); 7.1064 (2.11); 7.1024 (2.11); 7.0308 (4); 7.021 (4.76); 6.9091 (4.77); 6.8993 (4.18); 4.0597 (10.04); 4.0229 (0.98); 3.9002 (16); 3.777 (1.65); 3.3629 (27.04); 3.3519 (7); 3.3389 (118.46); 2.8911 (1.46); 2.7325 (1.13); 2.7313 (1.14); 2.5255 (0.41); 2.5122 (9.62); 2.5077 (19.57); 2.5031 (26.13); 2.4985 (18.94); 2.494 (9.21); 0.008 (0.62); −0.0002 (17.36); −0.0085 (0.66)<br>Example 277<br>Solvent: DMSO |
| 10.751 (2.21); 8.2954 (2.37); 8.2939 (2.36); 8.2825 (2.42); 8.2809 (2.44); 8.1286 (2.39); 8.0612 (6.15); 8.051 (0.39); 7.9526 (0.99); 7.8951 (0.86); 7.3545 (0.84); 7.349 (1.15); 7.3333 (9.87); 7.3282 (5.4); 7.3162 (4.82); 7.3111 (1.2); 7.3015 (0.73); 7.2963 (1.12); 7.2823 (0.45); 7.2726 (0.69); 7.2616 (0.89); 7.2561 (1.19); 7.2476 (0.87); 7.2394 (1.7); 7.2323 (0.53); 7.2295 (0.83); 7.2243 (0.57); 7.2184 (0.34); 7.076 (2.18); 7.0721 (2.11); 7.0632 (2.15); 7.0592 (2.13); 7.006 (4.04); 6.9962 (4.63); 6.8829 (4.74); 6.8731 (4.15); 3.8767 (16); 3.765 (1.84); 3.7153 (7.67); 3.6828 (0.88); 3.3903 (0.49); 3.3429 (175.62); 2.8906 (8.28); 2.7321 (6.51); 2.7311 (6.35); 2.5253 (0.6); 2.5121 (13.17); 2.5076 (26.6); 2.503 (35.39); 2.4984 (25.53); 2.4938 (12.24); −0.0002 (6.87)<br>Example 278<br>Solvent: DMSO |
| 10.4531 (2.01); 8.2783 (2.13); 8.2769 (2.16); 8.2655 (2.2); 8.264 (2.25); 8.1667 (2.41); 8.07 (6.03); 7.906 (0.53); 7.2939 (0.34); 7.2563 (0.35); 7.0588 (2.15); 7.0549 (2.09); 7.046 (2.12); 7.042 (2.12); 7.0275 (4.19); 7.0177 (4.77); 6.9001 (4.92); 6.8902 (4.23); 3.895 (16); 3.7779 (1.14); 3.3919 (0.35); 3.3459 (135.79); 2.8913 (0.58); 2.7328 (0.45); 2.7316 (0.45); 2.5261 (0.4); 2.5128 (8.84); 2.5083 (17.87); 2.5037 (23.75); 2.4991 (17.09); 2.4945 (8.23); 2.4173 (1.18); 2.3985 (4.02); 2.3796 (4.16); 2.3608 (1.34); 1.0725 (4.8); 1.0603 (0.84); 1.0537 (10.56); 1.0419 (1.07); 1.0348 (4.67); 1.0231 (0.39); 0.008 (0.51); −0.0002 (13.73); −0.0085 (0.5)<br>Example 279<br>Solvent: DMSO |
| 10.8188 (2.14); 8.2867 (2.22); 8.2855 (2.28); 8.2739 (2.27); 8.2726 (2.33); 8.1465 (2.7); 8.1449 (2.72); 8.0585 (6.06); 8.0316 (0.61); 7.9527 (0.34); 7.8923 (0.71); 7.8696 (0.49); 7.281 (0.45); 7.241 (0.45); 7.0569 (2.06); 7.053 (2.02); 7.0441 (2.04); 7.0401 (2.05); 7.0256 (0.57); 7.0202 (3.83); 7.016 (0.82); 7.0104 (4.31); 6.9275 (0.47); 6.9176 (0.42); 6.8937 (0.44); 6.8883 (4.53); 6.8784 (3.96); 6.5276 (0.37); 3.8865 (16); 3.8714 (0.33); 3.7734 (1.65); 3.3448 (172.08); 2.9341 (3.3); 2.8913 (2.65); 2.7326 (2.1); 2.7315 (2.12); 2.5258 (0.46); 2.5126 (10.55); 2.5082 (21.27); 2.5036 (28.27); 2.499 (20.55); 2.4945 (9.98); 2.0225 (0.84); 2.0074 (1.06); 1.9916 (0.91); 1.9761 (0.33); 0.8058 (5.32); 0.7906 (8); 0.7771 (0.77); 0.008 (0.33); −0.0002 (9.65); −0.0085 (0.36)<br>Example 280<br>Solvent: DMSO |
| 10.4641 (2.48); 8.2815 (2.64); 8.2686 (2.68); 8.2671 (2.42); 8.191 (3.33); 8.1772 (0.41); 8.0875 (6.43); 7.9533 (0.75); 7.9173 (0.93); 7.2938 (0.4); 7.2864 (0.61); 7.2469 (0.38); 7.0655 (2.35); 7.0616 (2.21); 7.0527 (2.3); 7.0488 (2.18); 7.0447 (0.49); 7.0345 (0.36); 7.0223 (3.98); 7.0125 (4.54); 6.9237 (0.34); 6.9197 (0.35); 6.9066 (4.77); 6.8968 (3.91); 3.8955 (16); 3.8728 (1); 3.7844 (1.98); 3.4294 (0.48); 3.357 (256.87); 3.2918 (0.69); 2.8921 (5); 2.7332 (4.29); 2.6069 (0.52); 2.5897 (0.9); 2.5718 (0.95); 2.5545 (0.72); 2.5436 (0.42); 2.5134 (14.83); 2.509 (27.29); 2.5045 (34.33); 2.5 (24.94); 2.4956 (12.3); 1.6233 (0.49); 1.6046 (0.77); 1.5897 (0.88); 1.5709 (1.04); 1.5515 (0.71); 1.4116 (0.57); 1.3964 (0.89); 1.378 (1.14); 1.3629 (0.74); 1.3597 (0.76); 1.3447 (0.55); 1.0662 (7.97); 1.0491 (8.58); 1.0314 (1.06); 0.8641 (4.09); 0.8456 (9.05); 0.8271 (4.69); 0.8101 (0.67); −0.0002 (5.16)<br>Example 281<br>Solvent: DMSO |
| 10.397 (2.38); 10.2767 (0.32); 8.2808 (2.52); 8.268 (2.58); 8.1841 (2.84); 8.0981 (0.49); 8.0859 (5.93); 7.9155 (1); 7.3044 (0.41); 7.2947 (0.63); 7.2624 (0.64); 7.2527 (0.42); 7.0679 (2.09); |

|     | -continued |
| --- | --- |
|     | NMR peak list table |

7.0641 (2.03); 7.0551 (2.05); 7.0512 (2); 7.0297 (3.57); 7.0198 (4.08); 6.9223 (0.33);
6.913 (0.47); 6.9048 (4.22); 6.895 (3.65); 3.8969 (16); 3.7804 (2.29); 3.3238 (76.18); 2.8906 (0.58);
2.7316 (0.47); 2.671 (0.33); 2.5107 (19.92); 2.5064 (37.63); 2.5019 (48.36); 2.4974 (35.42);
2.4931 (17.73); 2.3285 (0.32); 2.284 (4.57); 2.2664 (4.69); 2.252 (0.76); 2.2343 (0.67);
1.0562 (0.6); 1.0489 (0.58); 1.0369 (1.01); 1.0291 (0.53); 1.0245 (0.68); 1.0173 (0.65); 1.0056 (0.4);
0.4839 (0.89); 0.4733 (2.56); 0.4691 (2.77); 0.4638 (1.55); 0.459 (1.51); 0.4531 (2.72);
0.4489 (2.59); 0.439 (1.04); 0.1992 (0.95); 0.1885 (2.97); 0.1855 (2.99); 0.1766 (3.07); 0.1736 (3.13);
0.1625 (1.13); 0.0077 (0.53); −0.0002 (10.46); −0.0084 (0.47)
Example 282
Solvent: DMSO 10.7057 (2.53); 10.5861 (0.44); 8.5672 (2.13); 8.5639 (2.32); 8.5599 (2.3); 8.5566 (2.18);
8.5355 (0.37); 8.5322 (0.4); 8.5282 (0.4); 8.5249 (0.39); 8.371 (2.33); 8.3695 (2.41); 8.3582 (2.4);
8.3566 (2.51); 8.27 (2.98); 8.2683 (3.03); 8.1755 (0.51); 8.1734 (0.51); 8.1189 (6.09); 7.9627 (1.43);
7.7054 (1.81); 7.7022 (1.81); 7.6928 (2.72); 7.6895 (2.68); 7.6837 (0.44); 7.6804 (0.38);
7.671 (0.51); 7.6677 (0.51); 7.6474 (2.53); 7.6401 (2.88); 7.6347 (1.83); 7.6274 (1.9); 7.6198 (0.32);
7.3185 (0.54); 7.3089 (0.97); 7.2853 (0.94); 7.2756 (0.55); 7.1489 (2.18); 7.145 (2.13);
7.1361 (2.14); 7.1321 (2.14); 7.0443 (3.99); 7.0345 (4.91); 7.0062 (0.39); 7.0022 (0.38); 6.9932 (0.39);
6.9892 (0.38); 6.959 (4.93); 6.9492 (4.04); 3.91 (16); 3.7925 (3.01); 3.384 (0.44);
3.3419 (184.02); 2.8911 (1.08); 2.7325 (0.84); 2.7314 (0.83); 2.5256 (0.53); 2.5124 (12.54);
2.5079 (25.4); 2.5033 (33.8); 2.4987 (24.43); 2.4941 (11.83); −0.0002 (8.59); −0.0085 (0.33)
Example 283
Solvent: DMSO 9.8162 (0.66); 8.2994 (0.73); 8.298 (0.71); 8.2866 (0.74); 8.2852 (0.73); 8.1209 (0.87);
8.1192 (0.87); 8.0859 (1.83); 7.9246 (0.35); 7.0841 (0.65); 7.0802 (0.64); 7.0713 (0.64); 7.0674 (0.63);
7.0328 (1.2); 7.0229 (1.37); 6.9086 (1.42); 6.8987 (1.24); 3.8959 (4.89); 3.7843 (0.75);
3.3419 (41.45); 2.8914 (1.42); 2.7325 (1.12); 2.7317 (1.06); 2.5125 (3.37); 2.5079 (6.79); 2.5034 (9.01);
2.4987 (6.49); 2.4942 (3.13); 1.2334 (16); 1.2146 (2.62); −0.0002 (2.51)
Example 284
Solvent: DMSO 10.5058 (1.78); 8.2811 (2.39); 8.2793 (2.44); 8.2682 (2.49); 8.2664 (2.54); 8.1855 (0.33);
8.1839 (0.34); 8.1725 (0.34); 8.1707 (0.36); 8.1386 (1.92); 8.1282 (7.09); 7.958 (1.2); 7.9529 (0.61);
7.3021 (0.51); 7.2925 (0.68); 7.241 (0.67); 7.2313 (0.52); 7.0801 (2.26); 7.0761 (2.2);
7.0673 (2.22); 7.0633 (2.22); 7.026 (4.36); 7.0162 (5.07); 6.9018 (5.23); 6.892 (4.62); 4.2114 (1.18);
4.1932 (3.74); 4.175 (3.78); 4.1568 (1.21); 4.0695 (0.46); 4.0514 (0.47); 3.3441 (144.1);
2.8912 (4.86); 2.7327 (3.92); 2.7313 (3.98); 2.5259 (0.41); 2.5211 (0.71); 2.5126 (10.09); 2.5081 (20.75);
2.5035 (27.82); 2.4989 (20.09); 2.4943 (9.68); 2.0819 (16); 2.0465 (2.16); 1.4466 (4.91);
1.4285 (11.37); 1.4102 (4.82); 1.3292 (0.55); 1.3112 (1.3); 1.2931 (0.54); −0.0002 (4.15)
Example 285
Solvent: DMSO 10.449 (1.89); 8.2773 (2.19); 8.2643 (2.27); 8.176 (0.45); 8.1658 (2.64); 8.1319 (5.77);
7.9575 (0.88); 7.9517 (0.44); 7.3002 (0.35); 7.2905 (0.49); 7.2412 (0.48); 7.2316 (0.36); 7.0746 (1.87);
7.0706 (1.86); 7.0617 (1.84); 7.0577 (1.85); 7.0295 (3.4); 7.0197 (3.92); 6.9018 (4.14);
6.8919 (3.67); 6.8854 (0.37); 4.2129 (1.08); 4.1947 (3.38); 4.1765 (3.41); 4.1583 (1.1); 4.0831 (0.39);
4.065 (0.4); 3.5496 (0.35); 3.4173 (313.75); 3.2925 (0.63); 2.8937 (3.4); 2.783 (0.33);
2.766 (0.94); 2.7489 (1.35); 2.7337 (3.2); 2.7148 (0.46); 2.5177 (8.47); 2.5132 (17.19); 2.5087 (23.07);
2.5041 (17.04); 2.4996 (8.57); 1.4491 (4.24); 1.431 (9.46); 1.4127 (4.18); 1.3368 (0.46);
1.3188 (1.03); 1.3008 (0.46); 1.0879 (15.16); 1.0709 (16); 1.0551 (2.09); −0.0002 (1.23)
Example 286
Solvent: DMSO 10.4515 (1.75); 8.2757 (2.03); 8.2742 (2.07); 8.2628 (2.09); 8.2613 (2.14); 8.1786 (2.13);
8.1426 (5.69); 7.9656 (0.74); 7.2806 (0.47); 7.2429 (0.46); 7.2333 (0.53); 7.075 (1.79); 7.0711 (1.76);
7.0621 (1.76); 7.0582 (1.77); 7.0199 (3.46); 7.0101 (4.02); 6.9062 (4.15); 6.8964 (3.58);
4.2132 (1); 4.195 (3.19); 4.1768 (3.24); 4.1586 (1.03); 4.0612 (0.33); 3.327 (70.73); 2.8906 (2.68);
2.7318 (2.08); 2.7308 (2.06); 2.5242 (0.8); 2.511 (15.96); 2.5065 (32.08); 2.5019 (42.69);
2.4973 (30.91); 2.4927 (15.12); 2.2712 (3.56); 2.2533 (4.29); 2.2281 (0.4); 2.2102 (0.48); 2.0883 (0.4);
2.0714 (0.77); 2.0545 (0.93); 2.0371 (0.74); 2.0199 (0.4); 1.4474 (4.09); 1.4292 (9.33);
1.411 (4.02); 1.3331 (0.39); 1.3151 (0.9); 1.2971 (0.39); 0.9231 (16); 0.9065 (15.86); 0.893 (1.97);
0.008 (0.93); −0.0002 (24.69); −0.0085 (0.98)
Example 287
Solvent: DMSO 10.509 (2.14); 8.2815 (2.48); 8.2694 (2.56); 8.1794 (0.32); 8.1396 (2.22); 8.0688 (6.02);
7.9102 (0.87); 7.301 (0.36); 7.2914 (0.53); 7.2522 (0.53); 7.2425 (0.38); 7.0672 (2.11); 7.0634 (2.11);
7.0544 (2.12); 7.0505 (2.1); 7.0248 (3.55); 7.015 (4.11); 6.9047 (4.14); 6.8908 (3.64);
3.8935 (16); 3.7711 (1.98); 3.3267 (78.05); 2.8906 (1.86); 2.7315 (1.52); 2.5109 (15.16); 2.5067 (28.7);
2.5022 (37.13); 2.4978 (27.99); 2.4936 (14.75); 2.0814 (15.54); 2.0472 (1.95); −0.0002 (3.91)
Example 288
Solvent: DMSO 10.4533 (1.94); 8.2795 (2.22); 8.2782 (2.17); 8.2667 (2.27); 8.2653 (2.23); 8.1819 (0.51);
8.1733 (2.59); 8.1714 (2.72); 8.0953 (0.4); 8.079 (5.58); 7.9532 (0.64); 7.9061 (1.08); 7.3032 (0.45);
7.2935 (0.68); 7.2584 (0.67); 7.2487 (0.46); 7.0594 (1.98); 7.0555 (1.93); 7.0465 (1.95);
7.0426 (1.95); 7.028 (3.71); 7.0182 (4.16); 6.8981 (4.28); 6.8883 (3.79); 6.8815 (0.39); 3.8944 (14.73);

NMR peak list table 3.7828 (2.26); 3.3325 (89.08); 2.8912 (5.39); 2.7852 (0.34); 2.7681 (0.93); 2.7511 (1.35);
2.7324 (4.9); 2.7174 (0.6); 2.5119 (10.58); 2.5074 (21.23); 2.5028 (28.19); 2.4982 (20.4); 2.4937 (9.87);
1.0854 (15.5); 1.0684 (16); 1.0533 (2.48); 0.008 (0.57); −0.0002 (14.41); −0.0085 (0.57)
Example 289
Solvent: DMSO 8.5511 (0.37); 8.5383 (0.41); 8.4393 (1.24); 8.4261 (1.21); 8.2298 (0.86); 8.1416 (0.37);
8.1327 (3.36); 8.0931 (0.66); 7.4367 (0.51); 7.4342 (0.44); 7.3943 (0.88); 7.3904 (0.91); 7.3812 (0.85);
7.3772 (0.89); 7.3214 (1.47); 7.312 (1.93); 7.2948 (0.33); 7.2854 (0.65); 7.2794 (0.36);
7.2751 (0.76); 7.2594 (1.99); 7.2499 (2.02); 7.2448 (1.54); 7.2418 (1.55); 6.9848 (0.38); 6.9752 (0.72);
6.9568 (0.81); 6.9472 (0.41); 3.9226 (2.19); 3.9153 (0.49); 3.814 (7.37); 3.7991 (1.46);
3.3331 (5.83); 2.5288 (0.53); 2.5155 (6.21); 2.5111 (12.59); 2.5066 (16.89); 2.5021 (12.15);
2.4978 (5.68); 2.3165 (16); 2.2948 (1.85); 2.2899 (5.38); 2.2278 (0.41); 2.1766 (5.79); 2.1716 (1.67);
2.1299 (15.77); 2.0324 (0.51); 2.0169 (1.84); 1.9138 (0.38)
Example 290
Solvent: DMSO 11.9734 (0.68); 11.4839 (0.98); 11.2132 (1.4); 8.5238 (1); 8.5114 (0.96); 8.5095 (1);
8.4095 (1.01); 8.3964 (0.85); 8.1407 (2.78); 8.1155 (0.41); 8.0555 (2.3); 8.0293 (0.48); 7.4562 (0.74);
7.4523 (1.12); 7.4396 (3.11); 7.3581 (0.95); 7.3554 (0.97); 7.2327 (0.64); 7.2287 (0.6);
7.2195 (0.62); 7.2155 (0.58); 7.0875 (1.1); 7.0778 (1.13); 6.7752 (0.32); 6.7675 (1.6); 6.7576 (1.69);
6.7411 (1.13); 6.7315 (1.17); 6.5039 (1.74); 6.4941 (1.64); 4.3624 (0.4); 4.1283 (0.61);
4.1152 (1.83); 4.102 (1.88); 4.0889 (0.65); 3.8883 (6.97); 3.8824 (1.46); 3.758 (4.85); 3.7412 (1.14);
3.5716 (0.34); 3.3395 (30.93); 3.1787 (7.3); 3.1656 (7.01); 2.5289 (1.42); 2.5156 (13.42);
2.5112 (26.84); 2.5068 (35.76); 2.5022 (25.36); 2.4979 (11.48); 2.224 (1.1); 2.181 (16); 2.1385 (10.94);
2.0968 (5.19); 2.0843 (0.63); 2.0692 (7.84); 2.0342 (1.38); 2.0089 (0.46); 2.0023 (1.33);
1.9137 (5.96); 1.7717 (0.57); 1.0769 (0.62); 1.0594 (1.21); 1.0419 (0.59); 0.9936 (0.32)
Example 291
Solvent: DMSO 8.6057 (1.23); 8.593 (1.26); 8.3956 (2.82); 8.0699 (0.66); 8.044 (0.71); 7.8754 (0.6);
7.8495 (0.78); 7.7342 (0.72); 7.7056 (0.98); 7.6793 (0.56); 7.5356 (1.76); 7.5215 (1.09); 7.5178 (0.77);
7.5087 (0.99); 7.505 (0.77); 7.0863 (1.61); 7.0765 (1.74); 6.9237 (1.78); 6.9138 (1.57);
3.3387 (2.66); 2.5109 (13.3); 2.5066 (17.13); 2.5023 (12.48); 2.1931 (16)
Example 292
Solvent: DMSO 10.5838 (2.25); 8.4386 (0.38); 8.3282 (2.3); 8.3154 (2.39); 8.3013 (6.72); 8.1639 (2.18);
8.0662 (1.57); 8.0403 (1.64); 7.8713 (1.42); 7.8453 (1.78); 7.7098 (1.71); 7.6835 (1.87); 7.6806 (2.08);
7.6545 (1.26); 7.1058 (2.11); 7.102 (2.01); 7.093 (2.05); 7.0891 (1.96); 7.0732 (3.99);
7.0634 (4.5); 6.9584 (4.44); 6.9484 (3.8); 3.3402 (6.92); 2.6802 (0.56); 2.6757 (0.67); 2.6715 (0.52);
2.556 (0.59); 2.5513 (0.63); 2.5156 (47.07); 2.5112 (93.53); 2.5067 (124.25); 2.5022 (89.36);
2.498 (41.55); 2.4724 (0.39); 2.4464 (0.42); 2.4288 (0.34); 2.3383 (0.56); 2.3336 (0.74);
2.3293 (0.55); 2.1569 (0.6); 2.0915 (16); 2.0533 (0.4); 1.2385 (0.36); 0.9361 (0.55)
Example 293
Solvent: DMSO 10.585 (2.42); 8.3348 (2.8); 8.3173 (6.06); 8.168 (2.41); 7.1571 (2.27); 7.1533 (2.25);
7.1447 (3.23); 7.1406 (2.44); 7.1352 (1.57); 7.069 (3.77); 7.0591 (4.3); 6.9862 (1.51); 6.9757 (1.25);
6.9551 (1.37); 6.9463 (5.48); 6.9365 (3.83); 6.9039 (1.75); 6.8935 (1.01); 4.0051 (0.96);
3.3403 (3.34); 2.5111 (33.61); 2.5067 (43.72); 2.5023 (31.6); 2.0897 (16); 0.9334 (0.4)
Example 294
Solvent: DMSO 8.5449 (1.74); 8.5322 (1.73); 8.225 (6.23); 7.397 (3.36); 7.3932 (2.2); 7.3856 (2.2); 7.3818 (3.17);
7.0237 (3.3); 7.0144 (3.73); 6.8926 (3.62); 6.8833 (3.19); 5.7643 (0.64); 4.5709 (0.41);
4.5542 (1.04); 4.5376 (1.42); 4.5209 (1.06); 4.5043 (0.42); 3.3338 (5.84); 2.5457 (0.35); 2.5223 (22.3);
2.5156 (7.93); 2.5112 (15.28); 2.5066 (20.3); 2.5021 (14.37); 2.4977 (6.54); 1.485 (16);
1.4684 (15.76)
Example 295
Solvent: DMSO 8.4437 (2.52); 8.4294 (2.52); 8.2259 (0.73); 8.1006 (6.67); 7.3969 (0.42); 7.3818 (0.4);
7.2553 (1.43); 7.2461 (7.98); 7.243 (8.04); 7.2337 (1.62); 7.2261 (4.35); 7.2222 (2.8); 7.2145 (2.81);
7.2107 (4.13); 7.0242 (0.41); 7.0149 (0.44); 6.8926 (0.41); 6.8832 (3.19); 5.7643 (0.42);
4.4493 (0.4); 4.4328 (1.04); 4.4164 (1.42); 4.3999 (1.04); 4.3836 (0.4); 3.3323 (8.09); 2.5913 (26.11);
2.556 (0.36); 2.5459 (0.53); 2.5223 (5.32); 2.5155 (19.87); 2.5111 (39.99); 2.5066 (53.47);
2.502 (37.96); 2.4977 (17.34); 2.4743 (0.33); 2.3334 (0.34); 1.4851 (1.91); 1.4684 (1.87); 1.4013 (16);
1.3848 (15.7)
Example 296
Solvent: DMSO 8.1838 (16); 8.1412 (9.76); 8.014 (0.77); 7.9207 (7.61); 7.9062 (7.72); 7.3437 (0.35);
7.3341 (0.48); 7.2789 (0.58); 7.2689 (0.43); 7.0968 (10.6); 7.087 (12.09); 6.9703 (11.72); 6.9605 (10.12);
6.8382 (0.45); 6.7729 (3.5); 6.6565 (9.46); 6.6346 (6); 6.6201 (5.45); 6.6168 (4.64);
6.5563 (0.89); 5.7654 (5.72); 4.8957 (3.35); 4.8842 (5.59); 4.8726 (3.6); 4.7777 (3.27); 4.7664 (5.69);
4.7545 (3.7); 4.5427 (3.47); 4.5309 (5.29); 4.5193 (2.97); 4.4732 (3.72); 4.4615 (5.33);
4.4498 (2.82); 4.0663 (0.42); 4.0483 (0.45); 3.4682 (0.33); 3.4519 (0.44); 3.3394 (4.76); 2.8948 (0.51);

| NMR peak list table |
|---|
| 2.7347 (0.39); 2.6756 (1.15); 2.6712 (0.84); 2.511 (153.73); 2.5066 (202.43); 2.5021 (145.52); 2.4052 (0.32); 2.3336 (1.27); 2.3289 (0.94); 1.4351 (0.37); 1.4246 (0.51); 1.3249 (0.46); 1.3068 (1.07); 1.2884 (0.47); 1.2418 (0.32); 1.059 (0.54)<br>Example 297<br>Solvent: DMSO |
| 8.5997 (1.05); 8.5984 (1.04); 8.5869 (1.08); 8.5855 (1.08); 8.4849 (2.16); 7.5942 (1.22); 7.5921 (1.42); 7.5685 (1); 7.5645 (0.78); 7.5557 (0.94); 7.5517 (0.79); 7.1705 (0.53); 7.1601 (0.55); 7.0903 (1.75); 7.0805 (1.93); 7.0086 (0.58); 6.9981 (0.48); 6.9804 (0.45); 6.9699 (0.68); 6.9263 (0.84); 6.9228 (2.01); 6.9129 (1.8); 5.7653 (0.61); 3.3365 (6.02); 2.5293 (0.47); 2.5245 (0.71); 2.5159 (5.59); 2.5114 (11.55); 2.5069 (15.63); 2.5023 (11.13); 2.4978 (5.06); 2.1962 (16)<br>Example 298<br>Solvent: DMSO |
| 8.6657 (3.94); 8.6617 (2.31); 8.6547 (2.36); 8.6507 (3.99); 7.4306 (4.18); 7.4265 (2.44); 7.4196 (2.41); 7.4156 (3.99); 6.9848 (3.29); 6.9749 (3.39); 6.6127 (3.37); 6.6029 (3.22); 4.8404 (0.4); 4.8258 (0.58); 4.819 (0.5); 4.8096 (0.54); 4.8042 (0.57); 4.7881 (0.39); 3.3363 (8.95); 2.529 (0.74); 2.5157 (7.64); 2.5113 (15.49); 2.5068 (20.78); 2.5022 (14.74); 2.4978 (6.64); 2.2114 (16); 1.9409 (0.39); 1.925 (0.59); 1.9063 (0.64); 1.9041 (0.63); 1.8852 (0.54); 1.8655 (0.33); 1.8607 (0.5); 1.8464 (0.62); 1.8425 (0.58); 1.8279 (0.71); 1.8087 (0.39); 1.471 (5.8); 1.4544 (5.69); 0.8047 (2.83); 0.7863 (6.1); 0.7679 (2.57)<br>Example 299<br>Solvent: DMSO |
| 7.86 (2.16); 7.8554 (0.71); 7.85 (0.76); 7.8453 (2.23); 7.778 (5.12); 7.772 (2.48); 7.7586 (2.39); 7.7037 (7.54); 6.725 (3.54); 6.7158 (3.56); 6.5591 (2.99); 6.5498 (3.07); 6.4737 (1.21); 6.47 (2.27); 6.464 (2.65); 6.4596 (5.93); 6.4398 (2.86); 6.4382 (2.96); 6.3889 (2.07); 6.3851 (1.77); 6.3755 (1.99); 6.3718 (1.76); 5.9466 (3.44); 5.9373 (3.37); 5.8878 (5.97); 5.7877 (3.1); 5.7627 (3.83); 5.7477 (3.09); 5.7384 (2.98); 5.6266 (1.07); 4.1149 (0.41); 4.1021 (0.41); 3.8058 (12.54); 3.7299 (16); 3.4487 (0.32); 3.4432 (0.33); 3.3427 (2.6); 3.1798 (2.43); 3.1685 (2.38); 2.5289 (0.73); 2.5242 (1); 2.5157 (7.54); 2.5112 (15.54); 2.5066 (20.99); 2.5021 (14.9); 2.4976 (6.74); 1.0781 (1.27); 1.0606 (2.51); 1.0431 (1.23)<br>Example 300<br>Solvent: DMSO |
| 8.5246 (3.65); 8.5207 (2.34); 8.5134 (2.35); 8.5094 (3.69); 8.4091 (0.94); 8.4052 (0.62); 8.3977 (0.61); 8.3937 (0.95); 8.246 (6.09); 8.115 (1.36); 7.9197 (0.47); 7.9167 (0.49); 7.9069 (0.49); 7.904 (0.48); 7.5475 (1.76); 7.5445 (1.79); 7.535 (1.88); 7.532 (1.81); 7.3683 (4.29); 7.3643 (2.66); 7.3571 (2.87); 7.3531 (4.24); 7.3472 (0.76); 7.3188 (0.59); 7.31 (0.43); 7.3061 (0.56); 7.2973 (0.38); 7.1774 (1.11); 7.1733 (0.69); 7.1659 (0.68); 7.1619 (1.09); 7.0695 (1.38); 7.0606 (2.36); 7.0571 (1.29); 7.0481 (2.46); 7.038 (2.48); 7.0349 (2.66); 7.0291 (1.43); 7.026 (1.2); 5.7643 (0.64); 4.5816 (0.41); 4.5649 (1.05); 4.5482 (1.42); 4.5316 (1.06); 4.515 (0.41); 4.3684 (0.32); 3.335 (17.63); 2.5289 (0.68); 2.5156 (8.8); 2.5112 (17.76); 2.5067 (23.81); 2.5022 (17.11); 2.4978 (7.94); 1.4954 (16); 1.4788 (15.77); 1.3972 (3.64); 1.3807 (3.59)<br>Example 301<br>Solvent: DMSO |
| 8.3776 (0.45); 8.1958 (15.83); 8.1682 (5.81); 8.0359 (1.69); 8.0102 (1.48); 7.9367 (7.69); 7.9238 (7.72); 7.8409 (1.31); 7.8149 (1.69); 7.7017 (0.34); 7.6817 (1.68); 7.6555 (1.7); 7.6524 (1.98); 7.6263 (1.19); 7.5083 (0.35); 7.4891 (0.4); 7.4827 (0.4); 7.3965 (0.36); 7.3872 (0.38); 7.3819 (0.44); 7.3669 (0.49); 7.3605 (0.77); 7.3504 (0.69); 7.3462 (0.8); 7.3351 (0.51); 7.32 (0.4); 7.3109 (0.63); 7.3018 (0.34); 7.2728 (0.41); 7.2668 (0.58); 7.2633 (0.43); 7.2574 (0.44); 7.2422 (0.41); 7.1291 (0.77); 7.1215 (4.56); 7.1111 (4.73); 7.0884 (12.87); 7.0785 (14.28); 6.9566 (5.54); 6.9454 (16); 6.9354 (11.58); 6.931 (4.55); 6.9203 (5.48); 6.8741 (5.67); 6.8637 (3.32); 6.5433 (0.36); 6.5205 (5.87); 6.5169 (6.6); 6.5075 (5.58); 6.5039 (6.79); 6.4838 (12.29); 6.4703 (1.55); 6.4467 (1.95); 6.4504 (2.93); 6.3713 (0.39); 6.0109 (12); 5.7668 (4.42); 3.3349 (31.62); 3.3113 (0.9); 2.6802 (0.35); 2.6755 (0.45); 2.5288 (2.75); 2.524 (3.79); 2.5155 (28.21); 2.511 (57.47); 2.5065 (77.29); 2.502 (54.69); 2.4975 (24.76); 2.3378 (0.35); 2.3334 (0.49); 2.329 (0.33); 1.9932 (0.7); 1.3671 (0.48); 1.1782 (0.37); 1.1271 (3.02); 1.0774 (0.34); 1.0599 (0.65)<br>Example 302<br>Solvent: DMSO |
| 8.2104 (2.58); 8.1974 (2.6); 8.1705 (0.46); 8.1576 (0.48); 8.1069 (0.66); 8.0937 (0.65); 8.0721 (0.54); 8.0585 (0.58); 7.9696 (6.36); 7.8921 (2.84); 7.8066 (1.59); 7.6968 (3.29); 7.6783 (3.93); 7.6498 (1.26); 7.6326 (0.73); 7.6284 (0.6); 7.5993 (0.85); 7.5898 (2.31); 7.5725 (1.61); 7.5633 (1.73); 7.5195 (2.87); 7.4994 (4.53); 7.4816 (3.04); 7.4643 (0.98); 7.4609 (1.11); 7.4532 (0.75); 7.4436 (0.44); 7.44 (0.5); 7.4343 (0.65); 7.3559 (3.3); 7.3476 (4.52); 7.3406 (4.42); 7.3315 (1.78); 7.3247 (2.29); 7.3149 (2.97); 7.3034 (1.2); 7.2952 (0.84); 7.29 (0.6); 7.2658 (0.58); 7.2603 (0.64); 7.2511 (0.61); 7.2421 (0.43); 7.1947 (1.16); 7.185 (1.08); 7.1687 (1.41); 7.1593 (2.53); 7.1544 (2.21); 7.1453 (2.02); 7.1394 (1.77); 7.0738 (0.57); 7.0598 (0.98); 7.0511 (0.81); 7.0416 (0.53); 7.0281 (4.1); 7.0183 (4.76); 7.0079 (0.76); 6.9741 (0.67); 6.9643 (0.69); 6.9015 (2.06); 6.8977 (2.05); 6.8885 (1.99); 6.8847 (1.99); 6.8134 (0.41); 6.8094 (0.47); 6.8059 (0.59); 6.8015 (0.75); 6.7965 (0.45); 6.7927 (0.54); 6.7886 (0.52); 6.6892 (0.51); 6.6853 (0.54); 6.6734 (3.57); 6.6721 (3.57); 6.6012 (0.61); 6.5769 (0.81); 6.5416 (0.7); 6.5007 (4.02); 6.4909 (3.86); 6.4157 (0.67); 6.4059 (0.64); 5.7639 (5.86); 4.0418 (0.49); 4.024 (0.49); 3.8573 (16); 3.7878 (2.63); 3.7273 (4.13); 3.5989 (3.15); 3.333 (11.39); 2.5286 (1.91); 2.5153 (18.26); 2.5109 (36.46); 2.5064 (48.52); 2.5019 (34.34); 2.4975 (15.51); 1.9934 (2.1); 1.1961 (0.56); 1.1784 (1.1); 1.1606 (0.55); 0.8612 (0.35) |

NMR peak list table

Example 303
Solvent: DMSO 8.5611 (1.07); 8.5483 (1.09); 8.1934 (2.65); 8.0791 (0.84); 7.49 (1.51); 7.4786 (1.08);
7.4747 (0.68); 7.4658 (0.97); 7.4619 (0.72); 7.3413 (0.47); 7.3149 (0.47); 7.0499 (1.67); 7.0401 (1.81);
6.8771 (1.79); 6.8673 (1.6); 6.8144 (0.38); 3.9094 (6.98); 3.8981 (0.97); 3.7965 (1.55); 3.7758 (0.33);
3.3327 (5.44); 2.5291 (0.5); 2.5158 (5.39); 2.5114 (10.87); 2.5068 (14.54); 2.5023 (10.21); 2.4979 (4.57);
2.1884 (16); 2.1544 (3.44); 2.0858 (0.83); 1.9941 (0.77); 1.1792 (0.41)

Example 304
Solvent: DMSO 8.549 (1.09); 8.5362 (1.11); 8.3192 (2.99); 8.1719 (0.56); 7.511 (1.49); 7.4973 (1.06);
7.4933 (0.69); 7.4844 (0.94); 7.4804 (0.71); 7.059 (1.71); 7.0492 (1.87); 7.0215 (0.34); 6.9028 (0.41);
6.8944 (1.94); 6.8847 (1.62); 5.7644 (2.33); 4.5691 (0.59); 4.5525 (0.79); 4.5358 (0.59);
3.3318 (8.21); 3.308 (0.36); 2.5159 (9.7); 2.5114 (19.81); 2.5069 (26.62); 2.5023 (18.78); 2.4979 (8.46);
2.1909 (16); 2.0844 (1.19); 1.9942 (1.24); 1.4886 (7.76); 1.4826 (2.05); 1.4719 (7.62);
1.4659 (1.77); 1.1971 (0.34); 1.1794 (0.66); 1.1616 (0.35)

Example 305
Solvent: DMSO 7.9379 (6.03); 7.8987 (2.48); 7.8858 (2.5); 7.8021 (2.21); 7.7874 (0.64); 7.3004 (0.82);
7.2907 (1.09); 7.2409 (1.1); 7.2312 (0.79); 7.0425 (3.64); 7.0327 (3.98); 6.8844 (3.97); 6.8746 (3.47);
6.4598 (1.87); 6.4563 (2.19); 6.4468 (1.68); 6.4433 (2.67); 6.4374 (3.54); 6.4358 (3.73);
6.3522 (0.91); 6.3399 (0.6); 6.3362 (0.38); 6.3266 (0.54); 6.3229 (0.39); 5.9497 (3.91); 5.8474 (0.96);
5.7628 (1.8); 4.37 (0.64); 4.3574 (1.29); 4.3447 (0.66); 4.1103 (0.47); 4.0972 (0.47); 3.8731 (16);
3.7616 (4.16); 3.4771 (0.33); 3.4644 (0.4); 3.4597 (0.96); 3.4469 (1); 3.4422 (0.99);
3.4295 (0.97); 3.4249 (0.37); 3.3342 (15.45); 3.3109 (0.35); 3.1794 (1.93); 3.1663 (1.88); 2.5283 (1.07);
2.5149 (10.17); 2.5106 (19.47); 2.5061 (25.03); 2.5017 (17.32); 2.4975 (7.74); 1.0771 (2.05);
1.0596 (4.02); 1.0421 (1.96)

Example 306
Solvent: DMSO 8.0467 (6.3); 7.8935 (1.96); 7.8804 (2.02); 7.8757 (1.17); 7.7812 (0.34); 7.7679 (0.34);
7.3068 (0.57); 7.2972 (0.69); 7.2177 (0.69); 7.2081 (0.55); 7.044 (3.38); 7.0342 (3.69); 6.8935 (3.24);
6.8837 (2.86); 6.4874 (1.55); 6.4838 (1.82); 6.4744 (1.45); 6.4708 (1.94); 6.4559 (3.01);
6.3506 (0.47); 5.9277 (3.11); 5.8262 (0.51); 5.7633 (3.27); 4.5506 (0.47); 4.5358 (1.05); 4.5191 (1.43);
4.5025 (1.06); 4.4858 (0.41); 4.3707 (0.39); 4.3581 (0.7); 4.3453 (0.36); 3.4604 (0.5);
3.4477 (0.51); 3.4429 (0.52); 3.4302 (0.5); 3.3347 (9.94); 3.1801 (1); 3.167 (0.98); 2.5289 (0.69);
2.5241 (0.96); 2.5156 (6.99); 2.5112 (14.26); 2.5066 (19.17); 2.5021 (13.56); 2.4976 (6.11); 1.4671 (16);
1.4504 (15.71); 1.3894 (2.19); 1.373 (2.16); 1.0778 (1.1); 1.0603 (2.16); 1.0428 (1.05)

Example 307
Solvent: DMSO 8.0045 (10.8); 7.8966 (3.64); 7.8836 (3.64); 7.85 (2.9); 7.7903 (0.88); 7.7769 (0.9); 7.3037 (1.38);
7.2941 (1.72); 7.2273 (1.7); 7.2176 (1.34); 7.0445 (6.08); 7.0347 (6.71); 6.8909 (6.5);
6.8811 (5.73); 6.4741 (2.79); 6.4704 (3.48); 6.4611 (2.52); 6.4574 (3.81); 6.4463 (5.47); 6.3487 (1.25);
6.3326 (0.86); 6.3288 (0.61); 6.3194 (0.77); 6.3156 (0.63); 5.9401 (5.69); 5.8358 (1.31);
5.7638 (0.61); 4.1885 (1.93); 4.1703 (6.05); 4.152 (6.1); 4.1339 (1.94); 4.0753 (0.43); 4.0573 (1.38);
4.0392 (1.4); 4.0212 (0.44); 3.3341 (15.22); 3.3102 (0.51); 2.5289 (1.06); 2.5156 (13.05);
2.5112 (26.61); 2.5066 (35.86); 2.5021 (25.51); 2.4976 (11.52); 1.4361 (7.26); 1.418 (16); 1.3997 (7.03);
1.3197 (1.56); 1.3017 (3.51); 1.2836 (1.53); 1.0779 (0.34); 1.0604 (0.67); 1.043 (0.33)

Example 308
Solvent: DMSO 8.1956 (2.7); 8.1826 (2.74); 8.0932 (7.27); 8.0753 (0.65); 8.0107 (1.45); 7.6931 (2.46);
7.675 (2.96); 7.6453 (0.73); 7.5982 (0.6); 7.5798 (1.63); 7.5678 (1.35); 7.5188 (2.28); 7.4997 (3.02);
7.4817 (1.3); 7.3584 (3.24); 7.3507 (3.98); 7.343 (3.6); 7.3389 (2.74); 7.3288 (1.99);
7.3204 (1.04); 7.3124 (0.91); 7.1716 (1.89); 7.1648 (2.06); 7.1568 (2.79); 7.1475 (2.2); 7.0648 (0.46);
7.058 (0.53); 7.0483 (0.55); 7.0342 (4.28); 7.0244 (4.28); 6.9384 (2.14); 6.9345 (2.13);
6.9253 (2.07); 6.9215 (2.11); 6.8104 (0.48); 6.8065 (0.47); 6.7971 (0.47); 6.7931 (0.47); 6.7217 (3.4);
6.5765 (0.77); 6.5457 (4.23); 6.536 (4.05); 5.7634 (16); 4.2864 (0.57); 4.2704 (0.94);
4.2517 (0.93); 4.235 (0.56); 3.3326 (16.34); 2.5287 (1.65); 2.5155 (16.11); 2.5111 (32.34);
2.5065 (43.14); 2.502 (30.55); 2.4976 (13.87); 1.8648 (0.45); 1.8459 (0.66); 1.83 (0.98); 1.8111 (1.2);
1.7921 (0.88); 1.7764 (0.79); 1.7612 (0.94); 1.7428 (1.08); 1.7243 (0.6); 1.7088 (0.39);
1.4367 (7.64); 1.4199 (7.49); 1.3573 (1.55); 1.3408 (1.51); 0.7973 (3.79); 0.7789 (8.16); 0.7605 (3.47);
0.6518 (0.79); 0.6335 (1.68); 0.6151 (0.73)

Example 309
Solvent: DMSO 8.3785 (0.49); 8.2487 (8.54); 8.2357 (8.59); 8.2195 (0.33); 8.1901 (16); 8.1797 (5.59);
8.1733 (0.65); 8.1221 (0.56); 8.0179 (1.24); 7.992 (1.31); 7.8292 (0.52); 7.8229 (1.33); 7.7971 (1.84);
7.7892 (0.53); 7.71 (7.62); 7.6918 (8.88); 7.6782 (3.4); 7.6514 (1.97); 7.6485 (2.07);
7.6346 (0.64); 7.6224 (1.41); 7.604 (1.98); 7.5857 (5.32); 7.5677 (4.25); 7.5243 (7.53); 7.5052 (9.93);
7.4866 (4.16); 7.4699 (1.21); 7.4652 (1.1); 7.4446 (0.53); 7.4334 (0.61); 7.425 (0.59);
7.3912 (1.04); 7.3576 (11.82); 7.3504 (14.7); 7.3426 (12.44); 7.3125 (0.9); 7.3028 (0.57); 7.2839 (0.41);
7.274 (0.55); 7.2642 (0.65); 7.2549 (0.44); 7.2426 (0.67); 7.2264 (0.6); 7.2168 (0.56);
7.1755 (6.05); 7.1689 (7.44); 7.1609 (7.16); 7.1528 (5.82); 7.1242 (4.03); 7.1137 (4.03); 7.0643 (14.2);
7.0545 (14.36); 7.041 (0.34); 6.967 (6.44); 6.9632 (6.46); 6.954 (6.55); 6.9499 (8.18);

US 8,685,974 B2

189                                                                                        190

-continued

NMR peak list table 6.937 (4.53); 6.9339 (4.74); 6.9233 (5.07); 6.9183 (2.41); 6.9143 (2); 6.8966 (0.38); 6.8656 (4.85);
6.8552 (2.95); 6.753 (10.1); 6.7261 (2.76); 6.5616 (0.5); 6.5422 (13); 6.5323 (12.28);
5.7638 (4.58); 4.0419 (0.39); 4.0239 (0.41); 3.3323 (27.62); 2.6801 (0.64); 2.6754 (0.82); 2.6708 (0.57);
2.5285 (5.17); 2.5152 (47.58); 2.5109 (94.14); 2.5064 (124.87); 2.5019 (88.4); 2.4976 (40.25);
2.4567 (0.49); 2.4521 (0.42); 2.3377 (0.64); 2.3333 (0.8); 2.3287 (0.6); 1.9933 (1.66);
1.3614 (0.45); 1.2467 (1.08); 1.1961 (0.47); 1.1783 (0.87); 1.1606 (0.41); 1.1273 (3.23); 0.8776 (0.51);
0.8607 (1.49); 0.8431 (0.58)
Example 310
Solvent: DMSO 8.1951 (2.28); 8.1821 (2.32); 8.0996 (6.33); 8.0877 (0.46); 8.0742 (0.41); 8.0363 (0.5);
7.9792 (0.97); 7.6935 (2.24); 7.6754 (2.68); 7.6538 (0.41); 7.647 (0.53); 7.6377 (0.35); 7.5988 (0.54);
7.5806 (1.45); 7.5627 (1.29); 7.5195 (2.05); 7.5006 (2.84); 7.4829 (1.34); 7.4701 (0.41);
7.466 (0.44); 7.3567 (2.81); 7.3489 (3.44); 7.3411 (3.21); 7.3285 (1.51); 7.3188 (0.85); 7.3128 (0.85);
7.1993 (0.71); 7.1898 (0.82); 7.1805 (0.48); 7.1677 (1.61); 7.1611 (1.73); 7.1521 (1.61);
7.1446 (1.36); 7.0649 (0.35); 7.0598 (0.43); 7.0501 (0.46); 7.0387 (3.83); 7.0289 (3.75); 6.9334 (1.83);
6.9295 (1.82); 6.9204 (1.81); 6.9165 (1.83); 6.7954 (0.33); 6.7914 (0.32); 6.7822 (0.32);
6.7782 (0.33); 6.717 (2.87); 6.5805 (0.51); 6.5444 (3.67); 6.5347 (3.52); 5.7638 (0.44); 4.5312 (0.41);
4.5147 (1.06); 4.4981 (1.46); 4.4814 (1.09); 4.4648 (0.42); 3.3325 (13.84); 2.5289 (1.23);
2.5155 (12.08); 2.5111 (24.34); 2.5066 (32.57); 2.5021 (23.03); 2.4976 (10.37); 1.4534 (16);
1.4367 (15.71); 1.3988 (1); 1.3821 (1.04); 1.3693 (2.11); 1.3529 (2.06); 1.278 (0.77); 1.2615 (0.91);
1.2499 (1); 0.878 (0.47); 0.8613 (1.43); 0.8436 (0.55)
Example 311
Solvent: DMSO 8.2033 (4.07); 8.1902 (4.17); 8.0966 (1.03); 8.083 (1.04); 8.0467 (10.95); 7.9481 (2.92);
7.6952 (4); 7.6771 (4.78); 7.649 (1.25); 7.599 (0.94); 7.5809 (2.58); 7.563 (2.25); 7.5194 (3.61);
7.5002 (4.91); 7.4823 (2.14); 7.3564 (4.92); 7.3484 (6.23); 7.341 (5.82); 7.332 (3.15); 7.3223 (3.24);
7.3119 (1.55); 7.1961 (1.74); 7.1864 (1.64); 7.1746 (0.84); 7.1654 (2.89); 7.1577 (3.19);
7.1488 (2.89); 7.1424 (2.39); 7.0682 (0.74); 7.0624 (0.9); 7.0538 (0.91); 7.0449 (0.79); 7.0337 (6.47);
7.024 (6.49); 6.9171 (3.21); 6.9133 (3.31); 6.9041 (3.11); 6.9003 (3.28); 6.7994 (0.78);
6.7954 (0.79); 6.7861 (0.75); 6.7822 (0.81); 6.6959 (5.21); 6.6944 (5.18); 6.5762 (1.26); 6.5739 (1.24);
6.5223 (6.36); 6.5126 (6.14); 5.7641 (0.89); 4.1721 (1.93); 4.1539 (5.99); 4.1357 (6.06);
4.1175 (1.95); 4.0414 (0.51); 4.0228 (1.38); 4.0046 (1.36); 3.9866 (0.43); 3.3329 (17.2); 2.6758 (0.35);
2.5618 (0.36); 2.5572 (0.41); 2.5526 (0.33); 2.5288 (1.81); 2.5155 (19.79); 2.5112 (40.72);
2.5067 (55.35); 2.5022 (40.18); 2.4978 (18.79); 2.3337 (0.33); 1.9936 (0.64); 1.4239 (7.37); 1.4057 (16);
1.3875 (7.15); 1.3493 (0.33); 1.2999 (1.65); 1.2819 (3.64); 1.2639 (1.8); 1.2489 (0.87);
1.1786 (0.38); 0.8777 (0.38); 0.8613 (1.14); 0.8437 (0.45)
Example 312
Solvent: DMSO 13.4009 (1); 8.3792 (2.6); 8.2989 (2.51); 8.2861 (2.57); 7.537 (1.59); 7.5274 (1.63);
7.0833 (1.66); 7.0737 (1.55); 6.7744 (2.44); 6.7617 (2.42); 3.3382 (6.96); 3.3145 (0.33); 3.0999 (16);
3.0684 (1.26); 2.5153 (6.74); 2.511 (13.27); 2.5065 (17.55); 2.5021 (12.51); 2.4978 (5.76)
CHECK
Example 312
Solvent: DMSO 13.8718 (0.59); 13.6952 (3.86); 8.7086 (8.63); 8.6962 (16); 8.6828 (15.8); 8.3358 (0.9);
7.8169 (7.04); 7.8071 (7.27); 7.7769 (7.02); 7.7636 (6.41); 7.5982 (0.78); 7.5125 (0.34); 7.2753 (0.79);
7.2289 (0.41); 7.2184 (0.42); 7.1803 (0.39); 7.1628 (0.89); 7.1484 (6.69); 7.1385 (6.22);
5.9937 (0.38); 4.1078 (0.52); 4.095 (0.51); 3.3325 (42.31); 3.3109 (0.65); 3.2786 (1.08); 3.1794 (2.47);
3.1665 (2.32); 3.1455 (0.42); 3.0657 (0.44); 3.052 (0.66); 3.0237 (0.4); 2.8946 (0.35);
2.6801 (0.59); 2.6757 (0.76); 2.6712 (0.55); 2.5529 (0.95); 2.5458 (1.34); 2.5156 (46.61); 2.5112 (92.89);
2.5067 (122.94); 2.5022 (86.5); 2.4978 (38.95); 2.3378 (0.57); 2.3336 (0.73); 2.3289 (0.51);
1.2829 (0.48); 1.2629 (0.37); 1.2326 (1.47); 1.1724 (0.79); 1.1568 (0.82); 1.077 (1.05);
1.0594 (1.69); 1.0419 (0.88); 0.8778 (0.69); 0.8644 (0.48); 0.8591 (0.46)
CHECK
Example 312
Solvent: DMSO 13.5757 (0.38); 13.3725 (2.49); 8.3377 (5.05); 8.2147 (3.5); 8.2021 (3.59); 8.0291 (0.49);
7.6669 (0.63); 7.2112 (0.43); 7.0671 (4.01); 7.0574 (3.8); 6.9087 (2); 6.8883 (2.08); 6.7278 (5.47);
6.715 (5.5); 4.1155 (0.36); 4.1001 (0.93); 4.0835 (1.46); 4.0645 (1.56); 4.06 (1.64); 4.0474 (1.1);
4.042 (2.58); 4.0242 (2.26); 4.0064 (0.75); 3.3353 (58.82); 3.1001 (0.48); 3.0635 (0.54); 2.6758 (0.36);
2.5291 (1.55); 2.5156 (21.74); 2.5114 (45.41); 2.5069 (62.33); 2.5024 (45.82); 2.4981 (21.82);
2.3338 (0.38); 1.9937 (8.99); 1.1965 (2.68); 1.1787 (5.5); 1.1578 (15.21); 1.1416 (16)
Example 313
Solvent: DMSO 8.3851 (2.53); 8.3723 (2.57); 8.3018 (1.05); 8.2887 (1.05); 8.2377 (5.7); 8.1517 (2.91);
7.9574 (1.64); 7.4979 (2.88); 7.4957 (2.99); 7.4046 (1.32); 7.3987 (2.32); 7.3949 (1.95); 7.3857 (2.03);
7.382 (1.86); 7.369 (1.28); 7.3593 (1.8); 7.3183 (1.8); 7.3087 (1.25); 7.2134 (0.83); 7.2096 (0.78);
7.2003 (0.8); 7.1964 (0.75); 7.0943 (3.64); 7.0845 (3.97); 6.9129 (3.97); 6.9031 (3.56);
3.9024 (16); 3.7729 (6.98); 3.3315 (13.03); 3.3078 (0.87); 2.8949 (12.31); 2.7357 (10.23); 2.5289 (0.92);
2.5155 (10.42); 2.5111 (21.24); 2.5065 (28.62); 2.502 (20.4); 2.4976 (9.33)

NMR peak list table

Example 314
Solvent: DMSO 8.4071 (6.88); 8.3942 (7.05); 8.3275 (16); 8.3211 (1.51); 8.3045 (3.16); 7.5283 (7.68); 7.5259 (8);
7.4202 (6.33); 7.4164 (5.07); 7.4072 (5.24); 7.4035 (4.86); 7.3788 (1.4); 7.3691 (1.71);
7.2946 (1.56); 7.2849 (1.26); 7.2063 (0.85); 7.2025 (0.78); 7.1932 (0.84); 7.1894 (0.78); 7.1108 (9.56);
7.101 (10.46); 6.9344 (10.46); 6.9246 (9.41); 6.5976 (0.7); 6.5885 (1.38); 6.5796 (0.63);
6.4611 (1.48); 6.4522 (3.09); 6.4433 (1.37); 6.3854 (0.52); 6.3248 (0.7); 6.3158 (1.55); 6.3068 (0.73);
4.7617 (2.16); 4.7529 (2.31); 4.7239 (4.8); 4.715 (4.56); 4.6859 (2.49); 4.6769 (2.23);
4.5791 (0.37); 4.5709 (0.39); 4.5427 (0.8); 4.5336 (0.79); 4.5056 (0.42); 4.4963 (0.38); 3.3309 (23.91);
3.3072 (2.1); 2.6799 (0.33); 2.6755 (0.45); 2.5287 (2.66); 2.5154 (27.35); 2.511 (54.85);
2.5065 (73.24); 2.502 (51.79); 2.4975 (23.46); 2.4617 (0.37); 2.4572 (0.37); 2.3332 (0.43); 2.329 (0.33);
1.9935 (1.14); 1.2823 (0.41); 1.2496 (1.77); 1.1965 (0.33); 1.1787 (0.59); 0.8783 (0.85);
0.8616 (2.53); 0.8439 (0.99)

Example 315
Solvent: DMSO 8.374 (6.48); 8.3705 (2.87); 8.3568 (2.44); 8.2868 (0.53); 8.2736 (0.54); 8.22 (1.17); 7.9574 (0.9);
7.5371 (2.8); 7.5347 (2.86); 7.4123 (1.93); 7.4086 (1.82); 7.3993 (1.88); 7.3956 (1.83);
7.3908 (0.73); 7.388 (0.68); 7.3763 (0.68); 7.3667 (0.89); 7.3145 (0.89); 7.3049 (0.66); 7.1915 (0.42);
7.1877 (0.4); 7.1783 (0.41); 7.1746 (0.39); 7.0995 (3.39); 7.0897 (3.73); 6.9332 (3.74);
6.9234 (3.35); 4.5715 (0.41); 4.5549 (1.05); 4.5383 (1.43); 4.5216 (1.06); 4.5049 (0.41); 3.332 (6.46);
3.3083 (0.49); 2.8947 (6.68); 2.7353 (5.53); 2.5287 (0.56); 2.5155 (5.9); 2.5111 (11.99);
2.5065 (16.13); 2.502 (11.52); 2.4976 (5.28); 1.8472 (0.64); 1.8304 (0.64); 1.4835 (16); 1.4669 (15.76);
1.3999 (2.84); 1.3835 (2.8)

Example 316
Solvent: DMSO 8.3785 (4.19); 8.3655 (4.25); 8.3139 (10.48); 8.2935 (1.14); 8.2804 (1.14); 8.1958 (3.12);
7.9573 (0.97); 7.5159 (4.76); 7.5135 (4.92); 7.4058 (3.48); 7.4021 (3.24); 7.3929 (4.4); 7.3894 (3.73);
7.3715 (1.41); 7.3619 (1.94); 7.316 (1.93); 7.3063 (1.38); 7.1988 (0.91); 7.195 (0.86);
7.1856 (0.88); 7.1818 (0.83); 7.0958 (6.03); 7.086 (6.59); 6.9228 (6.58); 6.913 (5.91); 4.2151 (2.01);
4.1969 (6.19); 4.1787 (6.23); 4.1605 (2.01); 4.0911 (0.49); 4.0731 (1.58); 4.055 (1.58);
4.037 (0.5); 3.333 (9.74); 3.3093 (0.72); 2.8944 (7.32); 2.7354 (6.06); 2.5289 (0.9); 2.5155 (8.81);
2.511 (17.76); 2.5065 (23.79); 2.502 (16.85); 2.4975 (7.63); 1.4551 (7.36); 1.4369 (16); 1.4187 (7.09);
1.3308 (1.74); 1.3127 (3.87); 1.2946 (1.7)

Example 317
Solvent: DMSO 8.0415 (13.83); 7.9041 (3.03); 7.8935 (5.14); 7.8805 (5.08); 7.7806 (1.1); 7.7674 (1.1);
7.3052 (1.59); 7.2957 (1.78); 7.1705 (1.81); 7.1609 (1.55); 7.0416 (7.39); 7.0318 (8.16); 6.8959 (8.12);
6.8861 (7.07); 6.4884 (3.74); 6.485 (4.43); 6.4753 (3.42); 6.4719 (4.76); 6.4601 (7.42);
6.3579 (1.47); 6.3301 (0.9); 6.3266 (0.74); 6.3167 (0.86); 6.3132 (0.71); 5.925 (7); 5.9105 (1.84);
5.8188 (1.45); 5.804 (0.41); 5.7629 (8.64); 4.3057 (1.11); 4.2895 (1.82); 4.2705 (1.76); 4.2539 (1.09);
3.3317 (30.48); 3.308 (2.37); 2.6757 (0.35); 2.5153 (22.33); 2.511 (44.21); 2.5066 (58.78);
2.5021 (41.89); 2.4978 (19.3); 2.3335 (0.35); 1.9938 (0.43); 1.8931 (0.36); 1.8819 (0.83); 1.8746 (0.48);
1.8632 (1.24); 1.8473 (1.81); 1.8282 (2.21); 1.8089 (1.81); 1.7899 (1.71); 1.7745 (1.81);
1.7716 (1.71); 1.7561 (2.08); 1.7376 (1.2); 1.7289 (0.41); 1.7221 (0.75); 1.6975 (0.39); 1.4518 (15.2);
1.435 (14.94); 1.3828 (3.17); 1.3663 (3.08); 1.0778 (0.4); 1.0603 (0.77); 1.0428 (0.37);
0.8015 (7.52); 0.7831 (16); 0.7647 (6.91); 0.6621 (1.56); 0.6439 (3.35); 0.6255 (1.51)

Example 318
Solvent: DMSO 8.3699 (6.47); 8.3659 (14.76); 8.3577 (5.56); 8.2875 (1.31); 8.2744 (1.32); 8.2508 (2.85);
7.9579 (1.68); 7.537 (6.19); 7.5347 (6.32); 7.4182 (4.43); 7.4144 (4.11); 7.4052 (4.28); 7.4014 (4.06);
7.3935 (1.59); 7.3909 (1.59); 7.3765 (1.81); 7.3669 (2.12); 7.274 (2.1); 7.2644 (1.76);
7.199 (1.05); 7.1951 (1.01); 7.1858 (1.01); 7.182 (0.96); 7.0984 (7.9); 7.0887 (8.66); 6.938 (8.74);
6.9282 (7.74); 4.3288 (1.03); 4.3126 (1.66); 4.2937 (1.68); 4.2772 (1.03); 3.3244 (23.42);
2.8954 (12.98); 2.736 (10.52); 2.6801 (0.41); 2.6755 (0.53); 2.671 (0.41); 2.5556 (0.32); 2.5289 (3.21);
2.5241 (4.31); 2.5155 (31.76); 2.5111 (64.67); 2.5065 (87.25); 2.5019 (61.72); 2.4975 (27.91);
2.338 (0.38); 2.3335 (0.5); 2.3289 (0.35); 1.9152 (0.37); 1.8969 (0.94); 1.8784 (1.31);
1.8623 (1.98); 1.8433 (2.27); 1.8242 (1.67); 1.8089 (1.46); 1.794 (1.69); 1.7907 (1.61); 1.7754 (1.97);
1.7566 (1.08); 1.7413 (0.71); 1.7328 (0.36); 1.7269 (0.36); 1.714 (0.37); 1.4668 (15.28);
1.45 (15); 1.3909 (3.44); 1.3744 (3.38); 0.8208 (7.38); 0.8024 (16); 0.7839 (6.77); 0.6771 (1.67);
0.6588 (3.66); 0.6404 (1.57)

Example 387
Solvent: DMSO 8.5531 (3.74); 8.5492 (2.49); 8.5419 (2.38); 8.5379 (3.88); 8.4588 (0.79); 8.4549 (0.54);
8.4473 (0.5); 8.4434 (0.82); 8.2452 (6.27); 8.113 (1.18); 7.4479 (0.72); 7.4384 (0.79); 7.3991 (4.3);
7.3951 (2.74); 7.3879 (2.56); 7.3839 (4.21); 7.2487 (0.79); 7.2392 (0.76); 7.2332 (0.95);
7.2292 (0.61); 7.2218 (0.56); 7.2177 (0.91); 7.1633 (3.4); 7.1536 (3.52); 6.8426 (3.52); 6.833 (3.35);
5.7649 (2.91); 4.5773 (0.41); 4.5607 (1.06); 4.544 (1.45); 4.5274 (1.08); 4.5107 (0.43);
3.3371 (21.83); 2.8947 (1.38); 2.7352 (1.19); 2.5156 (9.24); 2.5114 (19); 2.5069 (25.96); 2.5024 (19.09);
2.4981 (9.09); 2.0908 (0.74); 1.4851 (16); 1.4684 (15.76); 1.3996 (2.88); 1.3831 (2.83)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-d6 and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values); can isolate the peaks of the target compounds as needed optionally using additional intensity filters. This isolation would be similar to relevant peak picking at classical 1H-NMR interpretation.

Use Examples

Beispiel A

*Alternaria* Test (Tomato)/Protective

Solvent: 49 parts by weight of N,N-dimethylformamide
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. One day after the treatment, the plants are inoculated with a spore suspension of *Alternaria solani* and then remain at 100% rel. humidity and 22° C. for 24 h. The plants then remain at 96% rel. atmospheric humidity and a temperature of 20° C.

Evaluation is carried out 7 days after the inoculation. 0% means an efficacy which corresponds to that of the control, whereas an efficacy of 100% means that no infection is observed.

In this test, the compounds according to the invention 1, 4, 5, 7, 8, 11, 13, 15, 17, 18, 21, 24, 50, 55, 57, 46 (95%), 47 (95%), 64 (80%), 76 (89%), 80 (94%), 82 (78%), 95 (70%), 97 (90%), 106 (100%), 108 (100%), 110 (95%), 145 (100%), 146 (95%), 164 (90%), 165 (70%), 167 (90%), 168 (90%), 169 (95%), 170 (90%), 175 (80%), 177 (90%), 179 (80%), 190 (80%), 194 (95%), 199 (89%), 201 (78%), 204 (80%), 205 (90%), 206 (80%), 210 (90%), 211 (90%), 212 (70%), 213 (80%), 223 (95%), 224 (80%), 225 (95%), 226 (90%), 227 (80%), 228 (70%), 229 (95%), 232 (80%), 233 (90%), 234 (90%), 235 (95%), 236 (80%), 238 (70%), 239 (80%), 240 (95%), 242 (90%), 243 (90%), 246 (95%), 247 (95%), 248 (90%), 249 (95%), 250 (90%), 252 (95%), 253 (95%), 254 (70%), 255 (90%), 256 (100%), 257 (95%), 258 (95%), 259 (90%), 260 (80%), 261 (90%), 262 (80%), 263 (95%), 264 (90%), 270 (95%), 274 (80%), 276 (90%), 277 (90%), 278 (90%), 279 (80%), 280 (90%), 281 (90%), 282 (80%), 284 (95%), 285 (95%), 286 (90%), 287 (90%), 288 (90%), 291 (90%), 292 (90%), 293 (80%), 297 (90%), 298 (95%), 300 (95%), 303 (95%), 304 (95%), 305 (70%), 307 (80%), 307 (94%), 311 (70%), 323 (78%), 328 (94%), 329 (94%), 330 (94%), 332 (94%), 333 (94%), 334 (78%), 337 (94%), 340 (94%), 342 (89%), 344 (94%), 345 (94%), 347 (70%), 350 (80%), 353 (78%), 354 (90%), 358 (100%), 359 (94%), 360 (78%), 361 (94%), 363 (100%), 364 (100%), 365 (78%), 366 (78%), 367 (78%), 368 (78%), 369 (94%), 371 (78%), 373 (100%), 374 (94%), 375 (100%), 376 (100%), 377 (100%), 378 (100%), 379 (94%), 380 (89%), 381 (94%), 384 (94%), 385 (94%), 386 (89%), 387 (100%), 388 (100%), 389 (94%), 390 (100%), 391 (100%), 392 (100%), 394 (94%), 395 (78%), 396 (100%), 397 (100%), 399 (78%), 401 (78%), 405 (94%), 407 (90%), 408 (70%), 412 (90%), 421 (89%), 423 (94%) from Table I show, at an active compound concentration of 500 ppm, an efficacy of 70% or more.

Beispiel B

*Leptosphaeria nodorum* Test (Wheat)/Protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young wheat plants are sprayed with the preparation of active compound at the stated application rate. One day after the treatment, the plants are inoculated with an aqueous spore suspension of *Leptosphaeria nodorum* and then remain at 100% rel. atmospheric humidity and 22° C. for 48 h. The plants are then placed in a greenhouse at 90% rel. atmospheric humidity and a temperature of 22° C.

Evaluation is carried out 7-9 days after the inoculation. 0% means an efficacy which corresponds to that of the control, whereas an efficacy of 100% means that no infection is observed.

In this test, the examples Nos. 1, 2, 3, 4, 8, 11, 13, 15, 16, 17, 18, 21, 24, 55, 57, 64 (78%), 80 (70%), 95 (80%), 104 (80%), 110 (95%), 145 (95%), 146 (95%), 164 (95%), 167 (90%), 168 (90%), 169 (80%), 170 (90%), 171 (89%), 172 (89%), 173 (89%), 175 (70%), 179 (80%), 180 (70%), 181 (70%), 190 (70%), 225 (70%), 226 (80%), 234 (80%), 243 (90%), 246 (90%), 247 (80%), 248 (90%), 249 (80%), 252 (70%), 256 (80%), 257 (90%), 258 (70%), 263 (80%), 264 (80%), 269 (70%), 277 (70%), 278 (80%), 279 (70%), 280 (80%), 281 (80%), 284 (80%), 285 (80%), 286 (90%), 287 (80%), 288 (70%), 292 (70%), 304 (80%), 307 (78%), 318 (70%), 354 (70%), 359 (90%), 384 (90%), 386 (80%), 387 (90%), 388 (80%), 392 (70%), 405 (94%), 407 (94%), 408 (78%), 409 (78%), 410 (94%), 412 (70%), 413 (70%), 416 (70%), 417 (80%), 423 (80%) from Table I showed, at an active compound concentration of 500 ppm, an efficacy of 70% or more.

Example C

Pyricularia Test (Rice)/Protective

Solvent: 28.5 parts by weight of acetone
Emulsifier: 1.5 parts by weight of polyoxyethylene alkyl phenyl ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. One day after spraying, the plants are inoculated with an aqueous spore suspension of the causal agent of rice blast (*Pyricularia oryzae*). The plants are then placed in an incubator at approximately 25° C. and a relative atmospheric humidity of approximately 100% for 1 day.

The test is evaluated 5 days after the inoculation. 0% means an efficacy which corresponds to that of the control, while an efficacy of 100% means that no disease is observed.

In this test the compounds according to the invention of the following structures showed efficacy of 80% or even higher at a concentration of 250 ppm of active ingredient.

In this test, the examples Nos. 50, 38 (98%), 54, 46 (93%), 47 (86%) from Table I showed, at an active compound concentration of 500 ppm, an efficacy of 70% or more.

Example D

Rhizoctonia Test (Rice)/Protective

Solvent: 28.5 parts by weight of acetone
Emulsifier: 1.5 parts by weight of polyoxyethylene alkyl phenyl ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. One day after spraying, the plants are inoculated with a hypha of the causal agent of rice sheath blight (*Rhizoctonia solani*). The plants are then placed in an incubator at approximately 25° C. and a relative atmospheric humidity of approximately 100%.

The test is evaluated 4 days after the inoculation. 0% means an efficacy which corresponds to that of the control, while an efficacy of 100% means that no disease is observed.

In this test the compounds according to the invention of the following structures showed efficacy of 80% or even higher at a concentration of 250 ppm of active ingredient.

In this test, the examples Nos. 38 (97%), 50 (93%), 54 (100%), 61 (98%), 64 (100%) from Table I showed, at an active compound concentration of 500 ppm, an efficacy of 70% or more.

Example E

Cochliobolus Test (Rice)/Protective

Solvent: 28.5 parts by weight of acetone
Emulsifier: 1.5 parts by weight of polyoxyethylene alkyl phenyl ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. One day after spraying, the plants are inoculated with an aqueous spore suspension of the causal agent of rice brown spot (*Cochliobolus miyabeanus*). The plants are then placed in an incubator at approximately 25° C. and a relative atmospheric humidity of approximately 100% for 1 day.

The test is evaluated 4 days after the inoculation. 0% means an efficacy which corresponds to that of the control, while an efficacy of 100% means that no disease is observed.

In this test the compounds according to the invention of the following structures showed efficacy of 80% or even higher at a concentration of 250 ppm of active ingredient.

In this test the examples Nos. 38 (93%), 54 (90%), 61 (92%), 64 (97%) from Table I showed, at an active compound concentration of 500 ppm, an efficacy of 70% or more.

Example F

In Vivo Test on *Peronospora parasitica* (Crucifer Downy Mildew)

The active ingredients tested are prepared by homogenization in a mixture of acetone/Tween/DMSO, then diluted with water to obtain the desired active material concentration.

Cabbage plants (Eminence variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Peronospora parasitica* spores (50 000 spores per ml). The spores are collected from infected plant.

The contaminated cabbage plants are incubated for 5 days at 20° C., under a humid atmosphere.

Grading is carried out 5 days after the contamination, in comparison with the control plants.

Under these conditions, good (at least 70%) or total protection is observed at a dose of 500 ppm with the following compounds: 8 (92%), 20, 38 (97%), 46 (92%), 47 (100%), 60 (98%), 61 (100%), 62 (89%), 63 (94%), 86 (92%).

Example G

In Vivo Test on *Botrytis cinerea* (Grey Mould)

The active ingredients tested are prepared by homogenization in a mixture of acetone/Tween/DMSO, then diluted with water to obtain the desired active material Gherkin plants (Vert petit de Paris variety), sown on a 50/50 peat soil-pozzolana substrate in starter cups and grown at 18-20° C., are treated at the cotyledon Z11 stage by spraying with the active ingredient prepared as described above.

Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:
  20 g/L of gelatine;
  50 g/L of D-fructose;
  2 g/L of $NH_4NO_3$;
  1 g/L of $KH_2PO_4$.

The contaminated cucumber plants are settled for 5/7 days in a climatic room at 15-11° C. (day/night) and at 80% relative humidity.

Grading is carried out 5/7 days after the contamination, in comparison with the control plants.

Under these conditions, good (at least 70%) or total protection is observed at a dose of 500 ppm with the following compounds: 8 (100%), 15 (100%), 18 (100%), 21 (100%), 38 (100%), 52, 55 (75%), 62 (98%), 64 (98%).

Example H

In Vivo Test on *Sphaerotheca fuliginea* (Cucurbits Powdery Mildew)

The active ingredients tested are prepared by homogenization in a mixture of acetone/tween/DMSO, then diluted with water to obtain the desired active material.

Gherkin plants (Vert petit de Paris variety) in starter cups, sown on a 50/50 peat soil-pozzolana substrate and grown at 20° C./23° C., are treated at the cotyledon Z10 stage by spraying with the aqueous suspension described above. Plants, used as controls, are treated with an aqueous solution not containing the active material.

After 24 hours, the plants are contaminated by spraying them with an aqueous suspension of *Sphaerotheca fuliginea* spores (100 000 spores per ml). The spores are collected from a contaminated plants. The contaminated gherkin plants are incubated at about 20° C./25° C. and at 60/70% relative humidity.

Grading (% of efficacy) is carried out 12 days after the contamination, in comparison with the control plants.

Under these conditions, good (at least 70%) or total protection is observed at a dose of 500 ppm with the following compounds: 6 (75%), 7 (78%), 14 (78%), 15 (92%), 18 (83%), 21 (89%), 38 (83%), 51 (100%), 52 (90%), 56 (88%), 58 (81%), 58 (81%), 60 (75%), 60 (75%), 61 (94%), 62 (94%), 63 (88%), 64 (98%), 66 (95%), 92 (100%).

Example I

In Vivo Test on *Pyrenophora teres* (Barley Net Blotch)

The active ingredients tested are prepared by homogenization in a mixture of acetone/Tween/DMSO, then diluted with water to obtain the desired active material concentration.

Barley plants (Plaisant variety), sown on a 50/50 peat soil-pozzolana substrate in starter cups and grown at 12° C., are treated at the 1-leaf stage (10 cm tall) by spraying with the active ingredient prepared as described above.

Plants, used as controls, are treated with an aqueous solution not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 70%) is observed at a dose of 500 ppm with the following compound: 38, 1 (90%), 5 (70%), 8 (100%), 11 (89%), 13 (94%), 15 (89%), 17 (100%), 18 (100%), 21 (100%), 24 (90%), 26 (70%), 46 (70%), 47 (70%), 50 (70%), 55 (80%), 57 (95%), 64 (95%), 110 (100%), 145 (100%), 146 (100%), 150 (95%), 151 (90%), 164 (100%), 166 (80%), 167 (95%), 168 (90%), 169 (95%), 170 (80%), 171 (95%), 172 (100%), 173 (95%), 174 (90%), 175 (90%), 176 (90%), 177 (95%), 179 (90%), 180 (80%), 181 (80%), 183 (70%), 186 (70%), 187 (70%), 188 (78%), 190 (95%), 193 (95%), 194 (100%), 195 (95%), 199 (95%), 204 (80%), 205 (95%), 206 (90%), 207 (70%), 208 (80%), 210 (70%), 211 (95%), 212 (80%), 213 (70%), 223 (95%), 224 (95%), 225 (95%), 226 (100%), 227 (95%), 228 (90%), 229 (90%), 230 (70%), 232 (80%), 233 (90%), 234 (95%), 235 (95%), 236 (95%), 238 (80%), 240 (90%), 241 (80%), 242 (70%), 243 (95%), 245 (100%), 246 (100%), 247 (100%), 248 (100%), 249 (95%), 250 (100%), 252 (100%), 253 (100%), 254 (90%), 255 (100%), 256 (100%), 257 (95%), 258 (100%), 259 (80%), 261 (90%), 262 (90%), 263 (90%), 264 (90%), 265 (70%), 267 (80%), 269 (80%), 270 (95%), 271 (90%), 272 (70%), 274 (80%), 275 (90%), 276 (80%), 277 (90%), 278 (90%), 279 (95%), 280 (90%), 281 (90%), 282 (70%), 284 (100%), 285 (95%), 286 (80%), 287 (95%), 288 (95%), 291 (95%), 292 (95%), 293 (90%), 296 (70%), 297 (80%), 303 (70%), 304 (95%), 307 (80%), 307 (95%), 340 (70%), 350 (90%), 354 (95%), 358 (80%), 359 (70%), 363 (90%), 364 (70%), 387 (80%), 396 (70%), 397 (90%), 405 (70%), 407 (90%), 423 (75%), 38 (97%), 52 (86%), 66 (92%).

Example J

In Vivo Test on *Puccinia recondita* (Brown Rust)

The active ingredients tested are prepared by homogenization in a mixture of acetone/tween/DMSO, then diluted with water to obtain the desired active material.

Wheat plants (Scipion variety) sown on 50/50 peat soil-pozzolana substrate in starter cups and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by spraying the leaves with an aqueous suspension of *Puccinia recondita* spores (100,000 spores per ml). The spores are collected from a 10-day-old contaminated wheat and are suspended in water containing 2.5 ml/l of tween 80 10%. The contaminated wheat plants are incubated for 24 hours at 20° C. and at 100% relative humidity, and then for 10 days at 20° C. and at 70% relative humidity.

Grading is carried out 10 days after the contamination, in comparison with the control plants.

Under these conditions, good (at least 70%) or total protection is observed at a dose of 500 ppm with the following compounds: 21 (75%), 38 (72%), 51 (75%), 66 (89%), 86 (75%), 6 (70%), 8 (86%), 17 (70%), 18 (89%), 21 (85%), 47 (71%), 52 (97%), 61 (77%), 62 (88%), 64 (88%), 66 (95%).

Example K

In Vivo Test on *Mycosphaerella graminicola* (Wheat Leaf Spot)

The active ingredients tested are prepared by homogenization in a mixture of acetone/tween/DMSO, then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 1 (75%), 6 (70%), 18, 62, 3 (86%), 17 (70%), 18 (89%), 21 (85%), 45 (71%), 52 (97%), 61 (77%), 62 (88%), 64 (88%), 66 (%).

Example L

In Vivo Test on *Pyricularia grisea* (Rice Blast)

The active ingredients tested are prepared by homogenization in a mixture of acetone/tween/DMSO, then diluted with water to obtain the desired active material concentration.

Rice plants (Koshihikari variety), sown on a 50/50 peat soil-pozzolana substrate in starter cups and grown at 25° C., are treated at the 2-leaf stage (13-15 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyricularia grisea* spores (30,000 spores per ml). The spores are collected from a 17-day-old culture and are suspended in water containing 2.5 g/l of gelatin. The contaminated Rice plants are incubated for 72 hours at about 25° C. and at 100% relative humidity, and then for 3 days at 25° C. at 80% relative humidity during the day and 20% relative humidity during the night.

Grading (% of efficacy) is carried out 6 days after the contamination, in comparison with the control plants.

Under these conditions, good (at least 70%) or total protection is observed at a dose of 500 ppm with the following compound: 38 (98%), 46 (93%), 47 (86%).

Example M

In Vivo Test on *Plasmopara parasitica* (Vine Downy Mildew)

Vine plants (Cabernet variety) grown on a 50/50 peat soil-pozzolana substrate at 20-22° C., are treated at stage Z15 by spraying with the aqueous suspension described above. Plants, used as controls, are treated with an aqueous solution not containing the active material. After 24 hours, the plants are contaminated by spraying the lower surface of the leaves with an aqueous suspension of *Plasmopara viticola* spores (100 000 spores per ml). The spores are collected from infected plants. The contaminated vine plants are incubated for 7 to 8 days at 20° C., under humid atmosphere. Grading is carried out 7 to 8 days after the contamination, in comparison with the control plants.

Under these conditions, good protection (at least 70%) is observed at a dose of 500 ppm with the following compounds: 1, 7, 15 and 2.

Example N

In Vivo Test on *Phakopsora pachyrhizi* (Soya Bean Rust/Protective)

Solvent: 28.5 parts by weight acetone
Emulsifier: 1.5 parts by weight alkylaryl polyglycol ethers For the preparation of a suitable active substance preparation, 1 part by weight of active substance is mixed with the stated quantities of solvent and emulsifier and the concentrate is diluted to the desired concentration with water.

For the testing for protective activity, young rice plants are sprayed with the active substance preparation at the stated application dosage. One day after the treatment, the plants are inoculated with an aqueous spore suspension of *Phakopsora pachyrhizi*. Next, the plants are set out in a greenhouse at 80% relative atmospheric humidity and 20° C.

11 days after the inoculation, the assessment takes place. Here 0% means an activity level which corresponds to that of the control, while an activity level of 100% means that no infection is observed.

In this test the following compounds according to the invention at an active substance concentration of 250 ppm displayed an activity level of 80% or more: 8 (98%).

Example O

Production of Fumonisin FBI by *Fusarium proliferatum*

Compounds were tested in microtiter plates in fumonisin-inducing liquid media (0.5 g malt extract, 1 g yeast extract, 1 g bacto peptone, 20 g Fructose, 1 g $KH_2PO_4$, 0.3 g $MgSO_4 \times 7H_2O$, 0.3 g KCl, 0.05 g $ZnSO_4 \times 7H_2O$ and 0.01 g $CuSO_4 \times 5H_2O$ per liter) containing 0.5% DMSO, inoculated with a concentrated spore suspension of *Fusarium proliferatum* to a final concentration of 2000 spores/ml.

Plates were covered and incubated at high humidity at 20° C. for 5 days

At start and after 5 days OD measurement at OD620 multiple read per well (square: 3×3) was taken to calculate growth inhibition.

After 5 days samples of each culture medium were taken and diluted 1:1000 in 50% acetonitrile. The amounts of fumonisin FB1 of the samples were analysed per HPLC-MS/MS and results were used to calculate inhibition of FB1 production in comparison to a control without compound.

HPLC-MS/MS was done with the following parameters:

Ionization mode: ESI positive

Ionspray voltage: 5500V

Spraygas Temperature: 500° C.

Declustering potential: 114V

Collision energy: 51 eV

Collision gas: $N_2$

MRM trace: 722.3>352.3; dwell time 100 ms

HPLC column: Waters Atlantis T3 (trifunctional C18 bonding, fully endcapped)

Particle size: 3 μm

Column size: 50×2 mm

Temperature: 40° C.

Solvent A: Water+0.1% HCOOH (v/v)

Solvent B: Acetonitrile+0.1% HCOOH (v/v)

Flow: 400 μL/min

Injection volume: 5 μL

Gradient:

| Time [min] | A % | B % |
|---|---|---|
| 0 | 90 | 10 |
| 2 | 5 | 95 |
| 4 | 5 | 95 |
| 4.1 | 90 | 10 |
| 9 | 90 | 10 |

Examples for Inhibition of Fumonisin FB1 Production

Compounds listed below showed an activity of >=80% of inhibition of Fumonisin FB1 production at 50 μM. Growth inhibition of *Fusarium proliferatum* of these examples varied from 0 to 91% at 50 μM.

| Example | % inhibition FB1 production at 50 μM | % inhibition fungal growth at 50 μM |
|---|---|---|
| 1 | 82 | 41 |
| 3 | 99 | 46 |
| 4 | 89 | 22 |
| 5 | 81 | 0 |
| 21 | 100 | 91 |
| 38 | 100 | 88 |
| 97 | 99 | 17 |
| 98 | 97 | 4 |
| 101 | 87 | 0 |
| 106 | 98 | 39 |
| 107 | 80 | 1 |
| 108 | 100 | 25 |
| 110 | 99 | 86 |
| 420 | 90 | 21 |

Production of DON/Acetyl-DON by *Fusarium graminearum*

Compounds were tested in microtiter plates in DON-inducing liquid media (1 g $(NH_4)_2HPO_4$, 0.2 g $MgSO_4 \times 7H_2O$, 3 g $KH_2PO_4$, 10 g Glycerin, 5 g NaCl and 40 g Saccharose per liter), supplemented with 10% oat extract, containing 0.5% DMSO, inoculated with a concentrated spore suspension of *Fusarium graminearum* to a final concentration of 2000 spores/ml.

The plate was covered and incubated at high humidity at 28° C. for 7 days.

At start and after 3 days OD measurement at OD620 multiple read per well (square: 3×3) was taken to calculate the growth inhibition.

After 7 days 1 volume of 84/16 acetonitrile/water was added to each well and a sample of the liquid medium was taken and diluted 1:100 in 10% acetonitrile. The amounts of DON and Acetyl-DON of the samples were analysed per HPLC-MS/MS and results were used to calculate inhibition of DON/AcDON production in comparison to a control without compound.

HPLC-MS/MS was done with the following parameters:
Ionization mode: ESI negative
Ionspray voltage: −4500V
Spraygas Temperature: 500° C.
Declustering potential: −40V
Collision energy: −22 eV
Collision gas: $N_2$
MRM trace: 355.0>264.9; dwell time 150 ms
HPLC column: Waters Atlantis T3 (trifunctional C18 bonding, fully endcapped)
Particle size: 3 μm
Column size: 50×2 mm
Temperature: 40° C.
Solvent A: Water/2.5 mM $NH_4OAc$+0.05% $CH_3COOH$ (v/v)
Solvent B: Methanol/2.5 mM $NH_4OAc$+0.05% $CH_3COOH$ (v/v)
Flow: 400 μL/min
Injection volume: 11 μL
Gradient:

| Time [min] | A % | B % |
|---|---|---|
| 0 | 100 | 0 |
| 0.75 | 100 | 0 |
| 1.5 | 5 | 95 |
| 4 | 5 | 95 |
| 5 | 100 | 0 |
| 10 | 100 | 0 |

Examples for Inhibition of DON/AcDON Production

The compounds listed below showed an activity of >=80% of inhibition of DON/AcDON at 50 μM. Growth inhibition of *Fusarium graminearum* of these examples varied from 0 to 100% at 50 μM.

| Example | % Inhibition of DON/AcDON at 50 μM | % Inhibition of fungal growth at 50 μM |
|---|---|---|
| 21 | 100 | 96 |
| 105 | 88 | 0 |
| 106 | 99 | 98 |
| 107 | 100 | 86 |
| 108 | 100 | 99 |
| 109 | 100 | 49 |
| 110 | 100 | 99 |
| 194 | 99 | 90 |
| 195 | 99 | 94 |
| 196 | 99 | 83 |
| 197 | 90 | 73 |
| 199 | 99 | 100 |
| 201 | 94 | 39 |
| 204 | 95 | 56 |
| 205 | 98 | 84 |
| 214 | 99 | 89 |
| 223 | 99 | 79 |
| 225 | 99 | 87 |
| 226 | 99 | 93 |
| 227 | 99 | 100 |
| 228 | 92 | 49 |
| 229 | 98 | 82 |
| 234 | 96 | 45 |
| 235 | 86 | 0 |
| 240 | 99 | 37 |
| 243 | 99 | 31 |
| 244 | 99 | 100 |
| 246 | 99 | 91 |
| 247 | 99 | 91 |
| 249 | 99 | 11 |
| 250 | 99 | 29 |
| 251 | 99 | 100 |
| 252 | 99 | 99 |
| 253 | 99 | 100 |
| 256 | 99 | 100 |
| 257 | 99 | 81 |
| 258 | 94 | 54 |
| 261 | 98 | 96 |
| 263 | 99 | 100 |
| 264 | 99 | 100 |
| 265 | 87 | 23 |
| 267 | 89 | 47 |
| 269 | 87 | 58 |
| 270 | 98 | 49 |
| 271 | 94 | 20 |

-continued

| Example | % Inhibition of DON/AcDON at 50 µM | % Inhibition of fungal growth at 50 µM |
|---|---|---|
| 275 | 99 | 95 |
| 276 | 98 | 98 |
| 278 | 98 | 100 |
| 279 | 98 | 100 |
| 281 | 99 | 100 |
| 284 | 99 | 100 |
| 285 | 99 | 90 |
| 286 | 99 | 68 |
| 287 | 99 | 94 |
| 288 | 99 | 92 |
| 291 | 100 | 18 |
| 292 | 100 | 45 |
| 293 | 100 | 32 |
| 294 | 99 | 92 |
| 297 | 100 | 0 |
| 298 | 100 | 38 |
| 300 | 99 | 100 |
| 301 | 99 | 60 |
| 303 | 100 | 83 |
| 304 | 100 | 87 |
| 304 | 100 | 90 |
| 306 | 100 | 87 |
| 307 | 80 | 45 |
| 312 | 99 | 87 |
| 313 | 98 | 6 |
| 316 | 87 | 37 |
| 317 | 100 | 78 |
| 321 | 92 | 39 |
| 322 | 99 | 0 |
| 323 | 94 | 6 |
| 324 | 93 | 0 |
| 328 | 98 | 100 |
| 329 | 98 | 85 |
| 330 | 94 | 31 |
| 333 | 98 | 86 |
| 337 | 99 | 100 |
| 338 | 99 | 50 |
| 340 | 98 | 91 |
| 341 | 96 | 55 |
| 342 | 97 | 23 |
| 344 | 98 | 91 |
| 345 | 97 | 63 |
| 347 | 99 | 79 |
| 348 | 99 | 45 |
| 349 | 99 | 95 |
| 350 | 99 | 92 |
| 351 | 99 | 36 |
| 354 | 99 | 97 |
| 356 | 97 | 75 |
| 358 | 100 | 102 |
| 359 | 100 | 62 |
| 360 | 100 | 12 |
| 363 | 99 | 99 |
| 364 | 99 | 100 |
| 365 | 90 | 100 |
| 366 | 98 | 93 |
| 367 | 99 | 78 |
| 368 | 99 | 100 |
| 369 | 99 | 100 |
| 370 | 99 | 70 |
| 371 | 99 | 82 |
| 372 | 98 | 1 |
| 373 | 99 | 97 |
| 374 | 99 | 58 |
| 375 | 99 | 78 |
| 376 | 99 | 84 |
| 377 | 99 | 89 |
| 378 | 99 | 54 |
| 379 | 99 | 90 |
| 380 | 99 | 82 |
| 381 | 99 | 91 |
| 384 | 99 | 100 |
| 385 | 82 | 17 |
| 386 | 99 | 0 |
| 387 | 99 | 93 |
| 388 | 99 | 100 |

-continued

| Example | % Inhibition of DON/AcDON at 50 µM | % Inhibition of fungal growth at 50 µM |
|---|---|---|
| 389 | 99 | 96 |
| 390 | 99 | 100 |
| 391 | 99 | 97 |
| 392 | 99 | 97 |
| 393 | 99 | 96 |
| 394 | 100 | 92 |
| 395 | 99 | 0 |
| 396 | 100 | 30 |
| 397 | 97 | 32 |
| 399 | 90 | 0 |
| 400 | 99 | 0 |
| 401 | 99 | 0 |
| 405 | 99 | 90 |
| 406 | 95 | 0 |
| 407 | 100 | 99 |
| 408 | 97 | 0 |
| 410 | 83 | 0 |
| 411 | 99 | 98 |
| 412 | 93 | 98 |
| 414 | 84 | 11 |
| 416 | 91 | 8 |
| 423 | 99 | 91 |

Production of Aflatoxins by *Aspergillus parasiticus*

Compounds were tested in microtiter plates (96 well black flat and transparent bottom) in Aflatoxin-inducing liquid media (20 g sucrose, yeast extract 4 g, $KH_2PO_4$ 1 g, and $MgSO_4$ $7H_2O$ 0.5 g per liter), supplemented with 20 mM of Cavasol (hydroxypropyl-beta-cyclodextrin) and containing 1% of DMSO. The assay is started by inoculating the medium with a concentrated spore suspension of *Aspergillus parasiticus* at a final concentration of 1000 spores/ml.

The plate was covered and incubated at 20° C. for 7 days.

After 7 days of culture, OD measurement at $OD_{620nm}$ with multiple read per well (circle: 4×4) was taken with an Infinite 1000 (Tecan) to calculate the growth inhibition. In the same time bottom fluorescence measurement at $EM_{360nm}$ and $Ex_{426nm}$ with multiple read per well (square: 3×3) was taken to calculate inhibition of aflatoxin formation.

Examples for Inhibition of Production of Aflatoxins:

The compounds listed below showed an activity of >=70% of inhibition of aflatoxins at 50 µM. Growth inhibition of *Aspergillus parasiticus* of these examples was between 47 and 64% at 50 µM.

| Example | % Inhibition of Aflatoxin at 50 µM | % Inhibition of fungal growth at 50 µM |
|---|---|---|
| 296 | 74 | 47 |
| 298 | 99 | 64 |

The invention claimed is:
1. A compound of formula (I),

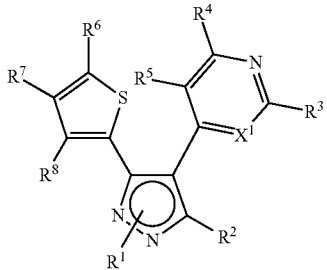

an N-oxide formed with the nitrogen in the pyridine ring, or a salt thereof;
in which
$X^1$ represents C—H or N;
$R^1$ represents $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, $C_3$-$C_8$-allenyl, $C_3$-$C_8$-trialkylsilyl, $C_4$-$C_8$-cycloalkenyl, $C_1$-$C_6$-alkoxy-$C_1$-$C_6$-alkyl, acyloxy-$C_1$-$C_6$-alkyl, heteroaryl-$C_1$-$C_6$-alkyl, aryl-$C_1$-$C_6$-alkyl, $C_1$-$C_6$-alkylthio-$C_1$-$C_6$-alkyl, $C_1$-$C_4$-alkyl-C(O)—$C_1$-$C_6$-alkyl, $C_3$-$C_6$-cycloalkyl-C(O)—$C_1$-$C_4$-alkyl, heterocyclyl-C(O)—$C_1$-$C_4$-alkyl, $C_1$-$C_4$-alkyl-C(O)O—$C_1$-$C_6$-alkyl, $C_3$-$C_6$-cycloalkyl-C(O)O—$C_1$-$C_4$-alkyl, heterocyclyl-C(O)O—$C_1$-$C_4$-alkyl, heterocyclyl-$C_1$-$C_6$-alkyl, $C_5$-$C_{10}$-aryl, heterocyclyl, or heteroaryl, any of which is optionally substituted by one or more $R^{16}$; H; C(O)$NR^{17}R^{18}$; C(O)$R^{17}$; C(O)$OR^{17}$; S(O)$_2R^{17}$; C(S)$NR^{17}R^{18}$; C(S)$R^{17}$; or S(O)$_2NR^{17}R^{18}$;
$R^2$ represents H; cyano; halogen; $C_1$-$C_6$-alkyl, $C_3$-$C_6$-cycloalkyl, heterocyclyl, $C_2$-$C_8$-alkenyl, $C_2$-$C_8$-alkynyl, $C_1$-$C_8$-alkoxy; $C_2$-$C_8$-alkynyloxy, $C_1$-$C_8$-alkylthio, or $C_3$-$C_8$-trialkylsilyl, any of which is optionally substituted by one or more substituents selected from the group consisting of halogen, cyano, amino, dimethylamino, and methoxy; $C_6$-$C_{14}$-aryl which is optionally substituted by one or more substituents selected from the group consisting of halogen, cyano, $C_1$-$C_6$ alkyl, $C_1$-$C_6$-alkylamino, $C_1$-$C_6$-dialkylamino, $NH_2$, heterocyclyl, C(O)O$C_1$-$C_6$-alkyl, OC(O)$C_1$-$C_6$-alkyl, $C_1$-$C_4$-alkoxy, and $C_6$-$C_{14}$-aryl; $C_1$-$C_6$-alkyl, $C_3$-$C_6$-cycloalkyl, $C_2$-$C_8$-alkenyl, $C_2$-$C_8$-alkynyl, $C_1$-$C_8$-alkoxy, $C_2$-$C_8$-alkynyloxy, $C_1$-$C_8$-alkylthio, or $C_3$-$C_8$-trialkylsilyl, any of which is optionally substituted by one or more substituents selected from the group consisting of $C_1$-$C_6$-alkyl, $C_1$-$C_6$-alkylamino, $C_1$-$C_6$-dialkylamino, heterocyclyl, C(O)O$C_1$-$C_6$-alkyl, OC(O)$C_1$-$C_6$-alkyl, $C_2$-$C_4$-alkoxy, and $C_6$-$C_{14}$-aryl; heterocyclyl which is optionally substituted by one or more substituents selected from the group consisting of $C_1$-$C_6$-alkylamino, $C_1$-$C_6$-dialkylamino, heterocyclyl, C(O)O$C_1$-$C_6$-alkyl, OC(O)$C_1$-$C_6$-alkyl, $C_2$-$C_4$-alkoxy, and $C_6$-$C_{14}$-aryl;
$R^3$ represents H; halogen; cyano; $OR^{11}$; C(O)$OR^{11}$; C(O)$SR^{11}$; C(S)$OR^{11}$; C(O)$R^{11}$; C(S)$R^{11}$; $SR^{11}$; $NR^9R^{10}$; C(O)$NR^{11}R^{20}$; C(S)$NR^{11}R^{20}$; N($R^{17}$)C(O)$OR^{11}$; N=CH—$NR^{17}R^{18}$; NH—CH—$NR^{17}R^{18}$; N=$CR^{17}R^{18}$; N($C_1$-$C_6$-alkyl)-$NHR^{17}$; N=C(H)$OR^{17}$; N=C(O$R^{17}$)$R^{18}$; N=C(S$R^{17}$)$R^{18}$; C(=$NR^{17}$)$NR^{17}R^{18}$; SO(=$NR^{17}$)$R^{18}$; SO$_2NR^{11}R^{20}$; $C_1$-$C_6$-alkyl, $C_3$-$C_8$-cycloalkyl, $C_2$-$C_6$-alkenyl, $C_2$-$C_8$-alkynyl, $C_6$-$C_{14}$-aryl, heterocyclyl, or heteroaryl, any of which is optionally substituted by one or more substituents selected from the group consisting of $R^{16}$; or SO$_2R^{11}$; with the proviso that if $X_1$ is N, then $R^3$ is not aniline;
$R^4$ and $R^5$ represent independently of each other H; F; Cl; Br; I; cyano; nitro; OH; SH; $NH_2$; $C_1$-$C_6$-alkyl, $C_3$-$C_6$-cycloalkyl, $C_2$-$C_6$-alkenyl, $C_2$-$C_6$-alkynyl, $C_6$-$C_{14}$-aryl, $C_1$-$C_4$-alkoxy, O—($C_6$-$C_{14}$-aryl), S—($C_1$-$C_4$-alky), S(O)—($C_1$-$C_6$-alkyl), C(O)—($C_1$-$C_6$-alkyl), $C_3$-$C_8$-trialkylsilyl, heteroaryl, or heterocyclyl, any of which is optionally substituted by one or more $R^{16}$; or $R^4$ and $R^5$ form, together with the carbon atoms to which they are bonded, a 5- to 8-membered ring which may contain one, two, three, or four heteroatoms selected from oxygen, sulphur, or $NR^{19}$, which may be optionally halogen, oxygen, cyano, $C_1$-$C_4$-alkyl, $C_1$-$C_4$-alkoxy, $C_1$-$C_6$-haloalkyl, $C_1$-$C_4$-haloalkoxy, or $C_3$-$C_6$-cycloalkyl;
$R^6$ represents H; halogen; OH; nitro; cyano; C(O)$NR^{11}R^{20}$; C(O)$OR^{11}$; SO$_2R^{11}$; $SR^{11}$; S(O)$R^{11}$; C(S)$R^{11}$; C(S)$NR^{11}R^{20}$; SO$_2NR^{11}R^{20}$; $NR^9R^{10}$; N=$CR^{17}R^{18}$; C(=$NR^{17}$)$R^{18}$; $OR^{11}$; C(O)$SR^{11}$; C(S)$OR^{11}$; C(O)OC(O)$R^{11}$; C(O)$R^{11}$; N($R^{17}$)C(O)$R^{11}$; N($R^{17}$)C(O)$OR^{11}$; N=C—$NR^{17}R^{18}$; N($C_1$-$C_6$-alkyl)-$NR^{17}$; N=C(H)$OR^{17}$; N=C(O$R^{17}$)$R^{18}$; N=C(S$R^{17}$)$R^{18}$; C(=$NR^{17}$)$NR^{17}R^{18}$; SO(=$NR^{17}$)$R^{18}$; SO$_2NR^{11}R^{20}$; or $C_1$-$C_6$-alkyl, $C_3$-$C_8$-cycloalkyl, $C_2$-$C_8$-alkenyl, $C_2$-$C_8$-alkynyl, C(O)—$C_1$-$C_6$-alkyl, $C_1$-$C_8$-alkoxy, $C_1$-$C_8$-alkylthio, $C_1$-$C_8$-halogenalkoxy, $C_1$-$C_6$-alkylsulphenyl, $C_1$-$C_6$-alkylsulfanyl, $C_3$-$C_8$-trialkylsilyl, $C_6$-$C_{10}$-aryl, heteroaryl, heterocyclyl, or $C_6$-$C_{10}$-aryloxy, any of which is optionally substituted by one or more $R^{16}$;
$R^7$ represents H; halogen; cyano; nitro; $C_1$-$C_6$-alkyl; $C_3$-$C_6$-cycloalkyl; $C_2$-$C_6$-alkenyl; $C_2$-$C_6$-alkynyl; $C_5$-$C_{10}$-aryl; heteroaryl; heterocyclyl;
or $R^6$ and $R^7$ form, together with the carbon atoms to which they are bonded, a 5- to 7-membered ring which may contain one, two, three, or four heteroatoms selected from oxygen, sulphur, or $NR^{19}$, and which may be optionally substituted with one or more substituents selected from the group consisting of $C_1$-$C_4$-alkyl, $C_1$-$C_4$-halogenoalkyl, $C_1$-$C_4$-alkoxy, $C_1$-$C_4$-halogenoalkoxy, halogen, hydroxyl, amino, cyano, and nitro;
$R^8$ represents H; halogen; cyano; $C_1$-$C_6$-alkyl; $C_3$-$C_6$-cycloalkyl; $C_2$-$C_6$-alkenyl; $C_2$-$C_6$-alkynyl; $C_6$-$C_{10}$-aryl; heteroaryl; heterocyclyl;
or $R^7$ and $R^8$ form, together with the carbon atoms to which they are bonded, a 5- to 7-membered ring which may contain one, two, three, or four heteroatoms selected from oxygen, sulphur, or $NR^{19}$, and which may be optionally substituted with one or more substituents selected from the group consisting of $C_1$-$C_4$-alkyl, $C_1$-$C_4$-halogenoalkyl, $C_1$-$C_4$-alkoxy, $C_1$-$C_4$-halogenoalkoxy, halogen, hydroxyl, amino, cyano, and nitro;
$R^9$ and $R^{10}$ represent H; C(S)$R^{14}$; C(O)$R^{14}$; SO$_2R^{14}$; C(O)$OR^{14}$; $OR^{14}$; C(O)$NR^{14}R^{15}$; $C_1$-$C_6$-alkyl, $C_3$-$C_6$-cycloalkyl, $C_2$-$C_6$-alkenyl, $C_2$-$C_6$-alkynyl, $C_3$-$C_8$-cycloalkyl, $C_6$-$C_{14}$-aryl, heterocyclyl, or heteroaryl, any of which is optionally substituted by one or more substituents selected from the group consisting of F, Cl, Br, OH, cyano, $C_1$-$C_6$-alkyl, O—C(O)$R^{17}$, O—P(O)(O$R^{17}$)$_2$, O—B(O$R^{17}$)$_2$, and O—($C_1$-$C_4$-alkyl); or $C_3$-$C_8$-cycloalkyl-$C_1$-$C_6$-alkyl, $C_6$-$C_{14}$-aryl-$C_1$-$C_6$-alkyl, heterocyclyl-$C_1$-$C_6$-alkyl, or heteroaryl-$C_1$-$C_6$-alkyl, any of which is optionally substituted by one or more substituents selected from the group consisting of F, Cl, Br, OH, cyano, $C_1$-$C_6$alkyl, O—C(O)$R^{17}$, O—P(O)(O$R^{17}$)$_2$, O—B(O$R^{17}$)$_2$, and O—($C_1$-$C_4$-alkyl);

$R^{11}$ and $R^{20}$ represent H; C(S)$R^{12}$; C(O)$R^{12}$; SO$_2R^{12}$; C(O)O$R^{12}$; O$R^{12}$; C(O)N$R^{12}R^{13}$; or $C_1$-$C_6$-alkyl, $C_2$-$C_6$-alkenyl, $C_2$-$C_6$-alkynyl, $C_3$-$C_8$-cycloalkyl, $C_6$-$C_{14}$-aryl, heterocyclyl, or heteroaryl, any of which is optionally substituted by one more substituents selected from the group consisting of F, Cl, Br, OH, cyano, $C_1$-$C_6$-alkyl, O—C(O)$R^{17}$, O—P(O)(O$R^{17}$)$_2$, O—B(O$R^{17}$)$_2$, and O—($C_1$-$C_4$-alkyl);

$R^{12}$ and $R^{13}$ represent H; or $C_1$-$C_6$-alkyl, $C_3$-$C_6$-cycloalkyl, $C_2$-$C_6$-alkenyl, $C_2$-$C_6$-alkynyl, $C_3$-$C_8$-cycloalkyl, $C_6$-$C_{14}$-aryl, heterocyclyl, or heteroaryl, any of which is optionally substituted by one or more substituents selected from the group consisting of F, Cl, Br, I, OH, carbonyl, cyano, $C_1$-$C_6$-alkyl, and $C_1$-$C_4$-alkoxy;

$R^{14}$ and $R^{15}$ represent H; $C_1$-$C_6$-alkyl, $C_3$-$C_6$-cycloalkyl, $C_2$-$C_6$-alkenyl, $C_2$-$C_6$-alkynyl, $C_3$-$C_8$-cycloalkyl, $C_6$-$C_{14}$-aryl, heterocyclyl, or heteroaryl, any of which is optionally substituted by one or more substituents selected from the group consisting of F, Cl, Br, I, OH, cyano, methoxy, nitro, trifluoromethyl, and difluoromethyl; $C_3$-$C_8$-cycloalkyl-$C_1$-$C_6$-alkyl, $C_6$-$C_{14}$-aryl-$C_1$-$C_6$-alkyl, heterocyclyl-$C_1$-$C_6$-alkyl, or heteroaryl-$C_1$-$C_6$-alkyl, any of which is optionally substituted by one or more substituents selected from the group consisting of F, Cl, Br, I, OH, cyano, methoxy, nitro, trifluoromethyl, difluoromethyl, $C_1$-$C_6$-alkyl, O—C(O)$R^{17}$, O—P(O)(O$R^{17}$)$_2$, O—B(O$R^{17}$)$_2$, and O—($C_1$-$C_4$-alkyl); or $C_1$-$C_6$-alkyl, $C_3$-$C_6$-cycloalkyl, $C_2$-$C_6$-alkenyl, $C_2$-$C_6$-alkynyl, $C_3$-$C_8$-cycloalkyl, $C_6$-$C_{14}$-aryl, heterocyclyl, or heteroaryl, any of which is optionally substituted by one or more substituents selected from the group consisting of $C_1$-$C_6$-alkyl, O—C(O)$R^{17}$, O—P(O)(O$R^{17}$)$_2$, O—B(O$R^{17}$)$_2$, or O—($C_1$-$C_4$-alkyl);

$R^{16}$ represents OH; F; Cl; Br; I; cyano; NH—C(O)$R^{17}$; N$R^{17}R^{18}$; C(O)$R^{17}$; C(O)O$R^{17}$; C(O)N$R^{17}R^{18}$; SO$_2R^{17}$; OC(O)$R^{17}$; or $C_1$-$C_6$-alkyl, $C_2$-$C_6$-alkenyl, $C_2$-$C_6$-alkynyl, $C_3$-$C_8$-cycloalkyl, $C_1$-$C_4$-alkoxy, S—($C_1$-$C_4$-alkyl), O—($C_3$-$C_8$-cycloalkyl), S—($C_3$-$C_8$-cycloalkyl), $C_6$-$C_{14}$-aryl, O—($C_6$-$C_{14}$-aryl), S—($C_6$-$C_{14}$-aryl), heterocyclyl, or heteroaryl, any of which is optionally substituted by one or more substituents selected from the group consisting of F, Cl, Br, I, OH, carbonyl, cyano, $C_1$-$C_6$-alkyl, and $C_1$-$C_4$-alkoxy;

$R^{17}$ and $R^{18}$ represent $C_1$-$C_6$-alkyl, $C_3$-$C_6$-cycloalkyl, $C_2$-$C_6$-alkenyl, $C_2$-$C_6$-alkynyl, or benzyl, any of which is optionally substituted with one or more substituents selected from the group consisting of F, Cl, Br, OH, and cyano; H; or aryl;

$R^{19}$ represents H, $C_1$-$C_6$-alkyl, $C_3$-$C_6$-cycloalkyl, $C_2$-$C_6$-alkenyl, $C_2$-$C_6$-alkynyl, C(S)$R^{14}$, C(O)$R^{14}$, SO$_2R^{14}$, or C(O)O$R^{14}$;

with the proviso that the compound of formula (I) is not 4-[3-(2-thienyl)-1H-pyrazol-4-yl]quinoline or phenyl substituted 4-phenyl-6-[1-phenyl-3-(2-thienyl)-1H-pyrazol-4-yl]pyrimidine-2(1H)-thiones.

2. The compound of claim 1, in which $X^1$ represents CH or N;

$R^1$ represents methyl, ethyl, n-propyl, iso-propyl, n-butyl, iso-butyl, sec-butyl, tert-butyl, n-pentyl, —CH=CH$_2$, —CH$_2$CH=CH$_2$, —CH$_2$C≡CH, —C≡CH, —CH=CHCH$_3$, —C≡CCH$_3$, but-2-en-1-yl, but-3-en-2-yl, but-2-yn-1-yl, cyclopropyl, cyclobutyl, cyclopentyl, cyclohexyl, —CH=C=CH$_2$, trimethylsilyl, tert-butyldimethylsilyl, cyclohexenyl, methoxymethyl, ethoxymethyl, methoxyethyl, tert-butoxy-methyl, trifluoromethyl, difluoromethyl, trifluoromethoxy, difluoromethoxy, methylacetate, ethylacetate, pyridin-2-ylmethyl, pyridin-3-ylmethyl, pyridin-4-ylmethyl, (1,3-thiazol-5-yl)methyl, (1,3-thiazol-4-yl)methyl, (1,3-thiazol-3-yl)methyl, (1,3-oxazol-5-yl)methyl, (1,3-oxa-4-yl)methyl, (1,3-oxa-3-yl)methyl, phenylmethyl, phenylethyl, methylthio, ethylthio, n-propylthio, iso-propylthio, tertbutylthio, n-butylthio, sec-butylthio, iso-butylthio, methylthioalkyl, phenyl, benzyl, naphthalenyl, oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydro-pyridazinyl, 4-hexahydropyridazinyl, 2-hexahydropyrimidinyl, 4-hexahydropyrimidinyl, 5-hexahydropyrimidinyl, 2-piperazinyl, furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, or morpholine, any of which is optionally substituted with one or more $R^{16}$; H; C(O)N$R^{17}R^{18}$; C(O)$R^{17}$; C(O)O$R^{17}$; S(O)$_2R^{17}$; C(S)N$R^{17}R^{18}$; C(S)$R^{17}$; or S(O)$_2$N$R^{17}R^{18}$;

$R^2$ represents H; cyano; Br; Cl; F; or methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH$_2$CH=CH$_2$, —C≡CH, —C≡CCH$_3$, —CH$_2$C≡CH, methoxy, ethoxy, n-propoxy, iso-propoxy, n-butoxy, tert-butoxy, —O—CH$_2$C≡CH, methylthio, ethylthio, n-propylthio, iso-propylthio, tertbutylthio, n-butylthio, sec-butylthio, iso-butylthio, or trimethylsilyl, any of which is optionally substituted by one or more substituents selected from the group consisting of F, Cl, Br, cyano, amino, dimethylamino, and methoxy;

$R^3$ represents H; F; Cl; Br; cyano; O$R^{11}$; C(O)O$R^{11}$; C(O)$R^{11}$; N$R^9R^{10}$; C(O)N$R^{11}R^{20}$; N=C(O$R^{17}$)$R^{18}$; N=C(S$R^{17}$)$R^{18}$; SO(=N$R^{17}$)$R^{18}$; N($C_1$-$C_6$-alkyl)-NH$R^{17}$; or methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —C$_2$C=CH, —C≡CH, —CH=CHCH$_3$, —C≡CCH$_3$, but-2-en-1-yl, but-3-en-2-yl, but-2-yn-1-yl, phenyl, or benzyl, any of which is optionally substituted by one or more $R^{16}$;

R⁴ and R⁵ represent independently of each other H; F; Cl; Br; cyano; nitro; OH; SH; or methyl, ethyl, cyclopropyl, CH=CH₂, —CH₂CH=CH₂, —CH₂C≡CH, —C≡CH, phenyl, or methoxy, any of which is optionally substituted with one or more R¹⁶;

or R⁴ and R⁵ form, together with the carbon atoms to which they are bonded, a 5- to 8-membered ring which may contain one, two, three, or four heteroatoms selected from oxygen, sulphur, or NR¹⁹, which may be optionally substituted by one or more F, Cl, Br, oxygen, cyano, methyl, ethyl, methoxy, trifluoromethyl, difluoromethyl, trifluoromethoxy, or cyclopropyl;

R⁶ represents H; F; Cl; Br; OH; nitro; cyano; C₂-alkynyl; or methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH₂, —CH₂CH=CH₂, —CH₂C≡CH, —C≡CH, methoxy, ethoxy, n-propoxy, iso-propoxy, n-butoxy, tert-butoxy, methylthio, ethylthio, n-propylthio, iso-propylthio, tertbutylthio, n-butylthio, sec-butylthio, or iso-butylthio, any of which is optionally substituted by one or more R¹⁶;

R⁷ represents H, F, Cl, Br, cyano, nitro, methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH₂, —CH₂CH=CH₂, —CH₂C≡CH, or —C≡CH;

R⁸ represents H; F; Cl; Br; cyano; methyl; ethyl; n-propyl; iso-propyl; n-butyl; iso-butyl; sec-butyl; tert-butyl; n-pentyl; cyclopropyl; cyclobutyl; cyclopentyl; cyclohexyl; CH=CH₂; —CH₂CH=CH₂; —CH₂C≡CH; —C≡CH;

or R⁷ and R⁸ form, together with the carbon atoms to which they are bonded, a 5- to 7-membered ring which may contain one, two, three, or four heteroatoms selected from oxygen, sulphur, or NR¹⁹, which may be optionally substituted with one or more substituents selected from the group consisting of methyl, ethyl, trifluoromethyl, methoxy, trifluoromethoxy, F, Cl, Br, hydroxyl, amino, cyano, and nitro;

R⁹ and R¹⁰ represent H; C(S)R¹⁴; C(O)R¹⁴; SO₂R¹⁴; C(O)OR¹⁴; OR¹⁴; C(O)NR¹⁴R¹⁵; or C₁-C₆-alkyl, C₃-C₆-cycloalkyl, C₂-C₆-alkenyl, C₂-C₆-alkynyl, C₃-C₈-cycloalkyl, C₆-C₁₄-aryl, heterocyclyl, or heteroaryl, ary of which is optionally substituted by one or more substituents selected from the group consisting of F, Cl, Br, OH, cyano, methyl, methoxy substituted methyl, ethyl, iso-propyl, sec-butyl, iso-butyl, tert-butyl, cyclopropyl, CH=CH₂, —CH₂CH=CH₂, —CH₂C≡CH, —C≡CH, —CH=CH—CH₃, —C≡CCH₃, but-2-en-1-yl, but-3-en-2-yl, but-2-yn-1-yl, phenyl, oxetanyl, methylcyclopropyl, and benzyl;

R¹¹ and R²⁰ represent H; C(S)R¹²; C(O)R¹²; SO₂R¹²; C(O)OR¹²; OR¹²; C(O)NR¹²R¹³; or methyl, ethyl, n-propyl, iso-propyl, n-butyl, iso-butyl, sec-butyl, tert-butyl, n-pentyl, O—C(O)Me, O—C(O)Et, O—P(O)(OMe)₂, O—B(OMe)₂, O—B(OEt)₂, methoxy, ethoxy, n-propoxy, iso-propoxy, n-butoxy, tert-butoxy substituted methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH₂, —CH₂CH=CH₂, —CH₂C≡CH, —C≡CH, or phenyl, any of which is optionally substituted by one or more substituents selected from the group consisting of F, Cl, Br, OH, and cyano;

R¹² and R¹³ represent H; or methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH₂, —CH₂CH=CH₂, —CH₂C≡CH, —C≡CH, or phenyl, any of which is optionally substituted by one or more substituents selected from the group consisting of F, Cl, Br, I, OH, carbonyl, cyano, methyl, ethyl, n-propyl, iso-propyl, n-butyl, iso-butyl, sec-butyl, tert-butyl, n-pentyl or methoxy, ethoxy, n-propoxy, iso-propoxy, n-butoxy, and tert-butoxy;

R¹⁴ and R¹⁵ represent methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH₂, —CH₂CH=CH₂, —CH₂C≡CH, —C≡CH, or phenyl, any of which is optionally substituted by one or more substituents selected from the group consisting of F, Cl, Br, I, OH, cyano, methoxy, nitro, trifluoromethyl, difluoromethyl, cyclopropylmethyl, benzyl, 3-thienyl, 2-thienyl; or hydrogen;

R¹⁶ represents OH; F; Cl; Br; I; cyano; NH—C(O)R¹⁷; NR¹⁷R¹⁸; C(O)R¹⁷; C(O)OR¹⁷; C(O)NR¹⁷R¹⁸; SO₂R¹⁷; or methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH₂, —CH₂CH=CH₂, —CH₂C≡CH, —C≡CH, phenyl, methoxy, ethoxy, tetrahydrofuranyl, 3-tetrahydrofuranyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2-piperidinyl, 3-piperidinyl, 4-piperidinyl, 2-piperazinyl, furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, or pyrazin-2-yl, any of which is optionally substituted by one or more substituents selected from the group consisting of F, Cl, Br, I, OH, carbonyl, cyano, methyl, ethyl, and methoxy;

R¹⁷ and R¹⁸ represent methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH₂, —CH₂CH=CH₂, —CH₂C≡CH, —C≡CH, or benzyl, any of which is optionally substituted by one or more substituents selected from the group consisting of F, Cl, Br, OH, and cyano; or H;

R¹⁹ represents H, methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH₂, —CH₂CH=CH₂, —CH₂C≡CH, —C≡CH, C(S)R¹⁴, C(O)R¹⁴, SO₂R¹⁴, or C(O)OR¹⁴;

an N-oxide formed with the nitrogen in the pyridine ring, or a salt thereof.

3. The compound of claim 1,
in which $X^1$ represents CH or N;

$R^1$ represents H, methyl, ethyl, propan-2-yl, isobutyl, butan-2-yl, 2-methylpropyl, 3-methylbut-2-en-1-yl, 4-methylpentan-2-yl, 3-methylbutyl, 2,2-dimethylpropyl, pentan-3-yl, terbutyl, 4-methylpentan-2-yl, 3-dimethylbutan-2-yl, 3-methylbutan-2-yl, 2,2,2-trifluoroethyl, 2-chloroethyl, 2-fluoroethyl, 2-methoxyethyl, methoxymethyl, 1-methoxypropan-2-yl, 2-(trifluoromethoxy)ethyl, cyanomethyl, benzyl, 2-phenylethyl, —CH$_2$C(O)OEt, tetrahydrofuran-2-ylmethyl, ethylmorpholine, 3-dimethylamino-2-methylpropyl, allyl, 3,3-dichloroprop-2-en-1-yl, but-3-en-2-yl, prop-2-yn-1-yl, but-2-yn-1-yl, cyclohexyl, cyclopropyl, cyclobutyl, cyclopentyl, (2,2-dichlorcyclopropyl)methyl, cyclopropylmethyl, cyanoethyl, 2,2-difluoroethyl, ethoxyethyl, orthocyanobenzyl, orthofluorobenzyl, methoxyethoxyethyl, trifluoromethoxyethyl, cyclopropylmethyl, tetrahydro-2H-pyran-2-yl, phenyl, 2-fluorobenzyl, acetyl, ethoxycarbonyl, methylsulfonyl, isopropylaminocarbonyl, 2-cyanoethyl, 2,2-difluoroethyl, 2-ethoxyethyl, cyclopropylmethyl, 2-cyanobenzyl, or 2,3-difluorobenzyl;

$R^2$ represents H, cyano, cyclopropyl, methyl, Br, methylthio, trimethylsilyl, methyl, prop-1-ynyl, propyl, F, or Cl;

$R^3$ represents H, Cl, Br, cyano, isopropylcarbamoyl, methoxy, propylamine, dimethylamino, hydrazine, benzylamino, amino, acetylamino, prop-2-yn-1-ylamino, N-Bis(cyclopropylcarbonyl)amino, N-benzyl-N-isopropylcarbonylamino, n-propionylamino, isobutyrylamino, (cyclobutylcarbonyl)amino, (cyclopropylcarbonyl)amino, (methoxyacetyl)amino, 2-methoxypropanoyl, (2-methylbutanoyl)amino, but-2-enoylamino, prop-2-enoylamino, 3-(dimethylamino)prop-2-enoyl]amino, (3,3,3-trifluoropropanoyl)amino, 3,3-difluoropropanoylamino, 2-(cyclopropylethynyl), (cyclopropylacetyl)amino; (3-methylbutanoyl)amino, 2-hydroxypropanoylamino, acetylacetamido, 3-oxetanylamino, cyclopropylamino, benzoylamino, 2,2-dimethylpropanoylamino, (3-thienylcarbonyl)amino, (2-thienylcarbonyl)amino, isopropylamino, allylamino, cyclopropylmethylamino, 1-methyl-2-methoxyethylamino, 1-methylpropylamino, or formamido;

$R^4$ represents H;

$R^5$ represents H;

$R^6$ represents H, Cl, F, acetyl, N-butylcarboxamido, methyl, cyano, $C_2$-$C_8$-alkynyl, or $C_3$-$C_8$-cycloalkyl;

$R^7$ represents H or Cl;

$R^8$ represents H or Cl;

an N-oxide formed with the nitrogen in the pyridine ring, or a salt thereof.

4. The compound of claim 1,
in which $X^1$ represents CH or N;

$R^1$ represents propan-2-yl, butan-2-yl, 2-methylpropyl, prop-2-yn-1-yl, cyclopropyl, cyclobutyl, cyclopentyl, 2,2,2-trifluoroethyl, 2-fluorobenzyl, 2-(trifluoromethoxy)ethyl, 2-fluoroethyl, ethyl, but-1-en-3-yl, cyanomethyl, 3-pentyl, 2-chloroethyl, methoxymethyl, 2-cyanoethyl, 2,2-difluoroethyl, 2-ethoxyethyl, cyclopropylmethyl, 2-cyanobenzyl, 2,3-difluorobenzyl, or methyl;

$R^2$ represents H, methyl, or prop-1-ynyl;

$R^3$ represents H, acetylamino, n-propionylamino, isobutyrylamino, (cyclopropylcarbonyl)amino, (methoxyacetyl)amino, 2-methoxypropanoylamino, (2-methylbutanoyl)amino, but-2-enoylamino, prop-2-enoylamino, 3-(dimethylamino)prop-2-enoylamino, 3,3,3-trifluoropropanoylamino, 3,3-difluoropropanoylamino, amino, (cyclobutylcarbonyl)amino, (cyclopropylacetyl)amino, (3-methylbutanoyl)amino, 2-hydroxypropanoylamino, acetylacetamido, 3-oxetanylamino, cyclopropylamino, benzoylamino, or 2,2-dimethylpropanoylamino;

$R^4$ represents H;

$R^5$ represents H;

$R^6$ represents Cl or F;

$R^7$ represents H; and $R^8$ represents H;

an N-oxide formed with the nitrogen in the pyridine ring, or a salt thereof.

5. A composition comprising at least one compound of formula (I) according to claim 1 and at least one extender or surfactant for controlling phytopathogenic harmful and mycotoxin producing fungi.

6. A method for controlling unwanted microorganisms, comprising applying one or more compounds of formula (I) according to claim 1 to a plant, plant part, or surroundings of a plant.

7. A method for controlling phytopathogenic harmful and mycotoxin producing fungi, comprising applying one or more compounds of formula (I) according to claim 1 to the microorganisms, their habitat, or both.

8. A composition comprising at least one compound of formula (I) according to claim 1 and an extender, surfactant, or both, for controlling unwanted microorganisms.

9. A method for treating transgenic plants comprising applying one or more compounds of formula (I) according to claim 1 to a plant, plant part, surroundings of a plant, or a mixture thereof.

10. A compound of claim 1, which is

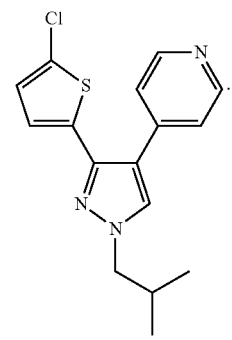 [SMILES: CC(C)Cn1cc(-c2ccncc2)c(-c2ccc(Cl)s2)n1]

* * * * *